US011293037B2

(12) United States Patent
Schalk et al.

(10) Patent No.: US 11,293,037 B2
(45) Date of Patent: Apr. 5, 2022

(54) METHOD FOR PRODUCING ALBICANOL AND/OR DRIMENOL

(71) Applicant: FIRMENICH SA, Geneva (CH)

(72) Inventors: Michel Schalk, Geneva (CH); Pauline Anziani, Geneva (CH); Christian Goerner, Geneva (CH); Daniel Solis Escalante, Geneva (CH)

(73) Assignee: FIRMENICH SA, Satigny (CH)

( * ) Notice: Subject to any disclaimer, the term of this patent is extended or adjusted under 35 U.S.C. 154(b) by 160 days.

(21) Appl. No.: 16/618,737

(22) PCT Filed: May 31, 2018

(86) PCT No.: PCT/EP2018/064344
§ 371 (c)(1),
(2) Date: Dec. 2, 2019

(87) PCT Pub. No.: WO2018/220113
PCT Pub. Date: Dec. 6, 2018

(65) Prior Publication Data
US 2020/0140898 A1  May 7, 2020

(30) Foreign Application Priority Data
Jun. 2, 2017 (EP) .................................... 17174399

(51) Int. Cl.
C12P 7/02 (2006.01)
C12N 9/88 (2006.01)

(52) U.S. Cl.
CPC .................. C12P 7/02 (2013.01); C12N 9/88 (2013.01); C12Y 402/03 (2013.01)

(58) Field of Classification Search
CPC ................................ C12P 7/02; C12Y 402/03
See application file for complete search history.

(56) References Cited

U.S. PATENT DOCUMENTS

2017/0362583 A1* 12/2017 Royer ..................... C07C 13/38

FOREIGN PATENT DOCUMENTS

WO  2013064411 A1  5/2013
WO  2017077125 A1  5/2017

OTHER PUBLICATIONS

International Search Report and Written Opinion for International Application No. PCT/EP2018/064344, dated Jul. 6, 2018, 18 pages.
EMBL-EBI, "HAD Superfamily IPR023214", Inter-Pro, Published 2017, http://www.ebi.ac.uk/interpro/entry/InterPro/IPR023214.
EMBL-EBI, "Family: HAD_2 (PF13419)", Pfam, http://pfam.xfam.org/family/PF13419.
Tatusova et al., "BLAST 2 Sequences, a new tool for comparing protein and nucleotide sequences", FEMS Microbiology Letters, Published 1999, pp. 247-250, vol. 174.
Zerbino et al., "Velvet: Algorithms for de novo short read assembly using de Bruign graphs", Published Mar. 18, 2008, pp. 821-829, vol. 18.
Schulz et al., "Oases: robust de novo RNA-seq assembly across the dynamic range of expression levels", Bioinformatics, Published 2012, pp. 1086-1092, vol. 28, No. 8.
Stanke et al., "AUGUSTUS: a web server for gene finding in eukaryotes", Nucleic Acids Research, Published 2004, pp. W309-W312, vol. 32.
Finn et al., "The Pfam protein families database: towards a more sustainable future", Nucleic Acids Research Database Issue, Published 2016, pp. D279-D285, vol. 44.
Henquet et al., "Identification of a drimenol synthase and drimenol oxidase from Persicaria hydropiper, involved in the biosynthesis of insect deterrent drimanes", The Plant Journal, Published 2017, pp. 1052-1063, vol. 90.
Kwon et al., "Molecular cloning and characterization of drimenol synthase from valerian plant (*Valeriana officinalis*)", FEBS Letters, Published 2014, pp. 4597-4603, vol. 588.
Shinohara et al., "Identification of a novel sesquiterpene biosynthetic machinery involved in astelloide biosynthesis", Scientific Reports, Published Sep. 15, 2016, pp. 1-11, vol. 6.
Morrone et al., "Gibberellin biosynthesis in bacteria: Separate ent-copalyl diphosphate and ent-kaurene synthases in Bradyrihizobium japonicum", FEBS Letters, Published 2009, pp. 475-480, vol. 583.
Finn et al., "HMMER web server: 2015 update", Nucleic Acids Research, Published 2015, Pages W30-W38, vol. 43.
Kuznetsova et al., "Functional Diversity of Haloacid Dehalogenase Superfamily Phasphatases from *Saccharomyces cerevisiae*", The Journal of Biological Chemistry, Published Jul. 24, 2015, pp. 18678-18698, vol. 390, No. 30.
Lu et al., "Nonmuscle myosin II powered transport of newly formed collagen fibrils at the plasma membrane", Proceedings of the National Academy of Sciences of the United States of America, Published Dec. 3, 2013, pp. E4743-E4752, vol. 110, No. 49.
Thompson et al., "Clustal W: improving the sensitivity of progressive multiple sequence alignment through sequence weighting, position-specific gap penalties and weight matrix choice", Nucleic Acids Research, Published 1994, pp. 4673-4680, vol. 22, No. 22.
Kuijpers et al., "A versatile, efficient strategy for assembly of multi-fragment expression vectors in *Saccaromyces cerevisiae* using 60bp synthetic recombination sequences", Microbial Cell Factories, Published 2013, pp. 1-13, vol. 12, No. 47.

(Continued)

Primary Examiner — Suzanne M Noakes
(74) Attorney, Agent, or Firm — Armstrong Teasdale LLP

(57) ABSTRACT

Described herein is a method of producing a drimane sesquiterpene such as albicanol, drimenol and/or derivatives thereof by contacting at least one polypeptide with farnesyl diphosphate (FPP) with a polypeptide comprising a Haloacid dehalogenase (HAD)-like hydrolase domain and having bifunctional terpene synthase activity. The method may be performed in vitro or in vivo. Also described herein are amino acid sequences of polypeptides useful in the methods and nucleic acids encoding the polypeptides described. The described method further provides host cells or organisms genetically modified to express the polypeptides and useful to produce a drimane sesquiterpene such as albicanol, drimenol and/or derivatives thereof.

18 Claims, 14 Drawing Sheets
Specification includes a Sequence Listing.

(56) References Cited

OTHER PUBLICATIONS

Paddon et al., "High-level semi-synthetic production of the potent antimalarial artemisinin" Nature, Published Apr. 25, 2013, pp. 528-532, vol. 496.

Griggs et al., "Regulated expression of the GAL4 activator gene in yeast provides a sensitive genetic switch for glucose repression", Proceedings of the National Academy of Sciences of the United States of America, Published 1991, pp. 8597-8601, vol. 88.

Westfall et al., "Production of amorphadiene in yeast, and its conversion to dihydroartemisinic acid, precursor to the antimalarial agent artemisinin", Proceedings of the National Academy of Sciences of the United States of America, Published 2012, pp. E111-E118, vol. 109.

Lee et al., "Transcriptomic analysis of the white rot fungus Polyporus brumalis provides insight into sesquiterpene biosynthesis", Microbiological Research, Published 2016, pp. 141-149, vol. 182.

Wang et al., "Four new spiroaxane sesquiterpenes and one new rosenonolactone derivative from cultures of Basidiomycete Trametes versicolor", Fitoterapia, Published 2015, pp. 127-131, vol. 105.

Xie et al., "Novel Sesquiterpenes from the Mycelial Cultures of Dichomitus squalens", Helvetica Chimica Acta, Published 2011, pp. 868-874, vol. 94.

Li et al., "Synthesis and bio-inspired optimization of drimenal: Discovry of chiral drimane fused oxazinones as promising antifungal and antibacterial candidates", European Journal of Medicinal Chemistry, Published 2018, pp. 558-567, vol. 143.

UniParc-UPI00032CBA96, "Dichomitus squalens (strain LYAD-421)(Western red white-rot fungus)", XP-002773242, 2 Pages.

UniParc-UPI00046216B7, "Trametes versicolor (strain FP-101664)(White-rot fungus)(Coriolus versicolor)", XP-002773243, 1 Page.

UniParc-UPI0002B3083B, "Ceriporiopsis subermispora (strain B)(White-rot fungus)(Gelatoporia subvermispora)", XP-002773244, 2 Pages.

\* cited by examiner drimane structure (+)-albicanol (-)-drimenol

Figure 6C

```
                          490        500        510        520        530        540        550        560
                   ....|....|....|....|....|....|....|....|....|....|....|....|....|....|....|....|
CvTps1             QDLERLAAAQCEDGGWDMCWFYAFGSTGIKAGNRGLTTALAVAAIRTAL----------------GRPPSPSPSNISSSS
LoTps1             RDLESLLAAQCEDGGWDLCWFYQYGSTGVKAGNRGLTTALAIKAIDSAI----------------ARPPSPALSVASSS-
OCH93767.1         PDMRKLLEMQCQDGGWDGGNLYRFGTTGLKVTNRGLTTAAAVQAIEATQ----------------LRPPSPAFSVESPKS
EMD37666.1         IDMRRLLEMQCEDGGWEGGNLYRFGTTGLKVTNRGLTTAAAVQAIEASQ----------------RRPPSPSPSVESTKS
EMD37666-B         IDMRRLLEMQCEDGGWEGGNLYRFGTTGLKVTNRGLTTAAAVQAIEASQ----------------RRPPSPSPSVESTKS
XP_001217376.1     D-MDSLRGKQCEDGGWPVEWVYRFASFGLNVGNRGLATAFAVRALE-------------------SPYG-ESAVK----
OJJ98394.1         D-ERALRDMQCEDGGFPTSWVLRFGSTGVKIGNRGLTTALAIKAIE-------------------MPLASLWKSWG---
GAO87501.1         VDVRELLALQCKDGSWEPGSFYRFGSSKMNVGNRGLTTALATRAVELYQ----------------GTRIRSKGTE-----
XP_008034151.1     RDLEKLLAAQCADGGWDLCWFYQYGSTGVKAGNRGLTTALAIKAIESAI----------------ARPPSPALSAVSSS-
XP_007369631.1     RDLERLTAGQCDDGGWDLCWFYVFGSTGVKAGNRGLTTALAVTAIQTAI----------------GRPPSPSPSAASSSF
ACg006372          VDLDKLFALQQNDGSWRDSAFYRFPSARQLASNDGLTTAIAIQAIQAAE----------------RLREDGNVL------
KIA75676.1         DDVATLTGMQCGDGGWPACVIYKYGAGGLGITNRGVSTAFAVKAITTTPLAVQPEVSVSAGAGGSSRPVGADAAAVSLRP
XP_001820867.2     VDLRELLSMQCEDGSWEHCPFTRYGLSKVSIGNRGLTTAFVVKAVEMCR----------------GS-------------
CEN60542.1         D-IATLITMQDEDGGWPAAVIYKYGAGGLGITNRGVSTAFAVKAITGSPVKTETNIG-----GDGARAVSAMSSLEARR-
XP_009547469.1     IDLRSLLPLQCEDGGWEAGWVYKYGSSGVKIGNRGLTTALALNAIEAVE----------------GRRTRPKSGKISRVS
KLO09124.1         VDCDALLQTQEDDGGFPIGWMYKYGATGMLLGNKGLSTALAIQAIKAVE----------------SFP------------
OJI95797.1         D-RSRLLALQETDGGWPAGWVYKFGSSGVQIGNRGLSTALALKSIE------------------RQKGPVEAISSEPE
                   Conserved domain D
```

```
                          570        580        590        600
                   ....|....|....|....|....|....|....|....|....|.
CvTps1             -------KLDAPNSFLGIPRPTSPIRFGELFRSWRKN-KPTAKSQ-
LoTps1             --------KSEIPKPIQRSLRPLSPRRFGGFLMPWRRSQRNGVAVSS
OCH93767.1         PVTPVTPMLEIPALGLSISRPSSP-LLGYFKLPWKKSAEVH-----
EMD37666.1         PITPVTPMLEVPSLGLSISRPSSP-LLGYFRLPWKKSAEVH-----
EMD37666-B         PITPVTPMLEVPSLGLSISRPSSP-LLGYFRLPWKKSAEVH-----
XP_001217376.1     --------VMRRIV--------------------------------
OJJ98394.1         --------LTTDIR--------------------------------
GAO87501.1         ----------------------------------------------
XP_008034151.1     --------KLEVPKPILQ--RPLSPRRLGDFLMPWRRAQR-EVAVSS
XP_007369631.1     --------RPSSPYKFLGISRPASPIRFGDLLRPWRKMSRSNLKSQ-
ACg006372          ----------------------------------------------
KIA75676.1         RWRAVVQSLHPLSRVGGLVAVIFAALHFNLAWLYNVSLASRIV---
XP_001820867.2     ----------------------------------------------
CEN60542.1         --------LQPISSVGDWVRFIIASLHVHLAWLWNVLLLSKVV---
XP_009547469.1     RHSEVAAAPRSSTSSHRSNRSISRTFQAYFKASWTSMKQVAVA---
KLO09124.1         ----------------------------------------------
OJI95797.1         AWWPSL-RLDRLLNVWPFIDWKGYSPS-------------------
```

METHOD FOR PRODUCING ALBICANOL AND/OR DRIMENOL

CROSS-REFERENCE TO RELATED APPLICATIONS

This application is a U.S. National Phase Application of PCT/EP2018/064344, filed on May 31, 2018, which claims the benefit of priority to European Patent Application Number 17174399.0, filed Jun. 2, 2017, the entire contents of which are hereby incorporated by reference herein.

TECHNICAL FIELD

Provided herein are biochemical methods of producing albicanol, drimenol and related compounds and derivatives, which method comprises the use of novel polypeptides.

BACKGROUND

Terpenes are found in most organisms (microorganisms, animals and plants). These compounds are made up of five carbon units called isoprene units and are classified by the number of these units present in their structure. Thus monoterpenes, sesquiterpenes and diterpenes are terpenes containing 10, 15 and 20 carbon atoms, respectively. Sesquiterpenes, for example, are widely found in the plant kingdom. Many sesquiterpene molecules are known for their flavor and fragrance properties and their cosmetic, medicinal and antimicrobial effects. Numerous sesquiterpene hydrocarbons and sesquiterpenoids have been identified. Chemical synthesis approaches have been developed but are still complex and not always cost-effective.

Biosynthetic production of terpenes involves enzymes called terpene synthases. There are numerous sesquiterpene synthases present in the plant kingdom, all using the same substrate (farnesyl diphosphate, PPP), but having different product profiles. Genes and cDNAs encoding sesquiterpene synthases have been cloned and the corresponding recombinant enzymes characterized.

Many of the main sources for sesquiterpenes, for example drimenol, are plants naturally containing the sesquiterpene; however, the content of sesquiterpenes in these natural sources can be low. There still remains a need for the discovery of new terpenes, terpene synthases and more cost-effective methods of producing sesquiterpenes such as albicanol and/or drimenol and derivatives therefrom.

SUMMARY

Provided herein is a method for producing a drimane sesquiterpene comprising:
a. contacting an acyclic farnesyl diphosphate (PPP) precursor with a polypeptide comprising aHaloacid dehalogenase (HAD)-like hydrolase domainand having bifunctional terpene synthase activity to produce a drimane sesquiterpene, wherein the polypeptide comprises
  i. a class I terpene synthase-like motif as set forth in SEQ ID NO: 53 (DDxx(D/E)); and
  ii. a class II terpene synthase-like motifas set forth in SEQ ID NO: 56 (DxD(T/S)T); and
b. optionally isolating the drimane sesquiterpene or a mixture comprising the drimane sesquiterpene.

In one aspect, the drimane sesquiterpene comprises albicanol and/or drimenol.

In a further aspect, in the above method, the polypeptide having bifunctional terpene synthase activity comprises
a. an amino acid sequence having at least 40%, 45%, 50%, 55%, 60%, 65%, 70%, 75%, 80%, 85%, 90%, 95%, 96%, 97%, 98% or 99% sequence identity to SEQ ID NO: 1, SEQ ID NO: 5, SEQ ID NO: 9, SEQ ID NO: 12, SEQ ID NO: 15, SEQ ID NO: 17, SEQ ID NO: 20, SEQ ID NO: 23, SEQ ID NO: 26, SEQ ID NO: 29, SEQ ID NO: 32, SEQ ID NO: 35, SEQ ID NO: 38, SEQ ID NO: 41, SEQ ID NO: 44, SEQ ID NO: 47, SEQ ID NO: 50, or SEQ ID NO: 63; and
b. the sequence as set forth in SEQ ID NO: 53, SEQ ID NO: 54, or SEQ ID NO: 55; and
c. the sequence as set forth in SEQ ID NO: 56, SEQ ID NO: 57, or SEQ ID NO: 58.

In one embodiment, the above method comprises contacting the drimane sesquiterpene with at least one enzyme to produce a drimane sesquiterpene derivative. In another embodiment, the above method comprises converting the drimane sesquiterpene to a drimane sesquiterpene derivative using chemical synthesis or biochemical synthesis.

In one aspect, the above method comprises transforming a host cell or non-human host organism with a nucleic acid encoding the above polypeptide.

In one aspect, the method further comprises culturing a non-human host organism or a host cell capable of producing FPP and transformed to express a polypeptide comprising a HAD-like hydrolase domain under conditions that allow for the production of the polypeptide, wherein the polypeptide
a. comprises the amino acid sequence of SEQ ID NO: 1, SEQ ID NO: 5, SEQ ID NO: 9, SEQ ID NO: 12, SEQ ID NO: 15, SEQ ID NO: 17, SEQ ID NO: 20, SEQ ID NO: 23, SEQ ID NO: 26, SEQ ID NO: 29, SEQ ID NO: 32, SEQ ID NO: 35, SEQ ID NO: 38, SEQ ID NO: 41, SEQ ID NO: 44, SEQ ID NO: 47, SEQ ID NO: 50, or SEQ ID NO: 63; or
b. comprises
  i. an amino acid sequence having at least 40%, 45%, 50%, 55%, 60%, 65%, 70%, 75%, 80%, 85%, 90%, 95%, 96%, 97%, 98%, or 99% sequence identity to SEQ ID NO: 1, SEQ ID NO: 5, SEQ ID NO: 9, SEQ ID NO: 12, SEQ ID NO: 15, SEQ ID NO: 17, SEQ ID NO: 20, SEQ ID NO: 23, SEQ ID NO: 26, SEQ ID NO: 29, SEQ ID NO: 32, SEQ ID NO: 35, SEQ ID NO: 38, SEQ ID NO: 41, SEQ ID NO: 44, SEQ ID NO: 47, SEQ ID NO: 50, or SEQ ID NO: 63; and
  ii. the sequence as set forth in SEQ ID NO: 53, SEQ ID NO: 54, or SEQ ID NO: 55; and
  iii. the sequence as set forth in SEQ ID NO: 56, SEQ ID NO: 57, or SEQ ID NO: 58.

In a further aspect, in the above method, the polypeptide comprises one or more conserved motif as set forth in SEQ ID NO: 59, SEQ ID NO: 60, SEQ ID NO: 61, and/or SEQ ID NO: 62.

In one embodiment, the class I terpene synthase-like motif of the above method comprises SEQ ID NO: 54 (DD(K/Q/R)(L/I/T)(D/E)), the class II terpene synthase-like motif comprises SEQ ID NO: 57 (D(V/M/L)DTT), and the drimane sesquiterpene is albicanol.

In a one embodiment, in the above method the polypeptide comprises
a. an amino acid sequence having at least 90% sequence identity to SEQ ID NO: 1, SEQ ID NO: 5, SEQ ID NO: 9, SEQ ID NO: 12, SEQ ID NO: 15, SEQ ID NO: 17, SEQ ID NO: 20, SEQ ID NO: 23, SEQ ID NO: 26, SEQ ID NO: 29, or SEQ ID NO: 32, and b. the sequence of SEQ ID NO: 54 (DD(K/Q/R)(L/I/T)(D/E)), and
c. the sequence of SEQ ID NO: 57 (D(V/M/L/F)DTTS); and the drimane sesquiterpene is albicanol.

In a further embodiment, in the above method the polypeptide comprises
a. an amino acid sequence having at least 90% sequence identity to SEQ ID NO: 35, SEQ ID NO: 38, SEQ ID NO: 41, SEQ ID NO: 44, SEQ ID NO: 47, SEQ ID NO: 50, or SEQ ID NO: 63, and
b. the sequence of SEQ ID NO: 55, and
c. the sequence of SEQ ID NO: 58; and
the drimane sesquiterpene is drimenol.

Also provided is an isolated polypeptide comprising a HAD-like hydrolase domains and having bifunctional terpene synthase activity comprising the amino acid sequence of SEQ ID NO: 1 or SEQ ID NO: 5 or comprising
a. an amino acid sequence having at least 40%, 45%, 50%, 55%, 60%, 65%, 70%, 75%, 80%, 85%, 90%, 95%, 96%, 97%, 98% or 99% sequence identity to SEQ ID NO: 1 or SEQ ID NO: 5; and
b. the sequence as set forth in SEQ ID NO: 53, SEQ ID NO: 54, or SEQ ID NO: 55; and
c. the sequence as set forth in SEQ ID NO: 56, SEQ ID NO: 57, or SEQ ID NO: 48.

In one aspect, the isolated polypeptide further comprises one or more conserved motif as set forth in SEQ ID NO: 59, SEQ ID NO: 60, SEQ ID NO: 61, and/or SEQ ID NO: 62.

Provided herein is an isolated nucleic acid molecule
a. comprising a nucleotide sequence encoding the polypeptide of claim 13 or 14; or
b. comprising a nucleotide sequence having at least 75%, 80%, 85%, 90%, 95%, 96%, 97%, 98% or 99% sequence identity to the nucleotide sequence of SEQ ID NO: 3, SEQ ID NO: 4, SEQ ID NO: 7, SEQ ID NO: 8, or SEQ ID NO: 68, or the reverse complement thereof; or
c. comprising a nucleotide molecule that hybridizes under stringent conditions to SEQ ID NO: 3, SEQ ID NO: 4, SEQ ID NO: 7, SEQ ID NO: 8, or SEQ ID NO: 68; or
d. comprising the nucleotide sequence of SEQ ID NO: 3, SEQ ID NO: 4, SEQ ID NO: 7, SEQ ID NO: 8, SEQ ID NO: 10, SEQ ID NO: 11, SEQ ID NO: 13, SEQ ID NO: 14, SEQ ID NO: 16, SEQ ID NO: 18, SEQ ID NO: 19, SEQ ID NO: 21, SEQ ID NO: 22, SEQ ID NO: 24, SEQ ID NO: 25, SEQ ID NO: 27, SEQ ID NO: 28, SEQ ID NO: 30, SEQ ID NO: 31, SEQ ID NO: 33, SEQ ID NO: 34, SEQ ID NO: 36, SEQ ID NO: 37, SEQ ID NO: 39, SEQ ID NO: 40, SEQ ID NO: 42, SEQ ID NO: 43, SEQ ID NO: 45, SEQ ID NO: 46, SEQ ID NO: 48, SEQ ID NO: 49, SEQ ID NO: 51, SEQ ID NO: 52, SEQ ID NO: 64, SEQ ID NO: 65, SEQ ID NO: 66, SEQ ID NO: 67, SEQ ID NO: 68, SEQ ID NO: 69, or SEQ ID NO: 70, or the reverse complement thereof.

Also provided is a vector comprising the above nucleic acid molecule or a nucleic acid encoding the above polypeptide. In one aspect, the vector is an expression vector. In another aspect, the vector is a prokaryotic vector, viral vector or a eukaryotic vector.

Further provided is a host cell or non-human organism comprising the above nucleic acid or above vector.

In one aspect, the host cell or non-human organism is a prokaryotic cell or a eukaryotic cell or a microorganism or fungal cell.

In one aspect, the prokaryotic cell is a bacterial cell. In a further aspect, the bacterial cell is *E. coli*.

In another aspect, the host cell or non-human organism is a eukaryotic cell. In one aspect, the eukaryotic cell is a yeast cell or plant cell. In a further aspect, the yeast cell is *Saccharomyces cerevisiae*.

Provided herein is the use of the above polypeptide for producing a drimane sesquiterpene or a mixture comprising a drimane sesquiterpene and one or more terpenes.

In one aspect, in the above use of the polypeptide, the drimane sesquiterpene is albicanol. In another aspect, in the above use of the polypeptide, the drimane sesquiterpene is drimenol.

DESCRIPTION OF THE DRAWINGS

FIG. 6A-C: Amino acid sequences alignment of putative terpene synthases containing class I and class II motifs: CvTps1 (SEQ ID NO: 1), LoTps1 (SEQ ID NO: 5), OCH93767.1 (SEQ ID NO: 9), EMD37666.1 (SEQ ID NO: 12), EMD37666-B (SEQ ID NO: 15), XP_001217376.1 (SEQ ID NO: 17), OJJ98394.1 (SEQ ID NO: 20), GAO87501.1 (SEQ ID NO: 23), XP_008034151.1 (SEQ ID NO: 26), XP_007369631.1 (SEQ ID NO: 29), ACg006372 (SEQ ID NO: 32), KIA75676.1 (SEQ ID NO: 35), XP_001820867.2 (SEQ ID NO: 38), CEN60542.1 (SEQ ID NO: 41), XP_009547469.1 (SEQ ID NO: 44), KLO09124.1 (SEQ ID NO: 47), and OJI95797.1 (SEQ ID NO: 50).

Figure 1:
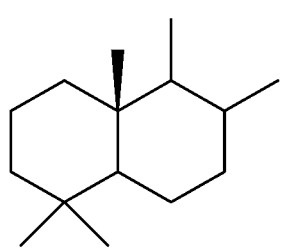
FIG. 1: Structure of drimane, (+)-albicanol and (−)-drimenol.
Figure 1:
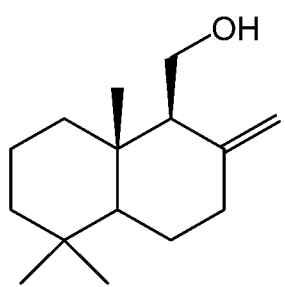
Figure 1:
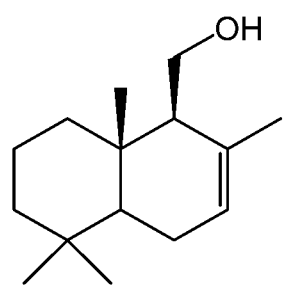

ABBREVIATIONS USED bp base pair
kb kilo base
DNA deoxyribonucleic acid
cDNA complementary DNA
DTT dithiothreitol
PPP farnesyl diphosphate
GC gas chromatograph
HAD Haloacid dehalogenase
IPTG isopropyl-D-thiogalacto-pyranoside
LB lysogeny broth
MS mass spectrometer/mass spectrometry
MVA mevalonic acid
PCR polymerase chain reaction
RNA ribonucleic acid
mRNA messenger ribonucleic acid
miRNA micro RNA
siRNA small interfering RNA
rRNA ribosomal RNA
tRNA transfer RNA

Definitions

The term "polypeptide" means an amino acid sequence of consecutively polymerized amino acid residues, for instance, at least 15 residues, at least 30 residues, at least 50 residues. In some embodiments herein, a polypeptide comprises an amino acid sequence that is an enzyme, or a fragment, or a variant thereof.

The term "protein" refers to an amino acid sequence of any length wherein amino acids are linked by covalent peptide bonds, and includes oligopeptide, peptide, polypeptide and full length protein whether naturally occurring or synthetic.

The term "isolated" polypeptide refers to an amino acid sequence that is removed from its natural environment by any method or combination of methods known in the art and includes recombinant, biochemical and synthetic methods.

The terms "bifunctional terpene synthase" or "polypeptide having bifunctional terpene synthase activity" relate to a polypeptide that comprises class I and class II terpene synthase domains and has bifunctional terpene synthase activity of protonation-initiated cyclization and ionization-initiated cyclization catalytic activities. A bifunctional terpene synthase as described herein comprises a HAD-like hydrolase domain which is characteristic of polypeptides belonging to the Haloacid dehalogenase (HAD)-like hydrolase superfamily (Interpro protein superfamily IPR023214, http://www.ebi.ac.uk/interpro/entry/IPR023214; Pfam protein superfamily PF13419, http://pfam.xfam.org/family/PF13419). A HAD-like hydrolase domain is a portion of a polypeptide having amino acid sequence similarities with the members of the HAD-like hydrolase family and related function. A HAD-like hydrolase domain can be identified in a polypeptide by searching for amino acid motifs or signatures characteristic of this protein family. Tools for performing such searches are available at the following web sites: ebi.ac.uk/interpro/or ebi.ac.uk/Tools/hmmer/. Proteins are generally composed of one or more functional regions or domains. Different combinations of domains give rise to the diverse range of proteins found in nature. The identification of domains that occur within proteins can therefore provide insights into their function. A polypeptide which comprises a HAD-like hydrolase domain and/or characteristic HAD-like hydrolase motifs functions in binding and cleavage of phosphate or diphosphate groups of a ligand. A bifunctional terpene synthase may also comprise one or more of conserved motifs A, B, C, and/or D as depicted in SEQ ID NO: 59, SEQ ID NO: 60, SEQ ID NO: 61, and/or SEQ ID NO: 62.

The term "drimane sesquiterpene" relates to a terpene having a drimane-like carbon skeleton structure as depicted in FIG. 1.

The term "class I terpene synthase" relates to a terpene synthase that catalyses ionization-initiated reactions, for example, monoterpene and sesquiterpene synthases.

The term "class I terpene synthase motif" or "class I terpene synthase-like motif" relates to an active site of a terpene synthase that comprises the conserved DDxx(D/E) motif. The aspartic acid residues of this class I motif bind, for example, a divalent metal ion (most often $Mg^{2+}$) involved in the binding of the diphosphate group and catalyze the ionization and cleavage of the allylic diphosphate bond of the substrate.

The term "class II terpene synthase" relates to a terpene synthase that catalyses protonation-initiated cyclization reactions, for example, typically involved in the biosynthesis of triterpenes and labdane diterpenes. In class II terpene synthases, the protonation-initiated reaction may involve, for example, acidic amino acids donating a proton to the terminal double-bond.

The term "class II terpene synthase motif" or "class II terpene synthase-like motif" relates to an active site of a terpene synthase that comprises the conserved DxDD or DxD(T/S)T motif.

The terms "albicanol synthase" or "polypeptide having albicanol synthase activity" or "albicanol synthase protein" relate to a polypeptide capable of catalyzing the synthesis of albicanol, in the form of any of its stereoisomers or a mixture thereof, starting from an acyclic terpene pyrophosphate, particularly farnesyl diphosphate (FPP). Albicanol may be the only product or may be part of a mixture of sesquiterpenes.

The terms "drimenol synthase" or "polypeptide having a drimenol synthase activity" or "drimenol synthase protein" relate to a polypeptide capable of catalyzing the synthesis of drimenol, in the form of any of its stereoisomers or a mixture thereof, starting from an acyclic terpene pyrophosphate, particularly farnesyl diphosphate (FPP). Drimenol may be the only product or may be part of a mixture of sesquiterpenes.

The terms "biological function," "function," "biological activity" or "activity" refer to the ability of the bifunctional terpene synthase to catalyze the formation of albicanol and/or drimenol or a mixture of compounds comprising albicanol and/or drimenol and one or more terpenes.

The terms "mixture of terpenes" or "mixture of sesquiterpenes" refer to a mixture of terpenes or sesquiterpenes that comprises albicanol and/or drimenol, and may also comprise one or more additional terpenes or sesquiterpenes.

The terms "nucleic acid sequence," "nucleic acid," "nucleic acid molecule" and "polynucleotide" are used interchangeably meaning a sequence of nucleotides. A nucleic acid sequence may be a single-stranded or double-stranded deoxyribonucleotide, or ribonucleotide of any length, and include coding and non-coding sequences of a gene, exons, introns, sense and anti-sense complimentary sequences, genomic DNA, cDNA, miRNA, siRNA, mRNA, rRNA, tRNA, recombinant nucleic acid sequences, isolated and purified naturally occurring DNA and/or RNA sequences, synthetic DNA and RNA sequences, fragments, primers and nucleic acid probes. The skilled artisan is aware that the nucleic acid sequences of RNA are identical to the DNA sequences with the difference of thymine (T) being replaced by uracil (U). The term "nucleotide sequence" should also be understood as comprising a polynucleotide molecule or an oligonucleotide molecule in the form of a separate fragment or as a component of a larger nucleic acid.

An "isolated nucleic acid" or "isolated nucleic acid sequence" relates to a nucleic acid or nucleic acid sequence that is in an environment different from that in which the nucleic acid or nucleic acid sequence naturally occurs and can include those that are substantially free from contaminating endogenous material. The term "naturally-occurring" as used herein as applied to a nucleic acid refers to a nucleic acid that is found in a cell of an organism in nature and which has not been intentionally modified by a human in the laboratory.

"Recombinant nucleic acid sequences" are nucleic acid sequences that result from the use of laboratory methods (for example, molecular cloning) to bring together genetic material from more than on source, creating or modifying a nucleic acid sequence that does not occur naturally and would not be otherwise found in biological organisms.

"Recombinant DNA technology" refers to molecular biology procedures to prepare a recombinant nucleic acid sequence as described, for instance, in Laboratory Manuals edited by Weigel and Glazebrook, 2002, Cold Spring Harbor Lab Press; and Sambrook et al., 1989, Cold Spring Harbor, N.Y., Cold Spring Harbor Laboratory Press.

The term "gene" means a DNA sequence comprising a region, which is transcribed into a RNA molecule, e.g., an mRNA in a cell, operably linked to suitable regulatory regions, e.g., a promoter. A gene may thus comprise several operably linked sequences, such as a promoter, a 5' leader sequence comprising, e.g., sequences involved in translation initiation, a coding region of cDNA or genomic DNA, introns, exons, and/or a 3'non-translated sequence comprising, e.g., transcription termination sites.

A "chimeric gene" refers to any gene which is not normally found in nature in a species, in particular, a gene in which one or more parts of the nucleic acid sequence are present that are not associated with each other in nature. For example the promoter is not associated in nature with part or all of the transcribed region or with another regulatory region. The term "chimeric gene" is understood to include expression constructs in which a promoter or transcription regulatory sequence is operably linked to one or more coding sequences or to an antisense, i.e., reverse complement of the sense strand, or inverted repeat sequence (sense and antisense, whereby the RNA transcript forms double stranded RNA upon transcription). The term "chimeric gene" also includes genes obtained through the combination of portions of one or more coding sequences to produce a new gene.

A "3' UTR" or "3' non-translated sequence" (also referred to as "3' untranslated region," or "3'end") refers to the nucleic acid sequence found downstream of the coding sequence of a gene, which comprises, for example, a transcription termination site and (in most, but not all eukaryotic mRNAs) a polyadenylation signal such as AAUAAA or variants thereof. After termination of transcription, the mRNA transcript may be cleaved downstream of the polyadenylation signal and a poly(A) tail may be added, which is involved in the transport of the mRNA to the site of translation, e.g., cytoplasm.

"Expression of a gene" encompasses "heterologous expression" and "over-expression" and involves transcription of the gene and translation of the mRNA into a protein. Overexpression refers to the production of the gene product as measured by levels of mRNA, polypeptide and/or enzyme activity in transgenic cells or organisms that exceeds levels of production in non-transformed cells or organisms of a similar genetic background.

"Expression vector" as used herein means a nucleic acid molecule engineered using molecular biology methods and recombinant DNA technology for delivery of foreign or exogenous DNA into a host cell. The expression vector typically includes sequences required for proper transcription of the nucleotide sequence. The coding region usually codes for a protein of interest but may also code for an RNA, e.g., an antisense RNA, siRNA and the like.

An "expression vector" as used herein includes any linear or circular recombinant vector including but not limited to viral vectors, bacteriophages and plasmids. The skilled person is capable of selecting a suitable vector according to the expression system. In one embodiment, the expression vector includes the nucleic acid of an embodiment herein operably linked to at least one regulatory sequence, which controls transcription, translation, initiation and termination, such as a transcriptional promoter, operator or enhancer, or an mRNA ribosomal binding site and, optionally, including at least one selection marker. Nucleotide sequences are "operably linked" when the regulatory sequence functionally relates to the nucleic acid of an embodiment herein.

"Regulatory sequence" refers to a nucleic acid sequence that determines expression level of the nucleic acid sequences of an embodiment herein and is capable of regulating the rate of transcription of the nucleic acid sequence operably linked to the regulatory sequence. Regulatory sequences comprise promoters, enhancers, transcription factors, promoter elements and the like.

"Promoter" refers to a nucleic acid sequence that controls the expression of a coding sequence by providing a binding site for RNA polymerase and other factors required for proper transcription including without limitation transcription factor binding sites, repressor and activator protein binding sites. The meaning of the term promoter also includes the term "promoter regulatory sequence". Promoter regulatory sequences may include upstream and downstream elements that may influences transcription, RNA processing or stability of the associated coding nucleic acid sequence. Promoters include naturally-derived and synthetic sequences. The coding nucleic acid sequences is usually located downstream of the promoter with respect to the direction of the transcription starting at the transcription initiation site.

The term "constitutive promoter" refers to an unregulated promoter that allows for continual transcription of the nucleic acid sequence it is operably linked to.

As used herein, the term "operably linked" refers to a linkage of polynucleotide elements in a functional relationship. A nucleic acid is "operably linked" when it is placed into a functional relationship with another nucleic acid sequence. For instance, a promoter, or rather a transcription regulatory sequence, is operably linked to a coding sequence if it affects the transcription of the coding sequence. Operably linked means that the DNA sequences being linked are typically contiguous. The nucleotide sequence associated with the promoter sequence may be of homologous or heterologous origin with respect to the plant to be transformed. The sequence also may be entirely or partially synthetic. Regardless of the origin, the nucleic acid sequence associated with the promoter sequence will be expressed or silenced in accordance with promoter properties to which it is linked after binding to the polypeptide of an embodiment herein. The associated nucleic acid may code for a protein that is desired to be expressed or suppressed throughout the organism at all times or, alternatively, at a specific time or in specific tissues, cells, or cell compartment. Such nucleotide sequences particularly encode proteins conferring desirable phenotypic traits to the host cells or organism altered or transformed therewith. More particularly, the associated nucleotide sequence leads to the production of albicanol and/or drimenol or a mixture comprising albicanol and/or drimenol or a mixture comprising albicanol and/or drimenol and one or more terpenes in the cell or organism. Particularly, the nucleotide sequence encodes a bifunctional terpene synthase.

"Target peptide" refers to an amino acid sequence which targets a protein, or polypeptide to intracellular organelles, i.e., mitochondria, or plastids, or to the extracellular space (secretion signal peptide). A nucleic acid sequence encoding a target peptide may be fused to the nucleic acid sequence encoding the amino terminal end, e.g., N-terminal end, of the protein or polypeptide, or may be used to replace a native targeting polypeptide.

The term "primer" refers to a short nucleic acid sequence that is hybridized to a template nucleic acid sequence and is used for polymerization of a nucleic acid sequence complementary to the template.

As used herein, the term "host cell" or "transformed cell" refers to a cell (or organism) altered to harbor at least one nucleic acid molecule, for instance, a recombinant gene encoding a desired protein or nucleic acid sequence which upon transcription yields a bifunctional terpene synthase protein useful to produce albicanol and/or drimenol. The host cell is particularly a bacterial cell, a fungal cell or a plant cell. The host cell may contain a recombinant gene which has been integrated into the nuclear or organelle genomes of the host cell. Alternatively, the host may contain the recombinant gene extra-chromosomally.

Homologous sequences include orthologous or paralogous sequences. Methods of identifying orthologs or paralogs including phylogenetic methods, sequence similarity and hybridization methods are known in the art and are described herein.

Paralogs result from gene duplication that gives rise to two or more genes with similar sequences and similar functions. Paralogs typically cluster together and are formed by duplications of genes within related plant species. Paralogs are found in groups of similar genes using pair-wise Blast analysis or during phylogenetic analysis of gene families using programs such as CLUSTAL. In paralogs, consensus sequences can be identified characteristic to sequences within related genes and having similar functions of the genes.

Orthologs, or orthologous sequences, are sequences similar to each other because they are found in species that descended from a common ancestor. For instance, plant species that have common ancestors are known to contain many enzymes that have similar sequences and functions. The skilled artisan can identify orthologous sequences and predict the functions of the orthologs, for example, by constructing a polygenic tree for a gene family of one species using CLUSTAL or BLAST programs. A method for identifying or confirming similar functions among homologous sequences is by comparing of the transcript profiles in host cells or organisms, such as plants or microorganisms, overexpressing or lacking (in knockouts/knockdowns) related polypeptides. The skilled person will understand that genes having similar transcript profiles, with greater than 50% regulated transcripts in common, or with greater than 70% regulated transcripts in common, or greater than 90% regulated transcripts in common will have similar functions. Homologs, paralogs, orthologs and any other variants of the sequences herein are expected to function in a similar manner by making the host cells, organism such as plants or microorganisms producing bifunctional terpene synthase proteins.

The term "selectable marker" refers to any gene which upon expression may be used to select a cell or cells that include the selectable marker. Examples of selectable markers are described below. The skilled artisan will know that different antibiotic, fungicide, auxotrophic or herbicide selectable markers are applicable to different target species.

"Drimenol" for purposes of this application relates to (−)-drimenol (CAS: 468-68-8).

"Albicanol" for the purpose of this application relates to (+)-albicanol (CAS: 54632-04-1).

The term "organism" refers to any non-human multicellular or unicellular organisms such as a plant, or a micro-organism. Particularly, a micro-organism is a bacterium, a yeast, an algae or a fungus.

The term "plant" is used interchangeably to include plant cells including plant protoplasts, plant tissues, plant cell tissue cultures giving rise to regenerated plants, or parts of plants, or plant organs such as roots, stems, leaves, flowers, pollen, ovules, embryos, fruits and the like. Any plant can be used to carry out the methods of an embodiment herein.

A particular organism or cell is meant to be "capable of producing FPP" when it produces FPP naturally or when it does not produce FPP naturally but is transformed to produce FPP, either prior to the transformation with a nucleic acid as described herein or together with said nucleic acid. Organisms or cells transformed to produce a higher amount of FPP than the naturally occurring organism or cell are also encompassed by the "organisms or cells capable of producing FPP".

For the descriptions herein and the appended claims, the use of "or" means "and/or" unless stated otherwise. Similarly, "comprise," "comprises," "comprising", "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

DETAILED DESCRIPTION

Provided herein is a nucleic acid molecule comprising a nucleotide sequence having at least 75%, 80%, 85%, 90%, 95%, 96%, 97%, 98% or 99% sequence identity to the nucleotide sequence of SEQ ID NO: 3, SEQ ID NO: 4, SEQ ID NO: 7, SEQ ID NO: 8, or SEQ ID NO: 68 or comprising the nucleotide sequence of SEQ ID NO: 3, SEQ ID NO: 4, SEQ ID NO: 7, SEQ ID NO: 8, SEQ ID NO: 10, SEQ ID NO: 11, SEQ ID NO: 13, SEQ ID NO: 14, SEQ ID NO: 16, SEQ ID NO: 18, SEQ ID NO: 19, SEQ ID NO: 21, SEQ ID NO: 22, SEQ ID NO: 24, SEQ ID NO: 25, SEQ ID NO: 27, SEQ ID NO: 28, SEQ ID NO: 30, SEQ ID NO: 31, SEQ ID NO: 33, SEQ ID NO: 34, SEQ ID NO: 36, SEQ ID NO: 37, SEQ ID NO: 39, SEQ ID NO: 40, SEQ ID NO: 42, SEQ ID NO: 43, SEQ ID NO: 45, SEQ ID NO: 46, SEQ ID NO: 48, SEQ ID NO: 49, SEQ ID NO: 51, SEQ ID NO: 52, SEQ ID NO: 64, SEQ ID NO: 65, SEQ ID NO: 66, SEQ ID NO: 67, SEQ ID NO: 68, SEQ ID NO: 69, or SEQ ID NO: 70, or the reverse complement thereof.

According to one embodiment, the nucleic acid molecule consists of the nucleotide sequence SEQ ID NO: 3, SEQ ID NO: 4, SEQ ID NO: 7, SEQ ID NO: 8, SEQ ID NO: 10, SEQ ID NO: 11, SEQ ID NO: 13, SEQ ID NO: 14, SEQ ID NO: 16, SEQ ID NO: 18, SEQ ID NO: 19, SEQ ID NO: 21, SEQ ID NO: 22, SEQ ID NO: 24, SEQ ID NO: 25, SEQ ID NO: 27, SEQ ID NO: 28, SEQ ID NO: 30, SEQ ID NO: 31, SEQ ID NO: 33, SEQ ID NO: 34, SEQ ID NO: 36, SEQ ID NO: 37, SEQ ID NO: 39, SEQ ID NO: 40, SEQ ID NO: 42, SEQ ID NO: 43, SEQ ID NO: 45, SEQ ID NO: 46, SEQ ID NO: 48, SEQ ID NO: 49, SEQ ID NO: 51, SEQ ID NO: 52, SEQ ID NO: 64, SEQ ID NO: 65, SEQ ID NO: 66, SEQ ID NO: 67, SEQ ID NO: 68, SEQ ID NO: 69, or SEQ ID NO: 70, or the reverse complement thereof.

In one embodiment, the nucleic acid of an embodiment herein can be either present naturally in *Cryptoporus* or *Laricifomes* or in other fungal species, or be obtained by modifying SEQ ID NO: 3 or SEQ ID NO: 7 or the reverse complement thereof.

In another embodiment, the nucleic acid is isolated or is derived from fungi of the genus *Cryptoporus* or *Laricifomes*. In a further embodiment the nucleic acid is isolated or derived from *Cryptoporus volvatus* or *Laricifomes officinalis*.

Further provided is a nucleotide sequence obtained by modifying SEQ ID NO: 3 or SEQ ID NO: 7 or the reverse complement thereof which encompasses any sequence that has been obtained by modifying the sequence of SEQ ID NO: 3 or SEQ ID NO: 7, or of the reverse complement thereof using any method known in the art, for example, by introducing any type of mutations such as deletion, insertion and/or substitution mutations. The nucleic acids comprising a sequence obtained by mutation of SEQ ID NO: 3 or SEQ ID NO: 7 or the reverse complement thereof are encompassed by an embodiment herein, provided that the sequences they comprise share at least the defined sequence identity of SEQ ID NO: 3 or SEQ ID NO: 7 as defined in any of the above embodiments or the reverse complement thereof and provided that they encode a polypeptide comprising a HAD-like hydrolase domain and having a bifunctional terpene synthase activity to produce a drimane sesquiterpene, wherein the polypeptide comprises (1) a class I terpene synthase-like motif as set forth in SEQ ID NO: 53 (DDxx(D/E)) and (2) a class II terpene synthase-like motif as set forth in SEQ ID NO: 56 (DxD(T/S)T). The polypeptide having bifunctional terpene synthase activity may further comprise one or more conserved motif as set forth in SEQ ID NO: 59, SEQ ID NO: 60, SEQ ID NO: 61, and/or SEQ ID NO: 62. Mutations may be any kind of mutations of these nucleic acids, for example, point mutations, deletion mutations, insertion mutations and/or frame shift mutations of one or more nucleotides of the DNA sequence of SEQ ID NO: 3 or SEQ ID NO: 7. In one embodiment, the nucleic acid of an embodiment herein may be truncated provided that it encodes a polypeptide as described herein.

A variant nucleic acid may be prepared in order to adapt its nucleotide sequence to a specific expression system. For example, bacterial expression systems are known to more efficiently express polypeptides if amino acids are encoded by particular codons.

Due to the degeneracy of the genetic code, more than one codon may encode the same amino acid sequence, multiple nucleic acid sequences can code for the same protein or polypeptide, all these DNA sequences being encompassed by an embodiment herein. Where appropriate, the nucleic acid sequences encoding the bifunctional terpene synthase may be optimized for increased expression in the host cell. For example, nucleotides of an embodiment herein may be synthesized using codons particular to a host for improved expression. In one embodiment, the nucleic acid molecule comprises the nucleotide sequence of SEQ ID NO: 4, SEQ ID NO: 8, SEQ ID NO: 11, SEQ ID NO: 14, SEQ ID NO: 16, SEQ ID NO: 19, SEQ ID NO: 22, SEQ ID NO: 25, SEQ ID NO: 28, SEQ ID NO: 31, SEQ ID NO: 34, SEQ ID NO: 37, SEQ ID NO: 40, SEQ ID NO: 43, SEQ ID NO: 46, SEQ ID NO: 49, SEQ ID NO: 52, SEQ ID NO: 64, SEQ ID NO: 65, SEQ ID NO: 66, SEQ ID NO: 67, SEQ ID NO: 68, SEQ ID NO: 69, or SEQ ID NO: 70, or the reverse complement thereof.

In one embodiment provided herein is an isolated, recombinant or synthetic nucleic acid sequence comprising the nucleotide sequence of SEQ ID NO: 3, SEQ ID NO: 4, SEQ ID NO: 7, SEQ ID NO: 8, SEQ ID NO: 10, SEQ ID NO: 11, SEQ ID NO: 13, SEQ ID NO: 14, SEQ ID NO: 16, SEQ ID NO: 18, SEQ ID NO: 19, SEQ ID NO: 21, SEQ ID NO: 22, SEQ ID NO: 24, SEQ ID NO: 25, SEQ ID NO: 27, SEQ ID NO: 28, SEQ ID NO: 30, SEQ ID NO: 31, SEQ ID NO: 33, SEQ ID NO: 34, SEQ ID NO: 36, SEQ ID NO: 37, SEQ ID NO: 39, SEQ ID NO: 40, SEQ ID NO: 42, SEQ ID NO: 43, SEQ ID NO: 45, SEQ ID NO: 46, SEQ ID NO: 48, SEQ ID NO: 49, SEQ ID NO: 51, SEQ ID NO: 52, SEQ ID NO: 64, SEQ ID NO: 65, SEQ ID NO: 66, SEQ ID NO: 67, SEQ ID NO: 68, SEQ ID NO: 69, or SEQ ID NO: 70, encoding for a bifunctional terpene synthase comprising the amino acid sequence of SEQ ID NO: 1, SEQ ID NO: 5, SEQ ID NO: 9, SEQ ID NO: 12, SEQ ID NO: 15, SEQ ID NO: 17, SEQ ID NO: 20, SEQ ID NO: 23, SEQ ID NO: 26, SEQ ID NO: 29, SEQ ID NO: 32, SEQ ID NO: 35, SEQ ID NO: 38, SEQ ID NO: 41, SEQ ID NO: 44, SEQ ID NO: 47, SEQ ID NO: 50, or SEQ ID NO: 63 or functional fragments thereof that catalyze production of a drimane sesquiterpene in a cell from a FPP precursor. In a further embodiment, the drimane sesquiterpene comprises albicanol and/or drimenol.

Provided herein are also cDNA, genomic DNA and RNA sequences. Any nucleic acid sequence encoding the bifunctional terpene synthase or variants thereof is referred herein as a bifunctional terpene synthase encoding sequence.

According to one embodiment, the nucleic acid of SEQ ID NO: 3, SEQ ID NO: 4, SEQ ID NO: 7, SEQ ID NO: 8, or SEQ ID NO: 68 is the coding sequence of a bifunctional terpene synthase gene encoding a bifunctional terpene synthase obtained as described in the Examples.

A fragment of a polynucleotide of SEQ ID NO: 3, SEQ ID NO: 4, SEQ ID NO: 7, SEQ ID NO: 8, or SEQ ID NO: 68 refers to contiguous nucleotides that is particularly at least 15 bp, at least 30 bp, at least 40 bp, at least 50 bp and/or at least 60 bp in length of the polynucleotide of an embodiment herein. Particularly the fragment of a polynucleotide comprises at least 25, more particularly at least 50, more particularly at least 75, more particularly at least 100, more particularly at least 150, more particularly at least 200, more particularly at least 300, more particularly at least 400, more particularly at least 500, more particularly at least 600, more particularly at least 700, more particularly at least 800, more particularly at least 900, more particularly at least 1000 contiguous nucleotides of the polynucleotide of an embodiment herein. Without being limited, the fragment of the polynucleotides herein may be used as a PCR primer, and/or as a probe, or for anti-sense gene silencing or RNAi.

It is clear to the person skilled in the art that genes, including the polynucleotides of an embodiment herein, can be cloned on basis of the available nucleotide sequence information, such as found in the attached sequence listing, by methods known in the art. These include e.g. the design of DNA primers representing the flanking sequences of such gene of which one is generated in sense orientations and which initiates synthesis of the sense strand and the other is created in reverse complementary fashion and generates the antisense strand. Thermo stable DNA polymerases such as those used in polymerase chain reaction are commonly used to carry out such experiments. Alternatively, DNA sequences representing genes can be chemically synthesized and subsequently introduced in DNA vector molecules that can be multiplied by e.g. compatible bacteria such as e.g. $E.$ $coli.$ In a related embodiment provided herein, PCR primers and/or probes for detecting nucleic acid sequences encoding a polypeptide having bifunctional terpene synthase activity are provided. The skilled artisan will be aware of methods to synthesize degenerate or specific PCR primer pairs to amplify a nucleic acid sequence encoding the bifunctional terpene synthase or functional fragments thereof, based on SEQ ID NO: 3, SEQ ID NO: 4, SEQ ID NO: 7, SEQ ID NO: 8, or SEQ ID NO: 68. A detection kit for nucleic acid sequences encoding the bifunctional terpene synthase may include primers and/or probes specific for nucleic acid sequences encoding the bifunctional terpene synthase, and an associated protocol to use the primers and/or probes to detect nucleic acid sequences encoding the bifunctional terpene synthase in a sample. Such detection kits may be used to determine whether a plant, organism, microorganism or cell has been modified, i.e., transformed with a sequence encoding the bifunctional terpene synthase.

To test a function of variant DNA sequences according to an embodiment herein, the sequence of interest is operably linked to a selectable or screenable marker gene and expression of the reporter gene is tested in transient expression assays, for example, with microorganisms or with protoplasts or in stably transformed plants. The skilled artisan will recognize that DNA sequences capable of driving expression are built as modules. Accordingly, expression levels from shorter DNA fragments may be different than the one from the longest fragment and may be different from each other. Provided herein are also functional equivalents of the nucleic acid sequence coding the bifunctional terpene synthase proteins provided herein, i.e., nucleotide sequences that hybridize under stringent conditions to the nucleic acid sequence of SEQ ID NO: 3, SEQ ID NO: 4, SEQ ID NO: 7, SEQ ID NO: 8, or SEQ ID NO: 68.

As used herein, the term hybridization or hybridizes under certain conditions is intended to describe conditions for hybridization and washes under which nucleotide sequences that are significantly identical or homologous to each other remain bound to each other. The conditions may be such that sequences, which are at least about 70%, such as at least about 80%, and such as at least about 85%, 90%, or 95% identical, remain bound to each other. Definitions of low stringency, moderate, and high stringency hybridization conditions are provided herein.

Appropriate hybridization conditions can be selected by those skilled in the art with minimal experimentation as exemplified in Ausubel et al. (1995, *Current Protocols in Molecular Biology*, John Wiley & Sons, sections 2, 4, and 6). Additionally, stringency conditions are described in Sambrook et al. (1989, *Molecular Cloning: A Laboratory Manual*, 2nd ed., Cold Spring Harbor Press, chapters 7, 9, and 11). As used herein, defined conditions of low stringency are as follows. Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5-20×10⁶ 32P-labeled probe is used. Filters are incubated in hybridization mixture for 18-20 h at 40° C., and then washed for 1.5 h at 55° C. In a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography.

As used herein, defined conditions of moderate stringency are as follows. Filters containing DNA are pretreated for 7 h at 50° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5-20×10⁶ 32P-labeled probe is used. Filters are incubated in hybridization mixture for 30 h at 50° C., and then washed for 1.5 h at 55° C. In a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography.

As used herein, defined conditions of high stringency are as follows. Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C. in the prehybridization mixture containing 100 µg/ml denatured salmon sperm DNA and 5-20×10⁶ cpm of 32P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 minutes. Other conditions of low, moderate, and high stringency well known in the art (e.g., as employed for cross-species hybridizations) may be used if the above conditions are inappropriate (e.g., as employed for cross-species hybridizations).

The skilled artisan will be aware of methods to identify homologous sequences in other organisms and methods to determine the percentage of sequence identity between homologous sequences. Such newly identified DNA molecules then can be sequenced and the sequence can be compared with the nucleic acid sequence of SEQ ID NO: 3 or SEQ ID NO: 7.

The percentage of identity between two peptide or nucleotide sequences is a function of the number of amino acids or nucleotide residues that are identical in the two sequences when an alignment of these two sequences has been generated. Identical residues are defined as residues that are the same in the two sequences in a given position of the alignment. The percentage of sequence identity, as used herein, is calculated from the optimal alignment by taking the number of residues identical between two sequences dividing it by the total number of residues in the shortest sequence and multiplying by 100. The optimal alignment is the alignment in which the percentage of identity is the highest possible. Gaps may be introduced into one or both sequences in one or more positions of the alignment to obtain the optimal alignment. These gaps are then taken into account as non-identical residues for the calculation of the percentage of sequence identity. Alignment for the purpose of determining the percentage of amino acid or nucleic acid sequence identity can be achieved in various ways using computer programs and for instance publicly available computer programs available on the world wide web. Preferably, the BLAST program (Tatiana et al, *FEMS Microbiol Lett.*, 1999, 174:247-250, 1999) set to the default parameters, available from the National Center for Biotechnology Information (NCBI) website at ncbi.nlm.nih.gov/BLAST/bl2seq/wblast2.cgi, can be used to obtain an optimal alignment of protein or nucleic acid sequences and to calculate the percentage of sequence identity.

A related embodiment provided herein provides a nucleic acid sequence which is complementary to the nucleic acid sequence according to SEQ ID NO: 3, SEQ ID NO: 4, SEQ ID NO: 7, SEQ ID NO: 8, or SEQ ID NO: 68 such as inhibitory RNAs, or nucleic acid sequence which hybridizes under stringent conditions to at least part of the nucleotide sequence according to SEQ ID NO: 3, SEQ ID NO: 4, SEQ ID NO: 7, SEQ ID NO: 8, or SEQ ID NO: 68. An alternative embodiment of an embodiment herein provides a method to alter gene expression in a host cell. For instance, the polynucleotide of an embodiment herein may be enhanced or overexpressed or induced in certain contexts (e.g. upon exposure to certain temperatures or culture conditions) in a host cell or host organism.

Alteration of expression of a polynucleotide provided herein may also result in ectopic expression which is a different expression pattern in an altered and in a control or wild-type organism. Alteration of expression occurs from interactions of polypeptide of an embodiment herein with exogenous or endogenous modulators, or as a result of chemical modification of the polypeptide. The term also refers to an altered expression pattern of the polynucleotide of an embodiment herein which is altered below the detection level or completely suppressed activity. In one embodiment, provided herein is also an isolated, recombinant or synthetic polynucleotide encoding a polypeptide or variant polypeptide provided herein.

In one embodiment is provided an isolated nucleic acid molecule encoding a polypeptide comprising a domain of the HAD-like hydrolase superfamily having bifunctional terpene synthase activity and comprising an amino acid sequence having at least 40%, 45%, 50%, 55%, 60%, 65%, 70%, 75%, 80%, 85%, 90%, 95%, 96%, 97%, 98%, or 99% sequence identity to SEQ ID NO: 1, SEQ ID NO: 5, SEQ ID NO: 9, SEQ ID NO: 12, SEQ ID NO: 15, SEQ ID NO: 17, SEQ ID NO: 20, SEQ ID NO: 23, SEQ ID NO: 26, SEQ ID NO: 29, SEQ ID NO: 32, SEQ ID NO: 35, SEQ ID NO: 38, SEQ ID NO: 41, SEQ ID NO: 44, SEQ ID NO: 47, SEQ ID NO: 50, or SEQ ID NO: 63; and the sequence as set forth in SEQ ID NO: 53, SEQ ID NO: 54, or SEQ ID NO: 55; and the sequence as set forth in SEQ ID NO: 56, SEQ ID NO: 57, or SEQ ID NO: 58 or comprising the amino acid sequence of SEQ ID NO: 1, SEQ ID NO: 5, SEQ ID NO: 9, SEQ ID NO: 12, SEQ ID NO: 15, SEQ ID NO: 17, SEQ ID NO: 20, SEQ ID NO: 23, SEQ ID NO: 26, SEQ ID NO: 29, SEQ ID NO: 32, SEQ ID NO: 35, or SEQ ID NO: 38, SEQ ID NO: 41, SEQ ID NO: 44, SEQ ID NO: 47, SEQ ID NO: 50, or SEQ ID NO: 63.

In one embodiment provided herein is an isolated polypeptide comprising a HAD-like hydrolase domain having bifunctional terpene synthase activity and comprising an amino acid sequence having at least 50%, 55%, 60%, 65%, 70%, 75%, 80%, 85%, 90%, 95%, 96%, 97%, 98%, or 99% sequence identity to SEQ ID NO: 1 or SEQ ID NO: 5 or comprising the amino acid sequence of SEQ ID NO: 1 or SEQ ID NO: 5.

According to one embodiment, the polypeptide consists of the amino acid sequence of SEQ ID NO: 1 or 5.

In one embodiment, the polypeptide of an embodiment herein can be present naturally in *Cryptoporus* or *Laricifomes* fungi or in other fungi species, or comprises an amino acid sequence that is a variant of SEQ ID NO: 1 or SEQ ID NO: 5, either obtained by genetic engineering or found naturally in *Cryptoporus* or *Laricifomes* fungi or in other fungi species.

According to another embodiment, the polypeptide is isolated or derived from fungi of the genus *Cryptoporus* or *Laricifomes*. In a further embodiment, the polypeptide is isolated or derived from *Cryptoporus volvatus* or *Laricifomes officinalis*.

In one embodiment, the at least one polypeptide having a bifunctional terpene synthase activity used in any of the herein-described embodiments or encoded by the nucleic acid used in any of the herein-described embodiments comprises an amino acid sequence that is a variant of SEQ ID NO: 1 or SEQ ID NO: 5, obtained by genetic engineering. In one embodiment the polypeptide comprises an amino acid sequence encoded by a nucleotide sequence that has been obtained by modifying SEQ ID NO: 3 or SEQ ID NO: 7 or the reverse complement thereof.

Polypeptides are also meant to include variants and truncated polypeptides provided that they have bifunctional terpene synthase activity.

According to another embodiment, the at least one polypeptide having a bifunctional terpene synthase activity used in any of the herein-described embodiments or encoded by the nucleic acid used in any of the herein-described embodiments comprises an amino acid sequence that is a variant of SEQ ID NO: 1 or SEQ ID NO: 5, obtained by genetic engineering, provided that said variant has bifunctional terpene synthase activity to produce a drimane sesquiterpene and has the required percentage of identity to SEQ ID NO: 1 or SEQ ID NO: 5 as described in any of the above embodiments and comprises (1) a class I terpene synthase-like motif as set forth in SEQ ID NO: 53 (DDxx(D/E)) and (2) a class II terpene synthase-like motif as set forth in SEQ ID NO: 56 (DxD(T/S)T) and comprises domains corresponding to Pfam domains PF13419.5 and PF13242.5. The polypeptide having bifunctional terpene synthase activity may further comprise one or more conserved motifs as set forth in SEQ ID NO: 59, SEQ ID NO: 60, SEQ ID NO: 61, and/or SEQ ID NO: 62.

According to another embodiment, the at least one polypeptide having a bifunctional terpene synthase activity used in any of the herein-described embodiments or encoded by the nucleic acid used in any of the herein-described embodiments is a variant of SEQ ID NO: 1 or SEQ ID NO: 5 that can be found naturally in other organisms, such as other fungal species, provided that it has bifunctional terpene synthase activity and comprises domains corresponding to Pfam domains PF13419.5 and PF13242.5. As used herein, the polypeptide includes a polypeptide or peptide fragment that encompasses the amino acid sequences identified herein, as well as truncated or variant polypeptides provided that they have bifunctional terpene synthase activity and that they share at least the defined percentage of identity with the corresponding fragment of SEQ ID NO: 1 or SEQ ID NO: 5 and comprise (1) a class I terpene synthase-like motif as set forth in SEQ ID NO: 53 (DDxx(D/E)) and (2) a class II terpene synthase-like motif as set forth in SEQ ID NO: 56 (DxD(T/S)T) and comprises domains corresponding to Pfam domains PF13419.5 and PF13242.5.

Examples of variant polypeptides are naturally occurring proteins that result from alternate mRNA splicing events or from proteolytic cleavage of the polypeptides described herein. Variations attributable to proteolysis include, for example, differences in the N- or C-termini upon expression in different types of host cells, due to proteolytic removal of one or more terminal amino acids from the polypeptides of an embodiment herein. Polypeptides encoded by a nucleic acid obtained by natural or artificial mutation of a nucleic acid of an embodiment herein, as described thereafter, are also encompassed by an embodiment herein.

Polypeptide variants resulting from a fusion of additional peptide sequences at the amino and carboxyl terminal ends can also be used in the methods of an embodiment herein. In particular such a fusion can enhance expression of the polypeptides, be useful in the purification of the protein or improve the enzymatic activity of the polypeptide in a desired environment or expression system. Such additional peptide sequences may be signal peptides, for example. Another aspect encompasses methods using variant polypeptides, such as those obtained by fusion with other oligo- or polypeptides and/or those which are linked to signal peptides. Polypeptides resulting from a fusion with another functional protein, such as another protein from the terpene biosynthesis pathway, can also be advantageously used in the methods of an embodiment herein.

A variant may also differ from the polypeptide of an embodiment herein by attachment of modifying groups which are covalently or non-covalently linked to the polypeptide backbone. The variant also includes a polypeptide which differs from the polypeptide provided herein by introduced N-linked or O-linked glycosylation sites, and/or an addition of cysteine residues. The skilled artisan will recognize how to modify an amino acid sequence and preserve biological activity.

In addition to the gene sequences shown in the sequences disclosed herein, it will be apparent for the person skilled in the art that DNA sequence polymorphisms may exist within a given population, which may lead to changes in the amino acid sequence of the polypeptides disclosed herein. Such genetic polymorphisms may exist in cells from different populations or within a population due to natural allelic variation. Allelic variants may also include functional equivalents.

Further embodiments also relate to the molecules derived by such sequence polymorphisms from the concretely disclosed nucleic acids. These natural variations usually bring about a variance of about 1 to 5% in the nucleotide sequence of a gene or in the amino acid sequence of the polypeptides disclosed herein. As mentioned above, the nucleic acid encoding the polypeptide or variants thereof of an embodiment herein is a useful tool to modify non-human host organisms, microorganisms or cells and to modify non-human host organisms, microorganisms or cells intended to be used in the methods described herein.

An embodiment provided herein provides amino acid sequences of bifunctional terpene synthase proteins including orthologs and paralogs as well as methods for identifying and isolating orthologs and paralogs of the bifunctional terpene synthases in other organisms. Particularly, so identified orthologs and paralogs of the bifunctional terpene synthase retain bifunctional terpene synthase activity, may be considered a polypeptide of the HAD-like hydrolase superfamily (Interpro protein superfamily IPR023214 or Pfam protein superfamily PF13419) and which comprises a HAD-like hydrolase domain and are capable of producing a drimane sesquiterpene, such as albicanol and/or drimenol, starting from an acyclic terpene pyrophosphate precursor, e.g. PPP.

The polypeptide to be contacted with an acyclic terpene pyrophosphate, e.g. FPP, in vitro can be obtained by extraction from any organism expressing it, using standard protein or enzyme extraction technologies. If the host organism is an unicellular organism or cell releasing the polypeptide of an embodiment herein into the culture medium, the polypeptide may simply be collected from the culture medium, for example by centrifugation, optionally followed by washing steps and re-suspension in suitable buffer solutions. If the organism or cell accumulates the polypeptide within its cells, the polypeptide may be obtained by disruption or lysis of the cells and optionally further extraction of the polypeptide from the cell lysate. The cell lysate or the extracted polypeptide can be used to contact the acyclic terpene pyrophosphate for production of a terpene or a mixture of terpenes.

The polypeptide having a bifunctional terpene synthase activity, either in an isolated form or together with other proteins, for example in a crude protein extract obtained from cultured cells or microorganisms, may then be suspended in a buffer solution at optimal pH. If adequate, salts, DTT, inorganic cations and other kinds of enzymatic co-factors, may be added in order to optimize enzyme activity. The precursor FPP is added to the polypeptide suspension, which is then incubated at optimal temperature, for example between 15 and 40° C., particularly between 25 and 35° C., more particularly at 30° C. After incubation, the drimane sesquiterpene, such as albicanol and/or drimenol, produced may be isolated from the incubated solution by standard isolation procedures, such as solvent extraction and distillation, optionally after removal of polypeptides from the solution.

According to another embodiment, the at least one polypeptide having a bifunctional terpene synthase activity can be used for production of a drimane sesquiterpene comprising albicanol and/or drimenol or mixtures of terpenes comprising albicanol and/or drimenol.

One particular tool to carry out the method of an embodiment herein is the polypeptide itself as described herein.

According to a particular embodiment, the polypeptide is capable of producing a mixture of sesquiterpenes wherein albicanol and/or drimenol represents at least 20%, particularly at least 30%, particularly at least 35%, particularly at least 90%, particularly at least 95%, more particularly at least 98% of the sesquiterpenes produced. In another aspect provided here, the albicanol and/or drimenol is produced with greater than or equal to 95%, more particularly 98% selectivity.

The functionality or activity of any bifunctional terpene synthase protein, variant or fragment, may be determined using various methods. For example, transient or stable overexpression in plant, bacterial or yeast cells can be used to test whether the protein has activity, i.e., produces albicanol and/or drimenol from FPP precursors. Bifunctional terpene synthase activity may be assessed in a microbial expression system, such as the assay described in Example 3 herein on the production of albicanol and/or drimenol, indicating functionality. A variant or derivative of a bifunctional terpene synthase polypeptide of an embodiment herein retains an ability to produce a drimane sesquiterpene such as albicanol and/or drimenol from FPP precursors. Amino acid sequence variants of the bifunctional terpene synthases provided herein may have additional desirable biological functions including, e.g., altered substrate utilization, reaction kinetics, product distribution or other alterations.

The ability of a polypeptide to catalyze the synthesis of a particular sesquiterpene (for example albicanol and/or drimenol) can be simply confirmed, for example, by performing the enzyme assay as detailed in Examples 3, 4 and 6.

Further provided is at least one vector comprising the nucleic acid molecules described herein.

Also provided herein is a vector selected from the group of a prokaryotic vector, viral vector and a eukaryotic vector.

Further provided here is a vector that is an expression vector.

In one embodiment, several bifunctional terpene synthases encoding nucleic acid sequences are co-expressed in a single host, particularly under control of different promoters. In another embodiment, several bifunctional terpene synthase proteins encoding nucleic acid sequences can be present on a single transformation vector or be co-transformed at the same time using separate vectors and selecting transformants comprising both chimeric genes. Similarly, one or more bifunctional terpene synthase encoding genes may be expressed in a single plant, cell, microorganism or organism together with other chimeric genes.

The nucleic acid sequences of an embodiment herein encoding bifunctional terpene synthase proteins can be inserted in expression vectors and/or be contained in chimeric genes inserted in expression vectors, to produce bifunctional terpene synthase proteins in a host cell or non-human host organism. The vectors for inserting transgenes into the genome of host cells are well known in the art and include plasmids, viruses, cosmids and artificial chromosomes. Binary or co-integration vectors into which a chimeric gene is inserted can also be used for transforming host cells.

An embodiment provided herein provides recombinant expression vectors comprising a nucleic acid sequence of a bifunctional terpene synthase gene, or a chimeric gene comprising a nucleic acid sequence of a bifunctional terpene synthase gene, operably linked to associated nucleic acid sequences such as, for instance, promoter sequences. For example, a chimeric gene comprising a nucleic acid sequence of SEQ ID NO: 3, SEQ ID NO: 4, SEQ ID NO: 7, SEQ ID NO: 8, SEQ ID NO: 10, SEQ ID NO: 11, SEQ ID NO: 13, SEQ ID NO: 14, SEQ ID NO: 16, SEQ ID NO: 18, SEQ ID NO: 19, SEQ ID NO: 21, SEQ ID NO: 22, SEQ ID NO: 24, SEQ ID NO: 25, SEQ ID NO: 27, SEQ ID NO: 28, SEQ ID NO: 30, SEQ ID NO: 31, SEQ ID NO: 33, SEQ ID NO: 34, SEQ ID NO: 36, SEQ ID NO: 37, SEQ ID NO: 39, SEQ ID NO: 40, SEQ ID NO: 42, SEQ ID NO: 43, SEQ ID NO: 45, SEQ ID NO: 46, SEQ ID NO: 48, SEQ ID NO: 49, SEQ ID NO: 51, SEQ ID NO: 52, SEQ ID NO: 64, SEQ ID NO: 65, SEQ ID NO: 66, SEQ ID NO: 67, SEQ ID NO: 68, SEQ ID NO: 69, or SEQ ID NO: 70 or a variant thereof may be operably linked to a promoter sequence suitable for expression in plant cells, bacterial cells or fungal cells, optionally linked to a 3' non-translated nucleic acid sequence.

Alternatively, the promoter sequence may already be present in a vector so that the nucleic acid sequence which is to be transcribed is inserted into the vector downstream of the promoter sequence. Vectors can be engineered to have an origin of replication, a multiple cloning site, and a selectable marker.

In one embodiment, an expression vector comprising a nucleic acid as described herein can be used as a tool for transforming non-human host organisms or host cells suitable to carry out the method of an embodiment herein in vivo.

The expression vectors provided herein may be used in the methods for preparing a genetically transformed non-human host organism and/or host cell, in non-human host organisms and/or host cells harboring the nucleic acids of an embodiment herein and in the methods for making polypeptides having a bifunctional terpene synthase activity, as described herein.

Recombinant non-human host organisms and host cells transformed to harbor at least one nucleic acid of an embodiment herein so that it heterologously expresses or overexpresses at least one polypeptide of an embodiment herein are also very useful tools to carry out the method of an embodiment herein. Such non-human host organisms and host cells are therefore provided herein.

In one embodiment is provided a host cell, microorganism or non-human host organism comprising at least one of the nucleic acid molecules described herein or comprising at least one vector comprising at least one of the nucleic acid molecules.

A nucleic acid according to any of the above-described embodiments can be used to transform the non-human host organisms and cells and the expressed polypeptide can be any of the above-described polypeptides.

In one embodiment, the non-human host organism or host cell is a prokaryotic cell. In another embodiment, the non-human host organism or host cell is a bacterial cell. In a further embodiment, the non-human host organism or host cell is *Escherichia coli*.

In one embodiment, the non-human host organism or host cell is a eukaryotic cell. In another embodiment, the non-human host organism or host cell is a yeast cell. In a further embodiment, the non-human host organism or cell is *Saccharomyces cerevisiae*.

In a further embodiment, the non-human organism or host cell is a plant cell or a fungal cell.

In one embodiment the non-human host organism or host cell expresses a polypeptide, provided that the organism or cell is transformed to harbor a nucleic acid encoding said polypeptide, this nucleic acid is transcribed to mRNA and the polypeptide is found in the host organism or cell. Suitable methods to transform a non-human host organism or a host cell have been previously described and are also provided herein.

To carry out an embodiment herein in vivo, the host organism or host cell is cultivated under conditions conducive to the production of a drimane sesquiterpene such as albicanol and/or drimenol. Accordingly, if the host is a transgenic plant, optimal growth conditions can be provided, such as optimal light, water and nutrient conditions, for example. If the host is a unicellular organism, conditions conducive to the production of a drimane sesquiterpene such as albicanol and/or drimenol may comprise addition of suitable cofactors to the culture medium of the host. In addition, a culture medium may be selected, so as to maximize drimane sesquiterpene, such as albicanol and/or drimenol, synthesis. Examples of optimal culture conditions are described in a more detailed manner in the Examples.

Non-human host organisms suitable to carry out the method of an embodiment herein in vivo may be any non-human multicellular or unicellular organisms. In one embodiment, the non-human host organism used to carry out an embodiment herein in vivo is a plant, a prokaryote or a fungus. Any plant, prokaryote or fungus can be used. Particularly useful plants are those that naturally produce high amounts of terpenes. In another embodiment the non-human host organism used to carry out the method of an embodiment herein in vivo is a microorganism. Any microorganism can be used, for example, the microorganism can be a bacteria or yeast, such as *E. coli* or *Saccharomyces cerevisiae*.

Some of these organisms do not produce FPP naturally. To be suitable to carry out the method of an embodiment herein, organisms or cells that do not produce an acyclic terpene pyrophosphate precursor, e.g. FPP, naturally are transformed to produce said precursor. They can be so transformed either before the modification with the nucleic acid described according to any of the above embodiments or simultaneously, as explained above. Methods to transform organisms, for example microorganisms, so that they produce an acyclic terpene pyrophosphate precursor, e.g. FPP, are already known in the art.

Isolated higher eukaryotic cells can also be used, instead of complete organisms, as hosts to carry out the method of an embodiment herein in vivo. Suitable eukaryotic cells may be any non-human cell, such as plant or fungal cells.

Further provided herein is a method of producing a drimane sesquiterpene comprising: contacting an acyclic terpene pyrophosphate, particularly farnesyl diphosphate (FPP) with a polypeptide which comprises a HAD-like hydrolase domain and having bifunctional terpene synthase activity to produce a drimane sesquiterpene, wherein the polypeptide comprises (1) a class I terpene synthase-like motif as set forth in SEQ ID NO: 53 (DDxx(D/E)); and (2) a class II terpene synthase-like motif as set forth in SEQ ID NO: 56 (DxD(T/S)T); and optionally isolating the drimane sesquiterpene.

Also provided is the above method wherein the drimane sesquiterpene comprises albicanol and/or drimenol.

Additionally provided is the above method, wherein the polypeptide comprises an amino acid sequence having at least 40%, 45%, 50%, 55%, 60%, 65%, 70%, 75%, 80%, 85%, 90%, 95%, 96%, 97%, 98%, or 99% sequence identity to SEQ ID NO: 1, SEQ ID NO: 5, SEQ ID NO: 9, SEQ ID NO: 12, SEQ ID NO: 15, SEQ ID NO: 17, SEQ ID NO: 20, SEQ ID NO: 23, SEQ ID NO: 26, SEQ ID NO: 29, SEQ ID NO: 32, SEQ ID NO: 35, SEQ ID NO: 38, SEQ ID NO: 41, SEQ ID NO: 44, SEQ ID NO: 47, SEQ ID NO: 50, or SEQ ID NO: 63 and (1) the sequence as set forth in SEQ ID NO: 53, SEQ ID NO: 54, or SEQ ID NO: 55; and (2) the sequence as set forth in SEQ ID NO: 56, SEQ ID NO: 57, or SEQ ID NO: 58 or comprising the amino acid sequence of SEQ ID NO: 1, SEQ ID NO: 5, SEQ ID NO: 9, SEQ ID NO: 12, SEQ ID NO: 15, SEQ ID NO: 17, SEQ ID NO: 20, SEQ ID NO: 23, SEQ ID NO: 26, SEQ ID NO: 29, SEQ ID NO: 32, SEQ ID NO: 35, SEQ ID NO: 38, SEQ ID NO: 41, SEQ ID NO: 44, SEQ ID NO: 47, SEQ ID NO: 50, or SEQ ID NO: 63 to produce a drimane sesquiterpene; and optionally isolating the drimane sesquiterpene. In another aspect, the polypeptide further comprises one or more conserved motif as set forth in SEQ ID NO: 59, SEQ ID NO: 60, SEQ ID NO: 61, and/or SEQ ID NO: 62.

In one aspect, the drimane sesquiterpene is albicanol and/or drimenol. In another aspect, the drimane sesquiterpene is isolated.

In another aspect provided here, the albicanol and/or drimenol is produced with greater than or equal to, 60%, 80%, or 90% or even 95% selectivity. In a further aspect the drimane sesquiterpene is albicanol.

Further provided here is a method comprising transforming a host cell, microorganism or a non-human host organism with a nucleic acid encoding a polypeptide comprising a HAD-like hydrolase domain having bifunctional terpene synthase activity and comprising an amino acid sequence having at least 40%, 45%, 50%, 55%, 60%, 65%, 70%, 75%, 80%, 85%, 90%, 95%, 96%, 97%, 98% or 99% sequence identity to SEQ ID NO: 1, SEQ ID NO: 5, SEQ ID NO: 9, SEQ ID NO: 12, SEQ ID NO: 15, SEQ ID NO: 17, SEQ ID NO: 20, SEQ ID NO: 23, SEQ ID NO: 26, SEQ ID NO: 29, SEQ ID NO: 32, SEQ ID NO: 35, or SEQ ID NO: 38, SEQ ID NO: 41, SEQ ID NO: 44, SEQ ID NO: 47, SEQ ID NO: 50, or SEQ ID NO: 63; and comprising (1) the sequence as set forth in SEQ ID NO: 53, SEQ ID NO: 54, or SEQ ID NO: 55; and (2) the sequence as set forth in SEQ ID NO: 56, SEQ ID NO: 57, or SEQ ID NO: 58 or comprising the amino acid sequence of SEQ ID NO: 1, SEQ ID NO: 5, SEQ ID NO: 9, SEQ ID NO: 12, SEQ ID NO: 15, SEQ ID NO: 17, SEQ ID NO: 20, SEQ ID NO: 23, SEQ ID NO: 26, SEQ ID NO: 29, SEQ ID NO: 32, SEQ ID NO: 35, or SEQ ID NO: 38, SEQ ID NO: 41, SEQ ID NO: 44, SEQ ID NO: 47, SEQ ID NO: 50, or SEQ ID NO: 63.

In one embodiment, a method provided herein comprises cultivating a non-human host organism or a host cell capable of producing FPP and transformed to express a polypeptide wherein the polypeptide comprises a sequence of amino acids that has at least 40%, 45%, 50%, 55%, 60%, 65%, 70%, 75%, 80%, 85%, 90%, 95%, 98%, 99% or 100% sequence identity to SEQ ID NO: 1 or SEQ ID NO: 5 under conditions that allow for the production of the polypeptide.

In a another embodiment, a method provided herein comprises contacting a sesquiterpene such as albicanol and/or drimenol with at least one enzyme to produce a sesquiterpene derivative. In one embodiment, the sesquiterpene derivative can be obtained biochemically or chemically. In one embodiment, a drimenol derivative is provided. Examples of such derivatives of drimenol include but not limited to drimenyl acetate (CAS 40266-93-1), drimenal (CAS 105426-71-9), drimenic acid (CAS 111319-84-7).

In one embodiment, an albicanol derivative is provided. Examples of such derivatives of albicanol include cryptoporic acid E (CAS 120001-10-7), cryptoporic acid D (CAS 119979-95-2), cryptoporic acid B (CAS 113592-88-4), cryptoporic acid A (CAS 113592-87-3), laricinolic acid (CAS 302355-23-3), albicanyl acetate (CAS 83679-71-4).

The albicanol and/or drimenol produced in any of the method described herein can be converted to derivatives such as, but not limited to hydrocarbons, esters, amides, glycosides, ethers, epoxides, aldehydes, ketons, alcohols, diols, acetals or ketals.

The albicanol and/or drimenol derivatives can be obtained by a chemical method such as, but not limited to oxidation, reduction, alkylation, acylation and/or rearrangement.

Alternatively, the albicanol and/or drimenol derivatives can be obtained using a biochemical method by contacting the albicanol and/or drimenol with an enzyme such as, but not limited to an oxidoreductase, a monooxygenase, a dioxygenase, a transferase. The biochemical conversion can be performed in-vitro using isolated enzymes, enzymes from lysed cells or in-vivo using whole cells.

According to another particularly embodiment, the method of any of the above-described embodiments is carried out in vivo. In such a case, step a) comprises cultivating a non-human host organism or a host cell capable of producing FPP and transformed to express at least one polypeptide comprising an amino acid comprising SEQ ID NO: 1 or SEQ ID NO: 5 or a functional variant thereof which may be considered a polypeptide of the HAD-like hydrolase superfamily (Interpro protein superfamily IPR023214 or Pfam protein superfamily PF13419) and which comprises a HAD-like hydrolase domain and having a bifunctional terpene synthase activity, under conditions conducive to the production of drimane synthase, for example, albicanol and/or drimenol. In one embodiment, albicanol may be the only product or may be part of a mixture of sesquiterpenes. In another aspect, drimenol may be the only product or may be part of a mixture of sesquiterpenes.

According to a further embodiment, the method further comprises, prior to step a), transforming a non-human organism or cell capable of producing FPP with at least one nucleic acid encoding a polypeptide comprising an amino acid comprising SEQ ID NO: 1 or SEQ ID NO: 5 or encoding a polypeptide having bifunctional terpene synthase activity and comprising an amino acid sequence having at least 40%, 45%, 50%, 55%, 60%, 65%, 70%, 75%, 80%, 85%, 90%, 95%, 96%, 97%, 98% or 99% sequence identity to SEQ ID NO: 1, SEQ ID NO: 5, SEQ ID NO: 9, SEQ ID NO: 12, SEQ ID NO: 15, SEQ ID NO: 17, SEQ ID NO: 20, SEQ ID NO: 23, SEQ ID NO: 26, SEQ ID NO: 29, SEQ ID NO: 32, SEQ ID NO: 35, or SEQ ID NO: 38, SEQ ID NO: 41, SEQ ID NO: 44, SEQ ID NO: 47, SEQ ID NO: 50, or SEQ ID NO: 63; and (1) the sequence as set forth in SEQ ID NO: 53, SEQ ID NO: 54, or SEQ ID NO: 55; and (2) the sequence as set forth in SEQ ID NO: 56, SEQ ID NO: 57, or SEQ ID NO: 58, so that said organism expresses said polypeptide. The polypeptide may further comprise one or more conserved motif as set forth in SEQ ID NO: 59, SEQ ID NO: 60, SEQ ID NO: 61, and/or SEQ ID NO: 62.

These embodiments of an embodiment herein are particularly advantageous since it is possible to carry out the method in vivo without previously isolating the polypeptide. The reaction occurs directly within the organism or cell transformed to express said polypeptide.

An embodiment herein provides polypeptides of an embodiment herein to be used in a method to produce a drimane sesquiterpene such as albicanol and/or drimenol contacting an FPP precursor with the polypeptides of an embodiment herein either in vitro or in vivo.

Further provided is the use of a polypeptide as described herein for producing a drimane sesquiterpene, for example, albicanol and/or drimenol.

The following examples are illustrative only and are not intended to limit the scope of the claims an embodiments described herein.

EXAMPLES

Example 1

Microorganism Cultivation and DNA and RNA Extraction.

Drimane sesquiterpenoids are widespread in nature (Jansen and Groot, 2004, *Nat. Prod. Rep.*, 21, 449-477). The compounds in the drimane sesquiterpeneoid family contain the sesquiterpene structure with the drimane carbon skeleton depicted in FIG. 1. For example, commonly found drimane sesquiterpene are drimenol and albicanol (FIG. 1) and compounds derived from drimenol and albicanol by enzymatic reactions such as oxidations, reduction, acylation, alkylation or rearrangement. The drimane sesquiterpenoid family contains also compounds were the drimane sesquiterpene is bound to a molecule derived from another biosynthetic pathway (Jansen and Groot, 2004, *Nat. Prod. Rep.*, 21, 449-477).

Cryptoporic acids A-H are drimane sequiterpenoid ethers of isocitric acid found in the fungus *Cryptoporus volvatus* (Hashimoto et al, 1987, *Tetrahedron Let.* 28, 6303-6304; Asakawa et al, 1992, *Phytochemistry* 31(2), 579-592; Hirotani et al, 1991, *Phytochemistry* 30(5), 1555-1559). In crypotoporic acids, the sesquiterpene moiety has the structure of albicanol and thus these compounds are putatively derived biosynthetically from albicanol. Laricinolic acid is a drimane type sesquiterpene which can be isolated from the wood-rotting fungus *Laricifomes officinalis* (Erb et al, 2000, *J. Chem. Soc., Perkin Trans.* 1, 2307-2309). Laricinolic acid is most likely derived from albicanol following several oxidative enzymatic steps.

We undertook to characterize albicanol synthases and to identify nucleotide sequences encoding for albicanol synthases from *Cryptoporus volvatus* and *Laricifomes officinalis*. Strains of *Laricifomes officinalis* (ATCC® 64430™) and *Cryptoporus volvatus* (ATCC®12212™) are conserved at the American Type Culture Collection (ATCC) under the collection numbers ATCC-64430 and ATCC-12212, respectively. The *Laricifomes officinalis* (ATCC® 64430™) and *Cryptoporus volvatus* (ATCC®12212™) strains were purchased from LGC Standards GmbH (46485 Wesel, Germany). The cells were grown in Yeast Mold (YM) medium (Wickerham, 1939, *J. Tropical Med. Hyg.* 42, 176).

For each of the two strains, genomic DNA and total RNA were extracted in order to sequence the full genome and a transcriptome. Cells propagated on YM-agar plates were used to inoculate 100 ml liquid YM medium in glass tubes. The cultures were incubated for 6 days with at 25° C. and 180 rpm agitation. For RNA extraction 0.5 ml of culture was taken, the cells (Approximately 100 mg) were recovered by centrifugation frozen in liquid nitrogen and grinded using a mortar and pestle. The total RNA pool was extracted using the ZR Fungal/Bacterial RNA MiniPrep™ from Zymo Research Corp (Irvine, Calif. 92614, U.S.A). From 100 mg of cells 18 and 23 micrograms of total RNA were obtained for ATCC-12212 and ATCC-64430, respectively. Genomic DNA was extracted using the NucleoSpin® Soil Kit from Machery-Nagel (Düren, Germany). Cells were recovered from the culture by centrifugation and the genomic DNA was extracted following the manufacturer protocol. From 500 mg of cells 1.05 and 0.93 micrograms of genomic DNA was extracted from ATCC-12212 and ATCC-64430, respectively.

Example 2

Genome and Transcriptome Sequencing.

The genomic DNA was sequenced using a paired read protocol (Illumina). The libraries were prepared to select insert sizes between 250 and 350 bp. The sequencing was performed on a HiSeq 2500 Illumina sequencer. The length of the reads was 125 bases. A total of 21.3 and 30.4 millions of paired-reads (clusters) were sequenced for ATCC-12212 and ATCC-64430, respectively.

For the transcriptomes the library was prepared from the total RNA using the TruSeq Stranded mRNA Library Preparation Kit (Illumina). An additional insert size selection step (160-240 bp) was performed. The libraries were sequenced in 2×125 bases paired-ends on a HiSeq 2500 Illumina sequencer. For ATCC-12212 and ATCC-64430, 19.9 million and 126 millions of reads were sequences, respectively.

For assembly of the *C. volvatus* transcriptome, the reads were first joined on their overlapping ends. The joined paired reads were then assembled using the Velvet V1.2.10 assembler (Zerbino D. R. and Birney E. 2008, *Genome Res.* 18(5), 821-829; www.ebi.ac.uk/~zerbino/velvet/) and the Oases software (Schulz M. H et al., 2012, *Bioinformatics* 28(8), 1086-1092; http://www.ebi.ac.uk/~zerbino/oases/). A total of 25'866 contigs with an average length of 1'792 bases was obtained for the *C. volvatus* transcriptome.

The *C. volvatus* genome was assembled using the Velvet V1.2.10 assembler (Zerbino D. R. and Birney E., 2008, *Genome Res.* 18(5), 821-829; www.ebi.ac.uk/~zerbino/velvet/). The genome could be assembled in 1'266 contigs with an average size 20'000 bases and a total size of 25'320'421 bases. An ab-initio gene prediction in the *C. volvatus* genomic contigs was performed by Progenus SA (Gembloux, Belgium) using the Augustus software (Stanke et al., *Nucleic Acids Res.* (2004) 32, W309-W312). A total of 7738 genes were predicted. Functional annotation was performed combining a Pfam domain search (Finn, R. D. et al., 2016, *Nucleic Acids Research* Database Issue 44:D279-D285) and a Blast search (Altschul et al., 1990, *J. Mol. Biol.* 215, 403-410).

The genome and transcriptome of *L. officinalis* were assembled using the CLC Genomic Workbench (Qiagen). The genome was assembled in 16'831 contigs for a total genome size of 90'591'190 bases. The transcriptome assembly provided 28'633 contigs with an average length of 1'962 bases.

Example 3

Identification of Drimane Sesquiterpene Synthases.

Using a tBlastn search (Altschul et al., 1990, *J. Mol. Biol.* 215, 403-410) with the amino acid sequences of known sesquiterpene synthases as query sequences, 6 and 10 putative sesquiterpene synthases sequences were identified in the *C. volvatus* genome and *L. officinalis* genome, respectively. The sequences were manually corrected, in particular for the intro-exon junction localizations, using a mapping of the RNA sequencing reads on the genomic contigs. The corresponding cDNAs were then codon-optimized for optimal *E. coli* expression, synthesized and cloned in an expression plasmid (pJ401, ATUM, Newark, Calif.). Functional expression *E. coli* cells and enzyme characterization assay showed sesquiterpene synthase activities but did not reveal any formation of albicanol from FPP.

Figure 2:
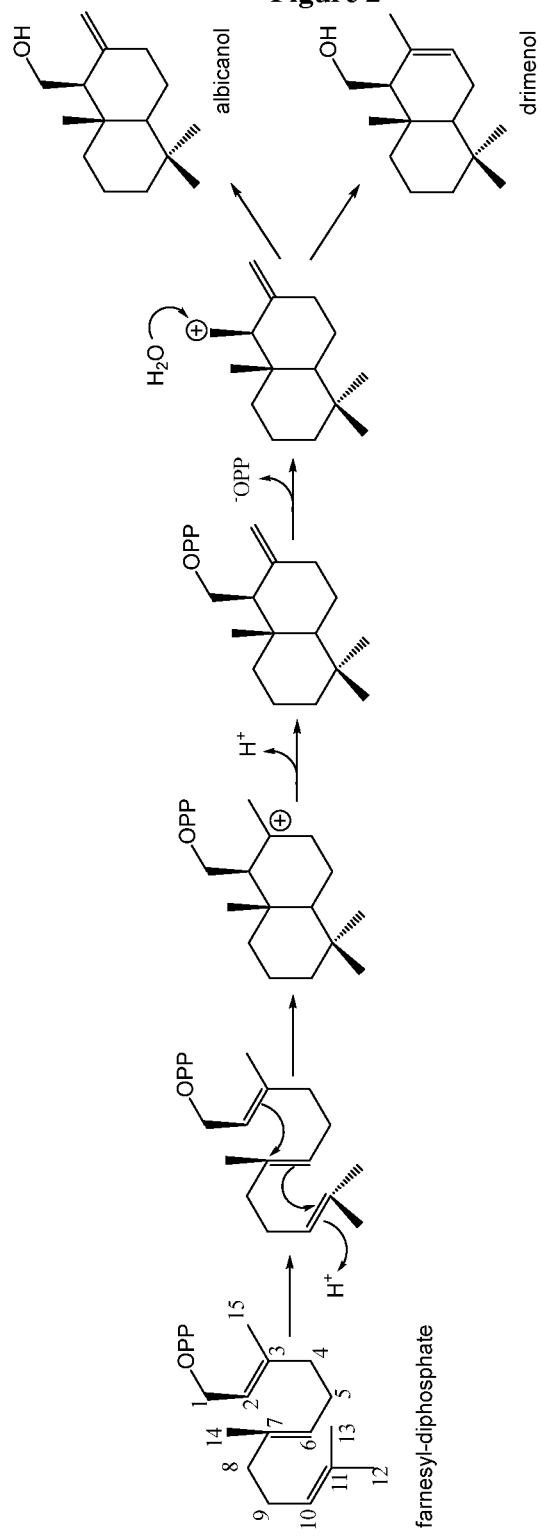
FIG. 2: Mechanism of cyclization of farnesyl-diphosphate by a class II terpene synthase and class I terpene synthase enzymatic activity.
Figure 3:
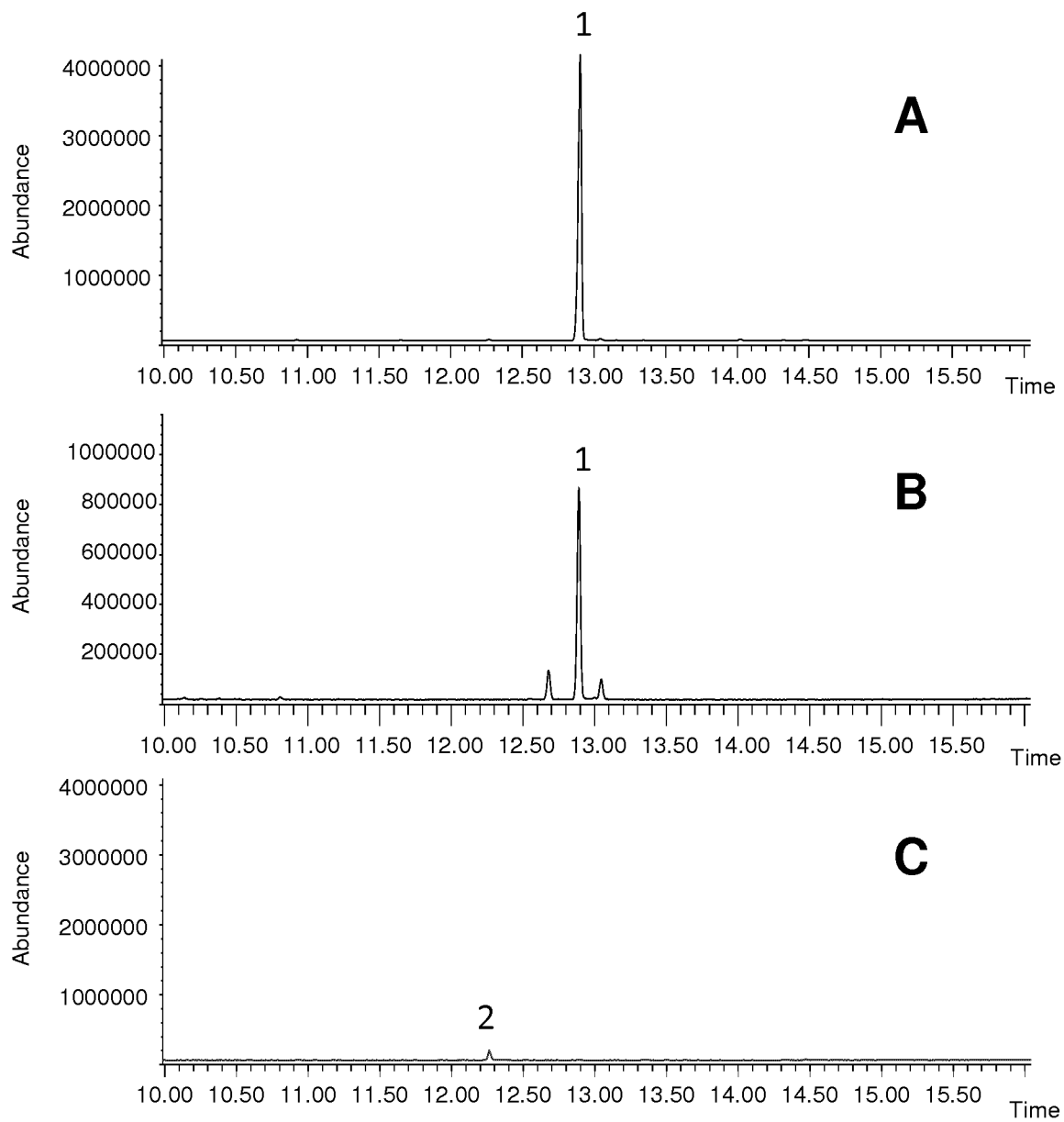
FIG. 3: GCMS analysis of the sesquiterpenes produced in-vivo by the recombinant CvTps1 enzyme in bacteria cells modified to overproduce farnesyl-diphosphate. A. Total ion chromatogram of an extract of *E. coli* cells expressing CvTps1 and the mevalonate pathway enzymes. B. Total ion chromatogram of an authentic standard of albicanol. C. Total ion chromatogram of an extract of *E. coli* cells expressing only the mevalonate pathway enzymes. 1, albicanol; 2, trans-farnesol (from hydrolysis of FPP by endogenous phosphatase enzymes).
Figure 4:
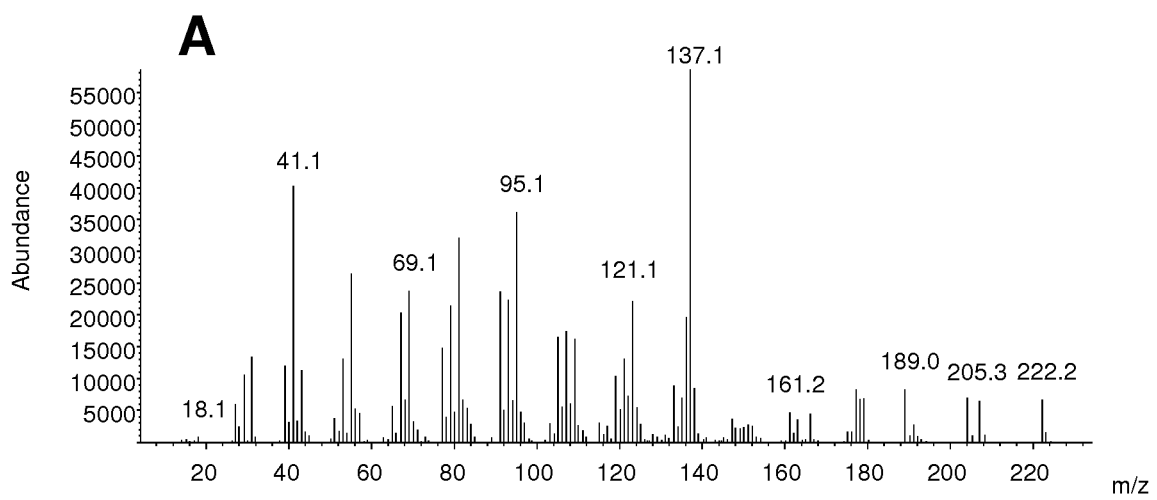
FIG. 4: Comparison of the mass spectra of the product of CvTps1 and of an authentic standard of albicanol. A. Mass spectra of peak 1 in FIG. 3A (product of CvTps1). B. Mass spectra of peak 1 in FIG. 3B (authentic standard of albicanol).
Figure 4:
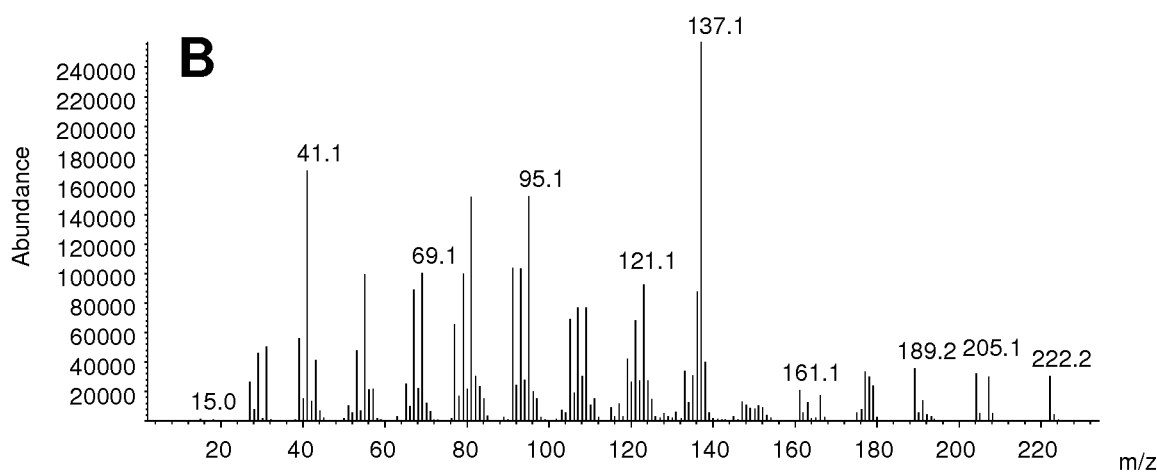
Figure 5:
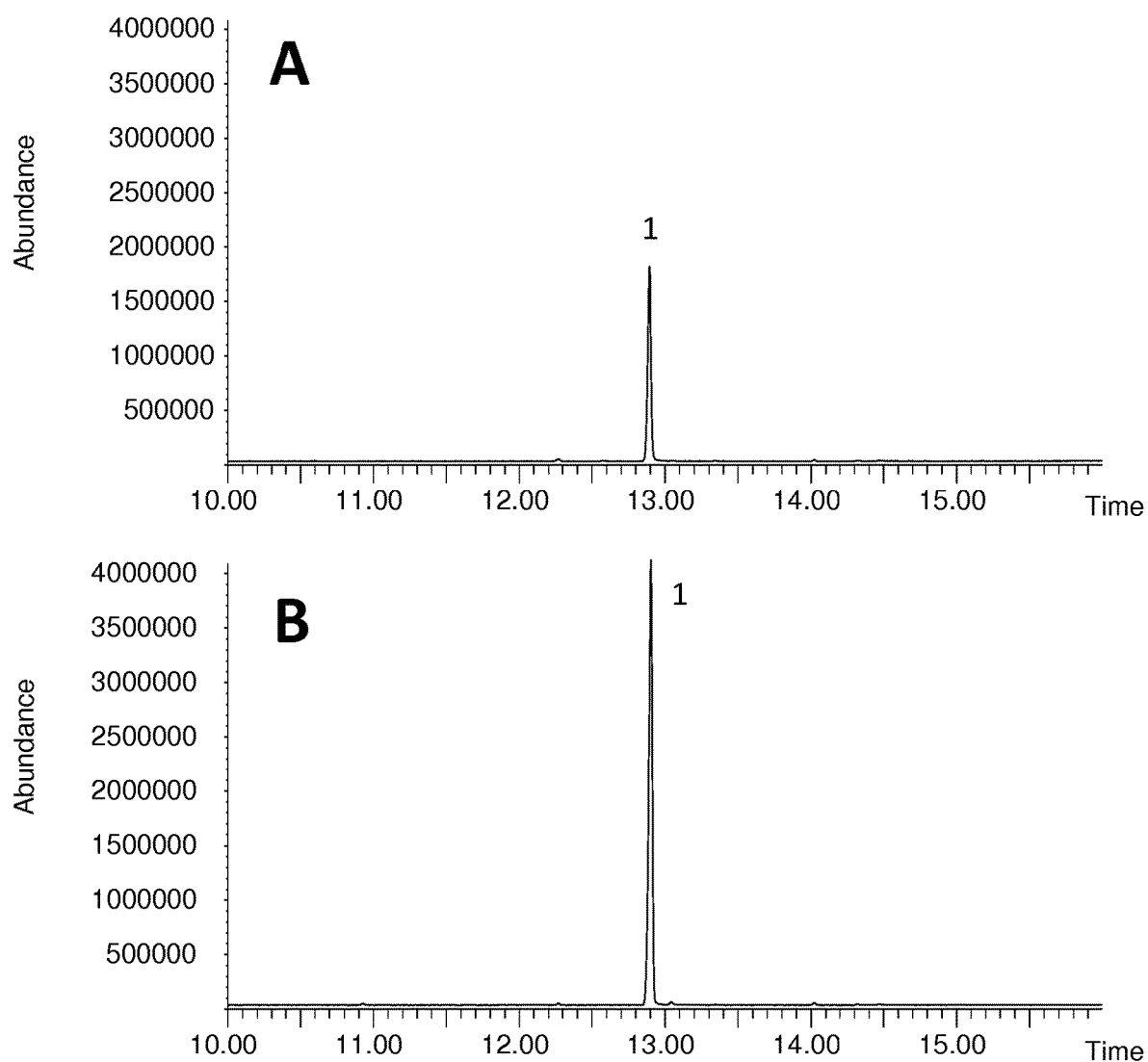
FIG. 5: GCMS analysis of the sesquiterpenes produced by the LoTps1 and CvTps1 recombinant protein. Total ion chromatogram of an extract of *E. coli* cells expressing LoTps1 (A) and CvTps1 (B). The peak labeled '1' is (+)-albicanol.

Drimane sesquiterpene are presumably produced from farnesyl-diphosphate (FPP) by an enzymatic mechanism involving a protonation-initiated cyclization followed by an ionization-initiated reaction (Henquet et al., 2017, *Plant J.* Mar 4. doi: 10.1111/tpj.13527; Kwon, M. et al., 2014, *FEBS Letters* 588, 4597-4603) (FIG. 2). This implies that the drimane synthases are composed of two catalytic domains, a protonation-initiated cyclization catalytic domain and an ionization-initiated cyclization catalytic domain.

Terpene synthases catalyzing protonation-initiated cyclization reaction are called class II (or type II) terpene synthases and are typically involved in the biosynthesis of triterpenes and labdane diterpenes. In class II terpene synthases the protonation-initiated reaction involves acidic amino acids donating a proton to the terminal double-bond. These residues, usually aspartic acids, are part of a conserved DxDD motif located in the active site of the enzyme.

Terpene synthases catalyzing ionization-initiated reactions are called class I (or type I) terpene synthases, generally monoterpene and sesquiterpene synthases, and the catalytic center contains a conserved DDxxD (part of SEQ ID NO: 53) motif. The aspartic acid residues of this class I motif bind a divalent metal ion (most often $Mg^{2+}$) involved in the binding of the diphosphate group and catalyze the ionization and cleavage of the allylic diphosphate bond of the substrate.

The putative cyclization mechanism of a farnesyl-diphosphate to a drimane sesquiterpene (such as albicanol or drimenol) starts with the protonation of the 10,11-double bond followed by the sequential rearrangements and carbon-bond formations. The carbocation intermediate of this first (class II) reaction can then undergo deprotonation at C15 or C4 (or eventually at C2) leading to an albicanyl-diphosphate or drimenyl-diphosphate intermediate. Finally the class I catalytic domain catalyzes the ionization of the allylic diphosphate bond and quenching of the carbocation intermediated by a water molecule leading to a drimane sesquiterpene containing a primary hydroxyl group (FIG. 2). If necessary, any traces of residual phosphorylated intermediates of the albicanol or drimenol synthesis, like any albicanyl- or drimenyl-monophosphate and/or -diphosphate, may be chemically converted to the respective final product albicanol or drimenol. Certain corresponding methods are known and may comprise, for example, the hydrolytic cleavage of the phosphoric acid ester bond. Additionally, certain intermediates can also be converted enzymatically as shown in Examples 7 and 8.

Based on the above considerations, we searched the *C. volvatus* and *L. officinalis* genome and transcriptome data for sequences encoding for polypeptides containing together a class I and a class II terpene synthase motif. Recently, a drimanyl-diphosphate synthase (AstC) was identified in the fungus *Aspergillus oryzea* (Shinohara Y. et al., 2016, *Sci Rep.* 6, 32865). The enzyme contains a class II terpene synthase domain and catalyzes the protonation-initiation cyclization of farnesyl-diphosphate to drimanyl-diphosphate. However, this enzyme does not have a class I terpene synthase activity and thus does not catalyze the ionization and cleavage of the allylic diphosphate group. Using the sequence of AstC, we first search the amino acid sequences deduced from the genes predicted in the *C. volvatus* genome. Using a Blastp search against the amino acid sequences deduced from the predicted genes, 5 sequences were retrieved with an E value between 0.77 and 3e-089 (Altschul et al., 1990, *J. Mol. Biol.* 215, 403-410).

Amongst these 5 sequences, CvTps1 was selected as the most relevant for a putative albicanol synthases. The amino acid sequence encoded by the CvTps1 gene shared 38% identity with the AstC amino acid sequence. Analysis of this sequence revealed the presence of a class II terpene synthase-like motif, DVDT, at position 275-279. This is a variant of the typical class II terpene synthase motif mentioned above, where the last Asp is replaced by a Thr. This DxDT class II motif is found in some class II diterpene synthases (Xu M. et al., 2014, *J. Nat. Prod.* 77, 2144-2147; Morrone D. et al., 2009, *J. FEBS Lett.,* 583, 475-480) and in AstC. Another interesting feature of the CvTps1 sequence is the presence of a typical class I motif in the N-terminal region (DDKLD at position 168-172). The presence of this class I motif, not present in AstC, suggests that CvTps1 can catalyze an ionization-initiated reaction in addition to the class II reaction. Another difference with AstC is the presence of a C-terminal extension, the CvTps1 peptide contains 46 additional amino acids at the C-terminal end. Thus CvTps1 was selected as putative candidate for a bi-functional albicanol synthase.

Protein family databases such as Pfam and Interpro (European Bioinformatic Institute (EMBL-EBI) are databases of protein families including functional annotation, protein domains and protein domain signatures. The amino acid sequence of CvTps1 was searched for the occurrence of motifs characteristic of protein domains using the HMMER algorithm available on the HMMER website (Finn R. D., 2015, *Nucleic Acids Research Web Server Issue* 43:W30-W38; www.ebi.ac.uk/Tools/hmmer/). No domain associated with classical terpene synthases was found in the CvTps1 amino acid sequence. The query identified a domain characteristic of the Haloacid dehalogenase (HAD)-like hydrolase protein superfamily (PF13419.5) in the region between residues 115 and 187. A similar search using the Interpro protein family database (see the ebi.ac.uk/interpro/web site) and the Conserved Domain Database (NCBI web site at ncbi.nlm.nih.gov/Structure/cdd/wrpsb.cgi) provided the same results: only the prediction of a domain of the HAD-like hydrolase superfamily in the N-terminal region (IPR 023214 and CL21460, respectively). The HAD-like hydrolase superfamily contains a large number of proteins with various functions including enzymes with phosphatase activity (Koonin and Tatusov, 1994, J. Mol. Biol 244, 125-132; Kuznetsova et al, 2015, J Biol Chem. 290(30), 18678-18698). The class I terpene synthase-like motif identified above in the CvTps1 polypeptide contains one of the HAD-like hydrolase motif signatures containing a conserved aspartic acid residues involved in the catalytic (phosphatase) activity. This analysis thus confirms that the N-terminal region of CvTps1 is involved in hydrolysis of the diphosphate group (class I terpene synthase activity).

No significant domain prediction was obtained in the C-terminal portion the polypeptide. Given the presence of a class II terpene synthase-like motif, the C-terminal part is likely involved in the protonation-initiated cyclization.

The CvTps1 amino acid sequence was used to search for homologous sequences in the *L. officinalis* genome and transcriptome. For this search the tBlastn algorithm was used (Altschul et al 1990, *J. Mol. Biol.* 215, 403-410). One transcript, LoTps1 showed sequence similarity with CvTps1: the length of the sequence (521 amino acid) was similar to the length of the CvTps1 amino acid sequence, the overall sequence identity between the two sequences was 71%, the N-terminal region contained a typical class I terpene synthase motif (DDKLD at position 162-166), a class II terpene synthase motif (DMDT) was found in position 267-270 and the N-terminal region contain a predicted HAD-like hydrolase domain.

Example 4

Heterologous Expression and Characterization of CvTps1 and LoTps1.

The CvTps1 and LoTps1 coding sequences were control and the intron-exon jonctions predictions were refined using mappings of the RNA sequencing reads against the genomic contigs. The coding sequences of the resulting cDNAs were codon optimized and cloned in the pJ401 *E. coli* expression plasmid (pJ401, ATUM, Newark, Calif.).

The enzymes were functionally characterized in *E. coli* cells engineered to overproduce farnesyl-diphosphate (FPP). Competent *E. coli* cells were transformed with the plasmid pACYC-29258-4506 (described in WO2013064411 or in Schalk et al., 2013, J. Am. Chem. Soc. 134, 18900-18903) and with the pJ401-CvTps1 or pJ401-LoTps1 expression plasmid. The pACYC-29258-4506 carries the cDNA encoding for a FPP synthase gene and the genes for a complete mevalonate pathway. The KRX *E. coli* cells (Promega) were used as a host. Transformed cells were selected on kanamycin (50 µg/ml) and chloramphenicol (34 µg/ml) LB-agarose plates. Single colonies were used to inoculate 5 mL liquid LB medium supplemented with the same antibiotics. The culture was incubated overnight at 37° C. The next day 2 mL of TB medium supplemented with the same antibiotics were inoculated with 0.2 mL of the overnight culture. After 6 hours incubation at 37° C., the culture was cooled down to 28° C. and 0.1 mM IPTG, 0.2% rhamnose and 10% in volume (0.2 ml) of dodecane were added to each tube. The cultures were incubated for 48 hours at 28° C. The cultures were then extracted twice with 2 volumes of tert-Butyl methyl ether (MTBE), the organic phase were concentrated to 500 µL and analyzed by GC-MS.

The GC-MS analysis were performed using an Agilent 6890 Series GC system connected to an Agilent 5975 mass detector. The GC was equipped with 0.25 mm inner diameter by 30 m DB-1MS capillary column (Agilent). The carrier gas was He at a constant flow of 1 mL/min. The inlet temperature was set at 250° C. The initial oven temperature was 80° C. followed by a gradient of 10° C./min to 220° C. and a second gradient of 30° C./min to 280° C. The identification of the products was based on the comparison of the mass spectra and retention indices with authentic standards and internal mass spectra databases.

In these conditions formation of a single product was observed with the recombinant CrVo07609 protein. The final concentration for this enzyme product was 200 mg/l of culture medium. The retention time in gas chromatography as well as the mass spectrum was in accordance with the GCMS data of an authentic (+)-albicanol standard. For structure confirmation, the recombinant cells were cultivated in a larger (500 ml) volume in the conditions described above. The MTBE was distilled form the extract and the resulting suspension in dodecane was subjected to flash chromatography. The product was eluted with a mixture 1:5 of MTBE and cyclohexane. The solvent was removed by distillation providing a product with 98% purity. The structure of albicanol was confirmed by 1H- and 13C-NMR analysis. The optical rotation was measured using a Bruker Avance 500 MHz spectrometer. The value of $[\alpha]^D_{20}=+3.8°$ (0.26%, CHCl3) confirmed the formation of (+)-albicanol (with the structure shown in FIG. 1) by the recombinant CvTps1 protein.

The activity of LoTps1 was evaluated in the same conditions. The product profile was identical to the profile of CvTps1 with (+)-albicanol as the only detected product of the recombinant LoTps1 enzyme.

This experiments show that the CvTps1 and LoTps1 are enzyme with bifunctional class II cyclase activity and class I phosphatase activity.

Example 5

Search for Sequences Homologous to CvTps1 and LoTps1 in Other Organisms.

The amino acid sequences of CvTps1 and LoTps1 were used to search for homologous sequences from other organisms present in public databases. A blastp search approach (Altschul et al., 1990, *J. Mol. Biol.* 215, 403-410) was first used to search in the protein database of the National Center for Biotechnology Information (NCBI, https://www.ncbi.nlm.nih.gov/) for sequences showing homology with CvTps1 and LoTps1. The retrieved amino acids were then analyzed for the presence of the CvTps1 and LoTps1 features described in Example 3. Fifteen sequences, all from fungi species, were selected for further analysis and enzymatic activity characterization: NCBI accession OCH93767.1 from *Obba rivulosa*, NCBI accession EMD37666.1 from *Gelatoporia subvermispora*, NCBI accession XP_001217376.1 from *Aspergillus terreus*, NCBI accession OJJ98394.1 from *Aspergillus aculeatus*, NCBI accession GA087501.1 from *Aspergillus udagawae*, NCBI accession XP_008034151.1 from *Trametes versicolor*, NCBI accession XP_007369631.1 from *Dichomitus squalens*, NCBI accession KIA75676.1 from *Aspergillus ustus*, NCBI accession XP_001820867.2 from *Aspergillus oryzae*, NCBI accession CEN60542.1 from *Aspergillus calidoustus*, NCBI accession XP_009547469.1 from *Heterobasidion irregulars*, NCBI accession KLO09124.1 from *Schizopora paradoxa*, NCBI accession OJI95797.1 from *Aspergillus versicolor*.

The sequence of EMD3766.1 was corrected by deleting the amino acids 261 to 266 present in the published sequence and probably resulting from incorrect splicing prediction (sequence EMD37666-B in table 1). Another sequence, ACg006372 was selected from the published annotated sequence of *Antrodia cinnamomea* (Lu et al., 2014, *Proc. Natl. Acad. Sci. USA.* 111(44):E4743-52, (Dataset S1)).

Figure 6A:
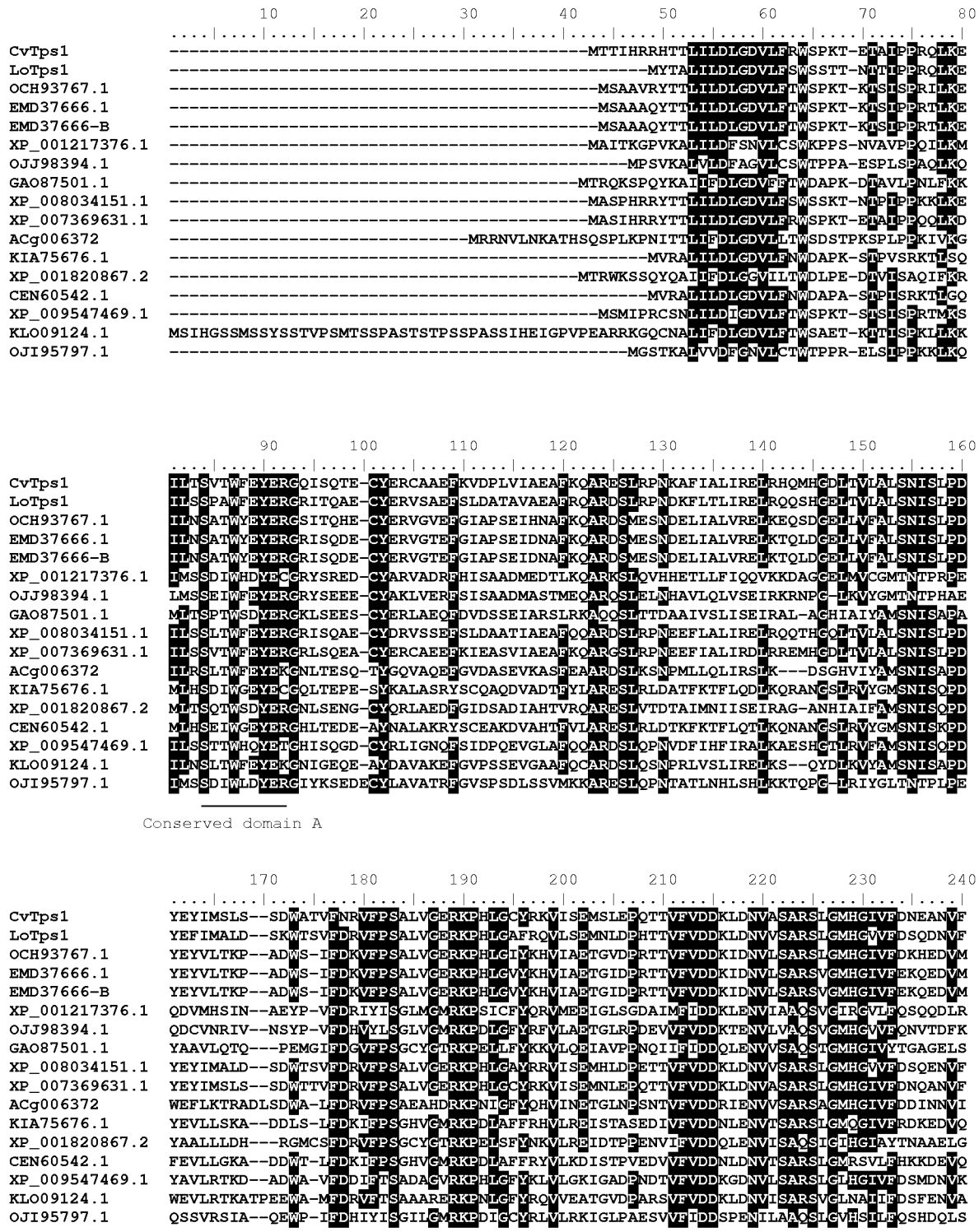
Figure 6B:
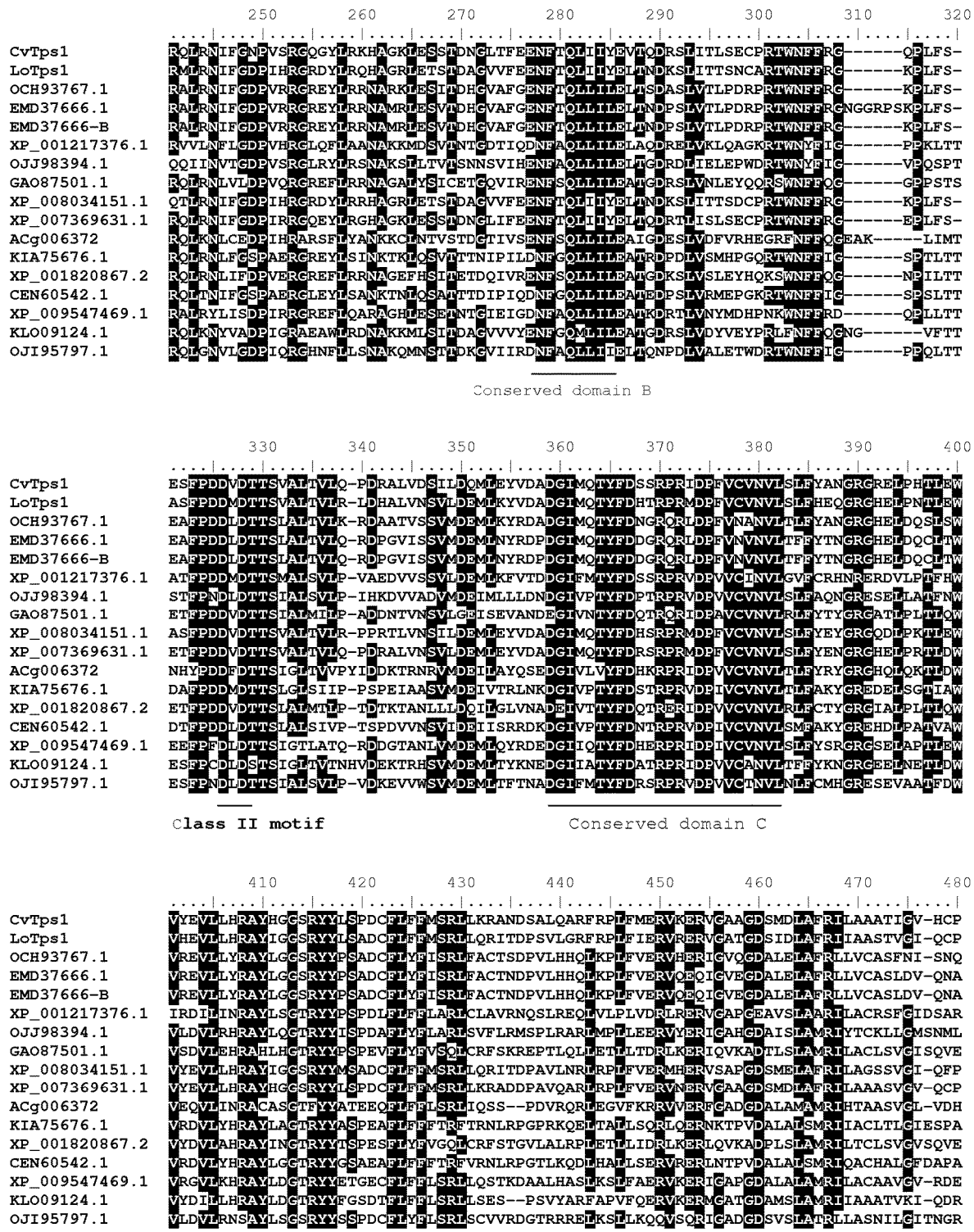

The 15 putative terpene synthases amino acid sequences contain a class II terpene synthase-like motif with the consensus sequence D(V/M/L/F)D(T/S) as well as a class I terpene synthase-like motif with the consensus sequence DD(K/N/Q/R/S)xD (were x is a hydrophobic residue L, I, G, T or P). The class I and class II motifs are easily localized using an alignment of the amino acid sequences with the sequences of CvTps1 and LoTps1 (FIG. 6). Such alignment can be made using for example the program Clustal W (Thompson J. D. et al., 1994, *Nucleic Acids Res.* 22(22), 4673-80). In addition, the presence of a HAD-like hydrolase domain was identified in the N-terminal region of the 15 amino acid sequences (between positions 1 and 183 to 243 of the sequences) (Table 3).

The features of the above sequences thus suggest that the proteins contain a phosphatase or class I terpene synthase domain and a class II terpene synthase domain in the N-terminal and C-terminal region, respectively and thus have bifunctional protonation-initiated cyclization and ionization-initiated catalytic activities. Alignment of the sequences and pairwise comparisons (Table 2) of the above amino acid sequences showed a lowest sequence identity value of 37% and a highest value of 89% (without considering the two EMD37666.1 variants). Compared to CvTps1 and LoTps1, the closest sequences shared 85% identity and the most distant sequence only 42% identity.

TABLE 1

List of selected sequences showing sequence homology with CvTps1 and LoTps1 and containing a class I and a class II motifs. The source (species) of the sequences, SEQ ID NO, length of the sequence, sequence region containing the class I and class II motifs, and positions of the class I and class II motifs are listed. The residues of class I and class II motifs are in bold

| Name or NCBI accession number | Source | Protein SEQ ID NO | Length (amino acids) | Putative function (database annotation) | Class I motif region sequence | Class I motif position | Class II motif region sequence | Class II motif position |
|---|---|---|---|---|---|---|---|---|
| CvTps1 | *Cryptoporus volvatus* | 1 | 525 | | VFVDDKLDNVA | 168-172 | FPDDVDTTS | 273-276 |
| LoTps1 | *Laricifomes officinalis* | 5 | 521 | | VFVDDKLDNVV | 162-166 | FPDDMDTTS | 267-270 |
| OCH93767.1 | *Obba rivulosa* | 9 | 527 | HAD-like protein | VFVDDKIDNVL | 166-170 | FPDDLDTTS | 271-274 |
| EMD37666.1 | *Gelatoporia subvermispora* | 12 | 533 | hypothetical protein | VFVDDKIDNVL | 166-170 | FPDDLDTTS | 277-280 |
| EMD37666-B | *Gelatoporia subvermispora* | 15 | 528 | hypothetical protein | VFVDDKIDNVL | 166-170 | FPDDLDTTS | 271-274 |
| XP_001217376.1 | *Aspergillus terreus* | 17 | 486 | Predicted protein | MFIDDKLENVI | 161-165 | FPDDMDTTS | 267-270 |
| OJJ98394.1 | *Aspergillus aculeatus* | 20 | 483 | Hypothetical protein | VFVDDKTENVL | 162-166 | FPNDLDTTS | 268-271 |
| GA087501.1 | *Aspergillus udagawae* | 23 | 485 | alpha-D-glucose-1-phosphate phosphatase YihX | IFIDDQLENVV | 167-171 | FPDDVDTTS | 273-276 |
| XP_008034151.1 | *Trametes versicolor* | 26 | 524 | HAD-like protein | VFVDDKLDNVV | 168-172 | FPDDVDTTS | 273-276 |
| XP_007369631.1 | *Dichomitus squalens* | 29 | 527 | HAD-like protein | FVFDDKLDNVA | 168-172 | FPDDVDTTS | 273-276 |
| ACg006372 | *Antrodia cinnamemea* | 32 | 496 | HAD-like protein | VFVDDRIENVV | 179-183 | YPDDFDTTS | 286-289 |

TABLE 1-continued

List of selected sequences showing sequence homology with CvTps1 and LoTps1 and containing a class I and a class II motifs. The source (species) of the sequences, SEQ ID NO, length of the sequence, sequence region containing the class I and class II motifs, and positions of the class I and class II motifs are listed. The residues of class I and class II motifs are in bold

| Name or NCBI accession number | Source | Protein SEQ ID NO | Length (amino acids) | Putative function (database annotation) | Class I motif region sequence | Class I motif position | Class II motif region sequence | Class II motif position |
|---|---|---|---|---|---|---|---|---|
| KIA75676.1 | Aspergillus ustus | 35 | 543 | Hypothetical protein | VFVDDNLENVTS | 161-165 | FPDDMDTTS | 267-270 |
| XP_001820867.2 | Aspergillus oryzae | 38 | 477 | Hypothetical protein | IFVDDQLENVIS | 167-171 | FPDDVDTTS | 273-276 |
| CEN60542.1 | Aspergillus calidoustus | 41 | 528 | Hypothetical protein | VFVDDNLDNVT | 161-165 | FPDDLDTTS | 267-270 |
| XP_009547469.1 | Heterobasidion irregulare | 44 | 531 | Hypothetical protein | VFVDDKGDNVL | 166-170 | FPFDLDTTS | 272-275 |
| KLO09124.1 | Schizopora paradoxa | 47 | 518 | Hypothetical protein | VFVDDKLDNVI | 209-213 | FPCDLDSTS | 315-318 |
| OJI95797.1 | Aspergillus versicolor | 50 | 507 | Hypothetical protein | VFIDDSPENIL | 163-167 | FPNDLDTTS | 269-272 |

TABLE 2

Pairwise sequence comparison of the selected putative bifunctional terpene synthases. The percentage of sequence identity is listed for each pairwise comparison.

|  | CvTps1 | LoTps1 | OCH93767.1 | EMD37666.1 | EMD37666-B | XP_001217376.1 |
|---|---|---|---|---|---|---|
| CvTps1 | 100 | 71 | 60 | 60 | 60 | 42 |
| LoTps1 | 72 | 100 | 60 | 58 | 59 | 43 |
| OCH93767.1 | 61 | 60 | 100 | 88 | 89 | 43 |
| EMD37666-B | 60 | 59 | 89 | 99 | 100 | 43 |
| EMD37666.1 | 60 | 58 | 88 | 100 | 99 | 43 |
| XP_001217376.1 | 42 | 43 | 43 | 43 | 43 | 100 |
| OJJ98394.1 | 47 | 48 | 47 | 47 | 47 | 54 |
| GAO87501.1 | 46 | 45 | 47 | 47 | 47 | 42 |
| XP_008034151.1 | 73 | 85 | 62 | 60 | 61 | 43 |
| XP_007369631.1 | 84 | 74 | 61 | 60 | 61 | 44 |
| ACg006372 | 45 | 48 | 47 | 46 | 47 | 37 |
| KIA75676.1 | 44 | 43 | 46 | 45 | 46 | 45 |
| XP_001820867.2 | 45 | 44 | 44 | 43 | 44 | 41 |
| CEN60542.1 | 44 | 45 | 45 | 46 | 46 | 44 |
| XP_009547469.1 | 54 | 55 | 54 | 53 | 54 | 43 |
| KLO09124.1 | 51 | 53 | 53 | 51 | 52 | 39 |
| OJI95797.1 | 45 | 43 | 45 | 45 | 46 | 55 |

|  | OJJ98394.1 | GAO87501.1 | XP_008034151.1 | XP_007369631.1 | ACg006372 | KIA75676.1 |
|---|---|---|---|---|---|---|
| CvTps1 | 47 | 46 | 72 | 84 | 45 | 44 |
| LoTps1 | 48 | 45 | 85 | 74 | 48 | 43 |
| OCH93767.1 | 47 | 47 | 62 | 62 | 48 | 46 |
| EMD37666-B | 47 | 47 | 61 | 62 | 47 | 46 |
| EMD37666.1 | 47 | 47 | 60 | 61 | 46 | 45 |
| XP_001217376.1 | 54 | 42 | 43 | 44 | 37 | 45 |
| OJJ98394.1 | 100 | 44 | 47 | 48 | 41 | 48 |
| GAO87501.1 | 44 | 100 | 46 | 47 | 45 | 46 |
| XP_008034151.1 | 47 | 46 | 100 | 77 | 49 | 44 |
| XP_007369631.1 | 48 | 48 | 77 | 100 | 48 | 45 |
| ACg006372 | 41 | 45 | 48 | 48 | 100 | 42 |
| KIA75676.1 | 48 | 46 | 44 | 43 | 42 | 100 |
| XP_001820867.2 | 44 | 69 | 45 | 46 | 44 | 47 |
| CEN60542.1 | 49 | 43 | 45 | 45 | 40 | 72 |
| XP_009547469.1 | 45 | 47 | 55 | 55 | 49 | 44 |
| KLO09124.1 | 44 | 45 | 51 | 51 | 55 | 45 |
| OJI95797.1 | 56 | 43 | 44 | 46 | 39 | 45 |

TABLE 2-continued

Pairwise sequence comparison of the selected putative bifunctional terpene synthases.
The percentage of sequence identity is listed for each pairwise comparison.

| | XP_001820867.2 | CEN60542.1 | XP_009547469.1 | KLO09124.1 | OJI95797.1 |
|---|---|---|---|---|---|
| CvTps1 | 45 | 44 | 55 | 52 | 45 |
| LoTps1 | 44 | 45 | 55 | 53 | 43 |
| OCH93767.1 | 44 | 45 | 54 | 53 | 45 |
| EMD37666-B | 44 | 46 | 58 | 52 | 46 |
| EMD37666.1 | 43 | 46 | 57 | 52 | 45 |
| XP_001217376.1 | 41 | 44 | 43 | 39 | 55 |
| OJJ98394.1 | 44 | 49 | 45 | 44 | 56 |
| GAO87501.1 | 69 | 43 | 47 | 45 | 43 |
| XP_008034151.1 | 45 | 45 | 55 | 52 | 44 |
| XP_007369631.1 | 46 | 46 | 56 | 52 | 46 |
| ACg006372 | 44 | 40 | 49 | 55 | 39 |
| KIA75676.1 | 46 | 72 | 44 | 45 | 45 |
| XP_001820867.2 | 100 | 47 | 46 | 42 | 41 |
| CEN60542.1 | 47 | 100 | 48 | 43 | 45 |
| XP_009547469.1 | 46 | 48 | 100 | 54 | 47 |
| KLO09124.1 | 42 | 44 | 54 | 100 | 44 |
| OJI95797.1 | 41 | 45 | 47 | 44 | 100 |

Example 6

Functional Characterisation of Other Fungal Hydrolase-Like Bifunctional Sesquiterpene Synthases.

Figure 7:
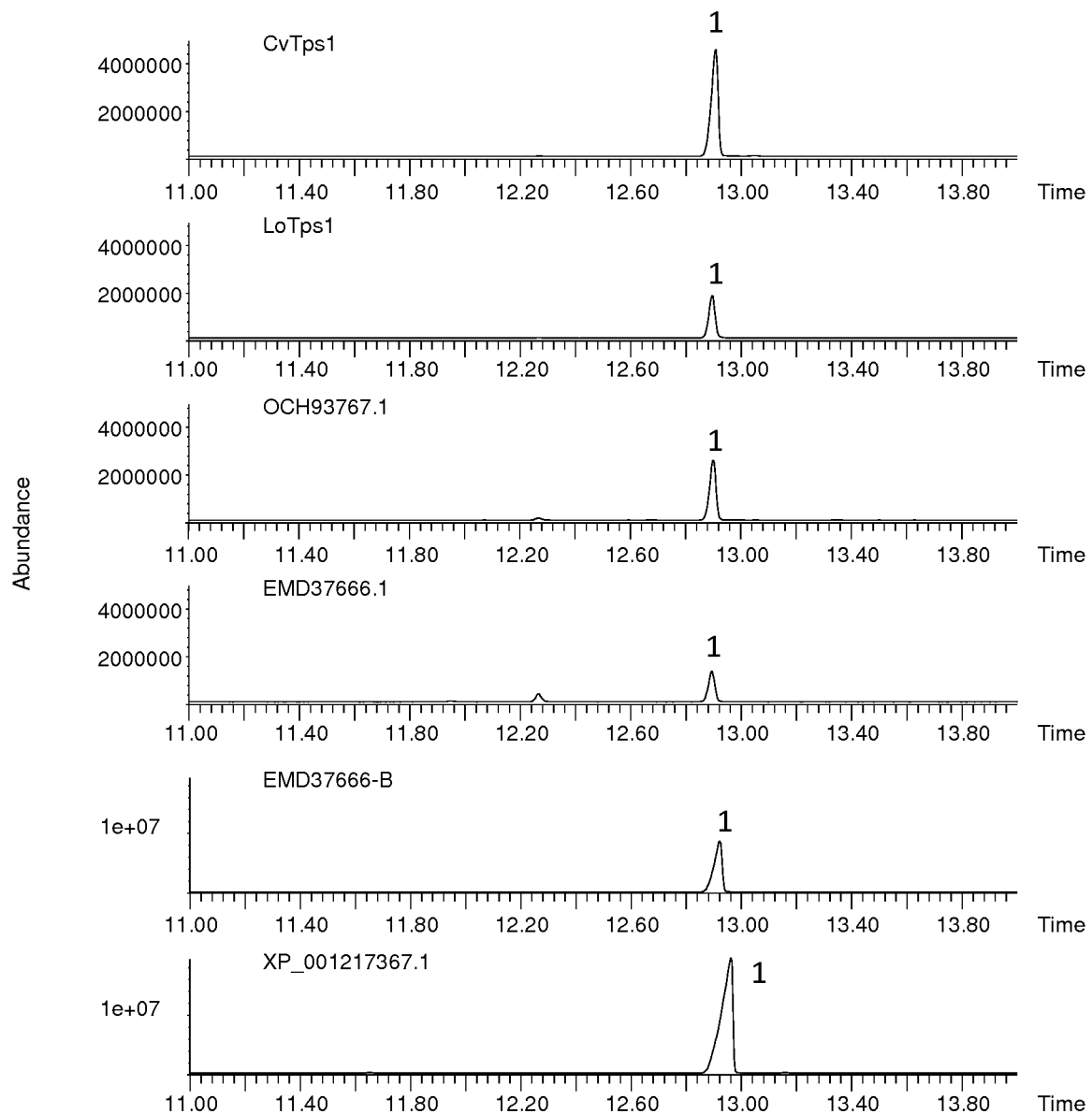
FIG. 7. GCMS chromatograms of the sesquiterpenes produced by the LoTps1, CvTps1, OCH93767.1, EMD37666.1, EMD37666-B, and XP_001217376.1, recombinant proteins. The peak labeled '1' is (+)-albicanol.
Figure 8:
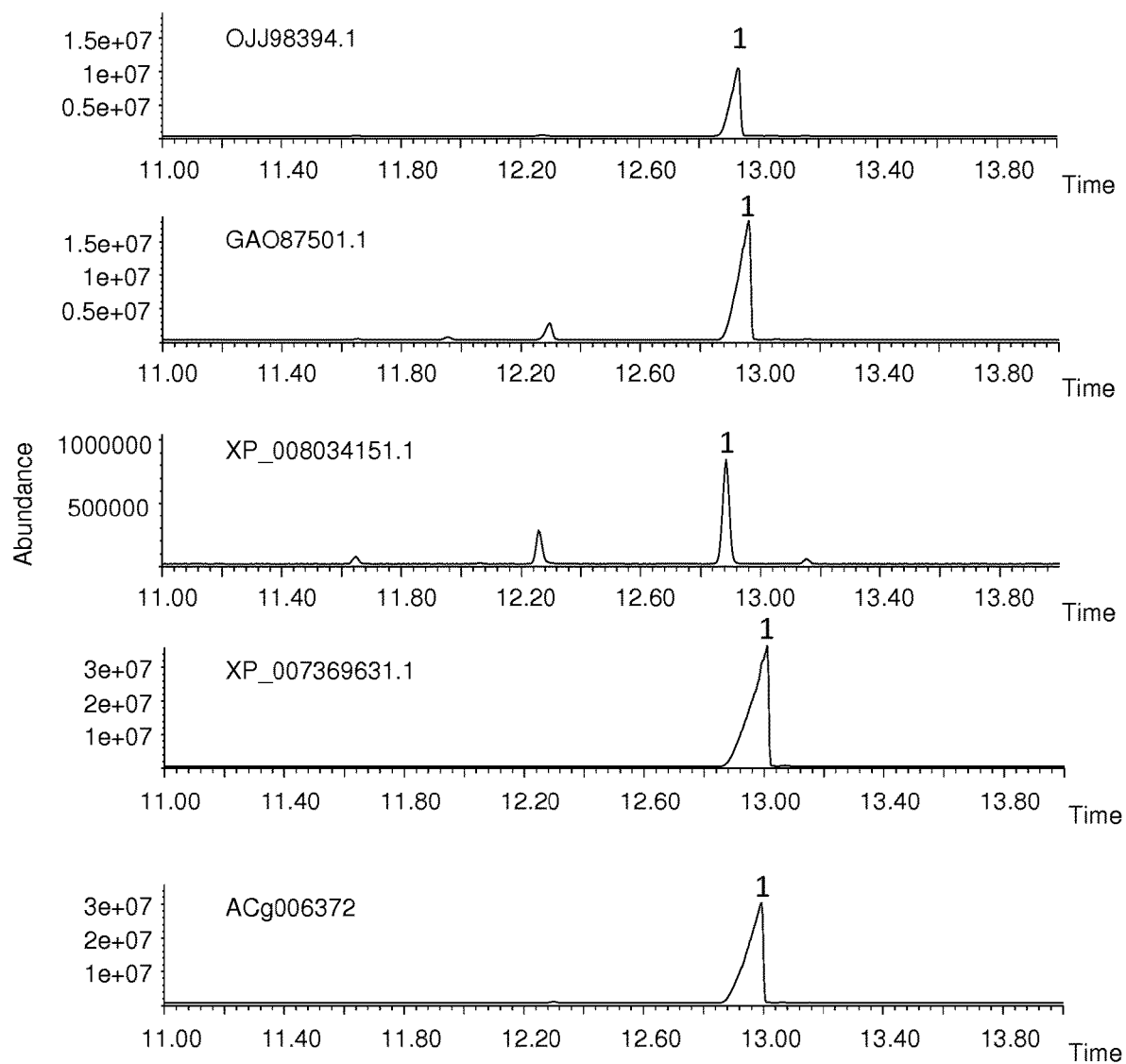
FIG. 8. GCMS chromatograms of the sesquiterpenes produced by the OJJ98394.1, GAO87501.1, XP_008034151.1, XP_007369631.1, and ACg006372 recombinant proteins. The peak labeled '1' is (+)-albicanol.
Figure 9:
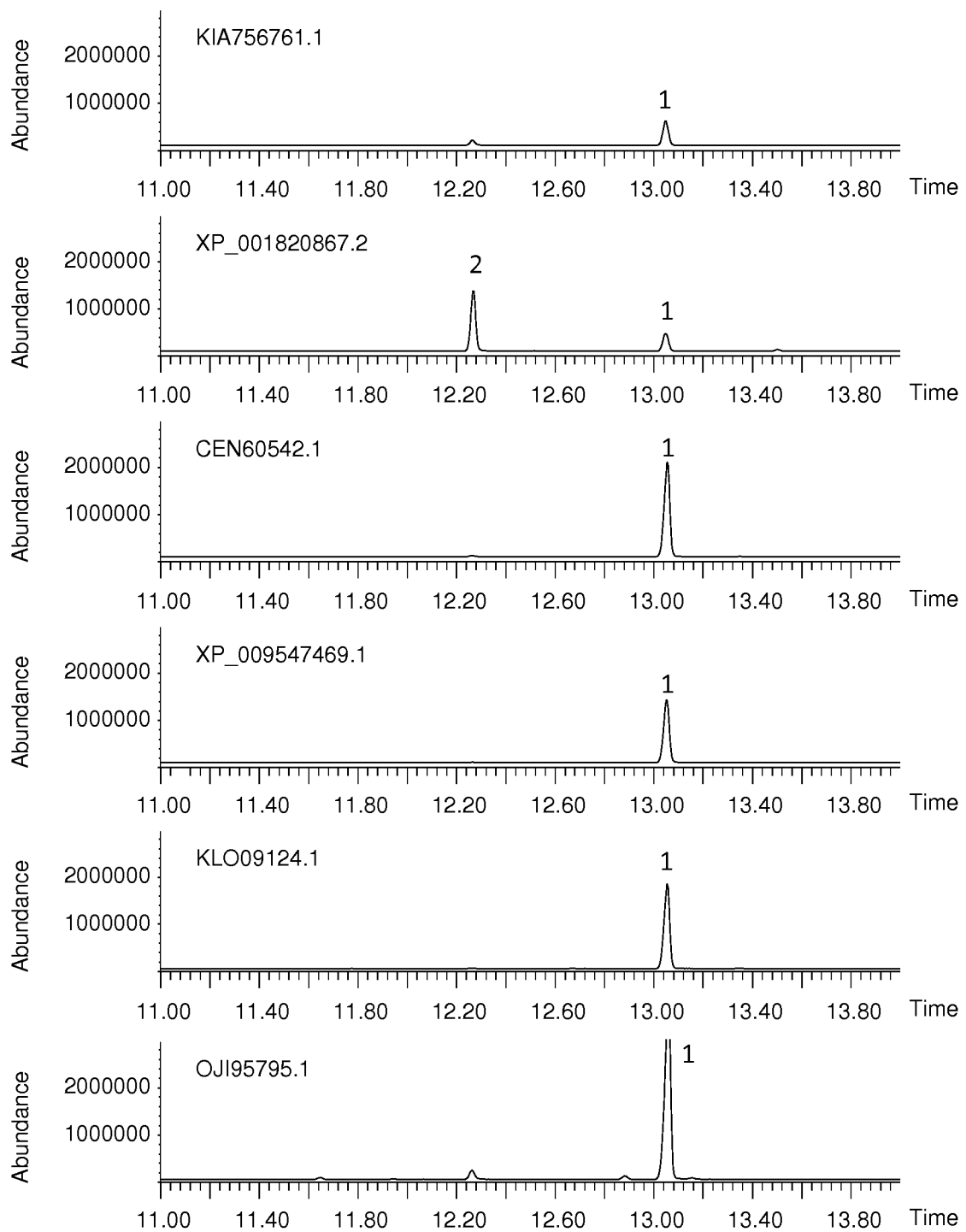
FIG. 9. GCMS chromatograms of the sesquiterpenes produced by the KIA75676.1, XP_001820867.2, CEN60542.1, XP_009547469.1, KLO09124.1 and OJI95797.1 recombinant proteins. The peak labeled '1' is (−)-drimenol and the peak labeled '2' is farnesol.

The cDNAs encoding for the 15 new putative synthases described in Example 5 were codon optimized and cloned in the pJ401 E. coli expression plasmid (pJ401, ATUM, Newark, Calif.). The enzymes were functionally characterized in E. coli cells engineered to overproduce farnesyl-diphosphate (FPP) following the procedure described in example 4. Amongst the 15 new recombinant enzymes, 9 produced (+)-albicanol as major product: OCH93767.1, EMD37666.1, EMD37666-B, XP_001217376.1, OJJ98394.1, GAO87501.1 XP_008034151.1, XP_007369631.1 and ACg006372 (FIGS. 7 and 8). These results confirm that these enzymes have bifunctional albicanol synthase enzymatic activities. The 6 other new synthases, KIA75676.1, XP_001820867.2, CEN60542.1, XP_009547469.1 and KLO09124.1 and OJI95797.1, produced (−)-drimenol as major product (FIG. 9). Drimenol is produced by a mechanism similar to the formation of albicanol and involving a class II followed by class I enzymatic activity.

For XP_001820867.2, the formation of a significant amount of trans-farnesol was detected (FIG. 9). This was likely due to lower enzymatic activity of this synthase and thus a significant amount of the farnesyl-diphosphate produced in the bacterial cell was not converted to drimenol. This excess farnesyl-diphosphate was hydrolyzed by the endogenous alkaline phosphatase and the trans-farnesol produced was released in the growing medium.

The two Pfam domains identified in CvTps1, i.e. PF13419.5 and PF13242.5 as described in Example 3, are also found in these new putative synthases as shown in Table 3.

TABLE 3

Locations of the haloacid dehalogenase-like hydrolase domain in each of the bifunctional synhtases described herein.

| Enzyme | Length | Product | HAD-like hydrolase domain Start | HAD-like hydrolase domain End |
|---|---|---|---|---|
| CvTps1 | 525 | Albicanol | 115 | 187 |
| LoTps1 | 521 | Albicanol | 62 | 181 |
| OCH93767.1 | 527 | Albicanol | 51 | 185 |
| EMD37666.1 | 533 | Albicanol | 54 | 185 |
| EMD37666-B | 528 | Albicanol | 54 | 185 |
| XP_001217376.1 | 486 | Albicanol | 61 | 186 |
| OJJ98394.1 | 483 | Albicanol | 25 | 181 |
| GAO87501.1 | 485 | Albicanol | 34 | 186 |
| XP_008034151.1 | 524 | Albicanol | 60 | 187 |
| XP_007369631.1 | 527 | Albicanol | 120 | 187 |
| ACg006372 | 496 | Albicanol | 60 | 198 |
| KIA75676.1 | 543 | Drimenol | 43 | 180 |
| XP_001820867.2 | 477 | Drimenol | 12 | 186 |
| CEN60542.1 | 528 | Drimenol | 20 | 180 |
| XP_009547469.1 | 531 | Drimenol | 77 | 185 |
| KLO09124.1 | 518 | Drimenol | 119 | 228 |
| OJI95797 | 507 | Drimenol | 48 | 180 |

Example 7

In-Vitro Assays.

Crude protein extracts containing the recombinant terpene synthases are prepared using KRX E. coli cells (Promega) or BL21 Star™ (DE3) E. coli (ThermoFisher). Single colonies of cells transformed with the expression plasmid are used to inoculate 5 ml LB medium. After 5 to 6 hours incubation at 37° C., the cultures are transferred to a 25° C. incubator and left 1 hour for equilibration. Expression of the protein is then induced by the addition of 1 mM IPTG and the cultures are incubated over-night at 25° C. The next day, the cells are collected by centrifugation, resuspended in 0.1 volume of 50 mM MOPSO pH 7 (3-Morpholino-2-hydroxypropanesulfonic acid (sigma-Aldrich), 10% glycerol and lyzed by sonication. The extracts are cleared by centrifugation (30 min at 20,000 g) and the supernatants containing the soluble proteins are used for further experiments.

These crude E. coli protein extracts containing the recombinant protein are used for the characterization of the enzymatic activities. The assays are performed in glass tubes in 2 mL of 50 mM MOPSO pH 7, 10% glycerol, 1 mM DTT, 15 mM MgCl2 in the presence of 80 μM of farnesyl-diphosphate (FPP, Sigma) and 0.1 to 0.5 mg of crude protein. The tubes are incubated 12 to 24 hours at 25° C. and extracted twice with one volume of pentane. After concentration under a nitrogen flux, the extracts are analyzed by GC-MS as described in Example 4 and compared to extracts from assays with control proteins. The aqueous phase is then treated by alkaline phosphatase (Sigma, 6 units/ml), followed by extraction with pentane and GC-MS analysis.

The assays without alkaline phosphatase treatment allow detecting and identifying the sesquiterpene compounds (hydrocarbons and oxygenated sesquiterpenes) present in the assay and produced by the recombinant enzymes. Albicanyl-diphosphate or drimenyl-diphosphate compounds are not soluble in the organic solvent and are thus not detected in the GC-MS analysis. Following the alkaline phosphatase treatment, allylic diphosphate bounds are cleaved and when albicanyl-diphosphate or drimenyl-diphosphate compounds are present, the sequiterpene moiety is released, extracted in the solvent phase and detected in the GC-MS analysis. This example allows to differentiate enzymes having only class II terpene synthase activity (such as AstC, NCBI accession XP_001822013.2, Shinohara Y. et al., 2016, *Sci Rep.* 6, 32865) from enzyme having class II terpene synthase-like activity and class I (phosphatase) activity such as CvTps1 and LoTps1.

Example 8

Co-Expression of Terpene Synthases and Phosphatases.

In Shinohara Y. et al., 2016, *Sci Rep.* 6, 32865 a drimane terpene synthase (AstC, NCBI accession XP_001822013.2) is described. This synthase produce a drimane sequiterpene bound to a diphosphate moiety. To produce a free drimane sesquiterpene the AstC enzyme must be combined with enzymes having phosphatase activity. The publication also describes two phosphatases AstI and AstK (XP_001822007.1 and XP_003189903.1) catalyzing the sequential cleavage of the phosphate moiety of the drimane-diphosphate produced by AstC.

Synthetic operons were designed to co-express the CvTps1 protein with the AstI and AstK proteins. The synthetic operon contains the optimized cDNA encoding for each of the 3 proteins separated by a ribosome binding sequence (RBS). A similar operon was designed to co-express AstC with AstI and AstK. The operons were synthesized and cloned in the pJ401 expression plasmid (ATUM, Newark, Calif.). *E. coli* cells were co-transformed with these expression plasmids and with the pACYC-29258-4506 plasmid (Example 4) and the cells were cultivated under conditions to produce sesquiterpenes as described in Example 4. The sequiterpenes produced were analyzed by GCMS as described in Example 4 and compared to the sequiterpene profile of cells expression only CvTps1 or AstC.

Figure 10:
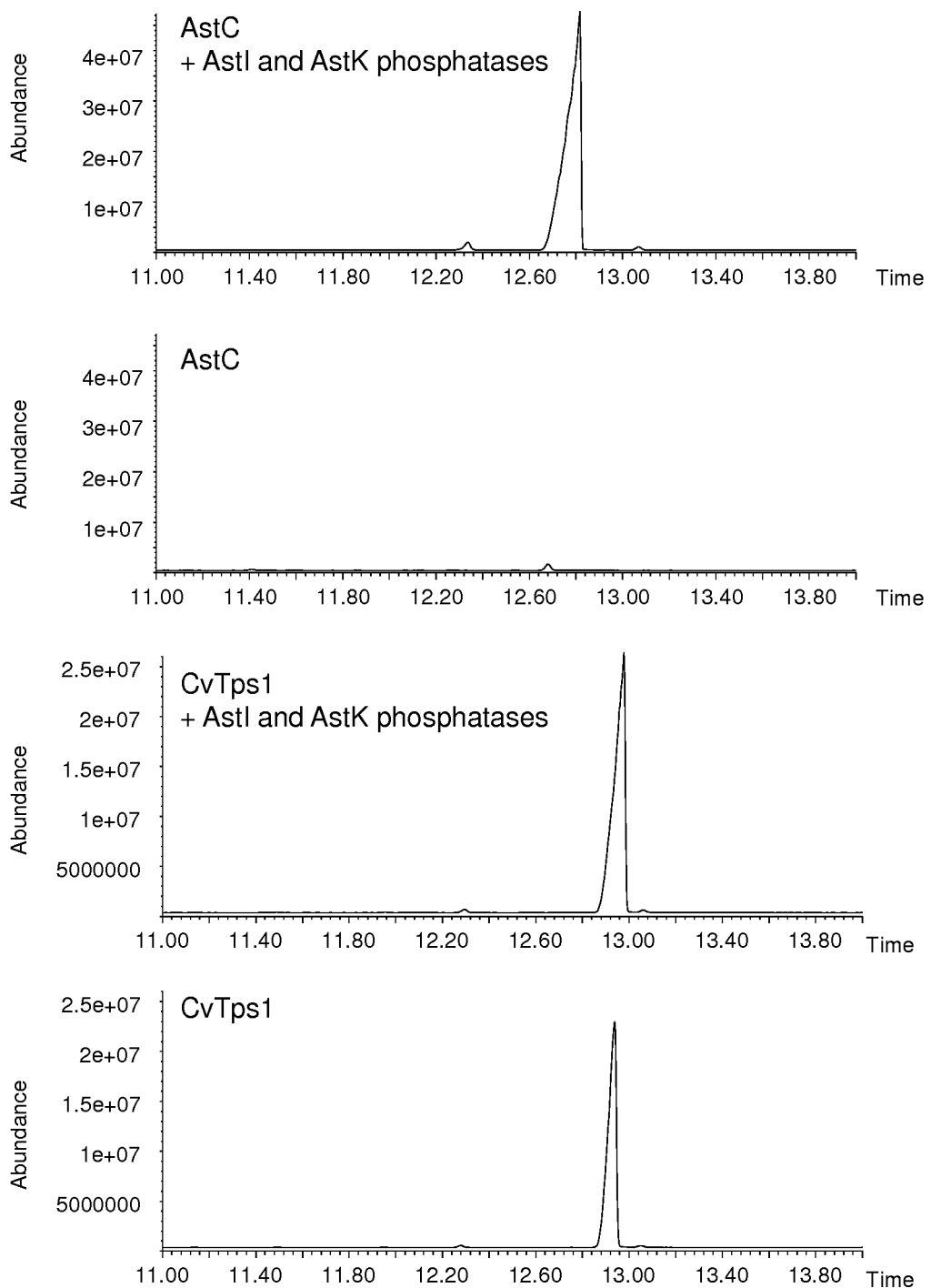
FIG. 10. GCMS chromatograms of the sesquiterpenes produced by CvTps1 and AstC expressed in *E. coli* cells with and without the AstI and AstK phosphatases. The major peak obtained with AstC is drim-8-ene-11-ol and the major peak obtained with CvTps1 is (+)-albicanol.

As shown FIG. 10, with AstC a significant higher amount (78-fold increase) of sesquiterpene is produced when the enzyme is co-expressed with enzymes (AstI and AstK) having phosphatase activity. Typical concentrations of drimane sesquiterpene in the *E. coli* cultures were 2'600 mg/ml with cells expressing AstC, AstI and AstK and 34 mg/ml with cells expressing AstC alone.

In contrast, with CvTps1 no significant difference is observed for the amount of drimane sesquiterpene produced when the enzyme is expressed alone (1'000 mg/ml) or co-expressed with the phosphatases (1'200 mg/ml). This experiment confirms that the CvTps1 polypeptide, in contrast to the previously known AstC synthase, carries phosphatase activity in addition to the cyclase activity (i.e. class I and class II terpene synthase activity).

Example 9

Functional Characterisation of XP_006461126.1.

The NCBI accession No XP_006461126.1 from *Agaricus bisporus* was selected using the method described in Example 5. The XP006461126.1 amino acid (SEQ ID NO: 63) shared 48.9% and 48.1% identity with the CvTps1 and LoTps1 amino acid sequences, respectively. The XP_006461126.1 contains a class II terpene synthase-like motif (DLDT) (part of SEQ ID NO: 56) located between position 278 and 271 and a class I terpene synthase-like motif (DDKLE) (part of SEQ ID NO: 55) located at position 167 to 171. The amino acid contains also motifs characteristic of the Haloacid dehalogenase-like hydrolase superfamily in the N-terminal region.

Figure 11:
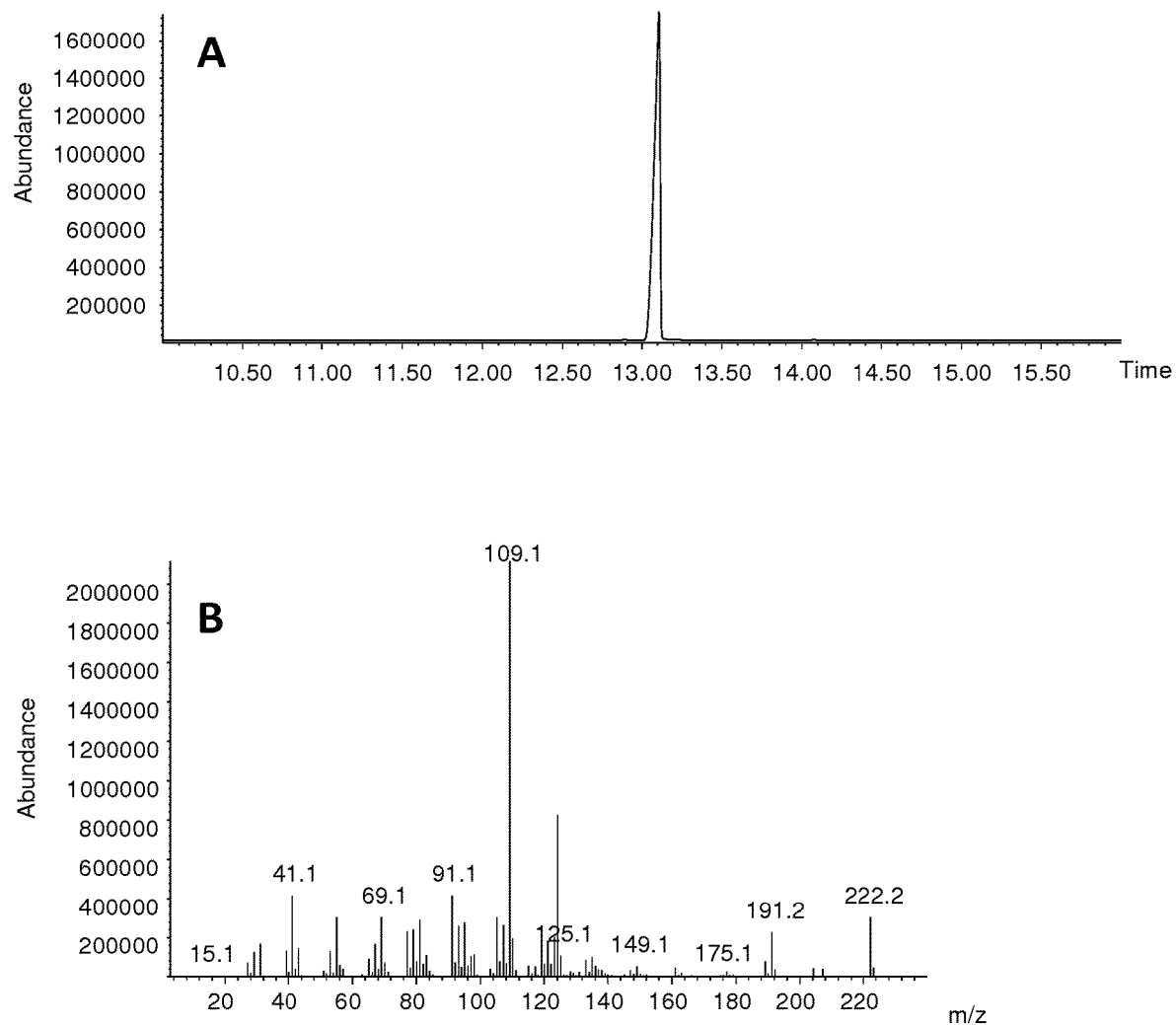
FIG. 11. GCMS analysis of the sesquiterpenes produced in-vivo by the recombinant XP_006461126.1 enzyme in bacteria cells modified to overproduce farnesyl-diphosphate. A. Total ion chromatogram of an extract of *E. coli* cells expressing XP_006461126.1 and the mevalonate pathway enzymes. B. Mass spectra of peak 13.1 minutes identified as drimenol.

The cDNA encoding for XP_006461126.1 was codon optimized and cloned in the pJ401 *E. coli* expression plasmid (pJ401, ATUM, Newark, Calif.). The enzyme was functionally characterized in *E. coli* cells engineered to overproduce farnesyl-diphosphate (FPP) following the procedure described in Example 4. The results show that XP_006461126.1 is a bifunctional drimenol synthase producing drimenol as major compound (FIG. 11).

Example 10

In Vivo Drimane Sesquiterpene Production in *Saccharomyces cerevisiae* Cells Using Fungal Hydrolase-Like Bifunctional Sesquiterpene Synthases.

Different hydrolase-like bifunctional sesquiterpene synthases were evaluated for the production of drimane sesquiterpenes in *S. cerevisiae* cells. The selected synthases were:

XP_007369631.1, NCBI accession No XP_007369631.1, from *Dichomitus squalens*

XP_006461126, NCBI accession No XP_006461126, from *Agaricus bisporus*

LoTps1, SEQ ID NO: 5, from *Laricifomes officinalis*

EMD37666.1, NCBI accession No EMD37666.1, from *Gelatoporia subvermispora*

XP_001217376.1, NCBI accession No XP_001217376.1, from *Aspergillus terreus*

The codon usage of the cDNA encoding for the different synthases was modified for optimal expression in *S. cerevisiae* (SEQ ID NO: 66, SEQ ID NO: 67, SEQ ID NO: 68, SEQ ID NO: 69, SEQ ID NO: 70).

For expression of the different genes in *S. cerevisiae*, a set of plasmids were constructed in vivo using yeast endogenous homologous recombination as previously described in Kuijpers et al., *Microb Cell Fact.*, 2013, 12:47. Each plasmid is composed by five DNA fragments which were used for *S. cerevisiae* co-transformation. The fragments were:

Fragment a: LEU2 yeast marker, constructed by PCR using the primers 5'-AGGTGCAGTTCGCGTGCAAT-TATAACGTCGTGGCAACTGTTATCAGTCGTACC GCGCCATTCGACTACGTCGTAAGGCC-3' (SEQ ID NO: 71) and 5'-TCGTGGTCAAGGCGTGCAAT-TCTCAACACGAGAGTGATTCTTCGGCGTT-GTTG CTGACCATCGACGGTCGAGGAGAACTT-3' (SEQ ID NO: 72) with the plasmid pESC-LEU (Agilent Technologies, California, USA) as template;

Fragment b: AmpR *E. coli* marker, constructed by PCR using the primers 5'-TGGTCAGCAACAACGCCG-AAGAATCACTCTCGTTGAGAATTGCACGC-CTT GACCACGACACGTTAAGGGATTTTGGTC-ATGAG-3' (SEQ ID NO: 73) and 5'-AACG-CGTACCCTAAGTACGGCACCACAGTGACTA-TGCAGTCCGCACTTTGCC AATGCCAAAAA-TGTGCGCGGAACCCCTA-3' (SEQ ID NO: 74) with the plasmid pESC-URA as template;

Fragment c: Yeast origin of replication, obtained by PCR using the primers 5'-TTGGCATTGGCAAAG-TGCGGACTGCATAGTCACTGTGGTGCCGTACT-TAGGG TACGCGTTCCTGAACGAAGCATCTGT-GCTTCA-3' (SEQ ID NO: 75) and 5'-CCAGATGC-CAAAGGATAGGTGCTATGTTGATGACTACGA-CACAGAACTGCG GGTGACATAATGATAGCATT-GAAGGATGAGACT-3' (SEQ ID NO: 76) with pESC-URA as template;

Fragment d: *E. coli* replication origin, obtained by PCR using the primers 5'-ATGTCACCCGCAGTTCTG-TGTCGTAGTCATCAACATAGCACCTATCCTTT-GGC ATCTCGGTGAGCAAAAGGCCAGCAAA-AGG-3' (SEQ ID NO: 77) and 5'-CTCA-GATGTACGGTGATCGCCACCATGTGACGGAA-GCTATCCTGACAGTGTA GCAAGTGCTGAGC-GTCAGACCCCGTAGAA-3' (SEQ ID NO: 78) with the plasmid pESC-URA as template and Fragment e: A fragment composed by the last 60 nucleotides of the fragment "d", 200 nucleotides downstream the stop codon of the yeast gene PGK1, one of the hydrolase-like bifunctional sesquiterpene synthase coding sequences tested, codon optimized for its expression in *S. cerevisiae*, the promoter of GAL1 and 60 nucleotides corresponding to the beginning of the fragment "a". These fragments were obtained by DNA synthesis (ATUM, Newark, Calif.).

To increase the level of endogenous farnesyl-diphosphate (FPP) pool in *S. cerevisiae* cells, an extra copy of all the yeast endogenous genes involved in the mevalonate pathway, from ERG10 coding for acetyl-CoA C-acetyltransferase to ERG20 coding for FPP synthetase, were integrated in the genome of the *S. cerevisiae* strain CEN.PK2-1C (Euroscarf, Frankfurt, Germany) under the control of galactose-inducible promoters, similarly as described in Paddon et al., *Nature*, 2013, 496:528-532. Briefly, three cassettes were integrated in the LEU2, TRP1 and URA3 loci respectively. A first cassette containing the genes ERG20 and a truncated HMG1 (tHMG1 as described in Donald et al., *Proc Natl Acad Sci USA*, 1997, 109:E111-8) under the control of the bidirectional promoter of GAL10/GAL1 and the genes ERG19 and ERG13 also under the control of GAL10/GAL1 promoter, the cassette was flanked by two 100 nucleotides regions corresponding to the up- and down-stream sections of LEU2. A second cassette where the genes ID11 and tHMG1 were under the control of the GAL10/GAL1 promoter and the gene ERG13 under the control of the promoter region of GAL7, the cassette was flanked by two 100 nucleotides regions corresponding to the up- and down-stream sections of TRP1. A third cassette with the genes ERG10, ERG12, tHMG1 and ERGS, all under the control of GAL10/GAL1 promoters, the cassette was flanked by two 100 nucleotides regions corresponding to the up- and down-stream sections of URA3. All genes in the three cassettes included 200 nucleotides of their own terminator regions. Also, an extra copy of GAL4 under the control of a mutated version of its own promoter, as described in Griggs and Johnston, *Proc Natl Acad Sci USA*, 1991, 88:8597-8601, was integrated upstream the ERG9 promoter region. In addition, the endogenous promoter of ERG9 was replaced by the yeast promoter region of CTR3 generating the strain YST035. Finally, YST035 was mated with the strain CEN.PK2-1D (Euroscarf, Frankfurt, Germany) obtaining a diploid strain termed YST045.

YST045 was transformed with the fragments required for in vivo plasmid assembly. Yeast transformations were performed with the lithium acetate protocol as described in Gietz and Woods, *Methods Enzymol.*, 2002, 350:87-96. Transformation mixtures were plated on SmLeu-media containing 6.7 g/L of Yeast Nitrogen Base without amino acids (BD Difco, New Jersey, USA), 1.6 g/L Dropout supplement without leucine (Sigma Aldrich, Missouri, USA), 20 g/L glucose and 20 g/L agar. Plates were incubated for 3-4 days at 30° C. Individual colonies were used to produce drimane sesquiterpenes in tubes or shake flasks containing media as described in Westfall et al., *Proc Natl Acad Sci USA*, 2012, 109:E111-118 and mineral oil ((2705-01, J. T. Baker, Avantor Performance Materials, Inc. Center Valley, Pa., USA) as organic overlay.

Figure 12:
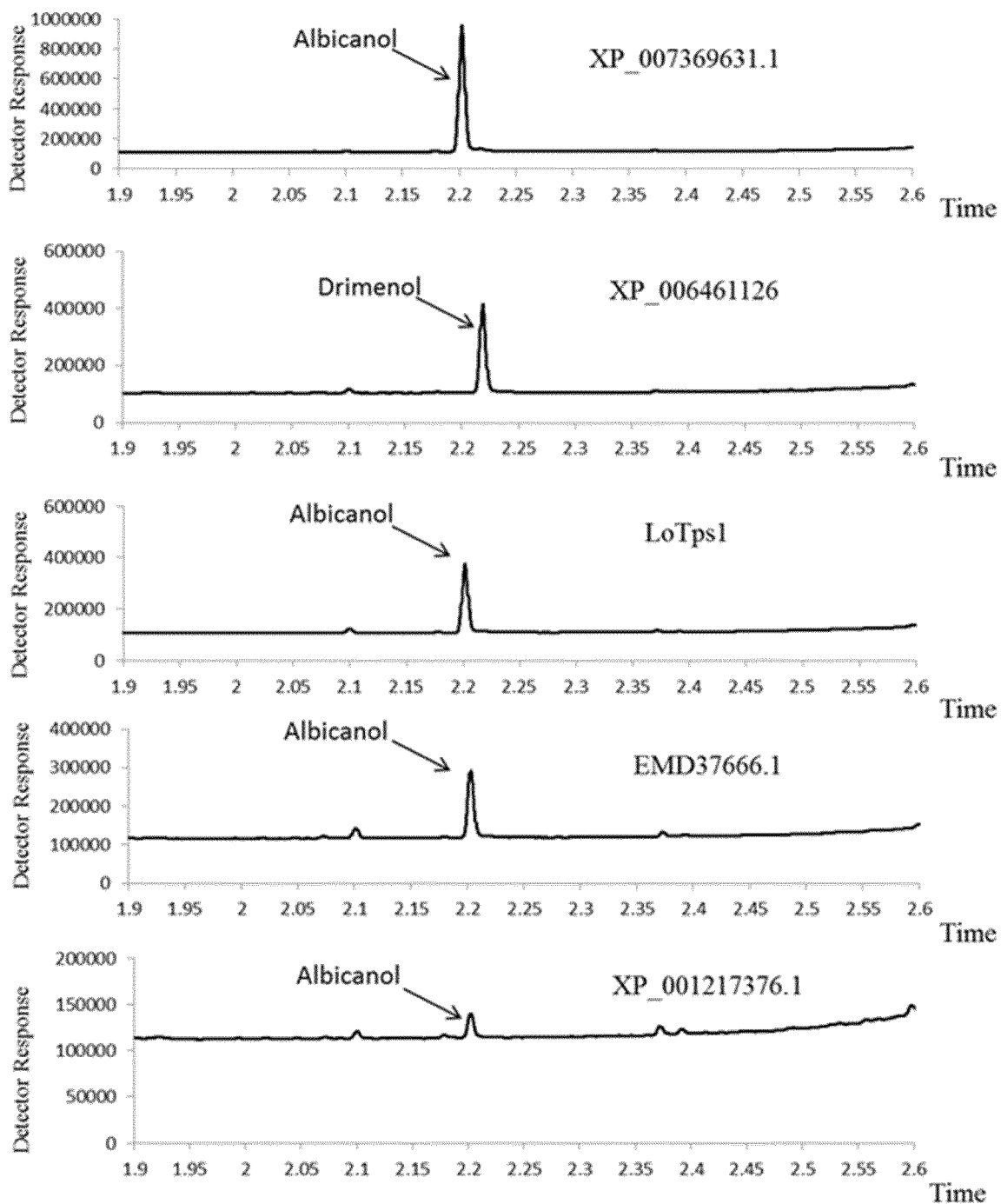
FIG. 12. GC-FID analysis of drimane sesquiterpenes produced using the modified *S. cereviciae* strain YST045 expressing five different synthases: XP_007369631.1 from *Dichomitus squalens*, XP_006461126 from *Agaricus bisporus*, LoTps1 from *Laricifomes officinalis*, EMD37666.1 from *Gelatoporia subvermispora* and XP_001217376.1 from *Aspergillus terreus*.

Under these culture conditions, albicanol or drimenol were produced with all hydrolase-like bifunctional sesquiterpene synthases tested. The production of drimane sesquiterpenes was identified using GC-MS analysis and quantified by GC-FID (see FIG. 12) with an internal standard. The table below shows the quantities of drimane sesquiterpene produced relative to the quantity obtained by the synthase XP_007369631.1 (under these experimental conditions, the concentration of drimane sesquiterpene produced by cells expressing XP_007369631.1 was 805 to 854 mg/L, the highest quantity produced).

| Enzyme | Product | Relative quantity of drimane sesquiterpene produced |
| --- | --- | --- |
| XP_007369631.1 | Albicanol | 100 |
| XP_006461126 | Drimenol | 39 |
| LoTps1 | Albicanol | 31 |
| EMD37666.1 | Albicanol | 23 |
| XP_001217376.1 | Albicanol | 3 |

Sequence Listings

SEQ ID NO: 1-CvTps1
MTTIHRRHTTLILDLGDVLFRWSPKTETAIPPRQLKEILTSVTWFEYERGQISQTECYERCAAEFKVDPLVIAEAFKQARES
LRPNKAFIALIRELRHQMHGDLTVLALSNISLPDYEYIMSLSSDWATVFNRVFPSALVGERKPHLGCYRKVISEMSLEPQTT
VFVDDKLDNVASARSLGMHGIVFDNEANVFRQLRNIFGNPVSRGQGYLRKHAGKLESSTDNGLTFEENFTQLIIYEVTQDRS
LITLSECPRTWNFFRGQPLFSESFPDDVDTTSVALTVLQPDRALVDSILDQMLEYVDADGIMQTYFDSSRPRIDPFVCNNVL
SLFYANGRGRELPHTLEWVYEVLLHRAYHGGSRYYLSPDCFLFFMSRLLKRANDSALQARFRPLFMERVKERVGAAGDSMDL
AFRILAAATIGVHCPQDLERLAAAQCEDGGWDMCWFYAFGSTGIKAGNRGLTTALAVAAIRTALGRPPSPSPSNISSSSKLD
APNSFLGIPRPTSPIRFGELFRWRKNKPTAKSQ

| Sequence Listings |
|---|

SEQ ID NO: 2-CvTps1 transcript (including non-coding sequences)
CATCCCGCCTTTTGAGCATGGCACACAAACAGCCTTTAAGGAGCTCCTTGGTTGCCTAGTCATGCCTCCACCTGCCCCCTCC
TCACTCATCCCCTCGCATCCTAAAACATGACCACGATTCACCGTCGGCACACCACTCTCATCTTGGACCTCGGCGACGTCCT
CTTCCGCTGGTCACCAAAGACCGAGACCGCCATCCCCCCTCGGCAGCTTAAGGAGATACTTACCTCCGTCACCTGGTTCGAG
TACGAACGAGGCCAGATATCCCAAACAGAATGTTACGAACGATGCGCTGCAGAATTCAAAGTCGACCCCTTAGTGATCGCTG
AAGCCTTCAAGCAAGCTCGCGAGTCATTACGGCCCAACAAAGCGTTCATCGCCTTGATTCGCGAACTTCGCCATCAAATGCA
TGGAGACCTCACGGTCCTCGCCCTTTCCAACATTTCCCTCCCCGATTACGAATATATCATGTCTCTGAGCTCGGATTGGGCA
ACCGTCTTCAATCGCGTATTCCCTTCTGCACTTGTTGGCGAGCGAAAACCCCATCTGGGGTGCTACCGCAAGGTCATTTCGG
AGATGAGCTTGGAACCCCAGACAACCGTATTTGTCGATGATAAGCTAGACAACGTCGCCTCTGCTCGCTCACTTGGCATGCA
CGGCATCGTATTCGACAACGAAGCCAATGTCTTCCGGCAACTGCGCAATATCTTCGGGAATCCGGTTAGCCGCGGTCAAGGC
TATCTTCGCAAGCATGCCGGAAAGCTTGAGTCTTCTACCGACAATGGCTTGACCTTTGAGGAGAACTTCACCCAGCTCATCA
TCTACGAGGTGACACAAGACAGGAGTCTCATCACGCTCTCAGAATGTCCCCGTACCTGGAATTTCTTTCGAGGTCAACCGCT
CTTCTCGGAGTCTTTCCCGGATGATGTGGACACAACATCCGTGGCATTGACAGTACTACAACCCGATAGAGCGCTCGTTGAT
TCTATTCTAGACCAAATGCTTGAATATGTTGACGCCGACGGCATCATGCAGACATACTTCGACAGCTCGCGACCACGCATAG
ACCCTTTTGTTTGCGTCAATGTGCTTTCTCTGTTCTACGCAAACGGCCGGGGTCGGGAGCTCCCTCACACACTGGAGTGGGT
CTATGAAGTACTCCTGCATCGCGCCTACCATGGAGGCTCACGTTACTACCTATCACCGGACTGCTTTTTATTCTTCATGAGC
CGCTTGCTCAAGCGCGCCAACGACTCGGCCCTCCAGGCTCGGTTCCGCCCACTGTTCATGGAGAGAGTGAAAGAACGAGTAG
GGGCAGCCGGAGACTCAATGGACCTGGCCTTCCGCATCCTCGCCGCGGCTACCATTGGCGTCCATTGCCCCCAAGATCTAGA
AAGATTGGCCGCCGCGCAATGCGAGGACGGTGGATGGGACATGTGCTGGTTCTACGCGTTCGGGTCGACAGGTATCAAGGCG
GGCAACCGCGGCCTCACCACGGCCCTTGCCGTCGCAGCTATACGAACCGCCCTCGGGCGCCCCCCCTCTCCCAGCCCCTCCA
ACATCTCGTCGTCGTCGAAGCTCGACGCTCCCAACAGCTTCTTGGGCATCCCGCGCCCAACCAGCCCCATTCGCTTTGGCGA
ACTTTTCCGTTCCTGGCGAAAGAACAAACCGACCGCAAAATCTCAATGAATCTCAGGTTCTCGTGCTCTCGTGCTATCTTCG
TACTTATGCTACTCGACATTACCCGTCGCTGTCTACAATGATACGGGTACTTTGATGAAACTGTAGATGTATTTGTATCATA
TTGACCTCCATCCATAGTCACCTAGCTACTGTTCGTGTTATCACCTGTTGCTGTTATATGATACAAGATGCCCAAACGAGAA
TGTAGAAATGTTCCGTACACTTGTGTACCTGTGATGAAGCTACATAGGCCTTCAATCGATCACTTGGTCC SEQ ID NO: 3-CvTps1 cDNA
ATGACCACGATTCACCGTCGGCACACCACTCTCATCTTGGACCTCGGCGACGTCCTCTTCCGCTGGTCACCAAAGACCGAGA
CCGCCATCCCCCCTCGGCAGCTTAAGGAGATACTTACCTCCGTCACCTGGTTCGAGTACGAACGAGGCCAGATATCCCAAAC
AGAATGTTACGAACGATGCGCTGCAGAATTCAAAGTCGACCCCTTAGTGATCGCTGAAGCCTTCAAGCAAGCTCGCGAGTCA
TTACGGCCCAACAAAGCGTTCATCGCCTTGATTCGCGAACTTCGCCATCAAATGCATGGAGACCTCACGGTCCTCGCCCTTT
CCAACATTTCCCTCCCCGATTACGAATATATCATGTCTCTGAGCTCGGATTGGGCAACCGTCTTCAATCGCGTATTCCCTTC
TGCACTTGTTGGCGAGCGAAAACCCCATCTGGGGTGCTACCGCAAGGTCATTTCGGAGATGAGCTTGGAACCCCAGACAACC
GTATTTGTCGATGATAAGCTAGACAACGTCGCCTCTGCTCGCTCACTTGGCATGCACGGCATCGTATTCGACAACGAAGCCA
ATGTCTTCCGGCAACTGCGCAATATCTTCGGGAATCCGGTTAGCCGCGGTCAAGGCTATCTTCGCAAGCATGCCGGAAAGCT
TGAGTCTTCTACCGACAATGGCTTGACCTTTGAGGAGAACTTCACCCAGCTCATCATCTACGAGGTGACACAAGACAGGAGT
CTCATCACGCTCTCAGAATGTCCCCGTACCTGGAATTTCTTTCGAGGTCAACCGCTCTTCTCGGAGTCTTTCCCGGATGATG
TGGACACAACATCCGTGGCATTGACAGTACTACAACCCGATAGAGCGCTCGTTGATTCTATTCTAGACCAAATGCTTGAATA
TGTTGACGCCGACGGCATCATGCAGACATACTTCGACAGCTCGCGACCACGCATAGACCCTTTTGTTTGCGTCAATGTGCTT
TCTCTGTTCTACGCAAACGGCCGGGGTCGGGAGCTCCCTCACACACTGGAGTGGGTCTATGAAGTACTCCTGCATCGCGCCT
ACCATGGAGGCTCACGTTACTACCTATCACCGGACTGCTTTTTATTCTTCATGAGCCGCTTGCTCAAGCGCGCCAACGACTC
GGCCCTCCAGGCTCGGTTCCGCCCACTGTTCATGGAGAGAGTGAAAGAACGAGTAGGGGCAGCCGGAGACTCAATGGACCTG
GCCTTCCGCATCCTCGCCGCGGCTACCATTGGCGTCCATTGCCCCCAAGATCTAGAAAGATTGGCCGCCGCGCAATGCGAGG
ACGGTGGATGGGACATGTGCTGGTTCTACGCGTTCGGGTCGACAGGTATCAAGGCGGGCAACCGCGGCCTCACCACGGCCCT
TGCCGTCGCAGCTATACGAACCGCCCTCGGGCGCCCCCCCTCTCCCAGCCCCTCCAACATCTCGTCGTCGTCGAAGCTCGAC
GCTCCCAACAGCTTCTTGGGCATCCCGCGCCCAACCAGCCCCATTCGCTTTGGCGAACTTTTCCGTTCCTGGCGAAAGAACA
AACCGACCGCAAAATCTCAATGA SEQ ID NO: 4-CvTps1 optimized cDNA
ATGACTACGATCCACCGCCGCCATACTACGCTGATCCTGGACCTGGGTGATGTTCTGTTCCGCTGGTCCCCGAAAACCGAAA
CCGCAATTCCGCCTCGTCAGCTGAAAGAAATCTTGACCAGCGTTACCTGGTTCGAGTATGAGCGTGGCCAAATTAGCCAGAC
CGAATGCTACGAGCGTTGTGCTGCCGAGTTTAAAGTTGATCCGCTGGTTATTGCCGAAGCGTTTAAACAAGCGCGTGAAAGC
CTGCGTCCGAACAAAGCGTTTATCGCGTTGATCCGTGAGTTGCGCCACCAGATGCATGGTGACCTGACGGTCCTGGCACTGA
GCAACATTAGCCTGCCTGATTATGAGTACATTATGTCGCTGAGCTCCGATTGGGCGACGGTCTTTAATCGCGTGTTTCCGAG
CGCACTGGTGGGTGAGCGTAAGCCACATCTGGGTGCTACCGCAAGGTCATCGACGAGATGTCTCTGGAGCCGCAGACCACG
GTTTTCGTCGATGACAAACTGGACAATGTCGCAAGCGCTCGTAGCCTGGGCATGCATGGCATCGTGTTCGACAACGAAGCCA
ACGTTTTTCGTCAGCTGCGTAATATCTTCGGTAACCCGGTTAGCCGCGGTCAAGGTTACTTGCGTAAACACGCCGGTAAACT
GGAATCTAGCACGGATAATGGTCTGACCTTCGAAGAGAACTTCACTCAATTAATTATTTACGAAGTCACGCAAGACCGCAGC
CTGATCACCCTGAGCGAGTGCCCGCGTACCTGGAACTTCTTCCGCGTCAACCACTGTTTTCTGAGAGCTTTCCGGACGACG
TGGACACCACCTCTGTGGCGTTGACCGTTCTGCAGCCGGATCGTGCGTTGGTGGATAGCATCCTGGACCAGATGTTGGAATA
TGTTGACGCGGATGGTATTATGCAAACCTACTTTGATTCATCCGTCCGCGCATTGACCCGTTCGTGTGCGTGAATGTCCTG
AGCCTGTTCTACGCCAATGGCAGAGGCCGCGAGCTGCCACACACGCTGGAATGGGTCTATGAAGTTCTGCTGCACCGTGCGT
ACCACGGCGGTAGCCGTTATTACCTGAGCCCGGACTGTTTCCTGTTCTTTATGAGCCGTCTGCTGAAGCGCGCGAATGACTC
GGCGCTGCAGGCCCGTTTTCGCCCGCTTTTCATGAACGTGTGAAAGAGCGTGTGGGCGCAGCCGGCGATAGCATGGACCTG
GCGTTCCGCATTCTGGCCGCTGCAACCATCGGCGTTCATTGCCCAAGATTGAGCGCTTGGCGGCCGCACAGTGCGAAG
ATGGTGGCTGGGATATGTGTTGGTTTTATGCGTTTGGCAGCACGGGTATCAAGGCTGGCAACCGCGGTCTGACCACCGCGTT
GGCTGTCGCCGCAATTCGTACCGCGCTGGGCGTCCGCCTTCCCCGAGCCCGAGCAATATTTCTAGCTCCAGCAAACTGGAC
GCGCCGAACTCCTTCCTGGGCATCCCGCGTCCGACCAGCCCGATCCGTTTCGGTGAACTGTTTCGTAGCTGGCGTAAGAACA
AGCCGACCGCGAAAAGCCAGTAA LoTps1
SEQ ID NO: 5-LoTps1 protein
MYTALILDLGDVLFSWSSTTNTTIPPRQLKEILSSPAWFEYERGRITQAECYERVSAEFSLDATAVAEAFRQARDSLRPNDK
FLTLIRELRQQSHGELTVLALSNISLPDYEFIMALDSKWTSVFDRVFPSALVGERKPHLGAFRQVLSEMNLDPHTTVFVDDK
LDNVVSARSLGMHGVVFDSQDNVFRMLRNIFGDPIHRGRDYLRQHAGRLETSTDAGVVFEENFTQLIIYELTNDKSLITTSN
CARTWNFFRGKPLFSASFPDDMDTTSVALTVLRLDHALVNSVLDEMLKYVDADGIMQTYFDHTRPRMDPFVCVNVLSLFHEQ Sequence Listings GRGHELPNTLEWVHEVLLHRAYIGGSRYYLSADCFLFFMSRLLQRITDPSVLGRFRPLFIERVREVGATGDSIDLAFRIIA
ASTVGIQCPRDLESLLAAQCEDGGWDLCWFYQYGSTGVKAGNRGLTTALAIKAIDSAIARPPSPALSVASSSKSEIPKPIQR
SLRPLSPRRFGGFLMPWRRSQRNGVAVSS SEQ ID NO: 6-LoTps1 transcript (including non-coding sequence)
GCGTCTGCTGCGGTCTCTCACCGCGCCGAGCGACGGGAAGCGGAGGCTTTTTGATGCAGCCAGCTCAGCGCCATCCTCTCAC
GCAGGGGGTTTGATCCAGATCTGATCGCCTCCGGGTTCTCATCTAGAACGCACGGCGGCTCCCAGGAAGTTCTATCGACCCT
CTGCGCGCTGGTCGGCGGCACGATGTGGCTACACCAGTCCCAATCATATCTCACACCCAGCACCATCATCTCGGGCCTCTTC
GTCATGTAACCCTCCCAAGCCTATTTTTCAGGGCGTTCCCCCTCACCGGCGCGCTTCTTAAAGAATCCCGAAATGTATACGG
CTCTTATCCTTGACCTCGGCGACGTTCTGTTCTCTTGGTCGTCGACGACCAACACGACTATTCCCCCTCGGCAGCTAAAGGA
GATCCTCTCATCTCCTGCCTGGTTTGAGTACGAGCGTGGTCGCATAACGCAAGCCGAATGCTACGAGCGTGTCAGCGCCGAG
TTCAGCCTAGACGCCACCGCCGTCGCGGAAGCATTCCGGCAAGCTCGCGACTCCTTGCGCCCGAACGACAAGTTCCTCACGT
TAATTCGCGAGCTTCGACAACAATCTCATGGGGAGCTCACGGTGCTTGCGCTGTCCAACATATCCCTTCCCGACTATGAATT
CATCATGGCCCTCGACTCGAAGTGGACTTCTGTCTTTGACCGCGTCTTCCCTTCTGCCCTCGTGGGCGAACGGAAGCCACAC
CTTGGAGCGTTTCGCCAGGTTCTGTCCGAGATGAATCTTGACCCGCACACAACTGTGTTCGTCGATGACAAGCTGGACAATG
TCGTCTCCGCACGGTCCCTCGGGATGCACGGCGTCGTGTTCGACTCTCCAAGACAATGTCTTTCGGATGCTGAGAAACATCTT
TGGCGATCCCATTCATCGGGGACGTGACTATCTCCGACAGCACGCCGGACGTCTGGAGACCTCCACGGATGCCGGTGTGGTC
TTCGAAGAGAATTTCACGCAACTCATCATCTACGAACTGACGAATGACAAGTCTCTCATCACGACATCAAACTGTGCTCGTA
CTTGGAATTTCTTTCGTGGGAAGCCTTTGTTCTCAGCATCGTTCCCTGACGACATGGACACGACCTCGGTTGCCTTGACTGT
ATTACGTTTAGACCACGCCCTCGTGAACTCGGTTTTGGACGAGATGCTAAAGTATGTCGACGCAGACGGCATCATGCAGACC
TACTTCGACCATACACGCCCACGCATGGATCCATTTGTCTGCGTCAATGTGCTCTCGTTGTTTCACGAACAAGGTCGTGGCC
ACGAGCTTCCGAACACCCTCGAATGGGTCCATGAGGTCCTCCTCCACCGCGCGTACATCGGGGGCTCGCGGTACTACCTCTC
CGCGGACTGCTTCCTCTTTTTTCATGAGCCGCCTCCTGCAGCGCATCACCGACCCGTCCGTCCTTGGCCGCTTCCGTCCACTA
TTCATAGAGCGCGTTCGGGAGCGTGTAGGTGCGACCGGGGACTCCATCGATCTCGCATTCCGCCATCATCGCCGCGTCCACAG
TAGGCATCCAGTGTCCACGCGACTTGGAAAGTCTCCTCGCCGCACAGTGTGAAGACGGTGGCTGGGACCTGTGCTGGTTCTA
CCAGTACGGATCGACCGGTGTCAAGGCGGGCAACCGCGGGCTCACCACCGCTCTGGCGATCAAAGCTATTGACTCCGCCATT
GCGAGGCCACCTTCGCCTGCCCTCTCAGTCGCTTCGTCGTCCAAATCGGAGATACCGAAACCCATACAACGGTCCCTTAGGC
CCCTTAGCCCCCGCCGGTTTGGCGGTTTCCTGATGCCGTGGCGCAGGTCACAGCGCAATGGCGTGGCGGTCTCTAGTTGAAC
ACTTGACCCTTGACACTTCGCTTTGCACTGCCTGCTCCCCTGCCAATCCTCCCCTACGATCGTATCATCCCTCTCTTGCCCT
CGCCTCCCCCTCGTACCCCCTCTCATGGGGTGCCATTTGTAGATATGTACGTAGCGTGATGTAGCGGTACTCGGATCGTTCT
CGTACTCGTCTTGCTCTGCCGTCGCTTCCAGCCCGTGCTGTTCTCTCGTTCAGGCTATTCGTTGGTTACGCGTATATCGTAA
TAGACCGCCCCGGTTCCTCGCCTACAGACACTCGCCCGTCTCGCCACGGACTCGGCTACGGAATTCAGACTACATGAGTGGC
AGTTATCACACGCAGATCCCTCCTTGGTCGTTCTGTAGTACCCACATATGTAATTGTACCAGTCCACTGTTGCAGATC SEQ ID NO: 7-LotTps1 cDNA
ATGTATACGGCTCTTATCCTTGACCTCGGCGACGTTCTGTTCTCTTGGTCGTCGACGACCAACACGACTATTCCCCCTCGGC
AGCTAAAGGAGATCCTCTCATCTCCTGCCTGGTTTGAGTACGAGCGTGGTCGCATAACGCAAGCCGAATGCTACGAGCGTGT
CAGCGCCGAGTTCAGCCTAGACGCCACCGCCGTCGCGGAAGCATTCCGGCAAGCTCGCGACTCCTTGCGCCCGAACGACAAG
TTCCTCACGTTAATTCGCGAGCTTCGACAACAATCTCATGGGGAGCTCACGGTGCTTGCGCTGTCCAACATATCCCTTCCCG
ACTATGAATTCATCATGGCCCTCGACTCGAAGTGGACTTCTGTCTTTGACCGCGTCTTCCCTTCTGCCCTCGTGGGCGAACG
GAAGCCACACCTTGGAGCGTTTCGCCAGGTTCTGTCCGAGATGAATCTTGACCCGCACACAACTGTGTTCGTCGATGACAAG
CTGGACAATGTCGTCTCCGCACGGTCCCTCGGGATGCACGGCGTCGTGTTCGACTCTCCAAGACAATGTCTTTCGGATGCTGA
GAAACATCTTTGGCGATCCCATTCATCGGGGACGTGACTATCTCCGACAGCACGCCGGACGTCTGGAGACCTCCACGGATGC
CGGTGTGGTCTTCGAAGAGAATTTCACGCAACTCATCATCTACGAACTGACGAATGACAAGTCTCTCATCACGACATCAAAC
TGTGCTCGTACTTGGAATTTCTTTCGTGGGAAGCCTTTGTTCTCAGCATCGTTCCCTGACGACATGGACACGACCTCGGTTG
CCTTGACTGTATTACGTTTAGACCACGCCCTCGTGAACTCGGTTTTGGACGAGATGCTAAAGTATGTCGACGCAGACGGCAT
CATGCAGACCTACTTCGACCATACACGCCCACGCATGGATCCATTTGTCTGCGTCAATGTGCTCTCGTTGTTTCACGAACAA
GGTCGTGGCCACGAGCTTCCGAACACCCTCGAATGGGTCCATGAGGTCCTCCTCCACCGCGCGTACATCGGGGGCTCGCGGT
ACTACCTCTCCGCGGACTGCTTCCTCTTTTTTCATGAGCCGCCTCCTGCAGCGCATCACCGACCCGTCCGTCCTTGGCCGCTT
CCGTCCACTATTCATAGAGCGCGTTCGGGAGCGTGTAGGTGCGACCGGGGACTCCATCGATCTCGCATTCCGCCATCATCGCC
GCGTCCACAGTAGGCATCCAGTGTCCACGCGACTTGGAAAGTCTCCTCGCCGCACAGTGTGAAGACGGTGGCTGGGACCTGT
GCTGGTTCTACCAGTACGGATCGACCGGTGTCAAGGCGGGCAACCGCGGGCTCACCACCGCTCTGGCGATCAAAGCTATTGA
CTCCGCCATTGCGAGGCCACCTTCGCCTGCCCTCTCAGTCGCTTCGTCGTCCAAATCGGAGATACCGAAACCCATACAACGG
TCCCTTAGGCCCCTTAGCCCCCGCCGGTTTGGCGGTTTCCTGATGCCGTGGCGCAGGTCACAGCGCAATGGCGTGGCGGTCT
CTAGTTGA SEQ ID NO: 8-LoTps1 optimized cDNA
ATGTACACGGCGCTGATTTTGGATTTGGGTGATGTTCTGTTTAGCTGGAGCTCAACGACTAACACCACCATTCCGCCGCGTC
AGCTGAAAGAAATCTTGAGCTCCCCGGCTGGTTCGAGTACGAGCGTGGCCGTATCACCCAGGCAGAGTGTTATGAGCGTGT
CAGCGCAGAGTTTAGCCTGGATGCGACGGCCGTGGCTGAGGCTTTTCGTCAGGCACGTGATAGCCTGCGTCCGAACGACAAA
TTTCTGACCCTGATCCGTGAGCTGCGTCAACAGAGCCACGGTGAATTGACCGTTCTGGCCTTGTCTAACATCAGCCTGCCGG
ATTACGAATTTATTATGGCACTGGACTCGAAGTGGACAAGCGTGTTTGATCGTGTTTCCCGAGCGCCCTGGTGGGCGAACG
CAAGCCGCACCTGGGCGCGTTCCGCCAAGTCCTGTCCGAGATGAATTTGGACCCGCATACCACCGTTTTTGTGGACGACAAA
CTGGACAATGTTGTCAGCGCACGCAGCCTGGGTATGCACGGTGTCGTGTTCGACAGCCAAGACAATGTTTTTCGTATGCTGC
GTAACATTTTCGGTGACCCAATTCACCGCGGTCGTGACTATCTGCGCCAGCACGCTGGTCGTCTTGAAACGTCCACCGATGC
GGGCGTTGTGTTCGAAGAGAACTTCACCCAACTGATCATTTACGAACTGACGAATGACAAGAGCCTGATCACCACCTCTAAT
TGCGCCCGCACCTGGAACTTCTTCCGCGGCAAACCTCTGTTCTCCGCGAGCTTTCCGGACGATATGGACACTACGTCGGTAG
CGCTGACCGTGCTGCGTCTGGACCATGCGCTGGTGAATAGCGTTCTGGATGAAATGCTGAAATACGTCGATGCTGACGGTAT
TATGCAGACCTACTTTGATCATACGCGTCCTCGTATGGACCCGTTCGTTTGCGTCAATGTGCTGAGCCTGTTTCACGAGCAA
GGTCGCGGTCATGAACTGCCGAATACGCTGGAATGGGTGCATGAAGTCCTGCTGCACCGTGCGTATATCGGTGGCAGCCGCT
ATTATCTGAGCGCGGATTGTTTCCTGTTCTTTATGAGCCGTCTGTTGCAACGTATTACCGACCCGAGCGTTTTAGGTAGATT
TCGCCCGCTGTTTATCGAGCGTGTTCGCGAGCGCGTTGGCGCGACTGGCGACAGCATCGACCTGGCATTCCGTATCATCGCG
GCCAGCACGGTCGGCATTCAATGGGCGTGACCTGGAGTCTCTGCTGGCAGCACAGTGCGAAGATGGTGGCTGGGATCTGTG
TTGGTTTTACCAGTACGGCAGCACGGGTGTTAAGGCCGGTAACCGTGGTCTGACCACGGCGTTGGCGATCAAAGCGATTGAC
AGCGCCATCGCGCGTCCGCCAAGCCCGGCCCTGTCCGTTGCAAGCTCCAGCAAGAGCGAGATTCCGAAGCCGATTCAGCGTA
GCCTCCGCCCGTTGAGCCCGCGTCGCTTCGGTGGCTTCCTGATGCCGTGGCGTCGTAGCCAACGCAATGGTGTCGCGGTGAG
CTCTTAA -continued Sequence Listings OCH93767.1
SEQ ID NO: 9-OCH93767.1 protein
MSAAVRYTTLILDLGDVLFTWSPKTKTSISPRILKEILNSATVYWYERGSTIQHECYERVGVEFGIAPSEIHNAFKQARDSM
ESNDELIALVRELKEQSDGELLVFALSNISLPDYEYVLTKPADWSIFDKVFPSALVGERKPHLGIYKHVIAETGVDPRTTVF
VDDKIDNVLSARSLGMHGIVFDKHEDVMRALRNIFGDPVRRGREYLRRNARKLESITDHGVAFGENFTQLLELELTSDASLV
TLPDRPRTWNFFRGKPLFSEAFPDDLDTTSLALTVLKRDAATVSSVMDEMLKRDADGIMQTYFDNGRQRLDPFVNANVLTLF
YANGRGHELDQSLSWVREVLLYRAYLGGSRYYPSADCFLYFISRLFACTSDPVLHHQLKPLFVERVHERIGVQGDALELAFR
LLVCASFNISNQPDMRKLLEMQCQDGGWDGGNLYRFGTTGLKVTNRGLTTAAAVQAIEATQLRPPSPAFSVESPKSPVTPVT
PMLEIPALGLSISRPSSPLLGYFKLPWKKSAEVH SEQ ID NO: 10-OCH93767.1 cDNA
ATGTCCGCAGCAGTTCGGTACACGACCCTCATCCTCGACCTTGGCGACGTCTTGTTCACTTGGTCACCGAAGACGAAGACCA
GCATCTCGCCTCGTATTCTGAAGGAGATCCTGAATTCCGCGACCTGGTATGAGTACGAGCGCGGTAGTATCACTCAGCACGA
ATGTTACGAACGCGTTGGCGTGGAGTTCGGTATTGCGCCGAGCGAGATCCACAACGCGTTCAAGCAGGCTCGGGACTCTATG
GAGTCGAATGACGAGCTGATCGCCCTTGTTCGGGAACTGAAGGAGCAGTCAGATGGAGAGCTTCTCGTCTTCGCATTATCGA
ACATCTCACTGCCGGACTACGAATACGTCCTGACGAAGCCCGCGGACTGGTCCATCTTCGACAAAGTCTTTCCTTCCGCTCT
CGTCGGCGAGCGCAAGCCCATCTCGGCATCTACAAACACGTCATCGCAGAGACGGGCGTTGATCCGCGAACAACCGTCTTC
GTGGACGACAAGATCGACAATGTGCTTTCGGCGCGGTCGCTCGGTATGCACGGCATTGTCTTCGACAAACACGAAGACGTAA
TGCGCGCTCTGCGAAACATTTTCGGTGACCCCGTGCGAAGAGGACGAGAATATTTGCGTCGAAATGCAAGGAAATTGGAATC
CATCACAGATCACGGCGTCGCCTTCGGGGAGAACTTCACCCAGCTTCTGATCCTCGAACTTACTAGTGATGCGTCCCTCGTT
ACTCTCCCTGATCGTCCTCGGACATGGAATTTTTTCCGAGGGAAGCCGCTCTTTTCGGAGGCCTTCCCCGATGACCTTGATA
CTACTTCCTTGGCACTCACTGTCCTGAAAAGAGATGCCGCCACTGTATCGTCCGTGATGGACGAGATGCTGAAATACAGGGA
CGCGGACGGCATCATGCAGACATACTTCGACAACGGTCGGCAACGACTCGATCCGTTCGTCAACGCCAACGTTTTGACCCTC
TTCTACGCCAACGGTCGCGGACACGAGCTGGATCAGGCCTCAGCTGGGTTCGCGAAGTCTTGCTCTACCGCGCTTACCTCG
GCGGTTCCCGCTACTACCCCTCCGCCGACTGCTTCCTATATTTCATCAGCCGCCTCTTCGCCTGCACCAGCGACCCGGTCCT
CCATCATCAACTTAAGCCCCTCTTTGTTGAGCGTGTGCACGAGCGGATAGGAGTGCAGGGCGACGCGCTGGAGCTCGCCTTC
CGCCTGCTTGTATGCGCGAGCTTCAACATCTCGAACCAGCCTGACATGCGCAAGCTGCTCGAGATGCAGTGCCAGGACGGAG
GCTGGGATGGCGGAAACCTGTATCGTTTCGGCACCACGGGCCTCAAGGTCACGAACCGGGGTCTGACCACCGCAGCAGCCGT
GCAAGCCATCGAGGCGACGCAGCTGCGTCCACCATCACCGGCGTTCTCTGTCGAGTCGCCTAAGAGCCCGGTGACGCCGGTG
ACGCCCATGCTGGAGATTCCAGCGCTGGGTCTCAGCATCTCGCGGCCCTCCAGTCCTCTGTTGGGGTATTTCAAGCTCCCGT
GGAAGAAGTCAGCCGAGGTTCATTGA SEQ ID NO: 11-OCH93767 optimized cDNA
ATGTCTGCAGCTGTTCGTTATACTACTCTGATCCTGGATTTGGGCGATGTTCTGTTCACCTGGTCCCCGAAAACCAAGACCT
CTATCAGCCCACGTATCCTGAAAGAAATCCTGAACAGCGCGACTGTATACTGGTACGAGCGCGGCAGCATCACCCAGCACGA
GTGCTACGAGCGTGTTGGCGTCGAATTTGGTATTGCGCCGAGCGAGATTCACAACGCGTTCAAACAAGCCCGCGACAGCATG
GAATCCAACGACGAACTGATTGCTCTGGTGCGTGAGCTGAAAGAACAGAGCGATGGTGAGCTGCTGGTCTTTGCCCTGAGCA
ATATCTCTCTGCCGGATTACGAATACGTTCTGACCAAACCAGCGGACTGGTCAATCTTCGATAAAGTCTTTCCGAGCGCTTT
GGTCGGTGAGCGTAAACCGCATCTGGGTATTTACAAACACGTTATTGCGGAAACCGGTGTTGACCCGAGAACGACCGTTTTT
GTTGACGATAAGATTGACAACGTCCTGAGCGCACGCAGCCTGGGTATGCATGGTATTGTCTTTGATAAGCACGAAGATGTGA
TGCGTGCTCTGCGCAATATCTTTGGCGACCCGGTGCGTCGCGGTCGTGAGTATTTGCGCCGCAACGCGCGCAAATTGGAGTC
CATTACCGATCATGGTGTCGCATTTGGTGAGAATTTCACCCAGCTCCTGATTCTGGAACTGACCAGCGACGCGTCCCTGGTG
ACGCTGCCGGATCGTCCGCGTACGTGGAACTTCTTCCGCGGCAAGCCGCTGTTTAGCGAAGCGTTCCCGGATGACCTGGACA
CCACGAGCCTGGCACTGACGGTGCTGAAACGCGATGCAGCAACTGTGAGCTCCGTCATGGACGAAATGCTGAAGTACCGCGA
CGCGGATGGCATCATGCAGACGTATTTCGACAACGGTCGTCAGCGTCTGGACCCGTTTGTCAACGCCAATGTTCTGACGCTG
TTTTACGCGAATGGCCGTGGTCATGAACTGGACCAGAGCTTATGTGGGTCGTGAAGTGCTGCTGTATCGCGCCTATCTGG
GTGGCAGCCGCTACTATCCGAGCGCGGACTGTTTTCTGTACTTCATTAGCCGCTTGTTCGCCTGCACCAGCGATCCGGTTCT
GCATCACCAACTGAAGCCATTGTTCGTCGAGCGTGTGCACGAGCGTATTGGTTTCAGGGCGACGCACTGGAACTGGCGTTC
CGTCTGTTGGTGTGTGCGAGCTTCAACATTAGCAATCAGCCGGATATGCGTAAGCTGCTGGAAATGCAATGCCAAGATGGCG
GCTGGGACGGTGGTAATCTGTACCGTTTTGGCACCACCGGTTTAAAAGTGACGAATCGTGGTTTGACCACCGCTGCGGCCGT
TCAAGCAATTGAAGCAACGCAACTGCGTCCGCCGAGCCCAGCATTTAGCGTAGAGTCGCCTAAGAGCCCGGTTACGCCGGTG
ACGCCGATGCTGGAAATCCCGGCGCTGGGTCTGTCTATCAGCCGTCCGTCGAGCCCGCTGCTGGGCTATTTCAAGTTGCCGT
GGAAGAAAAGCGCCGAAGTGCACTAA EMD37666.1
SEQ ID NO: 12-EMD37666.1 protein
MSAAQYTTLILDLGDVLFTWSPKTKTSIPPRTLKEILNSATWYEYERGRISQDECYERVGTEFGIAPSEIDNAFKQARDSM
ESNDELIALVRELKTQLDGELLVFALSNISLPDYEYVLTKPADWSIFDKVFPSALVGERKPHLGVYKHVIAETGIDPRTTVF
VDDKIDNVLSARSVGMHGIVFEKQEDVMRALRNIFGDPVRRGREYLRRNAMRLESVTDHGVAFGENFTQLLILELTNDPSLV
TLPDRPRTWNFFRGNGGRPSKPLFSEAFPDDLDTTSLALTVLQRDPVISSVMDEMLNYRDPDGIMQTYFDDGRQRLDPFVN
VNVLTFFYTNGRGHELDQCLTWVREVLLYRAYLGGSRYYPSADCFLYFISRLFACTNDPVLHHQLKPLFVERVQEQIGVEGD
ALELAFRLLVCASLDVQNAIDMRRLLEMQCEDGGWEGGNLYRFGTTGLKVTNRGLTTAAAVQAIEASQRRPPSPSPSVESTK
SPITPVTPMLEVPSLGLSISRPSSPLLGYFRLPWKKSAEVH SEQ ID NO: 13-EMD37666.1 cDNA
ATGTCCGCGGCAGCTCAATACACGACCCTCATTCTCGACCTTGGCGACGTCCTGTTCACCTGGTCACCGAAAAACCAAGACGA
GCATCCCCCCTCGGACTCTGAAGGAGATTCTCAATTCCGCGACATGGTATGAGTATGAGCGCGGCCGCATCTCTCAGGACGA
ATGTTACGAACGCGTTGGCACGGAGTTCGGAATCGCGCCTAGCGAAATCGACAACGCGTTCAAGCAAGCTCGGGATTCCATG
GAATCCAACGACGAACTGATCGCCCTTGTTCGGGAACTCAAGACGCAGTTGGACGGCGAACTCCTTGTCTTCGCACTCTCAA
ATATCTCGTTGCCTGACTACGAGTACGTTCTCACCAAACCGGCCGACTGGTCCATCTTCGACAAGGTCTTTCCTTCCGCCT
CGTGGGCGAGCGCAAGCCGCACCTCGGCGTTTACAAGCACGTCATTGCAGAACGGGCATTGATCCGCGAACACCGTTTTC
GTGGACGACAAGATCGACAACGTGCTCTCAGCGCGGTCTGTAGGTATGCATGGGATCGTTTTCGAGAAGCAGGAAGACGTAA
TGCGCGCTCTCCGAAACATCTTCGGAGACCCGGTTCGGCGAGGGCGCGAGTACTTGCGCCGTAATGCCATGAGGCTTGAATC
GGTTACAGACCATGGTGTGGCGTTTGGCGAGAACTTCACACAACTCCTTATCCTCGAACTAACGAACGATCCCTCCCTCGTT
ACGCTCCCTGATCGTCCTCGAACATGGAATTCTTCCGAGGTAACGGGGACGACCAAGCAAACCATTATTCTCGGAGGCCT
TCCCCGATGACTTGGACACTACTTCACTAGCGTTGACTGTCCTCCAAAGAGATCCCGGCGTCATCTCTTCTGTGATGGACGA

```
AATGTTGAACTACAGGGATCCGGACGGCATTATGCAGACATACTTCGACGATGGTCGGCAAAGACTCGATCCATTTGTCAAT
GTCAATGTCTTAACGTTCTTCTACACCAACGGACGTGGTCATGAACTGGACCAATGCCTTACATGGGTCCGCGAAGTTTTGC
TCTATCGCGCCTATCTCGGCGGCTCACGTTATTACCCCTCCGCCGACTGCTTTCTCTACTTCATCAGCCGCCTTTTCGCATG
CACGAATGACCCCGTGCTACACCACCAACTCAAACCGCTCTTCGTCGAGCGCGTGCAGGAGCAAATCGGCGTGGAGGGCGAT
GCGCTCGAGTTGGCGTTCCGATTGCTCGTCTGTGCAAGCCTGGACGTCCAAAACGCGATCGACATGCGCAGGCTGCTCGAGA
TGCAATGCGAAGATGGCGGCTGGGAGGGCGGGAACCTTTATAGGTTTGGCACGACCGGGCTCAAGGTACTAACCGGGGCCTG
ACGACTGCAGCGGCCGTACAGGCCATCGAGGCGTCCCAACGGCGCCCACCATCACCGTCCCCCTCCGTCGAATCTACAAAGA
GCCCAATAACCCCTGTGACGCCCATGCTGGAGGTCCCCTCGCTCGGCCTGAGCATCTCGAGGCCGTCCAGCCCTTTACTCGG
CTACTTCAGGCTCCCGTGGAAGAAGTCGGCCGAAGTACACTGA

SEQ ID NO: 14-EMD37666.1 optimized cDNA
ATGTCTGCGGCGGCTCAATACACGACTTTGATTCTGGATCTGGGTGATGTTCTGTTCACTTGGTCCCCGAAAACCAAGACCA
GCATCCCTCCGCGTACCCTGAAAGAAATCCTGAATAGCGCTACCTGGTATGAGTACGAGCGTGGTCGCATTTCCCAAGACGA
GTGTTACAACGTGTGGGCACCGAGTTCGGCATTGCGCCGAGCGAGATTGACAACGCGTTCAAACAAGCGCGCGATTCGATG
GAAAGCAATGATGAACTGATCGCACTGGTCCGTGAGCTGAAAACGCAGCTGGACGGTGACGCTGCTGGTTTTCGCACTGTCCA
ATATTAGCCTGCCGGATTACGAATACGTCTTGACCAAACCGGCGGACTGGAGCATCTTTGACAAAGTGTTCCCTAGCGCCTT
GGTGGGCGAGCGTAAGCCGCATCTGGGCGTTTATAAACACGTTATTGCGGAAACGGGCATTGATCCGCGCACGACGGTTTTC
GTGGACGACAAGATTGACAATGTGTTAAGCGCACGCAGCGTCGGTATGCATGGTATCGTGTTTGAGAAACAAGAAGATGTCA
TGCGTGCACTGCGTAACATCTTTGGTGATCCGGTCCGTCGTGGTCGTGAGTATCTGCGTAGAAACGAATGCGTCTGGAGTC
CGTGACCGACCACGGCGTGGCGTTTGGTGAGAACTTTACCCAGTTGCTGATTCTGGAATTGACGAACGACCCGAGCCTGGTC
ACCCTGCCTGATCGTCCGCGTACCTGGAACTTTTTTCGCGGCAATGGTGGCCGCCCGAGCAAGCCGCTGTTCAGCGAAGCGT
TCCCGGATGATCTGGATACCACGAGCCTGGCGCTGACCGTGCTGCAGCGCGACCCGGGTGTTATCAGCAGCGTTATGGACGA
AATGCTGAATTACCGTGACCCGGACGGTATCATGCAGACTTATTTCGATGACGGTCGCCAACGCTTGGACCCATTTGTGAAC
GTCAATGTTCTGACCTTTTTCTATACGAACGGCCGTGGTCACGAACTGGACCAGTGTTCTGACGTGGGTGCGTGAAGTCCTCT
TGTATCGTGCGTACCTTGGTGGCTCACGCTACTACCCATCGGCGGATTGCTTCCTGTACTTCATCTCTCGTCTGTTTGCGTG
TACCAATGACCCGGTGCTGCACCATCAGCTGAAGCCACTGTTTGTTGAGCGTGTCCAAGAGCAAATTGGTGTCGAGGGTGAT
GCACTGGAACTGGCTTTTCGTCTGCTGGTCTGCGCCAGCCTGGATGTCCAGAATGCCATCGACATGCGCCGTCTGCTGGAAA
TGCAGTGCGAAGATGGCGGTTGGGAGGGTGGTAACCTCTACCGCTTCGGCACCACGGGCCTGAAAGTTACCAACCGCGGTCT
GACGACCGCAGCCGCCGTTCAAGCGATCGAAGCGAGCCAACGCCGTCCGCCGAGCCCCGAGCCCGTCGTAGAGAGCACGAAA
AGCCCGATTACCCCGGTGACCCCGATGCTGGAAGTTCCAAGCCTGGGCTTATCTATCAGCCGTCCGTCCAGCCCGCTGCTGG
GTTATTTCCGTTTGCCGTGGAAGAAAAGCGCAGAAGTGCACTAA EMD37666-B
SEQ ID NO: 15-EMD37666-B protein
MSAAAQYTTLILDLDGVLFTWSPKTKTSIPPRTLKEILNSATWYEYERGRISQDECYERVGTEFGIAPSEIDNAFKQARDSM
ESNDELIALVRELKTQLDGELLVFALSNISLPDYEYVLTKPADWSIFDKVFPSALVGERKPHLGVYKHVIAETGIDPRTTVF
VDDKIDNVLSARSVGMHGIVFEKQEDVMRALRNIFGDPVRRGREYLRRNAMRLESVTDHGVAFGENFTQLLILELTNDPSLV
TLPDRPRTWNFFRGKPLFSEAFPDDLDTTSLALTVLQRDPGVISSVMDEMLNYRDPDGIMQTYFDDGRQRLDPFVNVNVLTF
FYTNGRGHELDQCLTWVREVLLYRAYLGGSRYYPSADCFLYFISRLFACTNDPVLHHQLKPLFVERVQEQIGVEGDALELAF
RLLVCASLDVQNAIDMRRLLEMQCEDGGWQEGGNLYRFGTTGLKVTNRGLTTAAAVQAIEASQRRPPSPSPSVESTKSPITP
VTPMLEVPSLGLSISRPSSPLLGYFRLPWKKSAEVH SEQ ID NO: 16-EMD37666-B optimized cDNA
ATGTCTGCGGCTGCTCAATATACTACTTTGATTCTGGATCTGGGCGACGTTCTGTTCACGTGGAGCCCGAAAACCAAGACCA
GCATTCCACCGCGTACCCTGAAGGAGATCCTCAATAGCGCGACTTGGTACGAGTATGAGCGTGGCCGCATCAGCCAAGACGA
GTGCTACGAACGCGTCGGTACGGAATTTGGCATTGCACCAAGCGAGATTGACAATGCGTTTAAACAAGCGCGTGACAGCATG
GAAAGCAATGACGAACTGATCGCGCTGGTCCGTGAGCTGAAAACCCAGCTGGATGGTGAGCTGTTGGTGTTTGCGCTGTCGA
ACATCTCTCTGCCGGACTACGAGTATGTTCTGACCAAACCGGCGGATTGGAGCATTTTTGATAAAGTGTTTCCGAGCGCGCT
GGTTGGTGAGCGCAAGCCGCATCTGGGTGTGTACAAACACGTTATTGCAGAGACTGGCATCGACCCGCGCACGACGGTTTTC
GTTGACGACAAGATCGATAACGTTCTGAGCGCACGTAGCGTCGGTATGCACGGTATTGTTTTCGAAAAACAAGAAGATGTTA
TGCGCGCACTGCGTAATATCTTCGGCGATCCGGTCAGACGTGGCCGTGAGTATCTGCGCCGCAATGCGATGCGTCTGGAATC
GGTGACCGATCATGGTGTCGCCTTTGGCGAGAATTTCACCCAGCTGCTGATTTTAGAGCTGACCAATGATCCTAGCCTGGTG
ACGCTGCCGGATCGTCCGCGTACCTGGAACTTTTTCCGCGGCAAGCCGTTGTTCTCCGAAGCCTTCCCGGACGACCTGGACA
CGACCAGCCTGGCGCTGACCGTGCTGCAACGTGATCCGGGTGTGATCTCTTCCGTAATGGACGAAATGCTGAACTACCGTGA
CCCGGACGGTATCATGCAGACCTATTTTGACGACGGTCGTCAGCGTCTGGACCCGTTTGTGAACGTGAATGTCCTGACGTTC
TTTTACACCAATGGTCGCGGTCACGAACTGGATCAGTGTCTGACCTGGGTCCGCGAAGTGCTGCTGTATCGTGCATACCTGG
GTGGCAGCCGTTATTACCCGAGCGCCGATTGCTTTCTGTACTTTATCAGCCGTCTGTTTGCGTGCACGAACGATCCGGTTCT
GCATCACCAGCTGAAGCCGCTTATTTGTTGAGCGCGTTCAGGAACAAATTGGTGTCGAGGGTGATGCACTGGAATTGGCATTC
CGCCTGTTGGTCTGCGCCAGCCTTGATGTCCAGAACGCCATTGACATGCGTCGCTTGCTCGAAATGCAGTGTGAGGACGGCG
GTTGGGAGGGTGGCAACCTGTACCGTTTCGGTACGACCGGCCTGAAAGTCACGAACCGTGGTCTGACGACGGCAGCTGCGGT
GCAAGCAATTGAAGCCAGCCAACGTCGTCCGCCATCCCCGTCACCGAGCGTTGAGTCCACCAAGAGCCCGATTACCCCTGTG
ACCCCGATGCTTGAAGTTCCGAGCCTGGGTCTGAGCATCTCCCGTCCTAGCAGCCCGCTGTTGGGTTACTTCCGCCTGCCGT
GGAAGAAAAGCGCTGAGGTGCATTAA XP_001217376.1
SEQ ID NO: 17-XP_001217376.1 protein
MAITKGPVKALILDFSNVLCSWKPPSNVAVPPQILKMIMSSDIWHDYECGRYSREDCYARVADRFHISAADMEDTLKQARKS
LQVHHETLLFIQQVKKDAGGELMVCGMTNTPRPEQDVMHSINAEYPVFDRIYISGLMGMRKPSICFYQRVMEEIGLSGDAIM
FIDDKLENVIAAQSVGIRGVLFQSQQDLRRVVLNFLGDPVHRGLQFLAANAKKMDSVTNTGDTIQDNFAQLLILELAQDREL
VKLQAGKRTWNYFIGPPKLTTATFPDDMDTTSMALSVLPVAEDVVSSVLDEMLKFVTDDGIFMTYFDSSRPVDPVVCINVL
GVFCRHNRERDVLPTFHWIRDILINRAYLSGTRYYPSPDLFLFFLARLCLAVRNQSLREQLVLPLVDRLRERVGAPGEAVSL
AARILACRSFGIDSARDMDSLRGKQCEDGGWPVEWVYRFASFGLNVGNRGLATAFAVRALESPYGESAVKVMRRIV SEQ ID NO: 18-XP_001217376.1 cDNA
ATGGCTATCACCAAGGGTCCAGTTAAGGCGCTTATTCTTGACTTTTCCAATGTTCTCTGCTCGTGGAAGCCTCCCAGCAATG
TTGCGGTGCCGCCCCAGATACTCAAAATGATCATGTCCTCTGACATATGGCATGACTACGAGTGCGGACGGTACTCGAGAGA
GGACTGCTATGCCAGAGTGGCAGACCGTTTTCATATCAGCGCCGCGGACATGGAAGACACGCTGAAACAGGCGCGCAAGAGC
```

```
CTGCAGGTTCACCATGAGACACTGTTGTTTATCCAGCAAGTCAAGAAGGATGCCGGGGGCGAGTTGATGGTGTGTGGGATGA
CCAACACGCCCCGGCCAGAGCAAGACGTAATGCATTCAATCAACGCGGAGTATCCTGTGTTTGATAGGATATATATATCCGG
TCTCATGGGCATGAGGAAGCCGAGCATCTGCTTCTACCAGCGGGTGATGGAGGAGATTGGCCTATCAGGCGATGCGATCATG
TTTATAGATGACAAGTTGGAGAATGTCATCGCCGCCCAGTCGGTAGGGATCCGAGGCGTTCTATTTCAGAGTCAGCAAGATC
TCCGTCGGGTTGTATTAAATTTCTTGGGCGATCCGGTCCATCGCGGCCTGCAGTTCCTAGCGGCCAATGCGAAAAAGATGGA
TAGTGTGACCAACACCGGCGATACTATCCAAGATAATTTTGCTCAGCTCCTCATCTTGGAGCTGGCCCAGGACAGGGAATTG
GTGAAGCTTCAGGCTGGAAAAAGGACTTGGAATTACTTCATAGGGCCTCCCAAGCTCACAACAGCCACGTTCCCCGATGACA
TGGACACCACATCTATGGCTCTCTCGGTCCTTCCTGTGGCCGAGGATGTGGTCTCTTCGTCCTGGATGAGATGCTTAAATT
CGTCACCGATGACGGTATCTTTATGACTTACTTCGATTCCTCGCGCCCTCGAGTCGACCCAGTCGTATGTATCAACGTCTTG
GGTGTTTTCTGCAGGCATAACCGAGAGCGAGACGTCCTTCCAACGTTCCATTGGATTCGAGACATCCTGATCAACCGGGCAT
ATCTCTCGGGCACCCGATACTACCCATCGCCCGATTTGTTTTTGTTTTTCCTTGCACGCCTCTGCCTGGCAGTCCGGAATCA
GAGCCTACGGGAACAACTTGTCTTGCCTCTGGTAGACCGACTGCGTGAGCGGGTGGGCGCACCTGGAGAAGCGGTCTCATTG
GCAGCGCGGATCCTTGCCTGCCGTAGCTTTGGTATCGACAGTGCGAGAGACATGGACAGCTTGAGGGGAAAACAATGCGAGG
ATGGCGGCTGGCCAGTGGAGTGGGTTTACCGGTTTGCCTCTTTCGGCCTGAACGTAGGCAATCGGGGTCTTGCTACTGCCTT
CGCGGTCAGGGCGCTCGAAAGCCCCTATGGTGAGTCGGCGGTGAAGGTTATGAGACGCATCGTCTGA

SEQ ID NO: 19-XP_001217376.1 optimized cDNA
ATGGCAATCACTAAGGGCCCAGTTAAAGCGCTGATTCTTGATTTTTCTAACGTTCTGTGTAGCTGGAAGCCGCCGAGCAATG
TTGCGGTCCCGCCTCAAATTCTGAAGATGATTATGTCGAGCGACATCTGGCATGATTATGAGTGTGGCCGTTACAGCCGTGA
GGACTGCTACGCCCGTGTTGCTGACCGTTTTCATATCAGCGCAGCGGACATGGAAGATACCCTGAAACAGGCACGTAAGTCC
CTGCAAGTGCACCACGAAACGCTGCTGTTCATCCAACAGGTGAAGAAAGACGCGGGTGGTGAGCTGATGGTTTGCGGCATGA
CCAACACGCCCGCGTCCGGAACAAGACGTGATGCATTCCATCAATGCTGAGTATCCGGTGTTCGACCGTATTTACATTAGCGG
CCGATGGGCATGCGTAAACCGAGCATTTGTTTCTACCAACGCGTAATGGAAGAGATTGGTCTGAGCGGTGACGCCATCATGT
TCATTGACGATAAACTGGAAAATGTGATTGCCGCACAGAGCGTGGATGTATCCGCGGTGGCTGCTGTTCCAAAGCCAGCAAGATCT
GCGTCGTGTCGTGCTGAACTTTCTGGGCGATCCGGTCCACCGTGGTCTGCAGTTCTTGGCGGCGAACGCAAAGAAAATGGAC
AGCGTCACGAATACCGGCGACACTATCCAAGACAATTTCGCACAGCTGTTGATCTTAGAGCTGGCGCAGGATCGCGAATTGG
TGAAATTGCAGGCCGGTAAACGTACCTGGAACTACTTTATTGGTCCGCCGAAGCTGACCACGGCGACGTTTCCGGATGATAT
GGACACGACCAGCATGGCGCTGTCGGTGCTGCCTGTCGGAAGATGTCGTGAGCTCTGTTCTGGACGAGATGCTGAAGTTC
GTGACCGATGATGGTATCTTTATGACCTATTTCGACTCTAGCCGTCCGCGTGTCGATCCGGTTGTCTGCATTAATGTGTTGG
GTGTTTTCTGCCGCCACAATCGTGAGCGCGACGTGTTGCCGACCTTTCACTGGATTCGTGATATTCTGATCAACCGCGCATA
TCTGAGCGGCACGCGCTATTACCCGTCCCCGGATCTGTTTCTGTTTTTCCTGGCTCGTCTGTGCCTGGCCGTTCGCAACCAG
AGCCTGCGCAACAACTGGTTCTCCCGCTGGTTGATCGTCTGCGCGAGCGTGTTGGTGCTCCGGGTGAGGCTGTGAGCCTGG
CGGCACGTATCCTGGCGTGCCGTAGCTTCGGTATCGACTCAGCCCGCGACATGGACTCCTTGCGTGGCAAACAGTGTGAAGA
TGGTGGTTTGGCCGGTCGAATGGGTCTATCGCTTCGCGAGCTTTGGTCTGAACGTTGGCAACCGTGGTTTGGCCACCGCGTTT
GCGGTTAGAGCGCTGGAGTCCCCATACGCGGAGAGCGCAGTTAAGGTTATGCGCCGTATCGTGTAA OJJ98394.1
SEQ ID NO: 20-OJJ98394.1 protein
MPSVKALVLDFAGVLCSWTPPAESPLSPAQLKQLMSSEIWFEYERGRYSEEECYAKLVERFSISAADMASTMEQARQSLELN
HAVLQLVSEIRKRNPGLKVYGMTNTPHAEQDCVNRIVNSYPVFDHVYLSGLVGMRKPDLGFYRFVLAETGLRPDEVVFVDDK
TENVLVAQSVGMHGVVFQNVTDFKQQIINVTGDPVSRGLRYLRSNAKSLLTVTSNNSVIHENFAQLLILELTGDRDLIELEP
WDRTWNYFIGVPQSPTSTFPNDLDTTSIALSVLPIHKDVVADVMDEIMLLLDNDGIVPTYFDPTRPRVDPVVCVNVLSLFAQ
NGRESELLATFNWVLDVLRHRAYLQGTRYYISPDAFLYFLARLSVFLRMSPLRARLMPLLEERVYERIGAHGDAISLAMRIY
TCKLLGMSNMLDERALRDMQCEDGGFPTSWVYRFGSTGVKIGNRGLTTALAIKAIEMPLASLWKSWGLTTDIR SEQ ID NO: 21-OJJ98394.1 cDNA
ATGCCCTCCGTCAAAGCACTGGTCCTGGACTTCGCCGGAGTTCTATGCTCATGGACCCCGCCAGCCGAGAGCCCGCTCTCCC
CAGCCCAGCTCAAACAACTCATGTCCTCCGAGATATGGTTCGAATACGAGCGCGGGAGATATTCCGAAGAAGAATGTTATGC
GAAGCTCGTCGAACGGTTCTCCATCAGCGCTGCGGACATGGCTTCCACCATGGAACAGGCCCGTCAGAGCCTGGAACTGAAC
CACGCCGTACTTCAGCTTGTCAGCGAGATAAGGAAGCGGAACCCCGGGCTCAAAGTTTATGGCATGACGAACACGCCCCATG
CGGAACAGGATTGTGTGAATCGCATCGTGAACAGCTATCCTGTTTTCGACCATGTGTATCTCTCCGGGCTCGTTGGGATGCG
CAAACCAGATCTTGGATTCTATCGGTTTGTTCTCGCAGAGACCGGGTTGAGGCCTGACGAGGTCGTGTTCGTCGACGACAAA
ACGGAGAATGTGTTGGTCGCGCAGTCCGTGGGCATGCACGGCGTGGTGTTCCAGAACGTTACGGATTTCAAGCAGCAGATCA
TAAACGTGACGGGAGACCCTGTCTCTCGGGGCTTGAGGTATCTCCGCTCGAATGCAAAGAGCTTCCTCACTGTGACTAGCAA
TAACTCCGTGATCCACGAAAACTTTGCGCAGTTGCTGATTCTGGAGCTGACGGGCGACCGAGACTTGATCGAACTCGAGCCT
TGGGATCGAACATGGAACTACTTCATCGGGGTTCCTCAGTCGCCGACGAGCACCTTCCCCAACGACCTGGACACCACCTCTA
TCGCGCTCTCGGTCCTTCCCATTCATAAGGACGTCGTTGCCGATGTGATGGACGAGATTATGCTTCTCCTAGACAACGACGG
GATAGTCCCAACATATTTTGATCCCACTCGCCCTCGAGTCGACCCAGTCGTGTGTGTGAATGTACTCAGCCTGTTTGCCCAA
AACGGCCGAGAATCCGAGTTACTCGCCACCTTCAACTGGGTGCTGGACGTGCTGCGACATAGAGCCTACCTGCAGGGCACGA
GATATTACATCAGTCCGGACGCCTTCTTGTACTTTCTAGCCAGACTCTCGGTCTTTCTGAGGATGAGTCCACTCCGCGCTCG
GCTAATGCCTCTCCTGGAAGAAAGAGTGTATGAGCGAATTGGTGCCCATGGCGACGCCATTTCGCTGGCTATGCGGATCTAT
ACGTGTAAGCTGCTCGGGATGTCGAATATGCTCGATGAAAGCAGCATTGCGGGACATGCAGTGTTGAGGATGGCGGCTTCCTA
CAAGTTGGGTCTATAGATTTGGATCGACCGGAGTGAAGATTGGGAACAGGGGGTTGACTACTGCACTTGCAATAAAGGCCAT
TGAGATGCCTCTCGCTTCGCTTTGGAAGTCGTGGGGATTGACGACTGACATTCGATAA SEQ ID NO: 22-OJJ98394.1 optimized cDNA
ATGCCGTCGGTTAAAGCGTTGGTTCTGGATTTTGCGGGTGTGTTGTGTTCTTGGACTCCACCGGCGGAAAGCCCGTTGTCCC
CAGCGCAGCTGAAGCAGCTGATGAGCAGCGAGATCTGGTTTGAGTATGAGCGTGGCCGTATAGCGAAGAAGAGTGTTATGC
AAAATTGGTGGAGCGTTTCTCTATCTCGGCCGCAGATATGGCGAGCACGATGGAACAGGCCCGTCAATCGCTGGAGTTGAAC
CACGCCGTGCTGCAATTAGTTTCCGAGATTCGTAAACGTAATCCGGGCTTAAAGGTTTACGGTATGACTAATACCCCGCATG
CAGAGCAAGATTGTGTGAACCGTATTGTCAATAGCTATCCGGTTTTTGATCATGTCTACCTGAGCGGTCTGGTGGGTATGCG
CAAACCGGATCTGGGCTTTTACCGTTTCGTTCTGGCAGAGACTGGTCTGCGCCCGGATGAAGTCGTGTTCGTTGACGACAAG
ACCGAAAATGTCCTGGTGGCTCAATCCGTTGGCATGCATGGTGTGGTGTTCCAAAATGTAACCGACTTCAAACAACAGATTA
TCAATGTCACGGGTGATCCTGTCAGCCGTGGTTTGCGCTACTTGCGTTCAAACGCGAAGTCTCTGCTCACTGTTACCAGCAA
TAACAGCGTTATCCATGAGAATTTCGCGCAGCTGCTGATCCTGGAACTGACGGGCGACCGTGACCTGATTGAACTGGAACCG
TGGGACCGTACGTGGAACTACTTTATCGGCGTGCCGCAAAGCCCGACCAGCACCTTTCCGAACGACCTGGATACGACCAGCA
TTGCCCTGAGCGTTCTGCCGATTCACAAAGATGTGGTTGCGGACGTGATGGATGAGATTATGCTGCTGCTGGACAATGACGG
```

Sequence Listings

```
TATTGTCCCGACCTACTTCGATCCAACCCGTCCGCGTGTTGATCCTGTTGTGTGCGTCAACGTTCTGAGCCTGTTCGCACAG
AACGGTCGCGAGTCCGAATTGCTGGCGACGTTCAACTGGGTTTTGGACGTTCTGAGACACCGTGCGTATTTGCAGGGTACGC
GCTATTATATCAGCCCGGATGCCTTTCTGTATTTTCTGGCGCGCGTCTGTGTTTCTGCGTATGTCTCCGTTGCGCGCTCG
TCTGATGCCGCTGCTGGAAGAACGCGTTTATGAGCGTATCGGCGCACACGGCGATGCTATTAGCCTGGCGATGCGCATTTAC
ACCTGTAAGCTGCTGGGCATGAGCAATATGCTGGACGAGCGTGCACTGCGTGACATGCAGTGTGAAGATGGTGGTTTCCCAA
CCAGCTGGGTGTACCGTTTTGGTAGCACGGGCGTGAAAATTGGTAACCGTGGCTTGACGACCGCACTGGCCATTAAGGCCAT
CGAAATGCCGCTGGCCAGCCTTTTGGAAAAGCTGGGGCCTGACCACCGATATTCGCTAA

GAO87501.1
SEQ ID NO: 23-GAO87501.1 protein
MTRKQSPQYKAIIFDLGDVFFTWDAPKDTAVLPNLFKKMLTSPTWSDYERGKLSEESCYERLAEQFDVDSSEIARSLRKAQQ
SLTTDAAIVSLISEIRALAGHIAIYAMSNISAPAYAAVLQTQPEMGIFDGVFPSGCYGTRKPELLFYKKVLQEIAVPPNQII
FIDDQLENVVSAQSTGMHGIVYGAGELSRQLRNLVLDPVQRGREFLRRNAGALYSICETGQVIRENFSQLLILEATGDRSLV
NLEYQQRSWNFFQGGPPSTSETFPDDVDTTSIALMILPADDNTVNSVLGEISEVANDEGIVNTYFDQTRQRIDPAVCVNVLR
LFYTYGRGATLPLTLQWVSDVLEHRAHLHGTRYYPSPEVFLYFVSQLCRFSKREPTLQLLETLLTDRLKERIQVKADTLSLA
MRILACLSVGISQVEVDVRELLALQCKDGSWEPGSFYRFGSSKMNVGNRGLTTALATRAVELYQGTRIRSKGTE SEQ ID NO: 24-GAO87501.1 cDNA
ATGACCCGACAGAAATCGCCTCAATACAAAGCAATCATCTTTGACCTAGGGGATGTCTTTTTCACCTGGGACGCCCCCAAAG
ACACTGCTGTCTTGCCCAACCTCTTCAAGAAAATGCTTACCTCGCCAACCTGGTCAGATTACGAGCGCGGCAAGTTGAGCGA
AGAAAGCTGCTACGAGAGACTGGCCGAACAGTTTGACGTTGACTCGTCGGAAATCGCGCGCAGCTTAAGGAAAGCACAGCAG
TCTCTTACCACAGACGCAGCAATCGTGAGCCTGATATCAGAGATCAGAGCGTTGGCCGGACATATTGCCATCTACGCCATGT
CCAACATTTCCGCCCCAGCTTATGCAGCTGTGCTCCAGACTCAGCCCGAAATGGGCATCTTTGACGGAGTGTTCCCGTCTGG
ATGCTATGGGACGAGGAAGCCGGAGCTGTTGTTCTATAAGAAAGTCTTGCAGGAGATTGCAGTGCCGCCAAATCAGATCATC
TTTATTGATGATCAGCTAGAGAATGTAGTTTCTGCGCAGTCAACAGGTATGCACGGCATTGTCTACACCGGTGCGGGTGAGC
TCAGTCGACAGCTCAGAAATCTGGTGTTGGACCCTGTACAAAGGGGTCGAGAGTTTCTACGGCGCAATGCTGGGGCATTGTA
TAGTATCTGCGAGACTGGTCAAGTCATCCGGGAAAACTTCTCGCAGCTGCTCATCCTAGAGGCGACGGGTGATAGAAGCCTG
GTCAACCTTGAATATCAGCAGCGGAGCTGGAATTTCTTTCAAGGAGGTCCCCCTTCTACGTCGGAAACATTCCAGATGATG
TCGACACAACATCCATTGCCTTGATGATTCTCCCTGCCGATGATAACACAGTCAACTCGGTTCTCGGCGAGATTTCCGAGGT
AGCTAATGACGAGGGCATTGTAAATACGTACTTTGACCAGACCCGACAGCGAATCGACCCAGCAGTCTGCGTCAATGTCCTC
CGTCTCTTTTATACCTACGGCCGGGGCGCCACTCTCCCATTGACCCTCCAGTGGGTGTCCGACGTTCTTGAGCATCGTGCGC
ACTTACATGGTACGCGATACTACCCCAGCCCGGAGGTTTTCCTCTACTTTGTCAGTCAACTCTGCCGGTTCTCCAAGAGGGA
ACCGACGCTGCAGCTGCTGGAGACGTTGCTCACGGATCGCCTCAAGGAGCGCATTCAGGTCAAGGCAGACACTCTGTCACTG
GCTATGCGGATCCTGGCATGCTTGTCTGTGGGTATATCACAAGTTGAAGTGGATGTCCGAGAGCTGCTCGCCTTGCAATGCA
AGGATGGATCGTGGGAACCCGGCTCGTTTTACCGGTTTGGGTCGTCCAAGATGAACGTTGGTAATCGAGGTCTTACGACTGC
GTTGGCGACTAGGGCGGTTGAGTTGTACCAGGGGACTAGAATACGCTCTAAGGGCACCGAGTAG SEQ ID NO: 25-GAO87501.1 optimized cDNA
ATGACTCGCCAAAAAAGCCCTCAATACAAAGCAATTATCTTCGATCTGGGTGACGTTTTCTTCACCTGGGATGCCGCCAAAG
ATACGGCCGTACTGCCGAACCTGTTCAAGAAAATGCTGACCTCGCCGACCTGGAGCGACTATGAGCGTGGTAAGCTGTCTGA
GGAAAGCTGTTACGAACGCTTGGCCGAGCAATTTGACGTGGACAGCAGCGAGATCGCGCGTAGCCTCCGTAAAGCGCAGCAA
AGCCTGACGACCGACGCAGCCATCGTGAGCCTGATCAGCGAGATCCGCGCATTGGCGGGTCACATTGCTATCTATGCTATGT
CTAACATTTCTGCGCCAGCATACGCAGCGGTGTTACAGACCCAGCCGGAAATGGGTATCTTTGATGGTGTTTTTCCGAGCGG
CTGCTATGGTACGCGTAAACCGGAACTGCTGTTTTACAAAAAAGTGCTTCAAGAAATTGCGGTTCCGCCGAATCAGATTATC
TTCATTGACGATCAGCTGGAAAACGTCGTCAGCGCACAGTCCACGGGCATGCATGGCATTGTTTACACCGGTGCCGGTGAAC
TGAGCCGTCAACTGCGTAATCTGGTCCTGGACCCGGTGCAGCGTGGTCGTGAGTTCCTGCGCCGTAATGCTGGCGCCCTGTA
CAGCATTTGTGAGACTGGCCAAGTTATCCGTGAGAACTTCAGCCAGCTGCTGATTCTGGAAGCAACCGGCGATCGTTCGCTG
GTGAACCTGGAGTATCAACAACGTTCCTGGAACTTCTTTCAGGGTGGCCCTCCATCCACGAGCGAAACTTTTCCGGATGATG
TTGACACGACCTCAATCGCGCTGATGATTTTACCGGCGACGATAACACCGTCAATAGCGTCCTGGGTGAAATCAGCGAAGT
CGCGAATGACGAGGGCATTGTGAATACCTATTTCGATCAGACCCGCCAACGTATCGATCCGGCCGTGTGTGTCAACGTGTTG
CGCCTGTTTTACACCTATGGTCGTGGCGCTACGCTGCCGTTGACCCTGCAATGGGTTAGCGACGTGCTGGAGCACCGTGCGC
ATCTGCACGGACCCGCTACTATCCGTCCCCAGAGGTTTTCCTGTACTTTGTCTCTCAGCTGTGCCGTTTTTCCAAGCGCGAA
CCGACCCTGCAGCTGCTGGAAACGCTGTTGACCGACAGACTGAAGGAACGCATCCAAGTTAAGGCAGATACGCTGAGCTTGG
CAATGCGTATTTTGGCGTGCCTGAGCGTGGGCATCAGCCAGGTTGAGGTTGACGTCCGCGAACTGCTGGCGCTGCAGTGCAA
GGACGGTAGCTGGGAGCCGGGTAGCTTCTACCGTTCGGTAGCAGCAAGATGAATGTCGGTAACCGCGGTCTGACGACCGCTT
TGGCGACCCGTGCGGTTGAGCTGTACCAGGGTACGCGTATTCGTAGCAAGGGCACCGAGTAA XP_008034151.1
SEQ ID NO: 26-XP_008034151.1 protein
MASPHRRYTTLILDLGDVLFSWSSKTNTPIPPKKLKEILSSLTWFEYERGRISQAEVYDRVSSEFSLDAATIAEAFQQARDS
LRPNEEFLALIRELRQQTHGQLTVLALSNISLPDYEYIMADLSDWTSVFDRVFPSALVGERKPHLGAYRRVISEMHLDPETT
VFVDDKLDNVVSARSLGMHGVVFDSQENVFQTLRNIFGDPIHRGRDYLRRHAGRLETSTDAGVVFEENFTQLIIYELTNDKS
LITTSDCPRTWNFFRGKPLFSASFPDDVDTTSVALTVLRPPRTLVNSILDEMLEYVDADGIMQTYFDHSRPRMDPFVCVNVL
SLFYEYGRGQDLPKTLEWVYEVLLHRAYIGGSRYYMSADCFLFFMSRLLQRITDPAVLNRLRPLFVERMHERVSAPGDSMEL
AFRILAGSSVGIQFPRDLEKLLAAQCADGGWDLCWFYQYGSTGVKAGNRGLTTALAIKAIESAIARPPSPALSAVSSSKLEV
PKPILQRPLSPRRLGDFLMPWRRAQREVAVSS SEQ ID NO: 27-XP_008034151.1-cDNA
ATGGCTTCACCTCACCGCAGGTATACGACACTCATCCTAGACCTGGGCGACGTCCTCTTCTCTTGGTCATCCAAGACCAACA
CACCTATCCCTCCCAAGAAGCTGAAGGAGATCCTCTCGTCCCTGACCTGGTTCGAGTACGAGCGCGGTCGGATATCACAGGC
CGAGTGCTATGACCGGGTCAGCTCCGAGTTCAGTCTTGACGCTGCCACCATCGCAGAAGCGTTCCAGCAGGCTCGCGACTCT
CTGCGACCGAACGAAGAGTTCCTGGCGTTGATTCGCGAACTCCGCCAACAAACGCATGGTCAGCTTACCGTCCTCGCGCTCT
CGAACATCTCACTCCCCGACTATGAATACATCATGGCTCTCGACTCGGACTGGACGTCGGTCTTCGACCGCGTCTTCCCTTC
TGCCCTCGTCGGCGAGCGCAAGCCACATCTGGGGGCGTACCGCCGTGTCATCTCTGAGATGCACCTAGACCCAGAAACGACC
GTCTTTGTGGACGACAAGCTGGACAACGTGGTGTCCGCGCGATCGCTCGGGATGCACGGCGTGGTCTTCGACTCCCAGGAGA
ACGTCTTCCAGACGCTGAGGAATATCTTCGGCGACCCCGATACATCGCGGACGTGACTATCTCCGCAGGCATGCCGGTCGTCT
```

Sequence Listings

```
GGAGACATCTACGGACGCCGGCGTTGTCTTCGAGGAAAACTTTACGCAGCTCATCATCTACGAACTAACAAATGACAAATCC
CTCATCACGACATCAGACTGTCCCCGCACTTGGAACTTCTTCCGCGGGAAGCCCTTGTTCTCGGCCTCGTTTCCCGACGATG
TGGACACGACGTCGGTTGCCCTGACAGTGTTGCGCCCACCCCGCACGCTTGTCAACTCGATCTTGGACGAGATGCTAGAGTA
TGTCGACGCCGACGGCATCATGCAGACCTACTTCGACCACTCGCGCCCGCGGATGGATCCGTTCGTCTGTGTCAACGTCCTG
TCGCTGTTCTACGAGTACGGCGGGGACAGGACCTCCCGAAGACCCTCGAATGGGTATACGAGGTTCTGCTGCACCGCGCCT
ACATCGGCGGCTCGCGGTACTACATGTCCGCGGACTGCTTCCTCTTCTTCATGAGCCGCCTTCTCCAACGTATCACCGACCC
AGCCGTCCTGAACCGCCTCCGCCCGTTGTTCGTCGAGCGCATGCACGAACGTGTCAGCGACACCGGGCGACTCCATGGAGCT
CGCGTTCCGCATCCTCGCTGGCTCGTCCGTCGGCATCCAGTTCCCACGTGACCTGGAGAAGCTCCTCGCCGCGCAGTGCGCC
GACGGCGGCTGGGACCTGTGCTGGTTCTACCAGTATGGGTCCACCGGCGTGAAGGCAGGCAACCGCGGGCTCACCACCGCGC
TCGCCATCAAGGCTATCGAGAGCGCTATCGCGCGCCCTCCGTCCCCGCTCTATCAGCTGTATCGTCGTCGAAACTGGAAGT
GCCGAAACCAATTCTCCAGCGTCCCCTCAGCCCGCGCCGGCTTGGCGACTTCCTGATGCCCTGGAGGAGAGCACAGCGCGAG
GTCGCGGTTTCCAGCTAG

SEQ ID NO: 28-XP_008034151-optimized cDNA
ATGGCTAGCCCGCACCGTCGCTATACTACTCTGATTCTGGATTTGGGTGATGTTTTGTTTAGCTGGAGCAGCAAAACCAATA
CGCCTATTCCGCCGAAAAAGCTGAAAGAAATCCTGTCTAGCCTGACCTGGTTCGAGTACGAGCGCGGTCGCATTTCTCAAGC
CGAGTGCTATGACCGTGTGAGCTCTGAGTTTAGCCTGGACGCAGCGACCATTGCAGAGGCATTCCAACAGGCTCGTGACTCG
CTGCGCCCGAACGAAGAATTTCTGGCGTTGATTCGTGAGCTGCGCCAGCAGACCCACGGCCAACTCACCGTTCTGGCACTGA
GCAACATCTCCCTGCCGGATTACGAGTACATCATGGCTCTGGATAGCGATTGGACCAGCGTCTTTGATAGAGTTTTCCCGAG
CGCGCTGGTTGGTGAGCGTAAGCCGCATCTGGGTGCTTACCGTCGTGTCATTAGCGAGATGCATCTGGACCCGGAGACTACG
GTGTTTGGACGACAAACTGGACAACGTTGTCTCCGCGCGCAGCCTGGGTATGCACGGCGTCGTTTTTGACTCACAAGAAA
ATGTTTTCCAGACGCTGCGTAACATTTTCGGTGACCCTATCCACCGTGGCCGCGACTATTGCGTCGTCATGCCGGTCGTTT
GGAAACCAGCACCGACGCGGGCGTTGTTTTGAAGAAAACTTCACCCAGCTGATCATCTACGAACTGACGAATGACAAGAGC
CTGATCACCACGAGCGATTGTCCGCGCACCTGGAACTTCTTCCGTGGTAAGCGCTGTTTAGCGCGTCCTTCCCAGACGATG
TCGATACGACTTCGGTGGCCCTGACCGTTCTGCGCCCACCGCACCCTGGTAAACAGCATCCTGGACGAAATGTTAGAATA
CGTCGATGCGGATGGTATTATGCAGACCTATTTCGACCACAGCCGTCCGCGCATGGACCCGTTTGTGTGTGTAATGTGTTG
AGCCTGTTCTATGAGTACGGCCGTGGTCAAGATCTGCCAAAAACCCTGGAATGGGTCTACGAAGTCCTTCTGCATCGTGCCT
ACATCGGTGGCTCCCGTTATTACATGAGCGCAGATTGCTTTTTGTTCTTTATGTCTCGTCTGCTGCAGCGCATCACGGACCC
TGCCGTGCTGAATCGTCTGCGTCCGCTGTTCGTGGAGCGTATGCACGAGCGCGTGTCTGCCCCGGGTGACAGCATGGAACTG
GCGTTCCGTATCCTGGCGGGCAGCAGCGTGGGTATTCAATTTCCGCGTGATTTGGAGAAACTGCTGGCTGCGCAGTGTGCGG
ACGGTGGCTGGGATCTGTGCTGGTTTTATCAATACGGTAGCACCGGCGTTAAGGCCGGCAATCGTGGCCTGACGACGGCACT
GGCAATTAAGGCCATTGAGTCCGCGATTGCGCGTCCGCCGAGCCCGGCATTGAGCGCGGTCAGCAGCAGCAAACTGGAAGTG
CCGAAGCCGATCTTGCAGCGTCCACTGAGCCCGCGTCGTCTGGGTGACTTCCTGATGCCGTGGCGCCGTGCGCAACGCGAAG
TCGCGGTTAGCTCCTAA XP_007369631.1
SEQ ID NO: 29-XP_007369631.1 protein
MASIHRRYTTLILDLGDVLFRWSPKTETAIPPQQLKDILSSVTWFEYERGRLSQEACYERCAEEFKIEASVIAEAFKQARGS
LRPNEEFIALIRDLRREMHGDLTVLALSNISLPDYEYIMSLSSDWTTVFDRVFPSALVGERKPHLGCYRKVISEMNLEPQTT
VFVDDKLDNVASARSLGMHGIVFDNQANVFRQLRNIFGDPIRRGQEYLRGHAGKLESSTDNGLIFEENFTQLIIYELTQDRT
LISLSECPRTWNFFRGEPLFSETFPDDVDTTSVALTVLQPDRALVNSVLDEMLEYVDADGIMQTYFDRSRPRMDPFVCNNVL
SLFYENGRGHELPRTLDWVYEVLLHRAYHGGSRYYLSPDCFLFFMSRLLKRADDPAVQARLRPLFVERVNERVGAAGDSMDL
AFRILAAASVGVQCPRDLERLTAGQCDDGGWDLCWFYVFGSTGVKAGNRGLTTALAVTAIQTAIGRPPSPSPSAASSSFRPS
SPYKFLGISRPASPRIRGDLLRPWRKMSRSNLKSQ SEQ ID NO: 30-XP_007369631.1 cDNA
ATGGCCTCAATCCACCGTCGATACACTACTCTCATCCTCGACCTCGGCGACGTACTCTTTCGTTGGTCTCCAAAGACTGAGA
CCGCCATTCCACCTCAACAACTCAAGGATATCCTCTCCTCTGTCACCTGGTTTGAGTACGAACGCGGCAGACTATCCCAGGA
AGCATGCTACGAGCGCTGCGCCGAGGAGTTCAAGATAGAGGCCTCGGTCATTGCAGAAGCCTTTAAGCAGGCTCGCGGGTCA
CTGCGGCCCAACGAGGAGTTCATCGCCCTTGATCCGTGACCTCCGCCGTGAGATGCACGGTGACCTTACCGTTCTTGCCCTCT
CCAACATCTCCCTCCCCGACTACGAATACATCATGTCGCTAAGCTCAGATTGGACGACCGTCTTCGATCGCGTATTCCCCTC
TGCACTCGTTGGCGAGCGCAAGCCTCATCGGGATGCTATCGCAAGGTCATCTCGGAGATGAACCTAGAACCTCAGACGACT
GTGTTCGTGGATGACAAGCTTGACAACGTCGCGTCTGCTCGCTCACTTGGTATGCACGGCATCGTGTTTGACAACCAAGCCA
ACGTCTTCCGCCAACTCCGCAATATCTTCGGAGACCCCATCCGCCGTGGCCAAGAGTATCTCCGTGGGCATGCTGGCAAACT
CGAGTCTTCGACCGACAACGGGTTGATCTTGAGGAGAACTTCACACAGCTGATCATCTACGAGTTGACGCAAGACAGGACT
CTCATCTCGCTTTCAGAATGTCCTCGTACTTGGAATTCTTCCGAGGCGAACCGCTATTCTCGGAGACCTTCCCGGATGATG
TCGACACAACATCTGTGGCGTTGACGGTATTGCAACCGGACAGGACTGGTCAACTCCGTTCTAGACGAGATGCTGGAGTA
TGTCGACGCCGATGGCATCATGCAGACATACTTCGATCGTTCACGACCACGCATGGACCCCTTCGTCTGCGTGAACGTACTC
TCCCTGTTCTACGAGAACGGTCGTGGTCACGAGCTCCCTCGCACATTGGACTGGGTCTACGAGGTGCTCCTCCATCGCGCGT
ACCACGGCGGTTCGCGTTATTACCTGTCGCCCGACTGCTTTCTATTCTTCATGAGCCGCCTACTCAAGCGCGCAGACGATCC
AGCAGTCCAGGCTCGGCTCCGCCCGCTCTTCGTCGAGCGGGTGAACGAGCGAGTAGGCGCCGCTGGCGACTCTGATGGACCTC
GCCTTCCGCATCCTCGCCGCAGCGTCTGTTGGCGTCCAGTGCCCCCGCGATCTGGAAAGGTTGACTGCCGGGCAATGCGACG
ACGGTGGATGGGACCTCTGCTGGTTCTACGTGTTCGGCTCGACGGGCGTGAAGGCGGGCAACCGCGGCCTCACAACGGCCCT
CGCTGTCACGGCCATACAGACGGCCATCGGACGCCCCCCTTCGCCCAGTCCCTCCGCGGCCTCCTCGTCTTTCAGACCTAGT
TCCCCTTACAAATTCCTAGGCATTTCGCGCCCAGCTAGCCCCATTCGCTTTGGCGACTTACTTCGCCCATGGCGGAAGATGA
GCAGGTCGAACTTGAAGTCTCAATGA SEQ ID NO: 31_XP_007369631.1 optimized cDNA
ATGGCAAGCATTCATCGTCGCTATACTACGCTGATTCTGGACCTGGGTGATGTTTTGTTCCGCTGGAGCCCGAAAACCGAGA
CTGCGATTCCTCCGCAACAACTGAAAGACATCCTGAGCAGCGTCACCTGGTTCGAGTACGAGCGTGGCCGTCTGAGCCAAGA
GGCTTGCTACGAGCGCTGCGCCGAAGAGTTCAAGATTGAAGCCAGCGTGATTGCGGAAGCGTTCAAACAAGCGCGTGGTAGC
CTGCGTCCGAACGAAGAATTTATCGCACTGATCCGTGATCTGCGTCGCGAGATGCATGGTGACCTGACCGTTCTGGCTCTGA
GCAATATCTCGTTGCCGGATTACGAGTATATTATGTCTCTGAGCAGCGACTGGACGACGGTCTTTGATCGTGTGTTCCCGTC
AGCTCTGGTGGGCGAGCGTAAACCGCACTTGGGTTGCTATCGCAAGGTCATCAGCGAGATGAACCTGGAACCTCAGACCACG
GTCTTTGTGGACGATAAACTGGATAATGTCGCAAGCGCGCGTAGCCTGGGTATGCACGGTATCGTGTTTGATAATCAAGCGA
ATGTTTTCGCCAGCTGCGTAATATTTTCGGTGATCCAATCCGTCGCGGTCAAGAGTATCTGCGTGGCCATGCCGGTAAATTG
GAGAGCAGCACGGACAATGGTTTGATCTTTGAAGAGAACTTCACCCAGCTGATCATTTATGAACTGACCCAGGACCGCACGT
```

```
TGATCAGCCTGTCGGAGTGTCCGCGTACCTGGAACTTCTTCCGTGGCGAGCCGTTGTTTTCTGAAACCTTCCCGGACGACGT
GGACACCACGTCCGTTGCACTGACGGTTCTGCAACCGGATCGCGCACTGGTTAACAGCGTGCTGGACGAAATGCTGGAATAT
GTCGATGCGGATGGCATCATGCAGACGTATTTCGACCGCTCGCGTCCGCGTATGGACCCGTTTGTTTGCGTCAACGTACTGA
GCCTGTTTTACGAGAACGGTCGTGGTCACGAACTGCCGCGCACTCTGGATTGGGTGTACGAAGTCCTGCTCCACCGCGCCTA
CCACGGTGGTTCCCGTTACTACCTGAGCCCGGACTGTTTCTTGTTTTTTATGAGCCGTCTGCTGAAACGTGCAGACGACCCA
GCGGTTCAGGCGAGATTGCGTCCGCTGTTTGTGGAACGCGTTAACGAACGTGTTGGCGCGGCCGGTGATAGCATGGACCTGG
CGTTTCGCATTCTGGCCGCAGCGAGCGTGGGTGTGCAGTGTCCGCGACCTGGAGCGTCTGACCGCTGGTCAATGCGATGA
TGGCGGCTGGGATCTGTGTTGGTTCTACGTTTTCGGCAGCACCGGCGTTAAGGCCGGTAATCGTGGTCTGACCACGGCGCTG
GCAGTCACCGCGATCCAGACCGCCATCGGCCGTCCGCCTAGCCCGAGCCCGTCCGCGGCAAGCTCCAGCTTCCGCCCGAGCA
GCCCGTACAAGTTTCTGGGTATTAGCCGTCCGGCGTCCCCAATTCGCTTCGGTGACCTTCTGCGTCCGTGGCGTAAAATGTC
TCGCTCTAACCTGAAGTCCCAGTAA

ACg006372
SEQ ID NO: 32-ACg006372 protein
MRRNVLNKATHSQSPLKPNITTLIFDLGDVLLTWSDSTPKSPLPPKIVKGILRSLTWFEYEKGNLTESQTYGVQAQEFGVDA
SEVKASFEAARDSLKSNPMLLQLIRSLKDSGHVIYAMSNISAPDWEFLKTRADLSDWALFDRVFPSAEAHDRKPNIGFYQHV
INETGLNPSNTVFVDDRIENVVSARSAGMHGIVFDDINNVIRQLKNLCEDPIHRARSFLYANKKCLNTVSTDGTIVSENFSQ
LLILEAIGDSELVDFVRHEGRFNFFQGEAKLIMTNHYPDDFDTTSIGLTVVPYIDDKTRNRVMDEILAYQSEDGIVLVYFDH
KRPRIDPVVCVNVLTLFYRYGRGHQLQKTLDWVEQVLINRACASGTFYYATEEQFLFFLSRLIQSSPDVRQRLEGVFKRRVV
ERFGADGDALAMAMRIHTAASVGLVDHVDLDKLFALQQNDGSWRDSAFYRFPSARQLASNDGLTTAIAIQAIQAAERLREDG
NVL SEQ ID NO: 33-ACg006372 cDNA
ATGAGGCGAAACGTACTCAACAAAGCAACACATTCTCAGTCACCATTGAAGCCCAACATCACGACGCTCATATTTGACTTGG
GCGACGTACTTCTCACGTGGTCCGACTCAACACCTAAATCTCCACTGCCCCAAAAATTGTCAAGGGAATACTACGTTCACT
GACCTGGTTTGAGTACGAGAAAGGGAACTTGACAGAGTCCCAGACCTACGGGCAAGTTGCTCAGGAATTTGGAGTGGATGCT
TCCGAAGTCAAAGCTTCCTTCGAAGCAGCTCGCGACTCGCTCAAGAGCAACCCAATGCTTCTCCAGTTGATCCGTAGCCTCA
AAGACTCTGGCCACGTCATTTACGCAATGTCTAACATATCTGCTCCCGACTGGGAATTTTTGAAGACGCGGGCAGACCTCTC
AGATTGGGCTCTTTTTGACAGAGTCTTCCCTTCTGCCGAAGCGCATGACCGCAAGCCGAACATTGGTTTCTATCAGCACGTC
ATAAACGAGACTGGTCTGAACCCGTCCAACACTGTCTTTGTCGATGACAGGATCGAGAATGTTGTATCCGCACGCTCAGCAG
GAATGCACGGGATCGTGTTTGACGACATAAATAATGTGATCCGACAGTTGAAAAACCTCTGCGAGGATCCGATTCACCGCGC
ACGATCTTTTCTTTATGCAAATAAGAAGTGTTTGAATACGGTTAGCACAGATGGCACAATTGTGAGCGAGAACTTCTCGCAA
TTGTTGATCCTTGAGGCCATTGGCGACGAAAGCCTAGTCGACTTTGTGAGGCATGAGGGCCGATTCAACTTCTTCCAGGGGG
AGGCCAAACTCATCATGACGAATCACTACCCCGATGATTTCGATACTACATCCATAGGTTTAACCGTTGTTCCATATATTGA
CGACAAGACTAGAAATAGAGTTATGGATGAGATCCTGGCCTACCAAAGCGAAGACGGCATTGTGCTGGTATACTTTGACCAC
AAGCGCCCCAGGATTGATCCTGTTGTCTGTGTCAATGTCCTCACCCTCTTCTATAGGTATGGCCGTGGGCACCAGCTTCAAA
AGACACTGGATTGGGTCGAACAGGTCCTGATCAACCGTGCGTGCGTCCGGCACGTTCTATTACGCAACAGAGGAACAATT
CCTCTTTTTCCTCTCCCGCCTGATCCAAAGCTCTCCGGACGTACGACAGCGGTTGGAAGGGGTCTTTAAAAGAAGAGTAGTC
GAGCGGTTTGGTGCAGACGGCGACGCTCTCGCTATGGCGATGCGCATTCACACCGCGGCGAGCGTGGGCCTCGTTGACCATG
TCGATCTTGACAAGCTGTTCGCATTGCAGCAAAATGACGGTTCTTGGAGAGACAGCGCTTTCTACAGATTTCCGTCGGCCAG
GCAACTGGCTAGTAACGACGGCTTGACGACTGCAATCGCTATTCAGGCCATTCAAGCTGCGGAGAGGCTCAGGGAGGATGGG
AACGTGCTTTGA SEQ ID NO: 34-ACg006372 optimized cDNA
ATGCGCCGTAATGTCCTGAACAAAGCAACCCATAGCCAGTCACCGTTGAAACCGAATATCACCACGCTGATTTTTGACTTGG
GCGATGTCCTGCTGACCTGGAGCGACAGCACTCCGAAATCTCCGTTGCCGCCGAAGATCGTCAAGGGCATCCTGCGTAGCCT
GACTTGGTTCGAGTACGAAAAGGGCAATTTGACCGAAAGCCAAACGTATGGTCAGGTCGCGCAAGAATTTGGTGTGGATGCC
TCTGAAGTCAAGGCCAGCTTTGAGGCTGCGCGTGATAGCTTGAAATCGAATCCGATGCTGCTGCAGCTGATTCGCAGCCTGA
AAGATTCCGGTCACGTGATCTACGCCATGAGCAACATCAGCGCGCCTGATTGGGAATTTCTGAAAACCCGCGCTGACCTGTC
TGACTGGGCCCTGTTTGACCGCGTGTTCCCGTCTGCCGAGGCACATGACCGCAAACCGAACATTGGCTTTTACCAACACGTG
ATCAATGAAACGGGTCTGAATCCATCCAATACCGTGTTCGTTGACGACCGTATTGAAAACGTTGTTAGCGCACGTAGCGCTG
GTATGCACGGTATCGTTTTCGATGACATTAACAACGTCATTCGCCAGCTGAAGAATCTGTGCGAGGACCCAATTCACCGTGC
ACGTTCCTTTTTGTATGCGAACAAAAAGTGCCTGAATACCGTGAGCACCGATGGTACGATCGTCAGCGAGAACTTTAGCCAG
CTTCTGATTCTGGAAGCCATTGGTGACGAGTCCCTGGTAGACTTCGTCCGCCATGAGGGCCGTTTTAACTTCTTCCAGGGTG
AGGCAAAGCTGATCATGACCAATCACTACCCGGACGATTTCGATACCACGAGCATTGGTCTGACCGTTGTCCCGTATATCGA
TGACAAAACGCGTAATCGTGTGATGGATGAAATCCTGGCGTATCAGTCCGAGGATGGTATCGTTCTGGTGTACTTCGATCAC
AAGCGTCCGCGCATTGACCCGGTCGTTTGTGTGAACGTTCTGACGCTGTTCTACCGCTATGGTCGTGGCCATCAACTGCAGA
AAACCCTGGACTGGGTTGAGCAAGTCCTGATTAATCGTGCGTGTGCGAGCGGCACGTTCTACTACGCGACCGAAGAACAGTT
CCTGTTTTTCCTGAGCCGTCTGATTCAGTCGAGCCCTGACGTGCGCCAACGTCTGGAAGGCGTGTTCAAGCGTCGTGTCGTT
GAGCGCTTTGGTGCGGACGGTGATGCCCTGGCAATGGCGATGCGTATCCATACCGCAGCGAGCGTTGGCCTGGTGGACCACG
TGGATCTGGATAAGCTGTTCGCGCTGCAACAGAACGACGGTAGCTGGCGCGATAGCGCGTTTATCGTTTTCCGAGCGCGCG
TCAACTCGCGAGCAACGACGGCTTGACCACGGCAATTGCTATTCAGGCCATCCAAGCGGCTGAGAGATTACGTGAGGATGGT
AACGTTCTGTAA KIA75676.1
SEQ ID NO: 35-KIA75676.1 protein
MVRALILDLGDVLFNWDAPKSTPVSRKTLSQMLHSDIWGEYECGQLTEPESYKALASRYSCQAQDVADTFYLARESLRLDAT
FKTFLQDLKQRANGSLRVYGMSNISQPDYEVLLSKADDLSLFDIKFPSGHVGMRKPDLAFFRHVLREISTASEDIVFVDDNL
ENVTSARSLGMQGIVFRDKEDVQRQLRNLFGSPAERGREYLSINKTKLQSVTTTNIPILDNFGQLLILEATRDPDLVSMHPG
QRTWNFFIGSPTLTTDAFPDDMDTTSLGLSIIPPSPEIAASVMDEIVTRLNKDGIVPTYFDSTRPRVDPIVCVNVLTLFAKY
GREDELSGTIAWVRDVLYHRAYLAGTRYYASPEAFLFFFTRFTRNLRPGPRKQELTALLSQRLQERNKTPVDALALSMRIIA
CLTLGIESPADDVATLTGMQCGDGGWPACVIYKYGAGGLGITNRGVSTAFAVKAITTTPLAVQPEVSVSAGAGGSSRPVGAD
AAAVSLRPRWRAVVQSLHPLSRVGGLVAVIFAALHFNLAWLYNVSLASRIV SEQ ID NO: 36-KIA75676.1 cDNA
ATGGTCCGCGCACTGATTCTCGATCTCGGCGACGTCCTCTTCAACTGGGACGCCCCAAAGTCAACCCCCGTTTCCCGCAAGA
CACTCAGCCAGATGCTGCATAGCGACATCTGGGGCGAATACGAATGTGGCCAACTGACAGAGCCGGAAAGCTACAAGGCGCT
```

```
TGCCAGCCGCTATTCTTGCCAGGCTCAAGATGTTGCAGATACCTTCTATCTAGCCCGCGAATCGCTGAGGCTCGATGCGACC
TTCAAGACCTTCCTGCAGGACTTGAAGCAGAGGGCCAACGGCTCACTTCGCTATATGGGATGTCCAACATCTCCCAGCCCG
ATTATGAGGTCCTGCTGTCCAAGGCGGATGACTTGAGCCTGTTTGACAAGATCTTCCATCCGGCCACGTCGGGATGCGTAA
GCCTGACCTTGCGTTTTTTCGACATGTCCTGCGTGAGATCTCGACGGCCAGCGAGGATATTGTGTTTGTTGACGACAACCTG
GAGAACGTGACATCTGCCCGGTCTCTGGGCATGCAGGGGATTGTCTTTCGCGACAAGGAGGATGTACAGAGACAGCTGCGGA
ACCTCTTTGGCAGTCCTGCTGAACGTGGAAGGGAGTATTTGTCCATCAACAAGACAAAGCTCCAGAGCGTCACGACGACCAA
TATCCCCATTCTCGACAACTTTGGCCAGCTCCTTATCCTCGAAGCCACCAGAGACCCAGACCTGGTGTCCATGCATCCTGGA
CAGAGGACCTGGAACTTTTTCATCGGATCTCCAACTCTGACAACGGACGCCTTCCCAGACGATATGGACACCACCTCACTTG
GCCTTTCTATTATACCCCAAGTCCCGAGATTGCAGCGTCCGTGATGGATGAGATTGTGACCCGCCTGAACAAGGACGGCAT
TGTCCCAACATATTTTGACAGCACCAGACCCCGCGTCGACCCGATCGTCTGCGTCAACGTTCTCACCCTCTTCGCTAAATAC
GGCCGCGAAGACGAGCTGTCCGGGACCATAGCCTGGGTGCCGCGATGTGCTGTATCACAGGGCGTACCTTGCAGGGACCAGAT
ACTACGCATCCCCAGAAGCATTCCTTTTCTTCTTCACGCGCTTCACCCGAAACCTGCGCCCGGGCCCGCGCAAGCAGGAGCT
CACGGCGCTGCTGTCCCAGCGCCTGCAGGAGCGCAACAAGACGCCCGTTGACGCACTTGCGCTCTCGATGCGGATTATTGCG
TGCCTCACGCTGGGTATTGAATCCCCGCTGACGACGTGGCTACCCTCACGGGCATGCAGTGTGGGGATGGCGGGTGGCCGG
CCTGTGTCATCTACAAGTACGGCGCCGGTGGGCTGGGGATCACGAACAGGGGGGTCTCGACCGCGTTTGCTGTCAAGGCAAT
CACTACTACTCCTTTGGCGGTGCAGCCTGAAGTTAGTGTCAGCGCAGGTGCAGGAGGCAGCAGTCGCCCTGTGGGTGCCGAT
GCTGCTGCAGTCTCGCTCCGCCCGAGATGGCGAGCTGTTGTGCAGAGTCTCCATCCGCTCTCTCGGGTTGGTGGGTTGGTGG
CCGTCATTTTTGCTGCACTGCATTTCAACTTGGCCTGGCTTTATAATGTGTCCCTTGCTAGTAGGATCGTTTAG
```

SEQ ID NO: 37-KIA75676.1 optimized cDNA
```
ATGGTTCGTGCATTGATTTTGGATTTGGGTGATGTGTTGTTTAACTGGGATGCGCCTAAGAGCACCCCGGTTTCCCGCAAGA
CTCTGAGCCAAATGCTGCACTCGGATATTTGGGGCGAGTACGAGTGTGGTCAACTGACTGAGCCGGAGTCCTATAAAGCCCT
GGCGAGCCGCTATAGCTGCCAGGCGCAAGATGTCGTGACACCTTTTACCTGGCGCGTGAGAGCCTGCGTCTGGACGCAACGT
TTAAGACCTTCCTGCAAGATCTGAAGCAACGCGCCAACGGTTCTCTGCGTGTCTATGGTATGAAGCAATATCAGCCAGCCGGA
TTACGAAGTCCTGCTGAGCAAAGCTGACGATCTCAGCCTGTTTGACAAAATCTTTCCGTCGGGTCACGTTGGTATGAGAAAG
CCTGACCTGGCGTTTTTCCGTCACGTTCTGCGTGAGATCAGCACGGCTAGCGAAGATATTGTGTTTGTTGACGACAATTTGG
AAAACGTCACGTCTGCACGCTCCCTGGGTATGCAAGGCATCGTCTTTCGTGATAAGGAAGATGTCCAGCGCCAGCTGCGCAA
TCTGTTCGGTTCCCCGGCAGAGCGCGGTCGTGAGTATCTGAGCATTAATAAGACCAAACTGCAGAGCGTGACCACCACCAAT
ATCCCGATTCTGGACAACTTCGGTCAGTTGCTGATCCTGGAAGCTACCCGTGACCCGGATTTAGTCAGCATGCATCCAGGCC
AACGTACGTGGAACTTCTTCATTGGCAGCCCGACCTTGACGACCGACGCGTTTCCGGACGATATGGACACGACTTCTCTGGG
CCTGAGCATCATCCCGCCGAGCCCGGAAATTGCAGCAAGCGTTATGGACGAAATCGTCACCCGTCTGAATAAAGATGGTATT
GTGCCGACCTACTTCGACAGCACGCGTCCACGTGTGGACCCGATCGTCTGCGTTAACGTCCTGACCTTGTTTGCGAAATATG
GTCGTGAAGATGAACTGAGCGGCACGATTGCGTGGGTCCGCGACGTTCTGTATCATCGCCCATACCTGGCGGGCACGCGCTA
CTACGCGTCCCCAGAGGCCTTCCTGTTCTTCTTTACGCGTTTCACCCGCAATCTGCGTCCGGGTCCGCGTAAACAAGAACTT
ACGGCGCTGCTGAGCCAGCGTCTGCAGGAACGCAACAAGACGCCGGTTGACGCTCTGGCCCTGAGCATGCGTATCATCGCCT
GTCTGACCCTGGGCATTGAGAGCCCCGACAGCGACGTGGCCACCCTGACCGGTATGCAGTGTGGTGATGGTGCTGGCCGGC
GTGCGTGATCTACAAATATGGTGCGGGTGGCTTGGGTATCACGAATCGTGGCGTTAGCACTGCCTTCGCGGTGAAAGCGATT
ACGACCACCCGCTGGCAGTGCAGCCAGAAGTCAGCGTCAGCGCTGGTGCCGGCGGCTCCAGCCGCCCGGTTGGTGCGGATG
CGGCAGCGGTTAGCTTGCGTCCGCGTTGGCGTGCGGTTGTGCAGAGCCTGCATCCGCTGAGCCGCGTGGGTGGCCTGGTTGC
CGTGATCTTCGCGGCACTGCACTTTAACCTGGCGTGGCTGTACAACGTAAGCCTGGCTAGCCGTATTGTGTAA
```

XP_001820867.2
SEQ ID NO: 38-XP_001820867.2 protein
```
MTRWKSSQYQAIIFDLVVGILTWDLPEDTVISAQIFKRMLTSQTWSDYERGNLSENGCYQRLAEDFGIDSADIAHTVRQARE
SLVTDTAIMNIISEIRAGANHIAIFAMSNISQPDYAALLLDHRGMCSFDRVFPSGCYGTRKPELSFYNKVLREIDTPPENVI
FVDDQLENVISAQSIGIHGIAYTNAAELGRQLRNLIFDPVERGREFLRRNAGEFHSITETDQIVRENFSQLLILEATGDKSL
VSLEYHQKSWNFFQGNPILTTETFPDDVDTTSLALMTLPTDTKTANLLLDQILGLVNADEIVTTYFDQTRERIDPVVCVNVL
RLFCTYGRGIALPLTLQWVYDVLAHRAYINGTRYYTSPESFLYFVGQLCRFSTGVLALRPLETLLIDRLKERLQVKADPLSA
MRILTCLSVGVSQVEVDLRELLSMQCEDGSWEHCPFTRYGLSKVSIGNRGLTTAFVVKAVEMCRGS
```

SEQ ID NO: 39-XP_001820867.2 cDNA
```
ATGACTCGATGGAAATCGTCCCAATACCAAGCAATTATCTTTGACCTAGGCGGTGTCATTTTAACATGGGACCTCCCGGAAG
ACACTGTGATATCGGCCCAGATCTTTAAGAGAATGCTCACATCGCAGACATGGTCAGATTATGAGCGCGGAAATCTCAGCGA
AAATGGTTGCTACCAGAGGTTGGCCGAGGATTTTGGCATTGACTCTGCCGACATTGCACATACCGTTAGACAAGCACGGGAA
TCCCTTGTCACTGATACCGCTATCATGAACATTATATCTGAGATCAGAGCTGGGGCTAACCATATTGCTATCTTCGCTATGT
CGAACATCTCCCAACCAGATTATGCGGCTCTGCTCCTTGATCATCGCGGGATGTGCAGTTTTGACCGGGTGTTCCCATCTGG
ATGCTACGGGACAAGGAAACCAGAGCTCTCATTCTATAACAAAGTCTTGCGGGAGATTGACACCGCCACCGGAAAACGTCATC
TTTGTCGATGATCAGCTGGAAAATGTGATCTCTGCGCAGTCCATTGGACATACACGGGATTGCCTATACGAATGCTGCTGAAC
TCGGTCGACAGCTTAGGAACCTAATATTTGACCCTGTAGAGAGGGGTAGGGAATTCTTACGGCGCAATGCTGGAGAGTTCCA
TAGCATCACTGAAACCGATCAAATTGTTCGGGAAAATTTCTCACAGTTGCTCATTCTAGAAGCGACTGGTGATAAGAGTCTG
GTATCTCTTGAATATCACCAGAAGAGCTGGAATTTCTTCCAAGGAAACCCTATTCTCACGACAGAGACATTCCCAGATGATG
TTGACAACATCTCTTGCCTTGATGACTCTACCTACGACACAAAAACTGCAAATTTGTTACTCGACCAGATTTTGGGGCT
AGTCAACGCTGATGAAATCGTAACAACATACTTTGACCAGACCCGAGAACGGATCGATCCAGTAGTCTGCGTCAATGTCCTT
CGTCTCTTTTGCACCTACGGCCGGGGCATTGCGCTCCCTTTGACTCTTCAGTGGGTGTACGACGTCCTGCTCATCGGGCAT
ATATAAACGGTACACGTTACTACACAAGTCCCGAAAGCTTCCTATACTTCGTCGGTCAACTTTGTCGATTCTCAACAGGGGT
ACTGGCACTTCGGCCGCTGGAAACGTTGCTTATAGATCGTCTCAAGGAACGTCTTCAGGTCAAAGCAGATCCTCTATCACTC
GCTATGCGGATCTTGACCTGTTTGTCCGTTGGTGTGTCTCAAGTTGAAGTCGATCTCCGAGAGTTGCTCTCGATGCAGTGTG
AAGATGGCTCGTGGGAACATTGTCCATTCACCCGGTATGGTTTGTCCAAAGTGAGCATTGGCAATCGGGGCCTTACAACTGC
TTTTGTGGTCAAGGCGGTTGAAATGTGTCGAGGCAGTTAG
```

SEQ ID NO: 40-XP_001820867.2 optimized cDNA
```
ATGACTCGTTGGAAAAGCTCTCAATATCAGGCAATCATTTTCGATCTGGGCGGTGTTATTCTGACCTGGGACTTGCCGGAAG
ATACGGTTATCTCCGCGCAAATCTTTAAGCGTATGCTGACCAGCCAGACCTGGTCCGATTATGAGCGCGGTAATCTGAGCGA
GAACGGCTGCTATCAACGTTTGGCGGAAGATTTCGGCATCGATAGCGCCGATATTGCCCACACCGTCCGTCAGGCACGTGAG
TCCCTGGTGACCGACACCGCCATCATGAATATCATCTCCGAGATCCGTGCAGGCGCGAACCACATCGCAATTTTCGCGATGA
GCAACATCTCACAGCCGGATTACGCTGCGCTGCTGCTGGACCATCGCGGTATGTGCAGCTTTGACCGCGTCTTTCCGAGCGG
TTGTTACGGCACCCGTAAGCCTGAGCTGAGCTTCTACAATAAAGTGCTGCGTGAAATTGACACCCCGCCGGAAAATGTTATT
```

Sequence Listings

```
TTCGTTGACGATCAATTGGAAAATGTGATTAGCGCGCAAAGCATTGGTATTCATGGCATTGCGTATACGAATGCCGCGGAAC
TGGGCCGCCAGCTGAGAAACCTGATCTTCGATCCGGTGGAGCGCGGTCGTGAGTTCCTGCGTCGTAACGCTGGTGAGTTTCA
CTCTATTACGGAAACGGACCAGATTGTGCGCGAGAACTTCAGCCAGCTGCTGATTCTGGAAGCGACCGGTGACAAAAGCCTG
GTTAGCCTGGAATACCACCAAAAGTCGTGGAACTTCTTCCAAGGTAACCCAATCCTGACGACGGAAACCTTCCCGGACGATG
TTGACACTACTAGCCTGGCTCTGATGACGCTGCCGACGGACACCAAGACCGCGAATCTGTTGCTGGACCAGATTCTGGGTTT
GGTTAATGCCGATGAAATTGTGACTACGTACTTCGACCAGACCCGTGAGCGTATCGATCCAGTGGTCTGTGTGAATGTCCTG
CGCCTGTTCTGTACGTACGGCCGCGGCATCGCGCTGCCGCTGACCCTGCAATGGGTCTACGATGTGCTGGCGCACCGCGCAT
ACATTAACGGTACGCGTTATTACACCAGCCCGGAGAGCTTTCTGTATTTTGTCGGTCAGCTCTGTCGTTTTAGCACCGGTGT
GCTGGCACTGCGTCCGCTGGAGACTCTGCTGATTGACGTCTGAAAGAGCGCCTGCAAGTTAAAGCTGACCCGCTGAGCCTG
GCAATGCGCATCCTTACGTGCTTATCTGTCGGTGTCAGCCAGGTTGAAGTGGACTTGCGTGAGTTGTTGAGCATGCAGTGCG
AGGACGTAGCTGGGAGCATTGCCCGTTCACCCGCTACGGCCTGAGCAAGGTTTCCATCGGTAACCGTGGCCTGACCACGGC
GTTTGTGGTTAAAGCCGTCGAGATGTGCCGTGGCAGCTAA
```

CEN60542.1
SEQ ID NO: 41-CEN60542.1 protein
```
MVRALILDLGDVLFNWDAPASTPISRKTLGQMLHSEIWGEYERGHLTEDEAYNALAKRYSCEAKDVAHTFVLARESLRLDTK
FKTFLQTLKQNANGSLRVYGMSNISKPDFEVLLGKADDWTLFDKIFPSGHVGMRKPDLAFFRYVLKDISTPVEDVVFVDDNL
DNVTSARSLGMRSVLFHKKDEVQRQLTNIFGSPAERGLEYLSANKTNLQSATTTDIPIQDNFGQLLILEATEDPSLVRMEPG
KRTWNFFIGSPSLTTDTFPDDLDTTSLALSIVPTSPDVVNSVIDEIISRRDKDGIVPTYFDNTRPRVDPIVCVNVLSMFAKY
GREHDLPATVAWVRDVLYHRAYLGGTRYYGSAEAFLFFTRFVRNLFPGTLKQDLHALLSERVRERLNTPVDALALSMRIQA
CHALGFDAPADIATLITMQDEDGGWPAAVIYKYGAGGLGITNRGVSTAFAVKAITGSPVKTETNIGGDGARAVSAMSSLEAR
RLQPISSVGDWVRFIIASLHVHLAWLWNVLLLSKVV
```

SEQ ID NO: 42-CEN60542.1 cDNA
```
ATGGTCCGCGCACTCATCCTCGATCTCGGCGATGTCCTCTTCAACTGGGACGCGCCTGCGTCCACCCCCATTTCACGCAAGA
CCCTCGGCCAGATGCTGCATAGTGAGATCTGGGGTGAGTATGAACGTGGCCATTTGACAGAAGACGAGGCATACAACGCACT
CGCGAAGCGGTATTCCTGCGAGGCAAGGATGTCGCACATACCTTTGTCCTGGCACGAGAATCGCTGCGGCTCGACACGAAA
TTCAAAACGTTTCTGCAGACTCTAAAGCAGAATGCCAACGGCTCCCTTCGTGTCTATGGCATGTCGAATATATCGAAACCGG
ATTTCGAAGTCCTGCTGGGCAAGGCCGATGACTGGACTCTGTTTGACAAGATCTTCCCCTCTGGCCATGTCGGTATGCGCAA
GCCAGATCTTGCCTTCTTCCGCTATGTGCTCAAGGACATTTCAACGCCTGTCGAGGATGTGGTGTTTGTTGACGATAACCTG
GACAACGTGACGAGTGCTCCGGTCTCTGGGCATGCGCAGCGTCCTCTTTCATAAGAAAGACGAGGTCCAGCGACAGCTCACCA
ACATCTTTGGCAGCCCTGCTGAGCGGGGCTTGGAGTATCTCTCCGCCAACAAGACGAATCTGCAGAGTGCTACCACGACAGA
TATCCCAATCCAGGATAACTTTGGCCAACTTCTGATTCTCGAGGCACTGAAGACCCATCGCTGGTCCGCATGGAGCCCGGT
AAGCGAACCTGGAATTTCTTCATCGGTTCTCCATCCCTCACAACCGACACCTTCCCCGACGATCTCGACACCACATCCCTTG
CCCTCTCCATCGTACCCACAAGCCCCGACGTCGTCAACTCGGTCATCGACGAGATTATCAGCCGTCGCGACAAGGACGGTAT
CGTCCCGACTTACTTCGACAACACCCGCCCCCGCGTGGACCCAATCGTCTGCGTAAACGTCCTCTCCATGTTCGCAAAGTAC
GGCCGCGAGCACGACCTCCCCGCAACAGTTGCGTGGGTCCGCGACGTCTTGTATCATCGAGCATACCTCGGCGGAACACGGT
ACTACGGGTCAGCTGAGGCCTTCCTCTTCTTCTTCACTCGCTTCGTTCGCAACCTCCGACCGGGAACTCTCAAGCAGGATCT
ACACGCATTGCTATCAGAGCGCGTGCGCGAGCGACTCAATACCCCCGTCGACGCACTCGCCCTGTCAATGCGCATCCAGGCC
TGTCATGCGCTGGGCTTTGACGCCCCCGCAGACATTGCGACGCTCATCACAATGCAGGACGAGGACGGCGGGTGGCCGGCAG
CCGTCATCTACAAGTACGGGGGCCGGGGGTTGGGGATCACGAACCGGGGTGTTTCGACTGCGTTGCCGTAAAGGCGATTAC
AGGGTCGCCCGTGAAGACTGAAACCAACATAGGCGGCGATGGAGCTCGCGCTGTCTCGGCCATGTCCTCCTTGGAGGCGAGG
AGGCTACAGCCGATCTCGTCGGTTGGGGACTGGGTGCGGTTTATCATTGCGTCGTTGCATGTCCATCTGGCTTGGCTTTGGA
ATGTTTTGCTTTTGAGCAAGGTTGTTTGA
```

SEQ ID NO: 43-CEN60542.1 optimized cDNA
```
ATGGTTCGTGCGTTGATTTTGGATTTGGGTGATGTGTTGTTTAATTGGGACGCCCCTGCAAGCACTCCGATCAGCCGTAAGA
CCCTGGGCCAGATGCTGCATTCCGAGATTTGGGGTGAGTATGAGCGTGGTCACCTGACCGAAGATGAAGCGTACAACGCGCT
GGCCAAAGCGCTACAGCTGCGAGGCAAAAGACGTGGCGCATACTTTTGTTTTGCGCTGGCGTGGAAAGCCTGCGCCTGGATACCAAG
TTTAAGACTTTTCTGCAGACCCTGAAACAGAACGCGAACGGCTCGCTGCGTGTTTATGGTATGTCCAATATCAGCAAACCGG
ATTTTGAAGTGCTGCTGGGTAAAGCTGACGACTGGACCTTGTTCGACAAGATCTTCCCGAGCGGTCATGTCGGTATGCGCAA
ACCGGACCTGGCTTTCTTTCGTTACGTGCTGAAAGACATCAGCACCCCGGTTGAGGATGTTGTGTTTGTTGACGATAACCTG
GATAATGTGACGTCTGCCCGTTCCCTGGGTATGCGTAGCGTCCTGTTTCACAAAAAAGACGAAGTCCAACGTCAGCTGACCA
ACATTTTCGGTAGCCCTGCTGAGCGCGGTCTGGAGTATCTGTCCGCGAACAAGACCAATCTGCAAAGCGCAACCACCACCGA
CATTCCCATCCAAGACAACTTTGGTCAATTACTGATTCTGGAAGCCACCGAAGATCCGAGCCTGGTACGCATGGAACCGGGC
AAGCGTACCTGGAATTTCTTCATTGGCTCTCCGAGCCTGACGACGGATACCTTCCCGGATGACCTGGACACGACGAGCCTCG
CACTGTCCATCGTGCCGACCAGCCCAGATGTTGTTAATAGCGTGATCGATGAAATTATCTCGCGACGAGGACAAGGACGGTAT
TGTGCCGACGTACTTTGATAACACGCGCCCGCGTGTGGACCCGATTGTTTGTGTTAACGTTCTGTCTATGTTCGCGAAATAT
GGCCGTGAGCACGATCTGCCGGCGACGGTCGCGTGGGTCCGCGACGTCCTCTATCATCGCGCATACCTGGGTGGCACCAGAT
ACTACGGTAGCGCGGAAGCCTTCCTTTTCTTCTTTACGCGCTTTGTGCGTAATCTGCGTCCGGGCACGCTGAAACAAGATCT
GCACGCGTTGCTGAGCGAGCGTGTCCGTGAGCGCCTGAATACCCCGGTGGATGCGCTGGCGCTGAGCATGCGCATTCAGGCT
TGCCACGCACTGGGCTTTGACGCCCCAGCTGACATCGCGACGCTGATTACCATGCAGGATGAAGATGGTGGCTGGCCGGCGG
CAGTTATCTACAAATATGGTGCGGGTGGCCTGGGCATTACGAACCGTGGTGTGTCCACGGCATTCGCGGTGAAGGCAATCAC
GGGTAGCCCGGTTAAAACCGAAACCAACATCGGCGGCGACGGTGCCCGTGCAGTGTCGGCCATGAGCAGCCTGGAAGCCCGT
CGTTTGCAGCCGATTTCTAGCGTCGGCGACTGGGTCCGTTTCATCATCGCATCACTGCACGTCCACCTGGCGTGGCTGTGGA
ATGTCCTGCTGCTGAGCAAAGTCGTTTAA
```

XP_009547469.1
SEQ ID NO: 44-XP_009547469.1 protein
```
MSMIPRSCNLILDIGVLFTWSPKTSTSISPRTMKSILSSTTWHQYETGHISQGDCYRLIGNQFSIDPQEVGLAFQQARDSLQ
PNVDFIHFIRALKAESHGTLRVFAMSNISQPDYAVLRTKDADWAVFDDIFTSADAGVDPNTVFV
DDKGDNVLSARSLGLHGIVFDSMDNVKRALRYISDPIRRGREFLQARAGHLESETNTGIEIGDNFAQLLILEATKDRTLVNY
MDHPNKWNFFRDQPLLTTEEFPFDLDTTSIGTLATQRDDGTANLVMDEMLQYRDEDGIIQTYFDHERPRIDPIVCVNVLSLF
YSRGRGSELAPTLEWVRGVLKHRAYLDGTRYYETGECFLFFLSRLLQSTKDAALHASKSLFAERVKERIGAPGDALALAMR
ILACAAVGVRDEIDLRSLLPLQCEDDGWEAGWVYKYGSSGVKIGNRGLTTALALNAIEAVEGRRTRPKSGKISRVSRHSEVA
AAPRSSTSSHRSNRSISRTFQAYFKASWTSMKQVAVA
```

| Sequence Listings |
| --- |

SEQ ID NO: 45-XP_009547469.1 cDNA
ATGTCCATGATACCCAGATGCTCGAATCTCATCCTCGACATCGGGGATGTTCTCTTCACATGGTCTCCGAAGACGTCCACTT
CGATCTCCCCCCGCACCATGAAGAGACATACTGTCATCGACGACCTGGCACCAATACGGACGCACATTTCACAGGGCG
ACTGCTACCGCCTCATAGGCAACCAGTTCTCCATCGATCCTCAGGAAGTCGGACTTGCATTCCAACAAGCTCGGGACTCATT
GCAGCCTAATGTTGACTTCATTCACTTCATCCGCGCCCTCAAGGCGGAATCACACGGGACGCTGCGCGTCTTCGCTATGTCC
AACATCTCTCAGCCCGATTACGCAGTTCTTCGGACTAAGGACGCCGACTGGGCCGTTTTGACGATATATTCACGTCTGCAG
ATGCTGGGGTTCGAAAGCCACACCTTGGGTTCTACAAGTTGGTACTCGGAAAGATCGGCGCCGATCCAAACGATACCGTCTT
CGTCGATGACAAGGGGGACAATGTCCTCTCTGCACGGTCTCTCGGCCTTCATGGAATCGTCTTTGACAGTATGGACAACGTC
AAGCGAGCCCTGCGCTACTTGATCAGCGACCCCATACGGCGAGGACGAGAGTTTCTCCAAGCGCGAGCCGGCCATTTGGAGT
CGGAGACCAATACGGGCATCGAAATCGGTGATAATTTTGCCCAGCTCCTTATTCTCGAGGCCACGAAGGATAGGACACTCGT
CAATTATATGGACCATCCGAACAAATGGAATTTCTTCCGAGATCAACCGCTCCTCACAACGGAGGAGTTCCCTTTCGATCTC
GATACGACATCTATTGGAACGCTTGCCGACGCAGCGCGATGATGGGACTGCCAATCTAGTAATGGATGAGATGCTTCAGTACC
GTGATGAGGATGGCATAATACAAACATATTTCGATCATGAACGACCGAGGATAGATCCCATCGTCTGTGTCAACGTCTTGAG
CCTTTTCTACTCCCGGGGTCGTGGTTCGGAGCTAGCACCGACACTAGAGTGGGTGCGTGGTGTCCTCAAGCACCGCGCGTAT
CTCGATGGAACGCGATACTACGAGACAGGCGAATGCTTCCTTTTCTTCCTCAGCCGGCTCTTGCAATCAACCAAGGACGCCG
CCTTGCACGCATCGTTGAAATCTTTGTTCGCCGAACGGGTCAAGGAGCGCATAGGGGCACCAGGGGACGCGCTGGCGCTGGC
GATGCGTATACTGGCATGCGCAGCAGTGGGCGTGCGGGACGAGATCGATCTTCGATCACTATTACCTCTGCAGTGCGAGGAT
GGGGGGTGGGAGGCAGGCTGGGTGTACAAGTATGGGTCTTCGGGAGTCAAGATCGGCAATCGTGGCCTCACGACTGCGCTTG
CGCTCAATGCCATCGAGGCTGTGGAGGGACGTCGCACGAGGCGAAGTCGGGTAAGATCAGCCGAGTCAGCCGTCATTCTGA
GGTCGCAGCAGCGCCACGGTCTTCCACCAGCAGTCATCGTTCTAATCGCTCGATCTCAAGGACATTCCAGGCGTACTTCAAG
GCGTCGTGGACATCGATGAAACAGGTGGCCGTGGCGTGA

SEQ ID NO: 46-XP_009547469.1 optimized cDNA
ATGAGCATGATTCCACGTTGTAGCAATCTGATTCTCGACATCGGTGATGTGTTGTTTACGTGGAGCCCGAAAACCAGCACCA
GCATTAGCCCGCGTACCATGAAATCTATCCTGAGCCTCTACCACCTGGCATCAATATGAGACTGGCCACATCAGCCAGGGTGA
TTGCTACCGCCTGATCGGTAATCAGTTCTCCATCGACCCGCAAGAGGTCGGTTTGGCCTTCCAGCAAGCCAGAGACAGCCTG
CAACCGAATGTTGATTTCATCCATTTCATTCGTGCCCTGAAAGCTGAGTCGCACGGCACCCTGCGCGTTTTTGCGATGAGCA
ATATCAGCCAACCTGACTATGCAGTCCTGCGTACGAAAGACGCGGACTGGGCTGTTTTTGATGATATCTTCACGAGCGCGGA
TGCTGGTGTTCGTAAACCGCACCTGGGTTTTTATAAACTGGTCTTAGGCAAGATTGGCGCGGACCCTAACGACACCGTTTTT
GTGGATGATAAGGGTGACAACGTCCTCTCTGCACGTTCCTGGGTCTGCACGGTATCGTTTTGATTCAATGGACAACGTGA
AGCGCGCACTGCGCTACCTGATTAGCGACCCGATCCGCCGCGGCCGTGAATTTCTGCAGGCCCGTGCGGGTCACCTGGAGTC
CGAAACGAACACGGGTATTGAGATTGGTGATAATTTCGCGCAATTGCTGATCCTGGAAGCGACCAAAGATCGTACTCTGGTG
AACTACATGGACCACCCGAACAAGTGGAACTTCTTCCGTGACCAGCCGCTCGTGACCACCGAAGAATTTCCGTTCGACCTGG
ACACGACCAGCATTGGCACGCTGGCCACCCAACGTGACGATGGTACGGCGAATCTGGTAATGGACGAAATGTTGCAGTATCG
TGACGAAGATGGCATCATTCAGACCTATTTCGATCATGAGCGCCCGCGTATTGATCCGATTGTTTGTGTGAATGTGCTGTCT
CTGTTCTACAGCCGTGGCCGTGGCTCTGAGTTGGCGCCGACGCTGGAATGGGTGCGCGGTGTGTTGAAACATCGTCGCGTACC
TGGATGGTACGCGTTATTACGAGACTGGTGAGTGTTTCCTGTTTTCCTGAGCCGTCTGCTGCAGAGCACCCAAAGACGCAGC
CCTGCACGCGAGCCTGAAGTCCCTGTTTGCAGAGCGTGTTAAAGAGCGCATCGGTGCGCCGGGCGATGCTCTGGCGCTGGCT
ATGCGCATCCTGGCGTGCGCCGCTGTTGGTGTGCGCGATGAAATTGATTTGCGTAGCCTGCTGCCGCTGCAATGCGAAGATG
GCGGCTGGGAAGCGGGCTGGGTCTACAAATACGGCAGCAGCGGTGTGAAGATTGGCAATCGCGGTCTTACCACGGCGCTGGC
ATTGAATGCTATCGAAGCCGTTGAGGGCCGTCGCACCCGCCCAAAGTCCGGTAAGATCAGCCGTGTTAGCCGTCATAGCGAA
GTCGCAGCGGCACCGCGTTCCTCGACGAGCAGCCACCGTAGCAACCGTAGCATTAGCCGCACCTTCCAGGCATATTTTAAAG
CGAGCTGGACCAGCATGAAACAAGTCGCAGTGGCGTAA KLO09124.1
SEQ ID NO: 47-KLO09124.1 protein
MSIHGSSMSSYSSTVPSMTSSPASTSTPSSPASSIHEIGPVPEARRKGQCNALIFDLGDVLFTWSAETKTTISPKLLKKILN
SLTWFEYEKGNIGEQEAYDAVAKEFGVPSSEVGAAFQCARDSLQSNPRLVSLIRELKSQYDLKVYAMSNISAPDWEVLRTKA
TPEEEWAMFDRVFTSAAARERKPNLGFYRQVVEATGVDPARSVFVDDKLDNVISARSVGLNAIIFDSFENVARQLKNYVADPI
GRAEAWLRDNAKKMLSITDAGVVVYENFGQMLILEATGDRSLVDYVEYPRLFNFFQGNGVFTTESFPCDLDSTSIGLTVTNH
VDEKTRHSVMEDMLTYKNEDGIIATYFDATRPRIDPVVCANVLTFFYKNGRGEELNETLDWVYDILLHRAYLDGTRYYFGSD
TFLFFLSRLLSESPSVYARFAPVFQERVKERMGATGDAMSLAMRIIAAATVKIQDRVDCDALLQTQEDDGGFPIGWMYKYGA
TGMLLGNKGLSTALAIQAIKAVESFP SEQ ID NO: 48-KLO09124.1 cDNA
ATGTCGATTCACGGTTCTTCTATGTCCTCCTATTCCTCGACTGTGCCGTCAATGACTTCCTCTCCCGCGTCCACTTCTACTC
CGTCGTCTCCTGCATCGTCGATCCATGAGATTGGTCCTGTCCCAGAAGCTCGACGAAAGGGACAGTGCAACGCGCTGATCTT
CGACCTCGGAGACGTCCTCTTCACCTGGTCGGCAGAGACTAAGACCACCATTTCCCCGAAACTCCTGAAAAAGATCCTTAAC
TCCTTAACATGGTTCGAATACGAGAAGGGAAACATCGGGGAGCAGGAGGCGTATGACGCAGTCGCAAAGGAGTTGGCGTCC
CGTCGTCCGAGGTCGGGGCCGCTTTCCAGTGCGCGCGCGATTCGCTACAGAGCAATCCCCGCCTCGTCTCGCTCATCCGTGA
GCTGAAGTCGCAATATGATCTCAAGGTGTACGCCATGTCCAACATCTCTGCCCGGACTGGGAAGTCCTAAGGACGAAGGCG
ACCCCTGAGGAGTGGGCAATGTTTGACCGCGTCTTCACGAGCGCGGCCGCGCGCGAGCGTAAGCCAAACCTCGGATTCTACA
GACAGGTTGTTGAGGCGACCGGCGTCGACCCCGCTCGCTCCGTGTTCGTCGACGATAAACTCGACAATGTCATCTCTGCGCG
TTCAGTCGGATTAAATGCGATCATCTTCGACTCATTTGAGAACGTCGCCCGGCAGCTCAAAAACTATGTCGCTGATCCTATC
GGACGGGCGGAGGCGTGGTTGCGCGATAACGCAAAGAAGATGTTGTCAATTACGGATGCCGGGGTGGTCGTATACGAGAATT
TCGGCCAGATGCTGATCTTGGAGGCAACAGGCGATAGGTCGCTTGTGGACTACGTCGAGTACCCTCGTCTCTTCAACTTCTT
CCAAGGCAATGGCGTCTTTACGACCGAGTCATTCCCTTGCGACCTTGATTCGACTTCCATCGGCTTAACCGTCACGAACCAC
GTCGATGAGAAACAAGGCACAGCGTCATGGATGAGATGCTGACCTACAAAAATGAGGATGGTATCATTGCGACTTACTTTG
ATGCCACGCGTCCCCGAATTGACCCCGTCGTCTGCGCAATGTCTTGACGTTCTTCTACAAGAACGGCCGTGGGGAGGAGCT
CAATGAAACACTTGACTGGGTCTACGACATCCTCCTTCATCGCGCGTACCTCGATGGCACACGTTATTTTCGGCTCAGAC
ACCTTCCTCTTCTTCCTTTCTCGACTTCTCTCCGAATCGCCATCCGTTTACGCCCGTTTCGCTCCGGTGTTCCAGGAGAGAG
TCAAGGAGCGCATGGGGCGACGGGAGATGCGATGTCCCTTGCGATGCGCATCATCGCGGCCGCAACTGTCAAGATCCAAGA
CCGAGTCGACTGCGACGCTCTGCTGCAGACGCAGGAAGACGACGGTGGATTCCCGATAGGTTGGATGTACAAGTACGGGGCG
ACCGGGATGCTTCTGGGTAACAAGGGCTTGTCGACAGCTCTGGCAATCCAAGCTATCAAAGCGGTCGAATCTTTCCCTTGA

Sequence Listings

SEQ ID NO: 49-KL009124.1 optimized cDNA
GGATCCAAGCTTAAGGAGGTAAAAAATGTCGATTCACGGTAGCAGCATGTCGTCTTATAGCAGCACGGTTCCATCTATGACT
AGCAGCCCGGCTTCCACGAGCACGCCGTCCAGCCCGGCCAGCAGCATCCACGAAATCGGCCCGGTCCCTGAGGCGCGTCGCA
AGGGCCAATGCAATGCACTGATCTTCGACCTGGGTGATGTTCTGTTTACCTGGAGCGCAGAAACCAAGACCACGATCAGCCC
GAAGCTGCTGAAAAAGATTCTGAACAGCTTGACCTGGTTTGAGTATGAGAAAGGCAACATCGGTGAACAAGAAGCCTATGAC
GCCGTTGCGAAAGAGTTCGGTGTGCCGAGCTCTGAGGTTGGCGCTGCGTTTCAATGTGCGCGTGACTCCCTGCAAAGCAATC
CGCGTTTGGTTAGCCTGATTCGTGAGCTGAAGTCCCAGTACGACCTGAAAGTGTACGCTATGAGCAATATTAGCGCGCCAGA
CTGGGAAGTGCTGCGTACTAAAGCGACCCCGGAAGAGTGGGCAATGTTCGATCGTGTCTTTACTTCTGCGGCGGCGCGTGAG
CGTAAGCCGAACTTGGGCTTTTACCGCCAAGTCGTGGAAGCAACCGGTGTCGATCCGGCGCGTAGCGTTTTCGTCGATGATA
AACTGGACAATGTGATCAGCGCGCGCTCTGTCGGTCTGAACGCTATTATCTTCGACTCCTTCGAAAACGTCGCCCGTCAGCT
GAAGAATTACGTCGCAGACCCGATTGGTCGCGCTGAGGCGTGGCTGCGCGACAACGCAAAGAAAATGCTGAGCATCACCGAT
GCGGGTGTTGTGGTTTACGAGAATTTTGGCCAGATGCTGATCCTGGAAGCTACCGGTGACCGTAGCCTGGTGGACTATGTGG
AGTATCCGCGCCTCTTTAACTTCTTCCAGGGTAACGGCGTTTTTACGACCGAGAGCTTTCCATGCGATCTGGACAGCACCAG
CATCGGTCTGACTGTGACCAATCATGTGGACAAAAGACTCGCCACAGCGTCATGGACGAAATGCTGACCTACAAAAATGAA
GATGGTATTATTGCGACGTACTTTGACGCGACGCGCCCGCGCATTGACCCTGTTGTCTGTGCCAATGTTCTGACCTTCTTCT
ACAAAAACGGTCGTGGTGAAGAATTGAACGAAACCCTGGATTGGGTGTACGACATTCTGCTGCATCGCGCGTATCTGGACGG
TACGCGTTATTATTTCGGCTCCGATACGTTCTTGTTTTTCCTGAGCCGTCTGCTGAGCGAGTCTTCCGAGCGTTTACGCGCGT
TTTGCCCCGGTGTTTCAAGAGCGCGTGAAAGAGCGTATGGGCGCGACCGGTGATGCGATGAGCCTGGCCATGCGTATCATTG
CAGCAGCAACCGTAAAGATCCAGGATCGTGTGGATTGCGACGCACTGTTGCAGACCCAAGAAGATGATGGCGGTTTCCCGAT
TGGTTGGATGTACAAATATGGTGCGACCGGTATGTTGCTGGGCAACAAAGGCCTGAGCACGGCCCTGGCGATCCAGGCAATT
AAAGCCGTCGAGTCGTTCCCGTAAGGTACCATATATGAATTCATTAATCTCGAG OJI95797.1
SEQ ID NO: 50-OJI95797.1 protein
MGSTKALVVDFGNVLCTWTPPRELSIPPKKLKQIMSSDIWLDYERGIYKSEDECYLAVATRFGVSPSDLSSVMKKARESLQP
NTATLNHLSHLKKTQPGLRIYGLTNTPLPEQSSVRSIAQEWPIFDHIYISGILGMRKPDIGCYRLVLRKIGLPAESVVFIDD
SPENILAAQSLGVHSILFQSHDQLSRQLGNVLGDPIQRGHNFLLSNAKQMNSTTDKGVIIRDNFAQLLIIELTQNPDLVALE
TWDRTWNFFIGPPQLTTESFPNDLDTTSIALSVLPVDKEVVWSVMDEMLTFTNADGIFMTYFDRSRPRVDPVVCTNVLNLFC
MHGRESEVAATFDWVLDVLRNSAYLSGSRYYSSPDCFLYFLSRLSCVVRDGTRRRELKSLLKQQVSQRIGADGDSVSLATRL
LASNILGITNGRDRSRLLALQETDGGWPAGWVYKFGSSGVQIGNRGLSTALALKSIERQKGPVEAISSEPEAWWPSLRLDRL
LNVWPFIDWKGYSPS SEQ ID NO: 51-OJI05797.1 cDNA
ATGGGTTCCACCAAGGCTCTTGTTGTTGACTTTGGGAATGTTTTGTGTACCTGGACACCACCCAGGGAGTTATCCATCCCGC
CCAAGAAGCTGAAACAAATCATGTCTTCTGACATTTGGCTCGACTATGAACGGGTATCTATAAGTCGGAGGACGAGTGCTA
CTTGGCGGTTGCAACTCGCTTCGGCGTCTCTCCCAGCGACCTCTCCTCGGTGATGAAAAAGGCCCGCGAGAGCCTGCAACCA
AACACCGCAACCCTGAATCATCTGTCTCATCTCAAAAAGACCCAGCCTGGCCTCAGGATATACGGTTTGACCAACACCCCTC
TCCCAGAACAAAGCAGTGTACGATCCATCGCCCAGGAATGGCCTATCTTCGACCATATCTACATATCAGGCATCCTCGGAAT
GCGCAAGCCGGACATTGGCTGCTACAGGCTGGTGCTGCGAAAGATTGGGCTTCCAGCGGAGTCCGTGGTCTTCATTGATGAT
TCACCCGAGAACATCCTGGCCGCGCAGTCACTGGGAGTACACAGCATACTGTTCCAAAGCCACGACCAGCTCTCTCGTCAGC
TTGGCAATGTGCTGGGTGATCCAATCCAGCGGGGCCATAACTTCCTACTCTCGAACGCAAAGCAAATGAATAGTACGACCGA
CAAGGGAGTTATTATCCGGGACAACTTTGCGCAACTGCTGATCATCGAGCTGACGCAGAACCCAGACCTTGTGGCGTTTAGA
ACATGGGACCGTACCTGGAATTTTTTTATTGGACCTCCACAATTGACAACTGAAAGCTTTCCCAATGATCTTGACACTACC
TCCATCGCTCTCTCGGTTCTTCCGGTTGACAAAGAAGTGGTATGGTCTGTGATGGACAGAGATGCTAACGTTTACCAATGCGG
ATGGGATTTTTATGACCTATTTCGACCGATCACGCCCTCGAGTTGATCCGGTAGTTTGCACCAATGTCCTGAATCTTTTCTG
CATGCATGGACGGGAAAGCGAAGTTGCAGCCACATTTGACTGGGTGCTGGACGTTCTTCGAAATTCGGCCTATTTATCAGGA
TCCAGATACTATTCTTCGCCTGATTGCTTTCTATACTTTCTTTCACCGGCTGAGCTGTGGTTCCGAGACGGCACGCGACGCA
GGGAGCTCAAGTCACTGTTGAAACAACAAGTGAGCCAGCGTATTGGCGCTGATGGTGATTCCGTCTCTCTCGCCACTAGGCT
ACTTGCATCGAACATTTTAGGAATCACAAATGGCCGTGATCGCTCCAGGCTTCTTGCTCTGCAGGAAACTGACGGTGGATGG
CCTGCTGGGTGGGTTTATAAATTCGGAAGCTCGGGGGTACAGATTGGCAATGGGGGCTCAGTACAGCCTTGGCGTTAAAAT
CAATTGAGCGTCAGAAGGGGCCTGTTGAGGCGATATCCAGTGAGCCAGAAGCGTGGTGGCCATCCCTCAGGCTTGACCGACT
TCTCAACGTTTGGCCTTTCATCGACTGGAAGGGATATTCGCCGAGTTGA SEQ ID NO: 52-OJI95797.1 optimized cDNA
ATGGGTTCTACGAAAGCGTTGGTTGTTGATTTTGGTAATGTTCTGTGCACTTGGACGCCACCACGTGAATTGTCCATCCCGC
CGAAGAAACTGAAGCAAATCATGAGCAGCGACATTTGGCTGGACTATGAGCGTGGTATCTACAAATCGGAAGATGAGTGCTA
CCTGGCAGTTGCGACGCGCTTTGGTGTCAGCCCGTCCGACCTGAGCTCCGTTATGAAAAAGCCCGTGAGAGCCTGCAGCCG
AATACCGCAACGCTGAACCACTTGAGCCATCTGAAGAAAACCCAGCCTGGCCTGCGTATCTACGGCCTGACGAACACCCCGT
TGCCGGAACAGAGCTCAGTCCGTAGCATTGCGCAGGAATGGCCGATTTTTGACCACATCTACATTAGCGGCATCTTGGGTAT
GCGCAAACCGGATATTGGTTGTTACCGTCTGGTTCTGCGTAAGATCGGTCTGCCAGCGGAGTCCGTCGTATTCATCGACGAC
AGCCCGGAGAACATTCTGGCAGCTCAATCGTTGGGTGTCCATAGCATCCTGTTCCAGTCCCACGATCAGCTGAGCCGTCAGC
TGGGCAATGTGCTGGGTGATCCGATTCAGCGCGGTCACAACTTCCTCCTGTCCAACGCGAAGCAAATGAACAGCACCACCGA
TAAGGGTGTGATTATCCGCGACAACTTCGCCCAGCTGCTGATTATTGAGCTGACCCAAAATCCGGATCTGGTTGCGCTGGAG
ACTTGGGACCGTACGTGGAATTTCTTTATTGGTCCGCCGCAACTGACCACCGAGAGCTTTCCGAACGACCTGGACACCACGA
GCATTGCCCTGAGCGTGTTGCCGGTGGATAAGAAGTCGTTTGGTCTGTGATGGATGAGATGCTGACCTTCACCAACGCAGA
CGGCATCTTCATGACCTATTTCGATCGTAGCCGTCCGCGTGTTGACCCGGTCGTTTGTACCAATGTCCTGAATCTGTTTTGC
ATGCATGGTCGCGAGAGCGAAGTGGCCGCGACGTTCGACTGGGTGCTGGACGTGCTGCGCAACAGCGCGTACCTGAGCGGTT
CCCGTTATTACAGCAGCCCGGATTGTTTTCTGTATTTCCTGTCTCGTCTGAGCTGCGTCGTCGATGGCACGCGTCGTCG
TGAACTGAAAAGCCTGCTGAAGCAACAAGTTTCTCAACGTATCGGCGCTGACGGTGATTCCGTCAGCCTGGCCACCCGTTTG
CTGGCGAGCAACATCCTGGGCATTACTAACGGTCGTGACCGCAGCCGTCTGCTGGCATTGCAAGAAACCGATGGTGGCTGGC
CTGCAGGCTGGGTCTATAAGTTTGGTAGCAGCGGCGTGCAAATTGGCAATCGCGGTCTGAGCACCGCGCTGGCTCTGAAGTC
TATCGAGCGCCAGAAAGGTCCGGTGGAAGCAATCAGCAGCGAGCCGGAAGCGTGGTGGCCTAGCTTACGCTTGGACCGCTTG
CTGAATGTTTGGCCATTTATCGACTGGAAGGGCTACTCCCCGAGCTAA -continued

| Sequence Listings |
|---|

Class I terpene synthase-like motif
SEQ ID NO: 53
DDxx(D/E), where x at position 3 is K, N, R, S, or Q and x at position 4 is L, I, G, P, or T Class I terpene synthase-like motif
SEQ ID NO: 54
DD(K/Q/R)(L/I/T)(D/E)NV Class I terpene synthase-like motif
SEQ ID NO: 55
DD(N/K/S/Q)(L/G/P)(D/E)N(V/I)

Class II terpene synthase-like motif
SEQ ID NO: 56
DxD(T/S)T, where x at position 2 is V, M, F or L Class II terpene synthase-like motif
SEQ ID NO: 57
D(V/M/L/F)DTTS Class II terpene synthase-like motif
SEQ ID NO: 58
D(V/M/L)D(T/S)TS Conserved motif A
SEQ ID NO: 59
SxxWxxYExG, where x is any amino acid Conserved motif B
SEQ ID NO: 60
NFxQx(I/L)IxE, where x is any amino acid Conserved motif C
SEQ ID NO: 61
(D/E)(G/E)Ixx(T/V)YFDxxRxRxDPxVxxNVL Conserved motif D
SEQ ID NO: 62
QxxDGx(W/F)

XP_006461126.1
SEQ ID NO: 63-XP_006461126.1 protein
MAPPQRPFTAIVFDIGDVLFQWSATTKTSISPKTLRSILNCPTWFDYERGRLAENACYAAISQEFNVNPDEVRDAFSQARDS
LQANHDFISLIRELKAQANGRLRVYAMSNISLPDWEVLRMKPADWDIFDHVFTSGAVGERKPNLAFYRHVIAATDLQPHQTI
FVDDKLENVLSARSLGFTGIVFDEPSEVKRALRNLIGDPVQRGGEFLVRNAGKLGSITRTTAKHESIPLDENFAQLLILEIT
GNRALVNLVEHPQTWNFFQGKGQLTTEEFPFDLDTTSLGLTILKRSREIADSVMDEMLEYVDPDGIIQTYFDHRRPRFDPVV
CVNALSLFYAYGRGEQLRSTLTWVHEVLLNRAYLDGTRYYETAECFLYFMSRLLATSGDPDLHSLLKPLLKERVQERIGADG
DSLALAMRILACDFVGIRDEVDLRTLLTLQCEDGGWEVGWMYKGSSGISIGNRGLATALAIKAVDTMFQPQIRFSESPTDTL
VENAIHKRRPSFSEKFLGKRPRSGSFRKPLQWILQGSKLRKSVEIGS SEQ ID NO: 64-XP_006461126.1 cDNA
ATGGCTCCGCCTCAGCGACCCTTTACTGCGATTGTCTTTGACATCGGGGATGTTCTATTCCAATGGTCTGCAACCACCAAAA
CCTCTATCTCACCAAAGACACTCCGCTCTATTCTCAACTGTCCGACATGGTTTGACTATGAACGTGGACGCCTGGCAGAAAA
CGCTTGTTATGCCGCTATCTCACAAGAATTCAACGTCAACCCAGACGAAGTTCGCGACGCTTTCAGCCAAGCGCGCGACTCT
CTCCAAGCAAACCACGACTTCATCAGTCTCATCCGTGAGCTGAAGGCACAAGCAAATGGTCGTTTACGTGTGTACGCCATGT
CGAACATATCTCTTCCTGATTGGGAAGTGCTGCGGATGAAACCTGCTGATTGGGATATTTTCGACCACGTCTTCACATCCGG
TGCGGTTGGGGAACGCAAGCCCAATCTCGCCTTTTATCGCCATGTTATCGCGGCCACCGATCTGCAGCCTCATCAGACAATA
TTTGTTGACGATAAGCTGGAGAATGTTCTCTCAGCACGTTCCCTCGGGTTCACAGGCATCGTGTTTGACGAGCCCTCCGAGG
TCAAACGTGCGCTTCGTAACCTCATTGGGGATCCTGTTCAACGAGGAGGTGAATTCTTGGTTCGGAATGCCGGAAAGCTTGG
CTCTATCACAAGGACTACTGCAAAGCACGAGTCAATCCCCCTCGACGAGAATTTTGCTCAGCTTCTTATTCTCGAGATAACG
GGGAACAGGTGCGTTAGCTTCTTGTAGGGTCTTCTGTCGTAATACTAAATTTTTTCTGGTGTTTAGGGCTTTGGTCAACCTC
GTTGAGCATCCTCAAACGTGGAATTTCTTCCAAGGTGCGCTGCTAAAATAAACATCCAGTTGCGTTTCGAAGCTCATTGTGG
GCGTCCCGTCACAGGCAAGGGCCAGCTGACAACAGAAGAATTTCCATTCGATCTCGATACAACTTCTCTTGGTCTCACGATC
CTCAAGCGAAGCAGGGAAATCGCCGATTCAGTCATGGATGAAATGCTGGAGTATGTCGATCCTGATGGTATCATTCAGGCAA
GTTTCATTTATCGGCTTGAGAAAATAAAGACAAAAACGTTCTGATGGGGGATGTTTCTAGACGTATTTCGATCATCGGAGA
CCACGTTTTGATCCAGTCGTGTGTGTCAATGCATTAAGCCTCTTCTATGCTTACGGCCGCGGGGAGCAACTGCGGTCGACTT
TGACATGGGTACATGAAGTCCTTCTCAATCGAGCCTACTTGGATGGCACACGGTACTACGAAACAGCCGAATGCTTCCTCTA
TTTCATGAGCCGACTTCTCGCCACTTCAGGCGACCCTGACCTTCACTCCCTTCTTAAACCTCTTCTCAAAGAACGGGTGCAA
GAACGCATTGGAGCTGATGGAGACTCTCTTGCACTCGCAATGCGTATTCTCGCCTGTGATTTCGTCGGAATCAGAGATGAAG
TGGATTTACGCACACTTCTGACTTTGCAATGTGAAGATGGAGGTTGGGAAGTGGGTTGGATGTACAAGTATGGATCTTCCGG
TATCAGTATCGGAAATCGTGGACTGGCCACCGCGCTCGCTATCAAGGCCGTCGACACGATGTTTCAACCCCAAATTCGGTTC
TCTGAATCACCCACAGATACTTTGGTTGAAAACGCTATCCACAAACGCCGTCCCTCATTTTCCGAAAAATTCCTCGGCAAAC
GTCCTCGCAGCGGATCGTTCAGGAAACCTTTACAGTGGATACTGCAAGGTTCCAAGCTTCGCAAATCTGTCGAAATAGGAAG
CTAA

Sequence Listings

SEQ ID NO: 65-xp_006461126.1 optimized cDNA
ATGGCACCACCGCAACGTCCGTTCACTGCAATTGTTTTCGATATTGGCGATGTTTTGTTCCAATGGTCTGCGACCACGAAAA
CCAGCATTAGCCCGAAAACCCTGCGCAGCATTCTGAATTGTCGACCTGGTTTATGAGCGGCCGTCTGCGGAAAA
TGCCGTGTTACGCTGCGATCAGCCAAGAATTTAACGTCAACCCGGACGAAGTTCGCGACGCCTTCAGCCAAGCGCGCGACAGC
CTGCAGGCGAATCACGACTTCATCAGCCTGATTCGTGAGCTGAAAGCTCAGGCGAACGGTCGTCTGCGTGTCTACGCCATGT
CTAATATCAGCCTGCCGGATTGGGAAGTCCTGCGTATGAAGCCAGCCGATTGGGACATCTTTGACCATGTATTTACCAGCGG
TGCGGTGGGTGAGCGCAAGCCGAACCTGGCCTTTTATCGTCACGTCATCGCCGGCCACGGATCTGCAGCCGCACCAGACGATC
TTCGTGGATGACAAACTGGAAAACGTGCTGTCTGCGCGCTCGCTGGGCTTCACGGGTATCGTGTTCGACGAGCCAAGCGAAG
TCAAACGTGCGCTGCGTAATCTGATCGGCGACCCGGTGCAGCGTGGTGGCGAGTTCCTGGTTCGTAATGCTGGCAAACTGGG
TTCTATCACCCGTACGACCGCAAAACATGAGAGCATCCCGCTGGATGAGAATTTTGCACAACTGTTGATTCTGGAAATTACT
GGTAACCGCGCACTGGTCAATCTGGTTGAGCACCCGCAGACGTGGAACTTCTTCCAGGGTAAGGGCCAGCTGACGACCGAAG
AATTTCCTTTTGACCTGGATACGACGAGCCTGGGTCTGACGATCCTGAAGCGTAGCCGCGAGATTGCCGACTCCGTCATGGA
CGAAATGTTGGAATACGTGGACCCTGACGGCATCATTCAGACCTACTTCGATATCGTCGCCCGCGCTTTGACCCGGTTGTT
TGCGTTAATGCCCTGAGCCTGTTCTATGCATACGGCCGTGGTGAGCAACTGCGTTCCACCTTGACCTGGGTGCACGAAGTTC
TGTTGAACCGTGCGTATTTGGATGGTACGCGTTACTATGAAACGGCCGAGTGCTTTCTGTATTTCATGTCCCGTCTGCTGGC
AACCAGCGGTGACCCGGATCTGCATTCCCTGCTGAAGCCGTTGCTGAAGGAACGCGTGCAAGAGCGCATCGGCGCTGACGGT
GACAGCCTGGCGCTGGCGATGCGCATTTTGGCATGTGATTTTGTTGGCATCCGTGATGAAGTGGATCTGCGTACCCTGCTGA
CCTTACAGTGCGAGGATGGCGGTTGGGAAGTGGGCTGGATGTACAAATACGGTAGCAGCGGTATTAGCATTGGTAACCGTGG
TCTGGCAACCGCATTGGCGATCAAAGCTGTTGACACCATGTTTCAACCGCAAATCCGTTTCAGCGAGAGCCCGACCGACACT
CTGGTGGAGAACGCGATTCACAAGCGCCGCCCGAGCTTTTCAGAGAAATTTTTAGGTAAGCGTCCGCGTTCCGGTTCGTTCC
GTAAACCGCTGCAATGGATTCTGCAGGGCAGCAAGCTGCGCAAGAGCGTCGAGATCGGTAGCTAA XP_007369631.1
SEQ ID NO: 66-XP_007369631.1 Optimized cDNA for *S. cerevisiae* expression
ATGGCTTCTATCCACAGAAGATACACTACTTTGATCTTGGACTTGGGTGACGTTTTGTTCAGATGGTCTCCAAAGACTGAAA
CTGCTATCCCACCACAACAATTGAAGGACATCTTGTCTTCTGTTACTTGGTTCGAATACGAAAGAGGTAGATTGTCTCAAGA
AGCTTGTTACGAAAGATGTGCTGAAGAATTCAAGATCGAAGCTTCTGTTATCGCTGAAGCTTTCAAGCAAGCTAGAGGTTCT
TTGAGACCAAACGAAGAATTCATCGCTTTGATCAGAGACTTGAAGAAGAAAATGCACGGTGACTTGACTGTTTTGGCTTTGT
CTAACATCTCTTTGCCAGACTACGAATACATCATGTCTTTGTCTTCTGACTGGACTACTGTTTTCGACAGAGTTTTCCCATC
TGCTTTGGTTGGTGAAAGAAAGCCACACTTGGGTTGTTACAGAAAGGTTATCTCTGAAATGAACTTGGAACCACAAACTACT
GTTTTCGTTGACGACAAGTTGGACAACGTTGCTTCTGCTAGATCTTTGGGTATGCACGGTATCGTTTTCGACAACCAAGCTA
ACGTTTTCAGACAATTGAGAAACATCTTCGGTGACCCAATCAGAAGAGGTCAAGAATACTTGAGAGGTCACGCTGGTAAGTT
GGAATCTTCTACTGACAACGGTTTGATCTTGAAGAAAACTTCACTCAATTGATCATCTACGAATTGACTCAAGACAGAACT
TTGATCTCTTTGTCTGAATGTCCAAGAACTTGGAACTTCTTCAGAGGTGAACCATTGTTCTCTGAAACTTTCCCAGACGACG
TTGACACTACTTCTGTTGCTTTGACTGTTTTGCAACCAGACAGAGCTTTGGTTAACTCTGTTTTGGACGAAATGTTGGAATA
CGTTGACGCTGACGGTATCATGCAAACTTACTTGCAACATGATCTAGACCAAGAATGGACCCATCGTTTGTTGTTAACGTTTTGT
CTTTGTTCTACGAAAACGGTAGAGGTCACGAATTGCCAAGAACTTTGGACTGGGTTTACGAAGTTTTGTTGCACAGAGCTTA
CCACGGTGGTTCTAGATACTACTTGTCTCCAGACTGTTTCTTGTTCTTCATGTCTAGATTGTTGAAGAGAGCTGACGACCCA
GCTGTTCAAGCTAGATTGAGACCATTGTTCGTTGAAAGAGTTAACGAAAGAGTTGGTGCTGCTGGTGACTCTATGGACTTGG
CTTTCAGAATCTTGGCTGCTGCTTCTGTTGGTGTTCAATGTCCAAGAGACTTGGAAAGATTGACTGCTGGTCAATGTGACGA
CGGTGGTTGGACTTGTGTTGGTTCTACGTTTTCGGTTCTACTGGTGTTAAGGCTGGTAACAGAGGTTTGACTACTGCTTTG
GCTGTTACTGCTATCCAAACTGCTATCGGTAGACCACCATCTCCATCTCCATCTGCTGCTTCTTCTTTTCAGACCATCTT
CTCCATACAAGTTCTTGGGTATCTCTAGACCAGCTTCTCCAATCAGATTCGGTGACTTGTTGAGACCATGGAGAAAGATGTC
TAGATCTAACTTGAAGTCTCAATAA XP_006461126
SEQ ID NO: 67-XP_006461126 Optimized cDNA for *S. cerevisiae* expression
ATGGCTCCACCACAAAGACCATTCACTGCTATCGTTTTCGACATCGGTGACGTTTTGTTCCAATGGTCTGCTACTACTAAGA
CTTCTATCTCTCCAAAGACTTTGATCTATCTTGAACTGTCGACCTGGTTCTGACTACGAAAGAGGTAGATTGGCTGAAAA
CGCTTGTTACGCTGCTATCTCTCAAGAATTCAACGTTAACCCAGACGAAGTTAGAGACGCTTTCTCTCAAGCTAGAGACTCT
TTGCAAGCTAACCACGACTTCATCTCTTTGATCAGAGAATTGAAGGCTCAAGCTAACGGTAGATTGAGAGTTTACGCTATGT
CTAACATCTCTTTGCCAGACTGGGAAGTTTTGAGAATGAAGCCAGCTGACTGGGACATCTTCGACCACGTTTTCACTTCTGG
TGCTGTTGGTGAAAGAAAGCCAAACTTGGCTTTCTACAGACATTATCGCTGCTCACGGTTGCAACCACACCAAAACATC
TTCGTTGACGACAAGTTGGAAAACGTTTTGTCTGCTAGATCTTTGGGTTTCACTGGTATCGTTTTCGACGAACCATCTGAAG
TTAAGAGAGCTTTGAGAAACTTGATCGGTGACCCAGTTCAAAGAGGTGGTGAATTCTTGGTTAGAAACGCTGGTAAGTTGGG
TTCTATCACTAGAACTACTGCTAAGACACGAATCTATCCCATTGGACGAAAACTTCGCTCAATTGTTGATCTTGGAAATCAC
TGGTAACAGAGCTTTGGTTAACTTGGTTGAACACCCACAAACTTGGAACTTCTTCCAAGGTAAGGGTCAATTGACTACTGAA
GAATTCCCATTCGACTTGGACACTACTTCTTTGGGTTTGACTATCTTGAAGAGATCTAGAGAAATCGCTGACTCTGTTATGG
ACGAAATGTTGGAATACGTTGACCCAGACGGTATCATCCAAACTTACTTCGACCACAGAAGACCAAGATTCGACCCAGTTGT
TTGTGTTAACGCTTTGTCTTTGTTCTACGCTTACGGTAGAGGTGAACAATTGAGATCTACTTTGACTTGGGTTCACGAAGTT
TTGTTGAACAGAGCTTACTTGGACGGTACTAGATACTACGAAACTGCTGAAGTTGCTTTTGTACTTCATGTCTAGATTGTTGG
CTACTTCTGGTGACCCAGACTTGCACTCTTTGTTGAAGCCATTGTTGAAGGAAAAGTTCAAGAAGAATCGGTGCTGACGG
TGACTCTTTGGCTTTGGCTATGAGAATCTTGGCTTGTGACTTCGTTGGTATCAGAGACGAAGTTGACTTGAGAACTTTGTTG
ACTTTGCAATGTGAAGACGGTGGTTGGGAAGTTGGTTGGATGTACAAGTACGGTTCTTCTGGTATCTCTATCGGTAACAGAG
GTTTGGCTACTGCTTTGGCTATCAAGGCTGTTGACACTATGTTCCAACCACAAATCAGATTCTCTGAATCTCCAACTGACAC
TTTGGTTGAAAACGCTATCCACAAGAGAAGACCATCTTTCTCTGAAAAGTTCTTGGGTAAGAGACCAAGATCGGTTCTTTC
AGAAAGCCATTGCAATGGATCTTGCAAGGTTCTAAGTTGAGAAAGTCTGTTGAAATCGGTTCTTAA LoTps1
SEQ ID NO: 68-LoTps1 Optimized cDNA for *S. cerevisiae* expression
ATGTACACTGCTTTGATCTTGGACTTGGGTGACGTTTTGTTCTCTGGTCTTCTACTACTAACACTACTATCCCACCAAGAC
AATTGAAGGAAATCTTGTCTTCTCCAGCTTGGTTCGAATACGAAAGAGGTAGACACTCAAGCTGAATGTTACGAAAGAGT
TTCTGCTGAATTCTCTTTGGACGCTACTGCTGTTGCTGAAGCTTTCAGAAGCTAGAGACTCTTTGAGACCAAACGACAAG
TTCTTGACTTTGATCAGAGAATTGAGACAACAATCTCACGGTGAATTGACTGTTTTGGCTTTGTCTAACATCTCTTTGCCAG
ACTACGAATTCATCATGGCTTTGGACTCTAAGTGGACTTCTGTTTTCGACAGAGTTTTCCCATCTGCTTTGGTTGGTGAAAG
AAAGCCACACTTGGGTGCTTTCAGACAAGTTTGTCTGAAATGAACTTGGACCCACACACTACTGTTTTCGTTGACGACAAG
TTGGACAACGTTGTTTCTGCTAGATCTTTGGGTATGCACGGTGTTGTTTTCGACTCTCAAGACAACGTTTTTCAGAATGTTGA

| Sequence Listings |
|---|
| GAAACATCTTCGGTGACCCAATCCACAGAGGTAGAGACTACTTGAGACAACACGCTGGTAGATTGGAAACTTCTACTGACGC
TGGTGTTGTTTTCGAAGAAAACTTCACTCAATTGATCATCTACGAATTGACTAACGACAAGTCTTTGATCACTACTTCTAAC
TGTGCTAGAACTTGGAACTTCTTCAGAGGTAAGCCATTGTTCTCTGCTTCTTTCCCAGACGACATGGACACTACTTCTGTTG
CTTTGACTGTTTTGAGATTGGACCACGCTTTGGTTAACTCTGTTTTGGACGAAATGTTGAAGTACGTTGACGCTGACGGTAT
CATGCAAACTTACTTCGACCACACTAGACCAAGAATGGACCCATTCGTTGTGTTAACGTTTTGTCTTTGTTCCACGAACAA
GGTAGAGGTCACGAATTGCCAAACACTTTGGAATGGGTTCACGAAGTTTTGTTGCACAGAGCTTACATCGGTGGTTCTAGAT
ACTACTTGTCTGCTGACTGTTTCTTGTTCTTCATGTCTAGATTGTTGCAAAGAATCACTGACCCATCTGTTTTGGGTAGATT
CAGACCATTGTTCATCGAAAGAGTTAGAGAAAGAGTTGGTGCTACTGGTGACTCTATCGACTTGGCTTTCAGAATCATCGCT
GCTTCTACTGTTGGTTATCCAATGTCCAAGAGACTTGGAATCTTTGTTGGCTGCTCAATGTGAAGACGGTGGTTGGGACTTG
TGTTGGTTCTACCAATACGGTTCTACTGGTGTTAAGGCTGGTAACAGAGGTTTGACTACTGCTTTGGCTATCAAGGCTATCG
ACTCTGCTATCGCTAGACCACCATCTCCAGCTTTGTCTGTTGCTTCTTCTTCTAAGTCTGAAATCCCAAAGCCAATCCAAAG
ATCTTTGAGACCATTGTCTCCAAGAAGATTCGGTGGTTTCTTGATGCCATGGAGAAGATCTCAAAGAAACGGTGTTGCTGTT
TCTTCTTAA EMD37666.1
SEQ ID NO: 69-EMD37666.1 Optimized cDNA for *S. cerevisiae* expression
ATGTCTGCTGCTGCTCAATACACTACTTTGATCTTGGACTTGGGTGACGTTTTGTTCACTTGGTCTCCAAAGACTAAGACTT
CTATCCCACCAAGAACTTTGAAGGAAATCTTGAACTCTGCTACTTGGTACGAATACGAAAGAGGTAGAATCTCTCAAGACGA
ATGTTACGAAAGAGTTGGTACTGAATTCGGTATCGCTCCATCTGAAATCGACAACGCTTTCAAGCAAGCTAGAGACTCTATG
GAATCTAACGACGAATTGATCGCTTTGGTTAGAGAATTGAAGACTCAATTGGACGGTGAATTGTTGGTTTTCGCTTTGTCTA
ACATCTCTTTGCCAGACTACGAATACGTTTTGACTAAGCCAGCTGACTGGTCTATCTTCGACAAGGTTTTCCCATCTGCTTT
GGTTGGTGAAAGAAAGCCACACTTGGGTGTTTACAAGCACGTTATCGCTGAAACTGGTATCGACCCAAGAACTACTGTTTTC
GTTGACGACAAGATCGACAACGTTTTGTCTGCTAGATCTGTTGGTATGCACGGTATCGTTTTCGAAAAGCAAGAAGACGTTA
TGAGAGCTTTGAGAAACATCTTCGGTGACCCAGTTAGAAGAGGTAGAGAATACTTGAGAGAGAACGCTATGAGATTGGAATC
TGTTACTGACCACGGTGTTGCTTTCGGTGAAAACTTCACTCAATTGTTGATCTTGGAATTGACTAACGACCCATCTTTGGTT
ACTTTGCCAGACAGACCAAGAACTTGGAACTTCTTCAGAGGTAACGGTGGTAGACCATCTAAGCCATTGTTCTCTGAAGCTT
TCCCAGACGACTTGGACACTACTTCTTTGGCTTTGACTGTTTTGCAAAGAGACCCAGGTGTTATCTCTTCTGTTATGGACGA
AATGTTGAACTACAGAGACCCAGACGGTATCATGCAAACTTACTTCGACGACGGTAGACAAAGATTGGACCCATTCGTTAAC
GTTAACGTTTTGACTTTCTTCTACACTAACGGTAGAGGTCACGAATTGGACCAATGTTTGACTTGGGTTAGAGAAGTTTTGT
TGTACAGAGCTTACTTGGGTGGTTCTAGATACTACCCATCTGCTGACTGTTTCTTGTACTTCATCTCTAGATTGTTCGCTTG
TACTAACGACCCAGTTTTGCACCACCAATTGAAGCCATTGTTCGTTGAAAGAGTTCAAGAACAAATCGGTGTTGAAGGTGAC
GCTTTGGAATTGGCTTTCAGATTGTTGGTTTGTGCTTCTTTGGACGTTCTCAAAACGCTATCGACATGAGAAGATTGTTGGAAA
TGCAATGTGAAGACGGTGGTTGGGAAGGTGGTAACTTGTACAGATTCGGTACTACTGGTTTGAAGGTTACTAACAGAGGTTT
GACTACTGCTGCTGCTGTTCAAGCTATCGAAGCTTCTCAAAGAAGACCACCATCTCCATCTCCATCTGTTGAATCTACTAAG
TCTCCAATCACTCCAGTTACTCCAATGTTGGAAGTTCCATCTTTGGGTTTGTCTATCTCTAGACCATCTTCTCCATTGTTGG
GTTACTTCAGATTGCCATGGAAGAAGTCTGCTGAAGTTCACTAA XP_001217376.1
SEQ ID NO: 70-XP_001217376.1 Optimized cDNA for *S. cerevisiae* expression
ATGGCTATCACTAAGGGTCCAGTTAAGGCTTTGATCTTGGACTTCTCTAACGTTTTGTGTTCTTGGAAGCCACCATCTAACG
TTGCTGTTCCACCACAAATCTTGAAGATGATCATGTCTTCTGACATCGTGGCACGACTACGAATGTGGTAGATACTCTAGAGA
AGACTGTTACGCTAGAGTTGCTGACAGATTCCACATCTCTGCTGCTGACATGGAAGACACTTTGAAGCAAGCTAGAAAGTCT
TTGCAAGTTCACCACGAAACTTTGTTGTTCATCCAACAAGTTAAGAAGGACGCTGGTGGTGAATTGATGGTTTGTGGTATGA
CTAACACTCCAAGACCAGAACAAGACGTTATGCACTCTATCAACGCTGAATACCCAGTTTTCGACAGAATCTACATCTCTGG
TTTGATGGGTATGAGAAAGCCATCTATCTGTTTCTACCAAAGAGTTATGGAAGAACATCCGTTTGTCTGGTGACGCTATCATG
TTCATCGACGACAAGTTGGAAAACGTTATCGCTGCTCAATCTGTTGGTATCAGAGGTGTTTTGTTCCAATCTCAACAAGACT
TGAGAAGAGTTGTTTTGAACTTCTTGGGTGACCCAGTTCACAGAGGTTTGCAATTCTTGGCTGCTAACGCTAAGAAGATGGA
CTCTGTTACTAACACTGGTGACACTATCCAAGACAACTTCGCTCAATTGTTGATCTTGGAATTGGCTCAAGACAGAGAATTG
GTTAAGTTGCAAGCTGGTAAGAGAACTTGGAACTACTTCATCGGTCCACCAAAGTTGACTACTGCTACTTTCCCAGACGACA
TGGACACTACTTCTATGGCTTTGTCTGTTTTGCCAGTTGCTGAAGACGTTGTTTCTTCTGTTTTGGACGAAATGTTGAAGTT
CGTTACTGACGACGGTATCTTCATGACTTACTTCGACTCTTCTAGACCAAGAGTTGACCCAGTTGTTTGTATCAACGTTTTG
GGTGTTTTCTGTAGACACAACAGAGAAAAGAGACGTTTTGCCAACTTTCCACTGGATCAGAGACATCTTGATCAACAGAGCTT
ACTTGTCTGGTACTAGATACTACCCATCTCCAGACTTGTTCTTGTTCTTGGGCTAGATTGTGTTTGGCTGTTAGAAACC
AATCTTTGAGAGAACAATTGGTTTTGCCATTGGTTGACAGATTGAGAGAAAGAGTTGGTGCTCCAGGTGAAGCTGTTTCTTT
GGCTGCTAGAATCTTGGCTTGAGATCTTTCGGTATCGACTCTGCTACTGCTTCTTTGAGAGGTAAGCAATGTGAA
GACGGTGGTTGGCCAGTTGAATGGGTTTACAGATTCGCTTCTTTCGGTTTGAACGTTGGTAACAGAGGTTTGGCTACTGCTT
TCGCTGTTAGAGCTTTGGAATCTCCATACGGTGAATCTGCTGTTAAGGTTATGAGAAGAATCGTTTAA Primers
SEQ ID NO: 71-Primer for construction of fragment "a" (LEU2 yeast marker)
AGGTGCAGTTCGCGTGCAATTATAACGTCGTGGCAACTGTTATCAGTCGTACCGCGCCATTCGACTACGTCGTAAGGCC SEQ ID NO: 72-Primer for construction of fragment "a" (LEU2 yeast marker)
TCGTGGTCAAGGCGTGCAATTCTCAACACGAGAGTGATTCTTCGGCGTTGTTGCTGACCATCGACGGTCGAGGAGAACTT SEQ ID NO: 73-Primer for construction of fragment "b" (AmpR *E. coli* marker)
TGGTCAGCAACAACGCCGAAGAATCACTCTCGTGTTGAGAATTGCACGCCTTGACCACGACACGTTAAGGGATTTTGGTCAT
GAG SEQ ID NO: 74-Primer for construction of fragment "b" (AmpR *E. coli* marker)
AACGCGTACCCTAAGTACGGCACCACAGTGACTATGCAGTCCGCACTTTGCCAATGCCAAAAATGTGCGCGGAACCCCTA SEQ ID NO: 75-Primer for construction of fragment "c" (Yeast origin of replication)
TTGGCATTGGCAAAGTGCGGACTGCATAGTCACTGTGGTGCCGTACTTAGGGTACGCGTTCCTGAACGAAGCATCTGTGCTT
CA

| Sequence Listings |
|---|
| SEQ ID NO: 76-Primer for construction of fragment "c" (Yeast origin of replication)<br>CCGAGATGCCAAAGGATAGGTGCTATGTTGATGACTACGACACAGAACTGCGGGTGACATAATGATAGCATTGAAGGATGAGACT |
| SEQ ID NO: 77-Primer for construction of fragment "d" (*E. coli* origin of replication)<br>ATGTCACCCGCAGTTCTGTGTCGTAGTCATCAACATAGCACCTATCCTTTGGCATCTCGGTGAGCAAAAGGCCAGCAAAAGG |
| SEQ ID NO: 78-Primer for construction of fragment "d" (*E. coli* origin of replication)<br>CTCAGATGTACGGTGATCGCCACCATGTGACGGAAGCTATCCTGACAGTGTAGCAAGTGCTGAGCGTCAGACCCCGTAGAA |

The invention claimed is:

1. A method for producing a drimane sesquiterpene comprising:
 a. contacting an acyclic farnesyl diphosphate (FPP) precursor with a polypeptide comprising a Haloacid dehalogenase (HAD)-like hydrolase domain and having bifunctional terpene synthase activity to produce a drimane sesquiterpene, wherein the polypeptide comprises
  i. a class I terpene synthase-like motif as set forth in SEQ ID NO: 53 (DDxx(D/E)); and
  ii. a class II terpene synthase-like motif as set forth in SEQ ID NO: 56 (DxD(T/S)T); and
 b. optionally isolating the drimane sesquiterpene or a mixture comprising the drimane sesquiterpene.

2. The method of claim 1, wherein the drimane sesquiterpene comprises albicanol and/or drimenol.

3. The method of claim 1, wherein the polypeptide having bifunctional terpene synthase activity comprises
 a. an amino acid sequence having at least 40%, 45%, 50%, 55%, 60%, 65%, 70%, 75%, 80%, 85%, 90%, 95%, 96%, 97%, 98% or 99% sequence identity to SEQ ID NO: 1, SEQ ID NO: 5, SEQ ID NO: 9, SEQ ID NO: 12, SEQ ID NO: 15, SEQ ID NO: 17, SEQ ID NO: 20, SEQ ID NO: 23, SEQ ID NO: 26, SEQ ID NO: 29, SEQ ID NO: 32, SEQ ID NO: 35, SEQ ID NO: 38, SEQ ID NO: 41, SEQ ID NO: 44, SEQ ID NO: 47, SEQ ID NO: 50, or SEQ ID NO: 63; and
 b. a sequence as set forth in SEQ ID NO: 53, SEQ ID NO: 54, or SEQ ID NO: 55; and
 c. a sequence as set forth in SEQ ID NO: 56, SEQ ID NO: 57, or SEQ ID NO: 58.

4. The method of claim 1, the method comprising transforming a host cell or non-human host organism with a nucleic acid encoding a polypeptide having bifunctional terpene synthase activity, wherein the polypeptide
 a. comprises an amino acid sequence of SEQ ID NO: 1, SEQ ID NO: 5, SEQ ID NO: 9, SEQ ID NO: 12, SEQ ID NO: 15, SEQ ID NO: 17, SEQ ID NO: 20, SEQ ID NO: 23, SEQ ID NO: 26, SEQ ID NO: 29, SEQ ID NO: 32, SEQ ID NO: 35, SEQ ID NO: 38, SEQ ID NO: 41, SEQ ID NO: 44, SEQ ID NO: 47, SEQ ID NO: 50, or SEQ ID NO: 63; or
 b. comprises
  i. an amino acid sequence having at least 40%, 45%, 50%, 55%, 60%, 65%, 70%, 75%, 80%, 85%, 90%, 95%, 96%, 97%, 98%, or 99% sequence identity to SEQ ID NO: 1, SEQ ID NO: 5, SEQ ID NO: 9, SEQ ID NO: 12, SEQ ID NO: 15, SEQ ID NO: 17, SEQ ID NO: 20, SEQ ID NO: 23, SEQ ID NO: 26, SEQ ID NO: 29, SEQ ID NO: 32, SEQ ID NO: 35, SEQ ID NO: 38, SEQ ID NO: 41, SEQ ID NO: 44, SEQ ID NO: 47, SEQ ID NO: 50, or SEQ ID NO: 63; and
  ii. a sequence as set forth in SEQ ID NO: 53, SEQ ID NO: 54, or SEQ ID NO: 55; and
  iii. a sequence as set forth in SEQ ID NO: 56, SEQ ID NO: 57, or SEQ ID NO: 58.

5. The method of claim 1, the method further comprising culturing a non-human host organism or a host cell capable of producing FPP and transformed to express a polypeptide comprising a Haloacid dehalogenase (HAD)-like hydrolase domain under conditions that allow for the production of the polypeptide, wherein the polypeptide
 a. comprises an amino acid sequence of SEQ ID NO: 1, SEQ ID NO: 5, SEQ ID NO: 9, SEQ ID NO: 12, SEQ ID NO: 15, SEQ ID NO: 17, SEQ ID NO: 20, SEQ ID NO: 23, SEQ ID NO: 26, SEQ ID NO: 29, SEQ ID NO: 32, SEQ ID NO: 35, SEQ ID NO: 38, SEQ ID NO: 41, SEQ ID NO: 44, SEQ ID NO: 47, SEQ ID NO: 50, or SEQ ID NO: 63; or
 b. comprises
  i. an amino acid sequence having at least 40%, 45%, 50%, 55%, 60%, 65%, 70%, 75%, 80%, 85%, 90%, 95%, 96%, 97%, 98%, or 99% sequence identity to SEQ ID NO: 1, SEQ ID NO: 5, SEQ ID NO: 9, SEQ ID NO: 12, SEQ ID NO: 15, SEQ ID NO: 17, SEQ ID NO: 20, SEQ ID NO: 23, SEQ ID NO: 26, SEQ ID NO: 29, SEQ ID NO: 32, SEQ ID NO: 35, SEQ ID NO: 38, SEQ ID NO: 41, SEQ ID NO: 44, SEQ ID NO: 47, SEQ ID NO: 50, or SEQ ID NO: 63; and
  ii. a sequence as set forth in SEQ ID NO: 53, SEQ ID NO: 54, or SEQ ID NO: 55; and
  iii. a sequence as set forth in SEQ ID NO: 56, SEQ ID NO: 57, or SEQ ID NO: 58.

6. The method of claim 3, wherein the polypeptide comprises one or more conserved motif as set forth in SEQ ID NO: 59, SEQ ID NO: 60, SEQ ID NO: 61, and SEQ ID NO: 62.

7. The method of claim 1, wherein the drimane sesquiterpene or the mixture comprising the drimane sesquiterpene is isolated.

8. The method as recited in claim 1, the method further comprising contacting the drimane sesquiterpene with at least one enzyme to produce a drimane sesquiterpene derivative.

9. The method as recited in claim 1, the method comprising converting the drimane sesquiterpene to a drimane sesquiterpene derivative by chemical synthesis or biochemical synthesis.

10. The method of claim 1, wherein the class I terpene synthase-like motif comprises SEQ ID NO: 54 (DD(K/Q/R)(L/I/T)(D/E)), the class II terpene synthase-like motif comprises SEQ ID NO: 57 (D(V/M/L)DTT), and the drimane sesquiterpene is albicanol.

11. The method of claim 1, wherein the polypeptide comprises
 a. an amino acid sequence having at least 90% sequence identity to SEQ ID NO: 1, SEQ ID NO: 5, SEQ ID NO: 9, SEQ ID NO: 12, SEQ ID NO: 15, SEQ ID NO: 17, SEQ ID NO: 20, SEQ ID NO: 23, SEQ ID NO: 26, SEQ ID NO: 29, or SEQ ID NO: 32,
 b. a sequence of SEQ ID NO: 54 (DD(K/Q/R)(L/I/T)(D/E)), and
 c. a sequence of SEQ ID NO: 57 (D(V/M/L/F)DTTS); and
wherein the drimane sesquiterpene is albicanol.

12. The method of claim 1, wherein the polypeptide comprises
   a. an amino acid sequence having at least 90% sequence identity to SEQ ID NO: 35, SEQ ID NO: 38, SEQ ID NO: 41, SEQ ID NO: 44, SEQ ID NO: 47, SEQ ID NO: 50, or SEQ ID NO: 63,
   b. a sequence of SEQ ID NO: 55, and
   c. a sequence of SEQ ID NO: 58; and
   wherein the drimane sesquiterpene is drimenol.

13. The method of claim 5, wherein the host cell is a prokaryotic cell.

14. The method of claim 13, wherein the prokaryotic cell is a bacterial cell.

15. The method of claim 14, wherein the bacterial cell is *E. coli*.

16. The method of claim 5, wherein the host cell is a eukaryotic cell.

17. The method of claim 16, wherein the eukaryotic cell is a yeast cell or a plant cell.

18. The method of claim 17, wherein the yeast cell is *Saccharomyces cerevisiae*.

\* \* \* \* \*

SEQUENCE LISTING

<160> NUMBER OF SEQ ID NOS: 78

<210> SEQ ID NO 1
<211> LENGTH: 526
<212> TYPE: PRT
<213> ORGANISM: Cryptoporus volvatus

<400> SEQUENCE: 1

```
Met Thr Thr Ile His Arg Arg His Thr Thr Leu Ile Leu Asp Leu Gly
1               5                   10                  15

Asp Val Leu Phe Arg Trp Ser Pro Lys Thr Glu Thr Ala Ile Pro Pro
            20                  25                  30

Arg Gln Leu Lys Glu Ile Leu Thr Ser Val Thr Trp Phe Glu Tyr Glu
        35                  40                  45

Arg Gly Gln Ile Ser Gln Thr Glu Cys Tyr Glu Arg Cys Ala Ala Glu
    50                  55                  60

Phe Lys Val Asp Pro Leu Val Ile Ala Glu Ala Phe Lys Gln Ala Arg
65                  70                  75                  80

Glu Ser Leu Arg Pro Asn Lys Ala Phe Ile Ala Leu Ile Arg Glu Leu
                85                  90                  95

Arg His Gln Met His Gly Asp Leu Thr Val Leu Ala Leu Ser Asn Ile
            100                 105                 110

Ser Leu Pro Asp Tyr Glu Tyr Ile Met Ser Leu Ser Ser Asp Trp Ala
        115                 120                 125

Thr Val Phe Asn Arg Val Phe Pro Ser Ala Leu Val Gly Glu Arg Lys
    130                 135                 140

Pro His Leu Gly Cys Tyr Arg Lys Val Ile Ser Glu Met Ser Leu Glu
145                 150                 155                 160

Pro Gln Thr Thr Val Phe Val Asp Asp Lys Leu Asp Asn Val Ala Ser
                165                 170                 175

Ala Arg Ser Leu Gly Met His Gly Ile Val Phe Asp Asn Glu Ala Asn
            180                 185                 190

Val Phe Arg Gln Leu Arg Asn Ile Phe Gly Asn Pro Val Ser Arg Gly
        195                 200                 205

Gln Gly Tyr Leu Arg Lys His Ala Gly Lys Leu Glu Ser Ser Thr Asp
    210                 215                 220

Asn Gly Leu Thr Phe Glu Glu Asn Phe Thr Gln Leu Ile Ile Tyr Glu
225                 230                 235                 240

Val Thr Gln Asp Arg Ser Leu Ile Thr Leu Ser Glu Cys Pro Arg Thr
                245                 250                 255

Trp Asn Phe Phe Arg Gly Gln Pro Leu Phe Ser Glu Ser Phe Pro Asp
```

|  |  |  | 260 |  |  |  | 265 |  |  |  | 270 |  |
|---|---|---|---|---|---|---|---|---|---|---|---|---|
Asp Val Asp Thr Thr Ser Val Ala Leu Thr Val Leu Gln Pro Asp Arg
       275              280              285

Ala Leu Val Asp Ser Ile Leu Asp Gln Met Leu Glu Tyr Val Asp Ala
   290              295              300

Asp Gly Ile Met Gln Thr Tyr Phe Asp Ser Ser Arg Pro Arg Ile Asp
305             310              315             320

Pro Phe Val Cys Val Asn Val Leu Ser Leu Phe Tyr Ala Asn Gly Arg
       325              330              335

Gly Arg Glu Leu Pro His Thr Leu Glu Trp Val Tyr Glu Val Leu Leu
   340              345              350

His Arg Ala Tyr His Gly Gly Ser Arg Tyr Tyr Leu Ser Pro Asp Cys
       355              360              365

Phe Leu Phe Phe Met Ser Arg Leu Leu Lys Arg Ala Asn Asp Ser Ala
   370              375              380

Leu Gln Ala Arg Phe Arg Pro Leu Phe Met Glu Arg Val Lys Glu Arg
385             390              395             400

Val Gly Ala Ala Gly Asp Ser Met Asp Leu Ala Phe Arg Ile Leu Ala
       405              410              415

Ala Ala Thr Ile Gly Val His Cys Pro Gln Asp Leu Glu Arg Leu Ala
   420              425              430

Ala Ala Gln Cys Glu Asp Gly Gly Trp Asp Met Cys Trp Phe Tyr Ala
       435              440              445

Phe Gly Ser Thr Gly Ile Lys Ala Gly Asn Arg Gly Leu Thr Thr Ala
   450              455              460

Leu Ala Val Ala Ala Ile Arg Thr Ala Leu Gly Arg Pro Pro Ser Pro
465             470              475             480

Ser Pro Ser Asn Ile Ser Ser Ser Lys Leu Asp Ala Pro Asn Ser
       485              490              495

Phe Leu Gly Ile Pro Arg Pro Thr Ser Pro Ile Arg Phe Gly Glu Leu
   500              505              510

Phe Arg Ser Trp Arg Lys Asn Lys Pro Thr Ala Lys Ser Gln
       515              520              525

<210> SEQ ID NO 2
<211> LENGTH: 1956
<212> TYPE: DNA
<213> ORGANISM: Cryptoporus volvatus

<400> SEQUENCE: 2

```
catcccgcct tttgagcatg gcacacaaac agcctttaag gagctccttg gttgcctagt      60
catgcctcca cctgccccct cctcactcat cccctcgcat cctaaaacat gaccacgatt     120
caccgtcggc acaccactct catcttggac ctcggcgacg tcctcttccg ctggtcacca     180
aagaccgaga ccgccatccc ccctcggcag cttaaggaga tacttacctc cgtcacctgg     240
ttcgagtacg aacgaggcca gatatcccaa acagaatgtt acgaacgatg cgctgcagaa     300
ttcaaagtcg accccttagt gatcgctgaa gccttcaagc aagctcgcga gtcattacgg     360
cccaacaaag cgttcatcgc cttgattcgc gaacttcgcc atcaaatgca tggagacctc     420
acggtcctcg cccttttccaa catttccctc cccgattacg aatatatcat gtctctgagc     480
tcggattggg caaccgtctt caatcgcgta ttcccttctg cacttgttgg cgagcgaaaa     540
ccccatctgg ggtgctaccg caaggtcatt tcggagatga gcttggaacc ccagacaacc     600
gtatttgtcg atgataagct agacaacgtc gcctctgctc gctcacttgg catgcacggc     660
```

```
atcgtattcg acaacgaagc caatgtcttc cggcaactgc gcaatatctt cgggaatccg    720
gttagccgcg gtcaaggcta tcttcgcaag catgccggaa agcttgagtc ttctaccgac    780
aatggcttga cctttgagga gaacttcacc cagctcatca tctacgaggt gacacaagac    840
aggagtctca tcacgctctc agaatgtccc cgtacctgga atttctttcg aggtcaaccg    900
ctcttctcgg agtctttccc ggatgatgtg gacacaacat ccgtggcatt gacagtacta    960
caacccgata gagcgctcgt tgattctatt ctagaccaaa tgcttgaata tgttgacgcc   1020
gacggcatca tgcagacata cttcgacagc tcgcgaccac gcatagaccc ttttgtttgc   1080
gtcaatgtgc tttctctgtt ctacgcaaac ggccggggtc gggagctccc tcacacactg   1140
gagtgggtct atgaagtact cctgcatcgc gcctaccatg gaggctcacg ttactaccta   1200
tcaccggact gcttttatt cttcatgagc cgcttgctca gcgcgccaa cgactcggcc   1260 ctccaggctc ggttccgccc actgttcatg gagagagtga agaacgagt aggggcagcc   1320 ggagactcaa tggacctggc cttccgcatc ctcgccgcgg ctaccattgg cgtccattgc   1380
ccccaagatc tagaaagatt ggccgccgcg caatgcgagg acggtggatg ggacatgtgc   1440
tggttctacg cgttcgggtc gacaggtatc aaggcgggca accgcggcct caccacggcc   1500
cttgccgtcg cagctatacg aaccgccctc gggcgccccc cctctcccag ccctccaac   1560 atctcgtcgt cgtcgaagct cgacgctccc aacagcttct tgggcatccc gcgcccaacc   1620
agccccattc gctttggcga acttttccgt tcctggcgaa gaacaaacc gaccgcaaaa   1680 tctcaatgaa tctcaggttc tcgtgctctc gtgctatctt cgtacttatg ctactcgaca   1740 ttaccccgtcg ctgtctacaa tgatacgggt actttgatga aactgtagat gtatttgtat   1800
catattgacc tccatccata gtcacctagc tactgttcgt gttatcacct gttgctgtta   1860
tatgatacaa gatgcccaaa cgagaatgta gaaatgttcc gtacacttgt gtacctgtga   1920
tgaagctaca taggccttca atcgatcact tggtcc                             1956
```

<210> SEQ ID NO 3
<211> LENGTH: 1581
<212> TYPE: DNA
<213> ORGANISM: Cryptoporus volvatus
<220> FEATURE:
<221> NAME/KEY: misc_feature
<223> OTHER INFORMATION: cDNA

<400> SEQUENCE: 3

```
atgaccacga ttcaccgtcg gcacaccact ctcatcttgg acctcggcga cgtcctcttc     60
cgctggtcac caaagaccga gaccgccatc cccctcggc agcttaagga gatacttacc    120
tccgtcacct ggttcgagta cgaacgaggc cagatatccc aaacagaatg ttacgaacga    180
tgcgctgcag aattcaaagt cgacccctta gtgatcgctg aagccttcaa gcaagctcgc    240
gagtcattac ggcccaacaa agcgttcatc gccttgattc gcgaacttcg ccatcaaatg    300
catggagacc tcacggtcct cgcccttttcc aacatttccc tccccgatta cgaatatatc    360
atgtctctga gctcggattg ggcaaccgtc ttcaatcgcg tattcccttc tgcacttgtt    420
ggcgagcgaa aacccatct ggggtgctac cgcaaggtca tttcggagat gagcttggaa    480
ccccagacaa ccgtatttgt cgatgataag ctagacaacg tcgcctctgc tcgctcactt    540
ggcatgcacg gcatcgtatt cgacaacgaa gccaatgtct ccggcaact gcgcaatatc    600 ttcgggaatc cggttagccg cggtcaaggc tatcttcgca agcatgccgg aaagcttgag    660
tcttctaccg acaatggctt gacctttgag gagaacttca cccagctcat catctacgag    720
```

```
gtgacacaag acaggagtct catcacgctc tcagaatgtc cccgtacctg gaatttcttt      780
cgaggtcaac cgctcttctc ggagtctttc ccggatgatg tggacacaac atccgtggca      840
ttgacagtac tacaacccga tagagcgctc gttgattcta ttctagacca aatgcttgaa      900
tatgttgacg ccgacggcat catgcagaca tacttcgaca gctcgcgacc acgcatagac      960 cctttgttt gcgtcaatgt gctttctctg ttctacgcaa acggccgggg tcgggagctc      1020
cctcacacac tggagtgggt ctatgaagta ctcctgcatc gcgcctacca tggaggctca     1080
cgttactacc tatcaccgga ctgctttta ttcttcatga ccgcttgct caagcgcgcc       1140 aacgactcgg ccctccaggc tcggttccgc ccactgttca tggagagagt gaaagaacga     1200 gtagggcag ccggagactc aatggacctg ccttccgca tcctcgccgc ggctaccatt       1260
ggcgtccatt gccccaaga tctagaaaga ttggccgccg cgcaatgcga ggacggtgga      1320
tgggacatgt gctggttcta cgcgttcggg tcgacaggta tcaaggcggg caaccgcggc    1380
ctcaccacgg cccttgccgt cgcagctata cgaaccgccc tcgggcgccc ccctctccc     1440 agcccctcca acatctcgtc gtcgtcgaag ctcgacgctc ccaacagctt cttgggcatc     1500
ccgcgcccaa ccagccccat tcgctttggc gaacttttcc gttcctggcg aaagaacaaa    1560
ccgaccgcaa aatctcaatg a                                              1581

<210> SEQ ID NO 4
<211> LENGTH: 1581
<212> TYPE: DNA
<213> ORGANISM: Artificial Sequence
<220> FEATURE:
<223> OTHER INFORMATION: codon optimized cDNA

<400> SEQUENCE: 4
atgactacga tccaccgccg ccatactacg ctgatcctgg acctgggtga tgttctgttc      60
cgctggtccc cgaaaaccga accgcaatt ccgcctcgtc agctgaaaga aatcttgacc       120
agcgttacct ggttcgagta tgagcgtggc caaattagcc agaccgaatg ctacgagcgt      180
tgtgctgccg agtttaaagt tgatccgctg gttattgccg aagcgtttaa acaagcgcgt     240
gaaagcctgc gtccgaacaa agcgttttat cgcgttgatc cgtgagttgcg ccaccagatg    300 catggtgacc tgacggtcct ggcactgagc aacattagcc tgcctgatta tgagtacatt     360
atgtcgctga gctccgattg ggcgacggtc tttaatcgcg tgtttccgag cgcactggtg     420
ggtgagcgta agccacacct gggttgctac cgcaaggtca tcagcgagat gtctctggag     480
ccgcagacca cggttttcgt cgatgacaaa ctggacaatg tcgcaagcgc tcgtagcctg    540 gcatgcatg gcatcgtgtt cgacaacgaa gcgaacgttt tcgtcagct gcgtaatatc      600 ttcggtaacc cggttagccg cggtcaaggt tacttgcgta aacacgccgg taaactggaa    660
tctagcacgg ataatggtct gaccttcgaa gagaacttca ctcaattaat tatttacgaa   720
gtcacgcaag accgcagcct gatcaccctg agcgagtgcc cgcgtacctg gaacttcttc   780
cgcggtcaac cactgttttc tgagagcttt ccggacgacg tggacaccac ctctgtggcg    840
ttgaccgttc tgcagccgga tcgtgcgttg gtggatagca tcctggacca gatgttggaa   900
tatgttgacg cggatggtat tatgcaaacc tactttgatt catcccgtcc gcgcattgac    960
ccgttcgtgt gcgtgaatgt cctgagcctg ttctacgcca atggcagagg ccgcgagctg   1020
ccacacacgc tggaatgggt ctatgaagtt ctgctgcacc gtgcgtacca cggcggtagc   1080
cgttattacc tgagcccgga ctgtttcctg ttctttatga gccgtctgct gaagcgcgcg   1140
```

-continued

```
aatgactcgg cgctgcaggc ccgttttcgc ccgcttttca tggaacgtgt gaaagagcgt    1200
gtgggcgcag ccggcgatag catggacctg gcgttccgca ttctggccgc tgcaaccatc    1260
ggcgttcatt gcccacaaga tctggagcgt ctggcagcag cgcagtgcga agatggtggc    1320
tgggatatgt gttggtttta tgcgtttggc agcacgggta tcaaggctgg caaccgcggt    1380
ctgaccaccg cgttggctgt cgccgcaatt cgtaccgcgc tgggtcgtcc gccttccccg    1440
agcccgagca atatttctag ctccagcaaa ctggacgcgc cgaactcctt cctgggcatc    1500
ccgcgtccga ccagcccgat ccgtttcggt gaactgtttc gtagctggcg taagaacaag    1560
ccgaccgcga aaagccagta a                                              1581
```

<210> SEQ ID NO 5
<211> LENGTH: 521
<212> TYPE: PRT
<213> ORGANISM: Laricifomes officinalis

<400> SEQUENCE: 5

```
Met Tyr Thr Ala Leu Ile Leu Asp Leu Gly Asp Val Leu Phe Ser Trp
1               5                   10                  15

Ser Ser Thr Thr Asn Thr Thr Ile Pro Pro Arg Gln Leu Lys Glu Ile
                20                  25                  30

Leu Ser Ser Pro Ala Trp Phe Glu Tyr Glu Arg Gly Arg Ile Thr Gln
            35                  40                  45

Ala Glu Cys Tyr Glu Arg Val Ser Ala Glu Phe Ser Leu Asp Ala Thr
        50                  55                  60

Ala Val Ala Glu Ala Phe Arg Gln Ala Arg Asp Ser Leu Arg Pro Asn
65                  70                  75                  80

Asp Lys Phe Leu Thr Leu Ile Arg Glu Leu Arg Gln Gln Ser His Gly
                85                  90                  95

Glu Leu Thr Val Leu Ala Leu Ser Asn Ile Ser Leu Pro Asp Tyr Glu
                100                 105                 110

Phe Ile Met Ala Leu Asp Ser Lys Trp Thr Ser Val Phe Asp Arg Val
            115                 120                 125

Phe Pro Ser Ala Leu Val Gly Glu Arg Lys Pro His Leu Gly Ala Phe
        130                 135                 140

Arg Gln Val Leu Ser Glu Met Asn Leu Asp Pro His Thr Thr Val Phe
145                 150                 155                 160

Val Asp Asp Lys Leu Asp Asn Val Val Ser Ala Arg Ser Leu Gly Met
                165                 170                 175

His Gly Val Val Phe Asp Ser Gln Asp Asn Val Phe Arg Met Leu Arg
                180                 185                 190

Asn Ile Phe Gly Asp Pro Ile His Arg Gly Arg Asp Tyr Leu Arg Gln
            195                 200                 205

His Ala Gly Arg Leu Glu Thr Ser Thr Asp Ala Gly Val Val Phe Glu
        210                 215                 220

Glu Asn Phe Thr Gln Leu Ile Ile Tyr Glu Leu Thr Asn Asp Lys Ser
225                 230                 235                 240

Leu Ile Thr Thr Ser Asn Cys Ala Arg Thr Trp Asn Phe Phe Arg Gly
                245                 250                 255

Lys Pro Leu Phe Ser Ala Ser Phe Pro Asp Asp Met Asp Thr Thr Ser
                260                 265                 270

Val Ala Leu Thr Val Leu Arg Leu Asp His Ala Leu Val Asn Ser Val
            275                 280                 285

Leu Asp Glu Met Leu Lys Tyr Val Asp Ala Asp Gly Ile Met Gln Thr
```

```
                290                 295                 300
Tyr Phe Asp His Thr Arg Pro Arg Met Asp Pro Phe Val Cys Val Asn
305                 310                 315                 320

Val Leu Ser Leu Phe His Glu Gln Gly Arg Gly His Glu Leu Pro Asn
                325                 330                 335

Thr Leu Glu Trp Val His Glu Val Leu Leu His Arg Ala Tyr Ile Gly
                340                 345                 350

Gly Ser Arg Tyr Tyr Leu Ser Ala Asp Cys Phe Leu Phe Phe Met Ser
                355                 360                 365

Arg Leu Leu Gln Arg Ile Thr Asp Pro Ser Val Leu Gly Arg Phe Arg
370                 375                 380

Pro Leu Phe Ile Glu Arg Val Arg Glu Arg Val Gly Ala Thr Gly Asp
385                 390                 395                 400

Ser Ile Asp Leu Ala Phe Arg Ile Ile Ala Ala Ser Thr Val Gly Ile
                405                 410                 415

Gln Cys Pro Arg Asp Leu Glu Ser Leu Leu Ala Ala Gln Cys Glu Asp
                420                 425                 430

Gly Gly Trp Asp Leu Cys Trp Phe Tyr Gln Tyr Gly Ser Thr Gly Val
                435                 440                 445

Lys Ala Gly Asn Arg Gly Leu Thr Thr Ala Leu Ala Ile Lys Ala Ile
                450                 455                 460

Asp Ser Ala Ile Ala Arg Pro Pro Ser Pro Ala Leu Ser Val Ala Ser
465                 470                 475                 480

Ser Ser Lys Ser Glu Ile Pro Lys Pro Ile Gln Arg Ser Leu Arg Pro
                485                 490                 495

Leu Ser Pro Arg Arg Phe Gly Gly Phe Leu Met Pro Trp Arg Arg Ser
                500                 505                 510

Gln Arg Asn Gly Val Ala Val Ser Ser
                515                 520

<210> SEQ ID NO 6
<211> LENGTH: 2291
<212> TYPE: DNA
<213> ORGANISM: Laricifomes officinalis

<400> SEQUENCE: 6
gcgtctgctg cggtctctca ccgcgccgag cgacgggaag cggaggcttt ttgatgcagc      60
cagctcagcg ccatcctctc acgcaggggg tttgatccag atctgatcgc ctccgggttc     120
tcatctagaa cgcacggcgg ctcccaggaa gttctatcga ccctctgcgc gctggtcggc     180
ggcacgatgt ggctacacca gtcccaatca tatctcacac ccagcaccat catctcgggc     240
ctcttcgtca tgtaaccctc ccaagccta t ttttcagggc gttcccccte accgcgcgc     300 ttcttaaaga atcccgaaat gtatacggct cttatccttg acctcggcga cgttctgttc     360
tcttggtcgt cgacgaccaa cacgactatt cccctcggc agctaaagga gatcctctca     420
tctcctgcct ggtttgagta cgagcgtggt cgcataacgc aagccgaatg ctacgagcgt     480
gtcagcgccg agttcagcct agacgccacc gccgtcgcgg aagcattccg gcaagctcgc     540
gactccttgc gcccgaacga caagttcctc acgttaattc gcgagcttcg acaacaatct     600
catggggagc tcacggtgct tgcgctgtcc aacatatccc ttcccgacta tgaattcatc     660
atggccctcg actcgaagtg gacttctgtc tttgaccgcg tcttcccctt cgccctcgtg     720
ggcgaacgga agccacacct tggagcgttt cgccaggttc gtccagagat gaatcttgac     780
ccgcacacaa ctgtgttcgt cgatgacaag ctggacaatg tcgtctccgc acggtccctc     840
```

```
gggatgcacg gcgtcgtgtt cgactcccaa gacaatgtct ttcggatgct gagaaacatc      900
tttggcgatc ccattcatcg gggacgtgac tatctccgac agcacgccgg acgtctggag      960
acctccacgg atgccggtgt ggtcttcgaa gagaatttca cgcaactcat catctacgaa     1020
ctgacgaatg acaagtctct catcacgaca tcaaactgtg ctcgtacttg gaatttcttt     1080
cgtgggaagc ctttgttctc agcatcgttc cctgacgaca tggacacgac ctcggttgcc     1140
ttgactgtat tacgtttaga ccacgccctc gtgaactcgg ttttggacga gatgctaaag     1200
tatgtcgacg cagacggcat catgcagacc tacttcgacc atacacgccc acgcatggat     1260
ccatttgtct gcgtcaatgt gctctcgttg tttcacgaac aaggtcgtgg ccacgagctt     1320
ccgaacaccc tcgaatgggt ccatgaggtc ctcctccacc gcgcgtacat cgggggctcg     1380
cggtactacc tctccgcgga ctgcttcctc tttttcatga gccgcctcct gcagcgcatc     1440
accgacccgt ccgtccttgg ccgcttccgt ccactattca tagagcgcgt tcgggagcgt     1500
gtaggtgcga ccggggactc catcgatctc gcattccgca tcatcgccgc gtccacagta     1560
ggcatccagt gtccacgcga cttggaaagt ctcctcgccg cacagtgtga agacggtggc     1620
tgggacctgt gctggttcta ccagtacgga tcgaccggtg tcaaggcggg caaccgcggg     1680
ctcaccaccg ctctggcgat caaagctatt gactccgcca ttgcgaggcc accttcgcct     1740
gccctctcag tcgcttcgtc gtccaaatcg gagataccga aacccataca acggtccctt     1800
aggcccctta gccccgccg gtttggcggt ttcctgatgc cgtggcgcag gtcacagcgc     1860
aatggcgtgg cggtctctag ttgaacactt gacccttgac acttcgcttt gcactgcctg     1920
ctcccctgcc aatcctcccc tacgatcgta tcatccctct cttgccctcg cctccccctc     1980
gtaccccctc tcatggggtg ccatttgtag atatgtacgt agcgtgatgt agcggtactc     2040
ggatcgttct cgtactcgtc ttgctctgcc gtcgcttcca gcccgtgctg ttctctcgtt     2100
caggctattc gttggttacg cgtatatcgt aatagaccgc cccggttcct cgcctacaga     2160
cactcgcccg tctcgccacg gactcggcta cggattcaga ctacatgagt ggcagttatc     2220
acacgcagat ccctccttgg tcgttctgta gtacccacat atgtaattgt accagtccac     2280
tgttgcagat c                                                         2291
```

<210> SEQ ID NO 7
<211> LENGTH: 1566
<212> TYPE: DNA
<213> ORGANISM: Laricifomes officinalis
<220> FEATURE:
<221> NAME/KEY: misc_feature
<223> OTHER INFORMATION: cDNA

<400> SEQUENCE: 7

```
atgtatacgg ctcttatcct tgacctcggc gacgttctgt tctcttggtc gtcgacgacc       60
aacacgacta ttccccctcg gcagctaaag gagatcctct catctcctgc ctggtttgag      120
tacgagcgtg gtcgcataac gcaagccgaa tgctacgagc gtgtcagcgc cgagttcagc      180
ctagacgcca ccgccgtcgc ggaagcattc cggcaagctc gcgactcctt gcgcccgaac      240
gacaagttcc tcacgttaat tcgcgagctt cgacaacaat ctcatgggga gctcacggtg      300
cttgcgctgt ccaacatatc ccttcccgac tatgaattca tcatggccct cgactcgaag      360
tggacttctg tctttgaccg cgtcttccct tctgccctcg tgggcgaacg gaagccacac      420
cttggagcgt ttcgccaggt tctgtccgag atgaatcttg acccgcacac aactgtgttc      480
gtcgatgaca agctggacaa tgtcgtctcc gcacggtccc tcgggatgca cggcgtcgtg      540
```

```
ttcgactccc aagacaatgt ctttcggatg ctgagaaaca tctttggcga tcccattcat    600
cggggacgtg actatctccg acagcacgcc ggacgtctgg agacctccac ggatgccggt    660
gtggtcttcg aagagaattt cacgcaactc atcatctacg aactgacgaa tgacaagtct    720
ctcatcacga catcaaactg tgctcgtact tggaatttct tcgtgggaa gcctttgttc     780 tcagcatcgt tccctgacga catggacacg acctcggttg ccttgactgt attacgttta    840
gaccacgccc tcgtgaactc ggttttggac gagatgctaa agtatgtcga cgcagacggc    900
atcatgcaga cctacttcga ccatacacgc ccacgcatgg atccatttgt ctgcgtcaat    960
gtgctctcgt tgtttcacga acaaggtcgt ggccacgagc ttccgaacac cctcgaatgg   1020
gtccatgagg tcctcctcca ccgcgcgtac atcggggct cgcggtacta cctctccgcg    1080
gactgcttcc tcttttttcat gagccgcctc ctgcagcgca tcaccgaccc gtccgtcctt   1140
ggccgcttcc gtccactatt catagagcgc gttcgggagc gtgtaggtgc gaccggggac   1200
tccatcgatc tcgcattccg catcatcgcc gcgtccacag taggcatcca gtgtccacgc   1260
gacttggaaa gtctcctcgc cgcacagtgt gaagacggtg gctgggacct gtgctggttc   1320
taccagtacg gatcgaccgg tgtcaaggcg ggcaaccgcg ggctcaccac cgctctggcg   1380
atcaaagcta ttgactccgc cattgcgagg ccaccttcgc ctgccctctc agtcgcttcg   1440
tcgtccaaat cggagatacc gaaacccata aacggtccc ttaggcccct tagccccgc     1500 cggtttggcg gtttcctgat gccgtggcgc aggtcacagc gcaatggcgt ggcggtctct   1560
agttga                                                             1566
```

<210> SEQ ID NO 8  
<211> LENGTH: 1566  
<212> TYPE: DNA  
<213> ORGANISM: Artificial Sequence  
<220> FEATURE:  
<223> OTHER INFORMATION: codon optimized cDNA

<400> SEQUENCE: 8

```
atgtacacgg cgctgatttt ggatttgggt gatgttctgt ttagctggag ctcaacgact     60
aacaccacca ttccgccgcg tcagctgaaa gaaatcttga gctccccggc gtggttcgag    120
tacgagcgtg gccgtatcac ccaggcagag tgttatgagc gtgtcagcgc agagtttagc    180
ctggatgcga cggccgtggc tgaggctttt cgtcaggcac gtgatagcct gcgtccgaac    240
gacaaatttc tgaccctgat ccgtgagctg cgtcaacaga gccacggtga attgaccgtt    300 ctggcccttgt ctaacatcag cctgccggat tacgaattta ttatggcact ggactcgaag    360
tggaccagcg tgtttgatcg tgtgttcccg agcgccctgg tgggcgaacg caagccgcac   420
ctgggcgcgt tccgccaagt cctgtccgag atgaatttgg accgcatac caccgttttt     480 gtggacgaca aactggacaa tgttgtcagc gcacgcagcc tgggtatgca cggtgtcgtg     540
ttcgacagcc aagacaatgt ttttcgtatg ctgcgtaaca ttttcggtga cccaattcac    600
cgcggtcgtg actatctgcg ccagcacgct ggtcgtcttg aaacgtccac cgatgcgggc    660
gttgtgttcg aagagaactt cacccaactg atcatttacg aactgaccaa cgataagagc    720
ctgatcacca cctctaattg cgcccgcacc tggaacttct ccgcggcaa acctctgttc     780 tccgcgagct ttccggacga tatggacact acgtcggtag cgctgaccgt gctgcgtctg    840
gaccatgcgc tggtgaatag cgttctggat gaaatgctga atacgtcga tgctgacggt    900 attatgcaga cctactttga tcatacgcgt cctcgtatgg acccgttcgt ttgcgtcaat    960
```

```
gtgctgagcc tgtttcacga gcaaggtcgc ggtcatgaac tgccgaatac gctggaatgg    1020
gtgcatgaag tcctgctgca ccgtgcgtat atcggtggca gccgctatta tctgagcgcg    1080
gattgtttcc tgttctttat gagccgtctg ttgcaacgta ttaccgaccc gagcgtttta    1140
ggtagatttc gcccgctgtt catcgagcgt gttcgcgagc gcgttggcgc gactggcgac    1200
agcatcgacc tggcattccg tatcatcgcg gccagcacgg tcggcattca atgcccgcgt    1260
gacctggagt ctctgctggc agcacagtgc gaagatggtg gctgggatct gtgttggttt    1320
taccagtacg gcagcacggg tgttaaggcc ggtaaccgtg gtctgaccac ggcgttggcg    1380
atcaaagcga ttgacagcgc catcgcgcgt ccgccaagcc cggccctgtc cgttgcaagc    1440
tccagcaaga gcgagattcc gaagccgatt cagcgtagcc tccgcccgtt gagcccgcgt    1500
cgcttcggtg gcttcctgat gccgtggcgt cgtagccaac gcaatggtgt cgcggtgagc    1560
tcttaa                                                                 1566
```

<210> SEQ ID NO 9
<211> LENGTH: 527
<212> TYPE: PRT
<213> ORGANISM: Obba rivulosa

<400> SEQUENCE: 9

```
Met Ser Ala Ala Val Arg Tyr Thr Thr Leu Ile Leu Asp Leu Gly Asp
1               5                   10                  15

Val Leu Phe Thr Trp Ser Pro Lys Thr Lys Thr Ser Ile Ser Pro Arg
                20                  25                  30

Ile Leu Lys Glu Ile Leu Asn Ser Ala Thr Trp Tyr Glu Tyr Glu Arg
            35                  40                  45

Gly Ser Ile Thr Gln His Glu Cys Tyr Glu Arg Val Gly Val Glu Phe
        50                  55                  60

Gly Ile Ala Pro Ser Glu Ile His Asn Ala Phe Lys Gln Ala Arg Asp
65                  70                  75                  80

Ser Met Glu Ser Asn Asp Glu Leu Ile Ala Leu Val Arg Glu Leu Lys
                85                  90                  95

Glu Gln Ser Asp Gly Glu Leu Leu Val Phe Ala Leu Ser Asn Ile Ser
            100                 105                 110

Leu Pro Asp Tyr Glu Tyr Val Leu Thr Lys Pro Ala Asp Trp Ser Ile
        115                 120                 125

Phe Asp Lys Val Phe Pro Ser Ala Leu Val Gly Glu Arg Lys Pro His
    130                 135                 140

Leu Gly Ile Tyr Lys His Val Ile Ala Glu Thr Gly Val Asp Pro Arg
145                 150                 155                 160

Thr Thr Val Phe Val Asp Asp Lys Ile Asp Asn Val Leu Ser Ala Arg
                165                 170                 175

Ser Leu Gly Met His Gly Ile Val Phe Asp Lys His Glu Asp Val Met
            180                 185                 190

Arg Ala Leu Arg Asn Ile Phe Gly Asp Pro Val Arg Arg Gly Arg Glu
        195                 200                 205

Tyr Leu Arg Arg Asn Ala Arg Lys Leu Glu Ser Ile Thr Asp His Gly
    210                 215                 220

Val Ala Phe Gly Glu Asn Phe Thr Gln Leu Leu Ile Leu Glu Leu Thr
225                 230                 235                 240

Ser Asp Ala Ser Leu Val Thr Leu Pro Asp Arg Pro Arg Thr Trp Asn
                245                 250                 255

Phe Phe Arg Gly Lys Pro Leu Phe Ser Glu Ala Phe Pro Asp Asp Leu
```

```
                    260                 265                 270
Asp Thr Thr Ser Leu Ala Leu Thr Val Leu Lys Arg Asp Ala Ala Thr
            275                 280                 285

Val Ser Ser Val Met Asp Glu Met Leu Lys Tyr Arg Asp Ala Asp Gly
        290                 295                 300

Ile Met Gln Thr Tyr Phe Asp Asn Gly Arg Gln Arg Leu Asp Pro Phe
305                 310                 315                 320

Val Asn Ala Asn Val Leu Thr Leu Phe Tyr Ala Asn Gly Arg Gly His
                325                 330                 335

Glu Leu Asp Gln Ser Leu Ser Trp Val Arg Glu Val Leu Leu Tyr Arg
            340                 345                 350

Ala Tyr Leu Gly Gly Ser Arg Tyr Tyr Pro Ser Ala Asp Cys Phe Leu
        355                 360                 365

Tyr Phe Ile Ser Arg Leu Phe Ala Cys Thr Ser Asp Pro Val Leu His
370                 375                 380

His Gln Leu Lys Pro Leu Phe Val Glu Arg Val His Glu Arg Ile Gly
385                 390                 395                 400

Val Gln Gly Asp Ala Leu Glu Leu Ala Phe Arg Leu Leu Val Cys Ala
                405                 410                 415

Ser Phe Asn Ile Ser Asn Gln Pro Asp Met Arg Lys Leu Leu Glu Met
            420                 425                 430

Gln Cys Gln Asp Gly Gly Trp Asp Gly Gly Asn Leu Tyr Arg Phe Gly
        435                 440                 445

Thr Thr Gly Leu Lys Val Thr Asn Arg Gly Leu Thr Thr Ala Ala Ala
450                 455                 460

Val Gln Ala Ile Glu Ala Thr Gln Leu Arg Pro Pro Ser Pro Ala Phe
465                 470                 475                 480

Ser Val Glu Ser Pro Lys Ser Pro Val Thr Pro Val Thr Pro Met Leu
                485                 490                 495

Glu Ile Pro Ala Leu Gly Leu Ser Ile Ser Arg Pro Ser Ser Pro Leu
            500                 505                 510

Leu Gly Tyr Phe Lys Leu Pro Trp Lys Lys Ser Ala Glu Val His
        515                 520                 525

<210> SEQ ID NO 10
<211> LENGTH: 1584
<212> TYPE: DNA
<213> ORGANISM: Obba rivulosa
<220> FEATURE:
<221> NAME/KEY: misc_feature
<223> OTHER INFORMATION: cDNA

<400> SEQUENCE: 10
atgtccgcag cagttcggta cacgaccctc atcctcgacc ttggcgacgt cttgttcact      60
tggtcaccga agacgaagac cagcatctcg cctcgtattc tgaaggagat cctgaattcc     120
gcgacctggt atgagtacga gcgcggtagt atcactcagc acgaatgtta cgaacgcgtt     180
ggcgtggagt tcggtattgc gccgagcgag atccacaacg cgttcaagca ggctcgggac     240
tctatggagt cgaatgacga gctgatcgcc cttgttcggg aactgaagga gcagtcagat     300
ggagagcttc tcgtcttcgc attatcgaac atctcactgc ggactacga atacgtcctg      360 acgaagcccg cggactggtc catcttcgac aaagtctttc cttccgctct cgtcggcgag     420
cgcaagcccc atctcggcat ctacaaaaca gtcatcgcag agacgggcgt tgatccgcga     480
acaaccgtct tcgtggacga caagatcgac aatgtgcttt cggcgcggtc gctcggtatg     540
```

| | | |
|---|---|---|
| cacggcattg tcttcgacaa acacgaagac gtaatgcgcg ctctgcgaaa cattttcggt | 600 | |
| gaccccgtgc gaagaggacg agaatatttg cgtcgaaatg caaggaaatt ggaatccatc | 660 | |
| acagatcacg gcgtcgcctt cggggagaac ttcacccagc ttctgatcct cgaacttact | 720 | |
| agtgatgcgt ccctcgttac tctccctgat cgtcctcgga catggaattt tttccgaggg | 780 | |
| aagccgctct tttcggaggc cttccccgat gaccttgata ctacttcctt ggcactcact | 840 | |
| gtcctgaaaa gagatgccgc cactgtatcg tccgtgatgg acgagatgct gaaatacagg | 900 | |
| gacgcggacg gcatcatgca gacatacttc gacaacggtc ggcaacgact cgatccgttc | 960 | |
| gtcaacgcca acgttttgac cctcttctac gccaacggtc gcggacacga gctggatcag | 1020 | |
| agcctcagct gggttcgcga agtcttgctc taccgcgctt acctcggcgg ttcccgctac | 1080 | |
| taccctccg ccgactgctt cctatatttc atcagccgcc tcttcgcctg caccagcgac | 1140 | |
| ccggtcctcc atcatcaact taagcccctc tttgttgagc gtgtgcacga gcggatagga | 1200 | |
| gtgcagggcg acgcgctgga gctcgccttc cgcctgcttg tatgcgcgag cttcaacatc | 1260 | |
| tcgaaccagc ctgacatgcg caagctgctc gagatgcagt gccaggacgg aggctgggat | 1320 | |
| ggcggaaacc tgtatcgttt cggcaccacg ggcctcaagg tcacgaaccg gggtctgacc | 1380 | |
| accgcagcag ccgtgcaagc catcgaggcg acgcagctgc gtccaccatc accggcgttc | 1440 | |
| tctgtcgagt cgcctaagag cccggtgacg ccggtgacgc ccatgctgga gattccagcg | 1500 | |
| ctgggtctca gcatctcgcg gccctccagt cctctgttgg ggtatttcaa gctcccgtgg | 1560 | |
| aagaagtcag ccgaggttca ttga | 1584 | |

<210> SEQ ID NO 11
<211> LENGTH: 1584
<212> TYPE: DNA
<213> ORGANISM: Artificial Sequence
<220> FEATURE:
<223> OTHER INFORMATION: codon optimized cDNA

<400> SEQUENCE: 11

| | | |
|---|---|---|
| atgtctgcag ctgttcgtta tactactctg atcctggatt tgggcgatgt tctgttcacc | 60 | |
| tggtccccga aaaccaagac ctctatcagc ccacgtatcc tgaaagaaat cctgaacagc | 120 | |
| gcgacctggt acgagtatga gcgtggcagc atcacccagc acgagtgcta cgagcgtgtt | 180 | |
| ggcgtcgaat tggtattgc gccgagcgag attcacaacg cgttcaaaca agcccgcgac | 240 | |
| agcatggaat ccaacgacga actgattgct ctggtgcgtg agctgaaaga cagagcgat | 300 | |
| ggtgagctgc tggtctttgc cctgagcaat atctctctgc ggattacga atacgttctg | 360 | |
| accaaaccag cggactggtc aatcttcgat aaagtctttc gagcgctttt ggtcggtgag | 420 | |
| cgtaaaccgc atctgggtat ttacaaacac gttattgcgg aaaccggtgt tgaccccgaga | 480 | |
| acgaccgttt ttgttgacga taagattgac aacgtcctga gcgcacgcag cctgggtatg | 540 | |
| catggtattg tctttgataa acacgaagat gtgatgcgtg ctctgcgcaa tatctttggc | 600 | |
| gacccggtgc gtcgcggtcg tgagtatttg cgccgcaacg cgcgcaaatt ggagtccatt | 660 | |
| accgatcatg gtgtcgcatt tggtgagaat ttcacccagc tcctgattct ggaactgacc | 720 | |
| agcgacgcgt ccctggtgac gctgccggat cgtccgcgta cgtggaactt cttccgcggc | 780 | |
| aagccgctgt ttagcgaagc gttcccggat gacctggaca ccacgagcct ggcactgacg | 840 | |
| gtgctgaaac gcgatgcagc aactgtgagc tccgtcatgg acgaaatgct gaagtaccgc | 900 | |
| gacgcggatg gcatcatgca gacgtatttc gacaacggtc gtcagcgtct ggaccccgttt | 960 | |
| gtcaacgcca atgttctgac gctgtttttac gcgaatggcc gtggtcatga actggaccag | 1020 | |

```
agcttatcat gggtgcgtga agtgctgctg tatcgcgcct atctgggtgg cagccgctac    1080
tatccgagcg cggactgttt tctgtacttc attagccgct tgttcgcctg caccagcgat    1140
ccggttctgc atcaccaact gaagccattg ttcgtcgagc gtgtgcacga gcgtattggt    1200
gttcagggcg acgcactgga actggcgttc cgtctgttgg tgtgtgcgag cttcaacatt    1260
agcaatcagc cggatatgcg taagctgctg gaaatgcaat gccaagatgg cggctgggac    1320
ggtggtaatc tgtaccgttt tggcaccacc ggtttaaaag tgacgaatcg tggtttgacc    1380
accgctgcgg ccgttcaagc aattgaagca acgcaactgc gtccgccgag cccagcattt    1440
agcgtagagt cgcctaagag cccggttacg ccggtgacgc cgatgctgga atcccggcg     1500 ctgggtctgt ctatcagccg tccgtcgagc ccgctgctgg gctatttcaa gttgccgtgg    1560
aagaaaagcg ccgaagtgca ctaa                                          1584
```

<210> SEQ ID NO 12
<211> LENGTH: 533
<212> TYPE: PRT
<213> ORGANISM: Gelatoporia subvermispora

<400> SEQUENCE: 12

```
Met Ser Ala Ala Ala Gln Tyr Thr Thr Leu Ile Leu Asp Leu Gly Asp
1               5                   10                  15

Val Leu Phe Thr Trp Ser Pro Lys Thr Lys Thr Ser Ile Pro Pro Arg
            20                  25                  30

Thr Leu Lys Glu Ile Leu Asn Ser Ala Thr Trp Tyr Glu Tyr Glu Arg
        35                  40                  45

Gly Arg Ile Ser Gln Asp Glu Cys Tyr Glu Arg Val Gly Thr Glu Phe
    50                  55                  60

Gly Ile Ala Pro Ser Glu Ile Asp Asn Ala Phe Lys Gln Ala Arg Asp
65                  70                  75                  80

Ser Met Glu Ser Asn Asp Glu Leu Ile Ala Leu Val Arg Glu Leu Lys
                85                  90                  95

Thr Gln Leu Asp Gly Glu Leu Leu Val Phe Ala Leu Ser Asn Ile Ser
            100                 105                 110

Leu Pro Asp Tyr Glu Tyr Val Leu Thr Lys Pro Ala Asp Trp Ser Ile
        115                 120                 125

Phe Asp Lys Val Phe Pro Ser Ala Leu Val Gly Glu Arg Lys Pro His
    130                 135                 140

Leu Gly Val Tyr Lys His Val Ile Ala Glu Thr Gly Ile Asp Pro Arg
145                 150                 155                 160

Thr Thr Val Phe Val Asp Asp Lys Ile Asp Asn Val Leu Ser Ala Arg
                165                 170                 175

Ser Val Gly Met His Gly Ile Val Phe Glu Lys Gln Glu Asp Val Met
            180                 185                 190

Arg Ala Leu Arg Asn Ile Phe Gly Asp Pro Val Arg Gly Arg Glu
        195                 200                 205

Tyr Leu Arg Arg Asn Ala Met Arg Leu Glu Ser Val Thr Asp His Gly
    210                 215                 220

Val Ala Phe Gly Glu Asn Phe Thr Gln Leu Leu Ile Leu Glu Leu Thr
225                 230                 235                 240

Asn Asp Pro Ser Leu Val Thr Leu Pro Asp Arg Pro Arg Thr Trp Asn
                245                 250                 255

Phe Phe Arg Gly Asn Gly Gly Arg Pro Ser Lys Pro Leu Phe Ser Glu
            260                 265                 270
```

Ala Phe Pro Asp Asp Leu Asp Thr Thr Ser Leu Ala Leu Thr Val Leu
            275                 280                 285

Gln Arg Asp Pro Gly Val Ile Ser Ser Val Met Asp Glu Met Leu Asn
        290                 295                 300

Tyr Arg Asp Pro Asp Gly Ile Met Gln Thr Tyr Phe Asp Asp Gly Arg
305                 310                 315                 320

Gln Arg Leu Asp Pro Phe Val Asn Val Asn Val Leu Thr Phe Phe Tyr
                325                 330                 335

Thr Asn Gly Arg Gly His Glu Leu Asp Gln Cys Leu Thr Trp Val Arg
            340                 345                 350

Glu Val Leu Leu Tyr Arg Ala Tyr Leu Gly Gly Ser Arg Tyr Tyr Pro
        355                 360                 365

Ser Ala Asp Cys Phe Leu Tyr Phe Ile Ser Arg Leu Phe Ala Cys Thr
370                 375                 380

Asn Asp Pro Val Leu His His Gln Leu Lys Pro Leu Phe Val Glu Arg
385                 390                 395                 400

Val Gln Glu Gln Ile Gly Val Glu Gly Asp Ala Leu Glu Leu Ala Phe
                405                 410                 415

Arg Leu Leu Val Cys Ala Ser Leu Asp Val Gln Asn Ala Ile Asp Met
            420                 425                 430

Arg Arg Leu Leu Glu Met Gln Cys Glu Asp Gly Gly Trp Glu Gly Gly
        435                 440                 445

Asn Leu Tyr Arg Phe Gly Thr Thr Gly Leu Lys Val Thr Asn Arg Gly
450                 455                 460

Leu Thr Thr Ala Ala Ala Val Gln Ala Ile Glu Ala Ser Gln Arg Arg
465                 470                 475                 480

Pro Pro Ser Pro Ser Pro Ser Val Glu Ser Thr Lys Ser Pro Ile Thr
                485                 490                 495

Pro Val Thr Pro Met Leu Glu Val Pro Ser Leu Gly Leu Ser Ile Ser
            500                 505                 510

Arg Pro Ser Ser Pro Leu Leu Gly Tyr Phe Arg Leu Pro Trp Lys Lys
        515                 520                 525

Ser Ala Glu Val His
    530

<210> SEQ ID NO 13
<211> LENGTH: 1602
<212> TYPE: DNA
<213> ORGANISM: Gelatoporia subvermispora
<220> FEATURE:
<221> NAME/KEY: misc_feature
<223> OTHER INFORMATION: cDNA

<400> SEQUENCE: 13
atgtccgcgg cagctcaata cacgaccctc attctcgacc ttggcgacgt cctgttcacc    60
tggtcaccga aaaccaagac gagcatcccc cctcggactc tgaaggagat tctcaattcc   120
gcgacatggt atgagtatga gcgcggccgc atctctcagg acgaatgtta cgaacgcgtt   180
ggcacggagt tcggaatcgc gcctagcgaa atcgacaacg cgttcaagca agctcgggat   240
tccatggaat ccaacgacga actgatcgcc cttgttcggg aactcaagac gcagttggac   300
ggcgaactcc ttgtcttcgc actctcaaat atctcgttgc ctgactacga gtacgtcctc   360
acgaaaccgg ccgactggtc catcttcgac aaggtcttcc cttccgccct cgtgggcgag   420
cgcaagccgc acctcggcgt ttacaagcac gtcattgcag aaacgggcat tgatccgcga   480

```
accaccgttt tcgtggacga caagatcgac aacgtgctct cagcgcggtc tgtaggtatg      540
catgggatcg ttttcgagaa gcaggaagac gtaatgcgcg ctctccgaaa catcttcgga      600
gacccggttc ggcgagggcg cgagtacttg cgccgtaatg ccatgaggct tgaatcggtt      660
acagaccatg gtgtggcgtt tggcgagaac ttcacacaac tccttatcct cgaactaacg      720
aacgatccct ccctcgttac gctccctgat cgtcctcgaa catggaattt cttccgaggt      780 aacggggggac gaccaagcaa accattattc tcggaggcct tccccgatga cttggacact      840
acttcactag cgttgactgt cctccaaaga gatcccggcg tcatctcttc tgtgatggac      900
gaaatgttga actacaggga tccggacggc attatgcaga catacttcga cgatggtcgg      960
caaagactcg atccatttgt caatgtcaat gtcttaacgt tcttctacac caacggacgt     1020
ggtcatgaac tggaccaatg ccttacatgg gtccgcgaag ttttgctcta tcgcgcctat     1080
ctcggcggct cacgttatta cccctccgcc gactgctttc tctacttcat cagccgcctt     1140
ttcgcatgca cgaatgaccc cgtgctacac caccaactca aaccgctctt cgtcgagcgc     1200
gtgcaggagc aaatcggcgt ggagggcgat gcgctcgagt tggcgttccg attgctcgtc     1260
tgtgcaagcc tggacgtcca aaacgcgatc gacatgcgca ggctgctcga gatgcaatgc     1320
gaagatggcg ctgggagggg cgggaacctt tataggtttg gcacgaccgg gctcaaggtg     1380
actaaccggg gcctgacgac tgcagcggcc gtacaggcca tcgaggcgtc ccaacggcgc     1440
ccaccatcac cgtcccccctc cgtcgaatct acaaagagcc caataacccc tgtgacgccc     1500
atgctggagg tccccctcgct cggcctgagc atctcgaggc cgtccagccc tttactcggc     1560
tacttcaggc tcccgtggaa gaagtcggcc gaagtacact ga                        1602

<210> SEQ ID NO 14
<211> LENGTH: 1602
<212> TYPE: DNA
<213> ORGANISM: Artificial Sequence
<220> FEATURE:
<223> OTHER INFORMATION: codon optimized cDNA

<400> SEQUENCE: 14
atgtctgcgg cggctcaata cacgactttg attctggatc tgggtgatgt tctgttcact       60
tggtccccga aaaccaagac cagcatccct ccgcgtaccc tgaaagaaat cctgaatagc      120
gctacctggt atgagtacga gcgtggtcgc atttcccaag acgagtgtta cgaacgtgtg      180
ggcaccgagt tcggcattgc gccgagcgag attgacaacg cgttcaaaca agcgcgcgat      240
tcgatggaaa gcaatgatga actgatcgca ctggtccgtg agctgaaaac gcagctggac      300
ggtgagctgc tggttttcgc actgtccaat attagcctgc cggattacga atacgtcttg      360
accaaaccgg cggactggag catctttgac aaagtgttcc ctagcgcctt ggtgggcgag      420
cgtaagccgc atctgggcgt ttataaacac gttattgcgg aaacgggcat tgatccgcgc      480
acgacggttt tcgtggacga caagattgac aatgtgttaa gcgcacgcag cgtcggtatg      540
catggtatcg tgtttgagaa acaagaagat gtcatgcgtg cactgcgtaa catctttggt      600
gatccggtcc gtcgtggtcg tgagtatctg cgtagaaacg caatgcgtct ggagtccgtg      660
accgaccacg gcgtggcgtt tggtgagaac tttacccagt tgctgattct ggaattgacg      720
aacgacccga gcctggtcac cctgcctgat cgtccgcgta cctggaactt ttttcgcggc      780
aatggtggcc gcccgagcaa gccgctgttc agcgaagcgt tcccggatga tctggatacc      840
acgagcctgg cgctgaccgt gctgcagcgc gacccggggtt tatcagcag cgttatggac      900 gaaatgctga attaccgtga cccggacggt atcatgcaga cttatttcga tgacggtcgc      960
```

```
caacgcttgg acccatttgt gaacgtcaat gttctgacct ttttctatac gaacggccgt    1020
ggtcacgaac tggaccagtg tctgacgtgg gtgcgtgaag tcctcttgta tcgtgcgtac    1080
cttggtggct cacgctacta cccatcggcg gattgcttcc tgtacttcat ctctcgtctg    1140
tttgcgtgta ccaatgaccc ggtgctgcac atcagctga agccactgtt tgttgagcgt     1200
gtccaagagc aaattggtgt cgagggtgat gcactggaac tggcttttcg tctgctggtc    1260
tgcgccagcc tggatgtcca gaatgccatc gacatgcgcc gtctgctgga aatgcagtgc    1320
gaagatggcg gttgggaggg tggtaacctc taccgcttcg gcaccacggg cctgaaagtt    1380
accaaccgcg gtctgacgac cgcagccgcc gttcaagcga tcgaagcgag ccaacgccgt    1440
ccgccgagcc cgagcccgtc tgtagagagc acgaaaagcc cgattacccc ggtgaccccg    1500
atgctggaag ttccaagcct gggcttatct atcagccgtc cgtccagccc gctgctgggt    1560
tatttccgtt tgccgtggaa gaaaagcgca gaagtgcact aa                       1602
```

<210> SEQ ID NO 15
<211> LENGTH: 527
<212> TYPE: PRT
<213> ORGANISM: Artificial Sequence
<220> FEATURE:
<223> OTHER INFORMATION: codon optimized cDNA

<400> SEQUENCE: 15

```
Met Ser Ala Ala Ala Gln Tyr Thr Thr Leu Ile Leu Asp Leu Gly Asp
1               5                   10                  15

Val Leu Phe Thr Trp Ser Pro Lys Thr Lys Thr Ser Ile Pro Pro Arg
            20                  25                  30

Thr Leu Lys Glu Ile Leu Asn Ser Ala Thr Trp Tyr Glu Tyr Glu Arg
        35                  40                  45

Gly Arg Ile Ser Gln Asp Glu Cys Tyr Glu Arg Val Gly Thr Glu Phe
    50                  55                  60

Gly Ile Ala Pro Ser Glu Ile Asp Asn Ala Phe Lys Gln Ala Arg Asp
65                  70                  75                  80

Ser Met Glu Ser Asn Asp Glu Leu Ile Ala Leu Val Arg Glu Leu Lys
                85                  90                  95

Thr Gln Leu Asp Gly Glu Leu Leu Val Phe Ala Leu Ser Asn Ile Ser
            100                 105                 110

Leu Pro Asp Tyr Glu Tyr Val Leu Thr Lys Pro Ala Asp Trp Ser Ile
        115                 120                 125

Phe Asp Lys Val Phe Pro Ser Ala Leu Val Gly Glu Arg Lys Pro His
    130                 135                 140

Leu Gly Val Tyr Lys His Val Ile Ala Glu Thr Gly Ile Asp Pro Arg
145                 150                 155                 160

Thr Thr Val Phe Val Asp Asp Lys Ile Asp Asn Val Leu Ser Ala Arg
                165                 170                 175

Ser Val Gly Met His Gly Ile Val Phe Glu Lys Gln Glu Asp Val Met
            180                 185                 190

Arg Ala Leu Arg Asn Ile Phe Gly Asp Pro Val Arg Arg Gly Arg Glu
        195                 200                 205

Tyr Leu Arg Arg Asn Ala Met Arg Leu Glu Ser Val Thr Asp His Gly
    210                 215                 220

Val Ala Phe Gly Glu Asn Phe Thr Gln Leu Leu Ile Leu Glu Leu Thr
225                 230                 235                 240

Asn Asp Pro Ser Leu Val Thr Leu Pro Asp Arg Pro Arg Thr Trp Asn
```

```
                    245                 250                 255
Phe Phe Arg Gly Lys Pro Leu Phe Ser Glu Ala Phe Pro Asp Asp Leu
            260                 265                 270

Asp Thr Thr Ser Leu Ala Leu Thr Val Leu Gln Arg Asp Pro Gly Val
        275                 280                 285

Ile Ser Ser Val Met Asp Glu Met Leu Asn Tyr Arg Asp Pro Asp Gly
    290                 295                 300

Ile Met Gln Thr Tyr Phe Asp Asp Gly Arg Gln Arg Leu Asp Pro Phe
305                 310                 315                 320

Val Asn Val Asn Val Leu Thr Phe Phe Tyr Thr Asn Gly Arg Gly His
            325                 330                 335

Glu Leu Asp Gln Cys Leu Thr Trp Val Arg Glu Val Leu Leu Tyr Arg
        340                 345                 350

Ala Tyr Leu Gly Gly Ser Arg Tyr Tyr Pro Ser Ala Asp Cys Phe Leu
    355                 360                 365

Tyr Phe Ile Ser Arg Leu Phe Ala Cys Thr Asn Asp Pro Val Leu His
370                 375                 380

His Gln Leu Lys Pro Leu Phe Val Glu Arg Val Gln Glu Gln Ile Gly
385                 390                 395                 400

Val Glu Gly Asp Ala Leu Glu Leu Ala Phe Arg Leu Val Cys Ala
            405                 410                 415

Ser Leu Asp Val Gln Asn Ala Ile Asp Met Arg Arg Leu Leu Glu Met
        420                 425                 430

Gln Cys Glu Asp Gly Gly Trp Glu Gly Asn Leu Tyr Arg Phe Gly
    435                 440                 445

Thr Thr Gly Leu Lys Val Thr Asn Arg Gly Leu Thr Thr Ala Ala Ala
450                 455                 460

Val Gln Ala Ile Glu Ala Ser Gln Arg Arg Pro Pro Ser Pro Ser Pro
465                 470                 475                 480

Ser Val Glu Ser Thr Lys Ser Pro Ile Thr Pro Val Thr Pro Met Leu
            485                 490                 495

Glu Val Pro Ser Leu Gly Leu Ser Ile Ser Arg Pro Ser Ser Pro Leu
        500                 505                 510

Leu Gly Tyr Phe Arg Leu Pro Trp Lys Lys Ser Ala Glu Val His
    515                 520                 525

<210> SEQ ID NO 16
<211> LENGTH: 1584
<212> TYPE: DNA
<213> ORGANISM: Artificial Sequence
<220> FEATURE:
<223> OTHER INFORMATION: codon optimized cDNA

<400> SEQUENCE: 16
atgtctgcgg ctgctcaata tactactttg attctggatc tgggcgacgt tctgttcacg     60
tggagcccga aaccaagac cagcattcca ccgcgtaccc tgaaggagat cctcaatagc    120
gcgacttggt acgagtatga gcgtggccgc atcagccaag acgagtgcta cgaacgcgtc    180
ggtacggaat tggcattgc accaagcgag attgacaatg cgtttaaaca agcgcgtgac    240
agcatggaaa gcaatgacga actgatcgcg ctggtccgtg agctgaaaac ccagctggat    300
ggtgagctgt tggtgtttgc gctgtcgaac atctctctgc ggactacga gtatgttctg    360 accaaaccgg cggattggag catttttgat aaagtgtttc gagcgcgct ggttggtgag    420 cgcaagccgc acctgggtgt gtacaaacac gttattgcag agactggcat cgacccgcgt    480
```

```
acgacggttt tcgttgacga caagatcgat aacgttctga gcgcacgtag cgtcggtatg    540
cacggtattg ttttcgaaaa acaagaagat gttatgcgcg cactgcgtaa tatcttcggc    600
gatccggtca gacgtggccg tgagtatctg cgccgcaatg cgatgcgtct ggaatcggtg    660
accgatcatg gtgtcgcctt tggcgagaat ttcacccagc tgctgatttt agagctgacc    720
aatgatccta gcctggtgac gctgccggat cgtccgcgta cctggaactt tttccgcggc    780
aagccgttgt tctccgaagc cttcccggac gacctggaca cgaccagcct ggcgctgacc    840
gtgctgcaac gtgatccggg tgtgatctct tccgtaatgg acgaaatgct gaactaccgt    900
gacccggacg gtatcatgca gacctatttt gacgacggtc gtcagcgtct ggacccgttt    960
gtgaacgtga atgtcctgac gttctttac accaatggtc gcggtcacga actggatcag    1020
tgtctgacct gggtccgcga agtgctgctg tatcgtgcat acctgggtgg cagccgttat    1080
tacccgagcg ccgattgctt tctgtacttt atcagccgtc tgttcgcgtg cacgaacgat    1140
ccggttctgc atcaccagct gaagccgtta tttgttgagc gcgttcagga acaaattggt    1200
gtcgagggtg atgcgctgga attggcattc cgcctgttgg tctgcgccag ccttgatgtc    1260
cagaacgcca ttgacatgcg tcgcttgctc gaaatgcagt gtgaggacgg cggttgggag    1320
ggtggcaacc tgtaccgttt cggtacgacc ggcctgaaag tcacgaaccg tggtctgacg    1380
acggcagctg cggtgcaagc aattgaagcc agccaacgtc gtccgccatc cccgtcaccg    1440
agcgttgagt ccaccaagag cccgattacc cctgtgaccc cgatgcttga agttccgagc    1500
ctgggtctga gcatctcccg tcctagcagc ccgctgttgg gttacttccg cctgccgtgg    1560
aagaaaagcg ctgaggtgca ttaa                                          1584
```

<210> SEQ ID NO 17
<211> LENGTH: 486
<212> TYPE: PRT
<213> ORGANISM: Aspergillus terreus

<400> SEQUENCE: 17

Met Ala Ile Thr Lys Gly Pro Val Lys Ala Leu Ile Leu Asp Phe Ser
1               5                   10                  15

Asn Val Leu Cys Ser Trp Lys Pro Pro Ser Asn Val Ala Val Pro Pro
            20                  25                  30

Gln Ile Leu Lys Met Ile Met Ser Ser Asp Ile Trp His Asp Tyr Glu
        35                  40                  45

Cys Gly Arg Tyr Ser Arg Glu Asp Cys Tyr Ala Arg Val Ala Asp Arg
    50                  55                  60

Phe His Ile Ser Ala Ala Asp Met Glu Asp Thr Leu Lys Gln Ala Arg
65                  70                  75                  80

Lys Ser Leu Gln Val His His Glu Thr Leu Leu Phe Ile Gln Gln Val
                85                  90                  95

Lys Lys Asp Ala Gly Gly Glu Leu Met Val Cys Gly Met Thr Asn Thr
            100                 105                 110

Pro Arg Pro Glu Gln Asp Val Met His Ser Ile Asn Ala Glu Tyr Pro
        115                 120                 125

Val Phe Asp Arg Ile Tyr Ile Ser Gly Leu Met Gly Met Arg Lys Pro
    130                 135                 140

Ser Ile Cys Phe Tyr Gln Arg Val Met Glu Glu Ile Gly Leu Ser Gly
145                 150                 155                 160

Asp Ala Ile Met Phe Ile Asp Asp Lys Leu Glu Asn Val Ile Ala Ala
                165                 170                 175

```
Gln Ser Val Gly Ile Arg Gly Val Leu Phe Gln Ser Gln Gln Asp Leu
            180                 185                 190
Arg Arg Val Val Leu Asn Phe Leu Gly Asp Pro Val His Arg Gly Leu
        195                 200                 205
Gln Phe Leu Ala Ala Asn Ala Lys Lys Met Asp Ser Val Thr Asn Thr
210                 215                 220
Gly Asp Thr Ile Gln Asp Asn Phe Ala Gln Leu Leu Ile Leu Glu Leu
225                 230                 235                 240
Ala Gln Asp Arg Glu Leu Val Lys Leu Gln Ala Gly Lys Arg Thr Trp
                245                 250                 255
Asn Tyr Phe Ile Gly Pro Pro Lys Leu Thr Thr Ala Thr Phe Pro Asp
            260                 265                 270
Asp Met Asp Thr Thr Ser Met Ala Leu Ser Val Leu Pro Val Ala Glu
        275                 280                 285
Asp Val Val Ser Ser Val Leu Asp Glu Met Leu Lys Phe Val Thr Asp
    290                 295                 300
Asp Gly Ile Phe Met Thr Tyr Phe Asp Ser Ser Arg Pro Arg Val Asp
305                 310                 315                 320
Pro Val Val Cys Ile Asn Val Leu Gly Val Phe Cys Arg His Asn Arg
                325                 330                 335
Glu Arg Asp Val Leu Pro Thr Phe His Trp Ile Arg Asp Ile Leu Ile
            340                 345                 350
Asn Arg Ala Tyr Leu Ser Gly Thr Arg Tyr Tyr Pro Ser Pro Asp Leu
        355                 360                 365
Phe Leu Phe Phe Leu Ala Arg Leu Cys Leu Ala Val Arg Asn Gln Ser
    370                 375                 380
Leu Arg Glu Gln Leu Val Leu Pro Leu Val Asp Arg Leu Arg Glu Arg
385                 390                 395                 400
Val Gly Ala Pro Gly Glu Ala Val Ser Leu Ala Ala Arg Ile Leu Ala
                405                 410                 415
Cys Arg Ser Phe Gly Ile Asp Ser Ala Arg Asp Met Asp Ser Leu Arg
            420                 425                 430
Gly Lys Gln Cys Glu Asp Gly Gly Trp Pro Val Glu Trp Val Tyr Arg
        435                 440                 445
Phe Ala Ser Phe Gly Leu Asn Val Gly Asn Arg Gly Leu Ala Thr Ala
    450                 455                 460
Phe Ala Val Arg Ala Leu Glu Ser Pro Tyr Gly Glu Ser Ala Val Lys
465                 470                 475                 480
Val Met Arg Arg Ile Val
                485

<210> SEQ ID NO 18
<211> LENGTH: 1461
<212> TYPE: DNA
<213> ORGANISM: Aspergillus terreus
<220> FEATURE:
<221> NAME/KEY: misc_feature
<223> OTHER INFORMATION: cDNA

<400> SEQUENCE: 18
atggctatca ccaagggtcc agttaaggcg cttattcttg acttttccaa tgttctctgc      60
tcgtggaagc ctcccagcaa tgttgcggtg ccgccccaga tactcaaaat gatcatgtcc     120
tctgacatat ggcatgacta cgagtgcgga cggtactcga gagaggactg ctatgccaga     180
gtggcagacc gttttcatat cagcgccgcg gacatggaag acacgctgaa acaggcgcgc     240
```

```
aagagcctgc aggttcacca tgagacactg ttgtttatcc agcaagtcaa gaaggatgcc      300
gggggcgagt tgatggtgtg tgggatgacc aacacgcccc ggccagagca agacgtaatg      360
cattcaatca acgcggagta tcctgtgttt gataggatat atatatccgg tctcatgggc      420
atgaggaagc cgagcatctg cttctaccag cgggtgatgg aggagattgg cctatcaggc      480
gatgcgatca tgtttataga tgacaagttg gagaatgtca tcgccgccca gtcggtaggg      540
atccgaggcg ttctatttca gagtcagcaa gatctccgtc gggttgtatt aaatttcttg      600
ggcgatccgg tccatcgcgg cctgcagttc ctagcggcca atgcgaaaaa gatggatagt      660
gtgaccaaca ccggcgatac tatccaagat aattttgctc agctcctcat cttggagctg      720
gcccaggaca gggaattggt gaagcttcag gctggaaaaa ggacttggaa ttacttcata      780
gggcctccca gctcacaac agccacgttc cccgatgaca tggacaccac atctatggct      840
ctctcggtcc ttcctgtggc cgaggatgtg gtctcttctg tcctggatga gatgcttaaa      900
ttcgtcaccg atgacggtat ctttatgact tacttcgatt cctcgcgccc tcgagtcgac      960
ccagtcgtat gtatcaacgt cttgggtgtt ttctgcaggc ataaccgaga gcgagacgtc     1020
cttccaacgt tccattggat tcgagacatc ctgatcaacc gggcatatct ctcgggcacc     1080
cgatactacc catcgcccga tttgttttg ttttccttg cacgcctctg cctggcagtc     1140
cggaatcaga gcctacggga acaacttgtc ttgcctctgg tagaccgact gcgtgagcgg     1200
gtgggcgcac ctggagaagc ggtctcattg gcagcgcgga tccttgcctg ccgtagcttt     1260
ggtatcgaca gtgcgagaga catggacagc ttgaggggaa acaatgcga ggatgcggc      1320 tggccagtgg agtgggttta ccggtttgcc tctttcggcc tgaacgtagg caatcggggt     1380
cttgctactg ccttcgcggt cagggcgctc gaaagcccct atggtgagtc ggcggtgaag     1440
gttatgagac gcatcgtctg a                                                1461

<210> SEQ ID NO 19
<211> LENGTH: 1461
<212> TYPE: DNA
<213> ORGANISM: Artificial Sequence
<220> FEATURE:
<223> OTHER INFORMATION: codon optimized cDNA

<400> SEQUENCE: 19
atggcaatca ctaagggccc agttaaagcg ctgattcttg attttttctaa cgttctgtgt       60 agctggaagc cgccgagcaa tgttgcggtc ccgcctcaaa ttctgaagat gattatgtcg      120
agcgacatct ggcatgatta tgagtgtggc cgttacagcc gtgaggactg ctacgcccgt      180
gttgctgacc gttttcatat cagcgcagcg gacatggaag atacc ctgaa acaggcacgt      240 aagtccctgc aagtgcacca cgaaacgctg ctgttcatcc aacaggtgaa gaaagacgcg      300
ggtggtgagc tgatggtttg cggcatgacc aacacgccgc gtccggaaca agacgtgatg      360
cattccatca tgctgagta tccggtgttc gaccgtattt acattagcgg cctgatgggc      420
atgcgtaaac cgagcatttg tttctaccaa cgcgtaatgg aagagattgg tctgagcggt      480
gacgccatca tgttcattga cgataaactg gaaaatgtga ttgccgcaca gagcgtgggt      540
atccgcggtg tgctgttcca aagccagcaa gatctgcgtc gtgtcgtgct gaactttctg      600
ggcgatccgg tccaccgtgg tctgcagttc ttggcggcga acgcaaagaa aatggacagc      660
gtcacgaata ccggcgacac tatccaagac aatttcgcac agctgttgat cttagagctg      720
gcgcaggatc gcgaattggt gaaattgcag gccggtaaac gtacctggaa ctactttatt      780
ggtccgccga agctgaccac ggcgacgttt ccggatgata tggacacgac cagcatggcg      840
```

-continued

```
ctgtcggtgc tgcctgtcgc ggaagatgtc gtgagctctg ttctggacga gatgctgaag    900
ttcgtgaccg atgatggtat ctttatgacc tatttcgact ctagccgtcc gcgtgtcgat    960
ccggttgtct gcattaatgt gttgggtgtt ttctgccgcc acaatcgtga gcgcgacgtg   1020
ttgccgacct tcactggat tcgtgatatt ctgatcaacc gcgcatatct gagcggcacg    1080
cgctattacc cgtccccgga tctgtttctg ttttcctgg ctcgtctgtg cctggccgtt    1140
cgcaaccaga gcctgcgcga caactggtt ctcccgctgg ttgatcgtct gcgcgagcgt    1200
gttggtgctc cgggtgaggc tgtgagcctg cggcacgta tcctggcgtg ccgtagcttc    1260
ggtatcgact cagcccgcga catggactcc ttgcgtggca aacagtgtga agatggtggt    1320
tggccggtcg aatgggtcta tcgcttcgcg agctttggtc tgaacgttgg caaccgtggt    1380
ttggccaccg cgtttgcggt tagagcgctg gagtccccat acggcgagag cgcagttaag    1440
gttatgcgcc gtatcgtgta a                                              1461
```

<210> SEQ ID NO 20
<211> LENGTH: 483
<212> TYPE: PRT
<213> ORGANISM: Aspergillus aculeatus

<400> SEQUENCE: 20

```
Met Pro Ser Val Lys Ala Leu Val Leu Asp Phe Ala Gly Val Leu Cys
1               5                   10                  15

Ser Trp Thr Pro Pro Ala Glu Ser Pro Leu Ser Pro Ala Gln Leu Lys
            20                  25                  30

Gln Leu Met Ser Ser Glu Ile Trp Phe Glu Tyr Glu Arg Gly Arg Tyr
        35                  40                  45

Ser Glu Glu Glu Cys Tyr Ala Lys Leu Val Glu Arg Phe Ser Ile Ser
    50                  55                  60

Ala Ala Asp Met Ala Ser Thr Met Glu Gln Ala Arg Gln Ser Leu Glu
65                  70                  75                  80

Leu Asn His Ala Val Leu Gln Leu Val Ser Glu Ile Arg Lys Arg Asn
                85                  90                  95

Pro Gly Leu Lys Val Tyr Gly Met Thr Asn Thr Pro His Ala Glu Gln
            100                 105                 110

Asp Cys Val Asn Arg Ile Val Asn Ser Tyr Pro Val Phe Asp His Val
        115                 120                 125

Tyr Leu Ser Gly Leu Val Gly Met Arg Lys Pro Asp Leu Gly Phe Tyr
    130                 135                 140

Arg Phe Val Leu Ala Glu Thr Gly Leu Arg Pro Asp Glu Val Val Phe
145                 150                 155                 160

Val Asp Asp Lys Thr Glu Asn Val Leu Ala Gln Ser Val Gly Met
                165                 170                 175

His Gly Val Val Phe Gln Asn Val Thr Asp Phe Lys Gln Gln Ile Ile
            180                 185                 190

Asn Val Thr Gly Asp Pro Val Ser Arg Gly Leu Arg Tyr Leu Arg Ser
        195                 200                 205

Asn Ala Lys Ser Leu Leu Thr Val Thr Ser Asn Asn Ser Val Ile His
    210                 215                 220

Glu Asn Phe Ala Gln Leu Leu Ile Leu Glu Leu Thr Gly Asp Arg Asp
225                 230                 235                 240

Leu Ile Glu Leu Glu Pro Trp Asp Arg Thr Trp Asn Tyr Phe Ile Gly
                245                 250                 255
```

```
Val Pro Gln Ser Pro Thr Ser Thr Phe Pro Asn Asp Leu Asp Thr Thr
                260                 265                 270

Ser Ile Ala Leu Ser Val Leu Pro Ile His Lys Asp Val Val Ala Asp
            275                 280                 285

Val Met Asp Glu Ile Met Leu Leu Leu Asp Asn Asp Gly Ile Val Pro
290                 295                 300

Thr Tyr Phe Asp Pro Thr Arg Pro Arg Val Asp Pro Val Val Cys Val
305                 310                 315                 320

Asn Val Leu Ser Leu Phe Ala Gln Asn Gly Arg Glu Ser Glu Leu Leu
                325                 330                 335

Ala Thr Phe Asn Trp Val Leu Asp Val Leu Arg His Arg Ala Tyr Leu
            340                 345                 350

Gln Gly Thr Arg Tyr Tyr Ile Ser Pro Asp Ala Phe Leu Tyr Phe Leu
        355                 360                 365

Ala Arg Leu Ser Val Phe Leu Arg Met Ser Pro Leu Arg Ala Arg Leu
370                 375                 380

Met Pro Leu Leu Glu Glu Arg Val Tyr Glu Arg Ile Gly Ala His Gly
385                 390                 395                 400

Asp Ala Ile Ser Leu Ala Met Arg Ile Tyr Thr Cys Lys Leu Leu Gly
                405                 410                 415

Met Ser Asn Met Leu Asp Glu Arg Ala Leu Arg Asp Met Gln Cys Glu
            420                 425                 430

Asp Gly Gly Phe Pro Thr Ser Trp Val Tyr Arg Phe Gly Ser Thr Gly
        435                 440                 445

Val Lys Ile Gly Asn Arg Gly Leu Thr Thr Ala Leu Ala Ile Lys Ala
450                 455                 460

Ile Glu Met Pro Leu Ala Ser Leu Trp Lys Ser Trp Gly Leu Thr Thr
465                 470                 475                 480

Asp Ile Arg

<210> SEQ ID NO 21
<211> LENGTH: 1452
<212> TYPE: DNA
<213> ORGANISM: Aspergillus aculeatus
<220> FEATURE:
<221> NAME/KEY: misc_feature
<223> OTHER INFORMATION: cDNA

<400> SEQUENCE: 21
atgccctccg tcaaagcact ggtcctggac ttcgccggag ttctatgctc atggaccccg      60
ccagccgaga gcccgctctc cccagcccag ctcaaacaac tcatgtcctc cgagatatgg     120
ttcgaatacg agcgcgggag atattccgaa gaagaatgtt atgcgaagct cgtcgaacgg     180
ttctccatca gcgctgcgga catggcttcc accatggaac aggcccgtca gagcctggaa     240
ctgaaccacg ccgtacttca gcttgtcagc gagataagga agcggaaccc cgggctcaaa     300
gtttatggca tgacgaacac gccccatgcg aacaggatt gtgtgaatcg catcgtgaac      360
agctatcctg ttttcgacca tgtgtatctc tccgggctcg ttgggatgcg caaaccagat     420
cttggattct atcggtttgt tctcgcagag accgggttga ggcctgacga ggtcgtgttc     480
gtcgacgaca aaacggagaa tgtgttggtc gcgcagtccg tggggatgca cggcgtggtg     540
ttccagaacg ttacggattt caagcagcag atcataaacg tgacgggaga ccctgtctct     600
cggggcttga ggtatctccg ctcgaatgca aagagcctcc tcactgtgac tagcaataac     660
tccgtgatcc acgaaaactt tgcgcagttg ctgattctgg agctgacggg cgaccgagac     720
```

```
ttgatcgaac tcgagccttg ggatcgaaca tggaactact tcatcggggt tcctcagtcg      780
ccgacgagca ccttccccaa cgacctggac accacctcta tcgcgctctc ggtccttccc      840
attcataagg acgtcgttgc cgatgtgatg gacgagatta tgcttctcct agacaacgac      900
gggatagtcc caacatattt tgatcccact cgccctcgag tcgacccagt cgtgtgtgtg      960
aatgtactca gcctgtttgc ccaaaacggc cgagaatccg agttactcgc caccttcaac     1020
tgggtgctgg acgtgctgcg acatagagcc tacctgcagg gcacgagata ttacatcagt     1080
ccggacgcct tcttgtactt tctagccaga ctctcggtct ttctgaggat gagtccactc     1140
cgcgctcggc taatgcctct cctggaagaa agagtgtatg agcgaattgg tgcccatggc     1200
gacgccattt cgctggctat gcggatctat acgtgtaagc tgctcgggat gtcgaatatg     1260
ctcgatgaaa gagcattgcg ggacatgcag tgtgaggatg gcggcttccc tacaagttgg     1320
gtctatagat ttggatcgac cggagtgaag attgggaaca gggggttgac tactgcactt     1380
gcaataaagg ccattgagat gcctctcgct tcgctttgga agtcgtgggg attgacgact     1440
gacattcgat aa                                                          1452

<210> SEQ ID NO 22
<211> LENGTH: 1452
<212> TYPE: DNA
<213> ORGANISM: Artificial Sequence
<220> FEATURE:
<223> OTHER INFORMATION: codon optimized cDNA

<400> SEQUENCE: 22
atgccgtcgg ttaaagcgtt ggttctggat tttgcgggtg tgttgtgttc ttggactcca       60
ccggcggaaa gcccgttgtc cccagcgcag ctgaagcagc tgatgagcag cgagatctgg      120
tttgagtatg agcgtggccg ctatagcgaa gaagagtgtt atgcaaaatt ggtggagcgt      180
ttctctatct cggccgcaga tatggcgagc acgatggaac aggcccgtca atcgctggag      240
ttgaaccacg ccgtgctgca attagttttc gagattcgta acgtaatccc gggcttaaag      300
gtttacggta tgactaatac cccgcatgca gagcaagatt gtgtgaaccg tattgtcaat      360
agctatccgg ttttttgatca tgtctacctg agcggtctgg tgggtatgcg caaaccggat      420
ctgggctttt accgtttcgt tctggcagag actggtctgc gcccggatga agtcgtgttc      480
gttgacgaca gaccgaaaaa tgtcctggtg gctcaatccg ttggcatgca tggtgtggtg      540
ttccaaaatg taaccgactt caaacaacag attatcaatg tcacgggtga tcctgtcagc      600 cgtggttttgc gctacttgcg ttccaacgcg aagtctctgc tcactgttac cagcaataac      660
agcgttatcc atgagaattt cgcgcagctg ctgatcctgg aactgacggg cgaccgtgac      720
ctgattgaac tggaaccgtg ggaccgtacg tggaactact ttatcggcgt gccgcaaagc      780
ccgaccagca ccttccgaa cgacctggat acgaccagca ttgccctgag cgttctgccg      840
attcacaaag atgtggttgc ggacgtgatg gatgagatta tgctgctgct ggacaatgac      900
ggtattgtcc cgacctactt cgatccaacc cgtccgcgtg ttgatcctgt tgtgtgcgtc      960
aacgttctga gcctgttcgc acagaacggt cgcgagtccg aattgctggc gacgttcaac     1020 tgggtttttgg acgttctgag cacccgtgcg tatttgcagg gtacgcgcta ttatatcagc     1080
ccggatgcct ttctgtattt tctggcgcgc ctgtctgtgt ttctgcgtat gtctccgttg     1140
cgcgctcgtc tgatgccgct gctggaagaa cgcgtttatg agcgtatcgg cgcacacggc     1200
gatgctatta gcctggcgat cgcatttac acctgtaagc tgctgggcat gagcaatatg     1260
ctggacgagc gtgcactgcg tgacatgcag tgtgaagatg gtggtttccc aaccagctgg     1320
```

-continued

```
gtgtaccgtt ttggtagcac gggcgtgaaa attggtaacc gtggcttgac gaccgcactg    1380
gccattaagg ccatcgaaat gccgctggcc agcctttgga aaagctgggg cctgaccacc    1440
gatattcgct aa                                                       1452
```

<210> SEQ ID NO 23
<211> LENGTH: 485
<212> TYPE: PRT
<213> ORGANISM: Aspergillus udagawae

<400> SEQUENCE: 23

```
Met Thr Arg Gln Lys Ser Pro Gln Tyr Lys Ala Ile Ile Phe Asp Leu
1               5                   10                  15

Gly Asp Val Phe Phe Thr Trp Asp Ala Pro Lys Asp Thr Ala Val Leu
            20                  25                  30

Pro Asn Leu Phe Lys Lys Met Leu Thr Ser Pro Thr Trp Ser Asp Tyr
        35                  40                  45

Glu Arg Gly Lys Leu Ser Glu Ser Cys Tyr Glu Arg Leu Ala Glu
    50                  55                  60

Gln Phe Asp Val Asp Ser Ser Glu Ile Ala Arg Ser Leu Arg Lys Ala
65                  70                  75                  80

Gln Gln Ser Leu Thr Thr Asp Ala Ala Ile Val Ser Leu Ile Ser Glu
                85                  90                  95

Ile Arg Ala Leu Ala Gly His Ile Ala Ile Tyr Ala Met Ser Asn Ile
            100                 105                 110

Ser Ala Pro Ala Tyr Ala Ala Val Leu Gln Thr Gln Pro Glu Met Gly
        115                 120                 125

Ile Phe Asp Gly Val Phe Pro Ser Gly Cys Tyr Gly Thr Arg Lys Pro
    130                 135                 140

Glu Leu Leu Phe Tyr Lys Lys Val Leu Gln Glu Ile Ala Val Pro Pro
145                 150                 155                 160

Asn Gln Ile Ile Phe Ile Asp Asp Gln Leu Glu Asn Val Val Ser Ala
                165                 170                 175

Gln Ser Thr Gly Met His Gly Ile Val Tyr Thr Gly Ala Gly Glu Leu
            180                 185                 190

Ser Arg Gln Leu Arg Asn Leu Val Leu Asp Pro Val Gln Arg Gly Arg
        195                 200                 205

Glu Phe Leu Arg Arg Asn Ala Gly Ala Leu Tyr Ser Ile Cys Glu Thr
    210                 215                 220

Gly Gln Val Ile Arg Glu Asn Phe Ser Gln Leu Leu Ile Leu Glu Ala
225                 230                 235                 240

Thr Gly Asp Arg Ser Leu Val Asn Leu Glu Tyr Gln Gln Arg Ser Trp
                245                 250                 255

Asn Phe Phe Gln Gly Gly Pro Pro Ser Thr Ser Glu Thr Phe Pro Asp
            260                 265                 270

Asp Val Asp Thr Thr Ser Ile Ala Leu Met Ile Leu Pro Ala Asp Asp
        275                 280                 285

Asn Thr Val Asn Ser Val Leu Gly Glu Ile Ser Glu Val Ala Asn Asp
    290                 295                 300

Glu Gly Ile Val Asn Thr Tyr Phe Asp Gln Thr Arg Gln Arg Ile Asp
305                 310                 315                 320

Pro Ala Val Cys Val Asn Val Leu Arg Leu Phe Tyr Thr Tyr Gly Arg
                325                 330                 335

Gly Ala Thr Leu Pro Leu Thr Leu Gln Trp Val Ser Asp Val Leu Glu
```

```
              340             345             350
His Arg Ala His Leu His Gly Thr Arg Tyr Tyr Pro Ser Pro Glu Val
            355                 360                 365

Phe Leu Tyr Phe Val Ser Gln Leu Cys Arg Phe Ser Lys Arg Glu Pro
        370                 375                 380

Thr Leu Gln Leu Leu Glu Thr Leu Leu Thr Asp Arg Leu Lys Glu Arg
385                 390                 395                 400

Ile Gln Val Lys Ala Asp Thr Leu Ser Leu Ala Met Arg Ile Leu Ala
                405                 410                 415

Cys Leu Ser Val Gly Ile Ser Gln Val Glu Val Asp Val Arg Glu Leu
            420                 425                 430

Leu Ala Leu Gln Cys Lys Asp Gly Ser Trp Glu Pro Gly Ser Phe Tyr
        435                 440                 445

Arg Phe Gly Ser Ser Lys Met Asn Val Gly Asn Arg Gly Leu Thr Thr
    450                 455                 460

Ala Leu Ala Thr Arg Ala Val Glu Leu Tyr Gln Gly Thr Arg Ile Arg
465                 470                 475                 480

Ser Lys Gly Thr Glu
            485

<210> SEQ ID NO 24
<211> LENGTH: 1458
<212> TYPE: DNA
<213> ORGANISM: Aspergillus udagawae
<220> FEATURE:
<221> NAME/KEY: misc_feature
<223> OTHER INFORMATION: cDNA

<400> SEQUENCE: 24
atgacccgac agaaatcgcc tcaatacaaa gcaatcatct ttgacctagg ggatgtcttt      60
ttcacctggg acgccccaa agacactgct gtcttgccca acctcttcaa gaaaatgctt     120
acctcgccaa cctggtcaga ttacgagcgc ggcaagttga gcgaagaaag ctgctacgag     180
agactggccg aacagtttga cgttgactcg tcggaaatcg cgcgcagctt aaggaaagca     240
cagcagtctc ttaccacaga cgcagcaatc gtgagcctga tatcagagat cagagcgttg     300
gccggacata ttgccatcta cgccatgtcc aacatttccg ccccagctta tgcagctgtg     360
ctccagactc agcccgaaat gggcatcttt gacggagtgt cccgtctgg atgctatggg     420 acgaggaagc cggagctgtt gttctataag aaagtcttgc aggagattgc agtgccgcca     480
aatcagatca tctttattga tgatcagcta gagaatgtag tttctgcgca gtcaacaggt     540
atgcacggca ttgtctacac cggtgcgggt gagctcagtc gacagctcag aaatctggtg     600
ttggaccctg tacaaagggg tcgagagttt ctacggcgca atgctgggc attgtatagt     660 atctgcgaga ctggtcaagt catccgggaa aacttctcgc agctgctcat cctagaggcg     720
acgggtgata gaagcctggt caaccttgaa tatcagcagc ggagctggaa tttcttcaa     780 ggaggtcccc cttctacgtc ggaaacattc ccagatgatg tcgacacaac atccattgcc     840
ttgatgattc tccctgccga tgataacaca gtcaactcgg ttctcggcga gatttccgag     900
gtagctaatg acgagggcat tgtaaatacg actttgacc agacccgaca gcgaatcgac     960
ccagcagtct gcgtcaatgt cctccgtctc ttttatacct acggccgggg cgccactctc    1020
ccattgaccc tccagtgggt gtccgacgtt cttgagcatc gtgcgcactt acatggtacg    1080
cgatactacc cagccccgga ggttttcctc tactttgtca gtcaactctg ccggttctcc    1140
aagagggaac cgacgctgca gctgctggag acgttgctca cggatcgcct caaggagcgc    1200
```

```
attcaggtca aggcagacac tctgtcactg gctatgcgga tcctggcatg cttgtctgtg    1260
ggtatatcac aagttgaagt ggatgtccga gagctgctcg ccttgcaatg caaggatgga    1320
tcgtgggaac ccggctcgtt ttaccggttt gggtcgtcca agatgaacgt tggtaatcga    1380
ggtcttacga ctgcgttggc gactagggcg gttgagttgt accaggggac tagaatacgc    1440
tctaagggca ccgagtag                                                 1458
```

<210> SEQ ID NO 25
<211> LENGTH: 1458
<212> TYPE: DNA
<213> ORGANISM: Artificial Sequence
<220> FEATURE:
<223> OTHER INFORMATION: codon optimized cDNA

<400> SEQUENCE: 25

```
atgactcgcc aaaaaagccc tcaatacaaa gcaattatct tcgatctggg tgacgttttc      60
ttcacctggg atgcgccgaa agatacggcc gtactgccga acctgttcaa gaaaatgctg    120
acctcgccga cctggagcga ctatgagcgt ggtaagctgt ctgaggaaag ctgttacgaa    180
cgcttggccg agcaatttga cgtggacagc agcgagatcg cgcgtagcct ccgtaaagcg    240
cagcaaagcc tgacgaccga cgcagccatc gtgagcctga tcagcgagat ccgcgcattg    300
gcgggtcaca ttgctatcta tgctatgtct aacatttctg cgccagcata cgcagcggtg    360
ttacagaccc agccggaaat gggtatcttt gatggtgttt ttccgagcgg ctgctatggt    420
acgcgtaaac cggaactgct gttttacaaa aaagtgcttc aagaaattgc ggttccgccg    480
aatcagatta tcttcattga cgatcagctg gaaaacgtcg tcagcgcaca gtccacgggc    540
atgcatggca ttgttttacac cggtgccggt gagctgagcc gtcaactgcg taatctggtc    600
ctggacccgg tgcagcgtgg tcgtgagttc ctgcgccgta atgctggcgc cctgtacagc    660
atttgtgaga ctggccaagt tatccgtgag aacttcagcc agctgctgat tctggaagca    720
accggcgatc gttcgctggt gaacctggag tatcaacaac gttcctggaa cttcttttcag    780 ggtggccctc catccacgag cgaaactttt ccggatgatg ttgacacgac ctcaatcgcg    840
ctgatgattt taccggcgga cgataatacc gtcaatagcc tcctgggtga aatcagcgaa    900
gtcgcgaatg acgagggcat tgtgaatacc tatttcgatc agaccccgcca acgtatcgat    960 ccggccgtgt gtgtcaacgt gttgcgcctg ttttacacct atggtcgtgg cgctacgctg   1020
ccgttgaccc tgcaatgggt tagcgacgtg ctggagcacc gtgcgcatct gcacggcacc   1080
cgctactatc cgtccccaga ggttttcctg tactttgtct ctcagctgtg ccgttttttcc   1140 aagcgcgaac cgaccctgca gctgctggaa acgctgttga ccgacagact gaaggaacgc   1200
atccaagtta aggcagatac gctgagcttg gcaatgcgta ttttggcgtg cctgagcgtg   1260
ggcatcagcc aggttgaggt tgacgtccgc gaactgctgg cgctgcagtg caaggacggt   1320
agctgggagc cgggtagctt ctaccgtttc ggtagcagca agatgaatgt cggtaaccgc   1380
ggtctgacga ccgctttggc gacccgtgcg gttgagctgt accagggtac gcgtattcgt   1440
agcaagggca ccgagtaa                                                1458
```

<210> SEQ ID NO 26
<211> LENGTH: 524
<212> TYPE: PRT
<213> ORGANISM: Trametes versicolor

<400> SEQUENCE: 26

```
Met Ala Ser Pro His Arg Arg Tyr Thr Thr Leu Ile Leu Asp Leu Gly
1               5                   10                  15

Asp Val Leu Phe Ser Trp Ser Ser Lys Thr Asn Thr Pro Ile Pro Pro
                20                  25                  30

Lys Lys Leu Lys Glu Ile Leu Ser Ser Leu Thr Trp Phe Glu Tyr Glu
            35                  40                  45

Arg Gly Arg Ile Ser Gln Ala Glu Cys Tyr Asp Arg Val Ser Ser Glu
        50                  55                  60

Phe Ser Leu Asp Ala Ala Thr Ile Ala Glu Ala Phe Gln Gln Ala Arg
65                  70                  75                  80

Asp Ser Leu Arg Pro Asn Glu Glu Phe Leu Ala Leu Ile Arg Glu Leu
                85                  90                  95

Arg Gln Gln Thr His Gly Gln Leu Thr Val Leu Ala Leu Ser Asn Ile
            100                 105                 110

Ser Leu Pro Asp Tyr Glu Tyr Ile Met Ala Leu Asp Ser Asp Trp Thr
        115                 120                 125

Ser Val Phe Asp Arg Val Phe Pro Ser Ala Leu Val Gly Glu Arg Lys
130                 135                 140

Pro His Leu Gly Ala Tyr Arg Arg Val Ile Ser Glu Met His Leu Asp
145                 150                 155                 160

Pro Glu Thr Thr Val Phe Val Asp Asp Lys Leu Asp Asn Val Val Ser
                165                 170                 175

Ala Arg Ser Leu Gly Met His Gly Val Val Phe Asp Ser Gln Glu Asn
            180                 185                 190

Val Phe Gln Thr Leu Arg Asn Ile Phe Gly Asp Pro Ile His Arg Gly
        195                 200                 205

Arg Asp Tyr Leu Arg Arg His Ala Gly Arg Leu Glu Thr Ser Thr Asp
210                 215                 220

Ala Gly Val Val Phe Glu Glu Asn Phe Thr Gln Leu Ile Ile Tyr Glu
225                 230                 235                 240

Leu Thr Asn Asp Lys Ser Leu Ile Thr Thr Ser Asp Cys Pro Arg Thr
                245                 250                 255

Trp Asn Phe Phe Arg Gly Lys Pro Leu Phe Ser Ala Ser Phe Pro Asp
            260                 265                 270

Asp Val Asp Thr Thr Ser Val Ala Leu Thr Val Leu Arg Pro Pro Arg
        275                 280                 285

Thr Leu Val Asn Ser Ile Leu Asp Glu Met Leu Glu Tyr Val Asp Ala
290                 295                 300

Asp Gly Ile Met Gln Thr Tyr Phe Asp His Ser Arg Pro Arg Met Asp
305                 310                 315                 320

Pro Phe Val Cys Val Asn Val Leu Ser Leu Phe Tyr Glu Tyr Gly Arg
                325                 330                 335

Gly Gln Asp Leu Pro Lys Thr Leu Glu Trp Val Tyr Glu Val Leu Leu
            340                 345                 350

His Arg Ala Tyr Ile Gly Gly Ser Arg Tyr Tyr Met Ser Ala Asp Cys
        355                 360                 365

Phe Leu Phe Phe Met Ser Arg Leu Leu Gln Arg Ile Thr Asp Pro Ala
370                 375                 380

Val Leu Asn Arg Leu Arg Pro Leu Phe Val Glu Arg Met His Glu Arg
385                 390                 395                 400

Val Ser Ala Pro Gly Asp Ser Met Glu Leu Ala Phe Arg Ile Leu Ala
                405                 410                 415

Gly Ser Ser Val Gly Ile Gln Phe Pro Arg Asp Leu Glu Lys Leu Leu
```

|  |  | 420 |  |  | 425 |  |  | 430 |  |  |  |
|--|--|--|--|--|--|--|--|--|--|--|--|

Ala Ala Gln Cys Ala Asp Gly Gly Trp Asp Leu Cys Trp Phe Tyr Gln
               435                 440                 445

Tyr Gly Ser Thr Gly Val Lys Ala Gly Asn Arg Gly Leu Thr Thr Ala
       450                 455                 460

Leu Ala Ile Lys Ala Ile Glu Ser Ala Ile Ala Arg Pro Pro Ser Pro
465                 470                 475                 480

Ala Leu Ser Ala Val Ser Ser Lys Leu Glu Val Pro Lys Pro Ile
               485                 490                 495

Leu Gln Arg Pro Leu Ser Pro Arg Arg Leu Gly Asp Phe Leu Met Pro
               500                 505                 510

Trp Arg Arg Ala Gln Arg Glu Val Ala Val Ser Ser
               515                 520

```
<210> SEQ ID NO 27
<211> LENGTH: 1575
<212> TYPE: DNA
<213> ORGANISM: Trametes versicolor
<220> FEATURE:
<221> NAME/KEY: misc_feature
<223> OTHER INFORMATION: cDNA

<400> SEQUENCE: 27
atggcttcac ctcaccgcag gtatacgaca ctcatcctag acctgggcga cgtcctcttc      60
tcttggtcat ccaagaccaa cacacctatc cctcccaaga agctgaagga gatcctctcg     120
tccctgacct ggttcgagta cgagcgcggt cggatatcac aggccgagtg ctatgaccgg     180
gtcagctccg agttcagtct tgacgctgcc accatcgcag aagcgttcca gcaggctcgc     240
gactctctgc gaccgaacga agagttcctg gcgttgattc gcgaactccg ccaacaaacg     300
catggtcagc ttaccgtcct cgcgctctcg aacatctcac tccccgacta tgaatacatc     360
atggctctcg actcggactg gacgtcggtc ttcgaccgcg tcttcccttc tgccctcgtc     420
ggcgagcgca agccacatct gggggcgtac cgccgtgtca tctctgagat gcacctagac     480
ccagaaacga ccgtctttgt ggacgacaag ctggacaacg tggtgtccgc gcgatcgctc     540
gggatgcacg gcgtggtctt cgactcccag gagaacgtct tccagacgct gaggaatatc     600
ttcggcgacc cgatacatcg cggacgtgac tatctccgca ggcatgccgg tcgtctggag     660
acatctacgg acgccggcgt tgtcttcgag gaaaacttta cgcagctcat catctacgaa     720
ctaacaaatg acaaatccct catcacgaca tcagactgtc cccgcacttg gaacttcttc     780
cgcgggaagc cttgttctc ggcctcgttt cccgacgatg tggacacgac gtcggttgcc     840
ctgacagtgt tgcgcccacc ccgcacgctt gtcaactcga tcttggacga gatgctagag     900
tatgtcgacg ccgacggcat catgcagacc tacttcgacc actcgcgccc gcggatggat     960
ccgttcgtct gtgtcaacgt cctgtcgctg ttctacgagt acggccgggg acaggacctc    1020
ccgaagaccc tcgaatgggt atacgaggtt ctgctgcacc gcgcctacat cggcggctcg    1080
cggtactaca tgtccgcgga ctgcttcctc ttcttcatga gccgccttct ccaacgtatc    1140
accgacccag ccgtcctgaa ccgcctccgc ccgttgttcg tcgagcgcat gcacgaacgt    1200
gtcagcgcac cggcgactc catggagctc gcgttccgca tcctcgctgg ctcgtccgtc    1260
ggcatccagt tcccacgtga cctggagaag ctcctcgccg cgcagtgcgc cgacggcggc    1320
tgggacctgt gctggttcta ccagtatggg tccaccggcg tgaaggcagg caaccgcggg    1380
ctcaccaccg cgctcgccat caaggctatc gagagcgcta tcgcgcgccc tccgtccccc    1440
```

```
gctctatcag ctgtatcgtc gtcgaaactg aagtgccga aaccaattct ccagcgtccc    1500
ctcagcccgc gccggcttgg cgacttcctg atgccctgga ggagagcaca gcgcgaggtc    1560
gcggtttcca gctag                                                    1575
```

<210> SEQ ID NO 28
<211> LENGTH: 1575
<212> TYPE: DNA
<213> ORGANISM: Artificial Sequence
<220> FEATURE:
<223> OTHER INFORMATION: codon optimized cDNA

<400> SEQUENCE: 28

```
atggctagcc cgcaccgtcg ctatactact ctgattctgg atttgggtga tgttttgttt     60
agctggagca gcaaaaccaa tacgccatt ccgccgaaaa agctgaaaga atcctgtct    120 agcctgacct ggttcgagta cgagcgcggt cgcatttctc aagccgagtg ctatgaccgt   180
gtgagctctg agtttagcct ggacgcagcg accattgcag aggcattcca acaggctcgt   240
gactcgctgc gcccgaacga agaatttctg gcgttgattc gtgagctgcg ccagcagacc   300
cacggccaac tcaccgttct ggcactgagc aacatctccc tgccggatta cgagtacatc   360
atggctctgg atagcgattg gaccagcgtc tttgatagag ttttcccgag cgcgctggtt   420
ggtgagcgta gccgcatct gggtgcttac cgtcgtgtca ttagcgagat gcatctggac    480
ccggagacta cggtgtttgt ggacgacaaa ctggacaacg ttgtctccgc gcgcagcctg   540
ggtatgcacg gcgtcgtttt tgactcacaa gaaaatgttt tccagacgct gcgtaacatt   600
ttcggtgacc ctatccaccg tggccgcgac tatttgcgtc gtcatgccgg tcgtttggaa   660
accagcaccg acgcgggcgt tgtttttgaa gaaaacttca cccagctgat catctacgaa   720
ctgacgaatg acaagagcct gatcaccacg agcgattgtc cgcgcacctg gaacttcttc   780
cgtggtaagc cgctgtttag cgcgtccttc ccagacgatg tcgatacgac ttcggtggcc   840
ctgaccgttc tgcgcccacc gcgcaccctg gtaaacagca tcctggacga atgttagaa    900 tacgtcgatg cggatggtat tatgcagacc tatttcgacc acagccgtcc gcgcatggac   960
ccgtttgtgt gtgtgaatgt gttgagcctg ttctatgagt acggccgtgg tcaagatctg   1020
ccaaaaaccc tggaatgggt ctacgaagtc cttctgcatc gtgcctacat cggtggctcc   1080
cgttattaca tgagcgcaga ttgcttttg ttctttatgt ctcgtctgct gcagcgcatc    1140
acggaccctg ccgtgctgaa tcgtctgcgt ccgctgttcg tggagcgtat gcacgagcgc   1200
gtgtctgccc cgggtgacag catggaactg gcgttccgta tcctggcggg cagcagcgtg   1260
ggtattcaat ttccgcgtga tttggagaaa ctgctggctg cgcagtgtgc ggacggtggc   1320
tgggatctgt gctggttta tcaatacggt agcaccggcg ttaaggccgg caatcgtggc   1380
ctgacgacgg cactggcaat taaggccatt gagtccgcga ttgcgcgtcc gccgagcccg   1440
gcattgagcg cggtcagcag cagcaaactg gaagtgccga agccgatctt gcagcgtcca   1500
ctgagcccgc gtcgtctggg tgacttcctg atgccgtggc gccgtgcgca acgcgaagtc   1560
gcggttagct cctaa                                                    1575
```

<210> SEQ ID NO 29
<211> LENGTH: 527
<212> TYPE: PRT
<213> ORGANISM: Dichomitus squalens

<400> SEQUENCE: 29

Met Ala Ser Ile His Arg Arg Tyr Thr Thr Leu Ile Leu Asp Leu Gly

-continued

```
1               5                   10                  15
Asp Val Leu Phe Arg Trp Ser Pro Lys Thr Glu Thr Ala Ile Pro Pro
                20                  25                  30

Gln Gln Leu Lys Asp Ile Leu Ser Ser Val Thr Trp Phe Glu Tyr Glu
                35                  40                  45

Arg Gly Arg Leu Ser Gln Glu Ala Cys Tyr Glu Arg Cys Ala Glu Glu
        50                  55                  60

Phe Lys Ile Glu Ala Ser Val Ile Ala Glu Ala Phe Lys Gln Ala Arg
65                  70                  75                  80

Gly Ser Leu Arg Pro Asn Glu Glu Phe Ile Ala Leu Ile Arg Asp Leu
                85                  90                  95

Arg Arg Glu Met His Gly Asp Leu Thr Val Leu Ala Leu Ser Asn Ile
                100                 105                 110

Ser Leu Pro Asp Tyr Glu Tyr Ile Met Ser Leu Ser Ser Asp Trp Thr
                115                 120                 125

Thr Val Phe Asp Arg Val Phe Pro Ser Ala Leu Val Gly Glu Arg Lys
        130                 135                 140

Pro His Leu Gly Cys Tyr Arg Lys Val Ile Ser Glu Met Asn Leu Glu
145                 150                 155                 160

Pro Gln Thr Thr Val Phe Val Asp Asp Lys Leu Asp Asn Val Ala Ser
                165                 170                 175

Ala Arg Ser Leu Gly Met His Gly Ile Val Phe Asp Asn Gln Ala Asn
                180                 185                 190

Val Phe Arg Gln Leu Arg Asn Ile Phe Gly Asp Pro Ile Arg Arg Gly
                195                 200                 205

Gln Glu Tyr Leu Arg Gly His Ala Gly Lys Leu Glu Ser Ser Thr Asp
        210                 215                 220

Asn Gly Leu Ile Phe Glu Glu Asn Phe Thr Gln Leu Ile Ile Tyr Glu
225                 230                 235                 240

Leu Thr Gln Asp Arg Thr Leu Ile Ser Leu Ser Glu Cys Pro Arg Thr
                245                 250                 255

Trp Asn Phe Phe Arg Gly Glu Pro Leu Phe Ser Glu Thr Phe Pro Asp
                260                 265                 270

Asp Val Asp Thr Thr Ser Val Ala Leu Thr Val Leu Gln Pro Asp Arg
        275                 280                 285

Ala Leu Val Asn Ser Val Leu Asp Glu Met Leu Glu Tyr Val Asp Ala
        290                 295                 300

Asp Gly Ile Met Gln Thr Tyr Phe Asp Arg Ser Arg Pro Arg Met Asp
305                 310                 315                 320

Pro Phe Val Cys Val Asn Val Leu Ser Leu Phe Tyr Glu Asn Gly Arg
                325                 330                 335

Gly His Glu Leu Pro Arg Thr Leu Asp Trp Val Tyr Glu Val Leu Leu
                340                 345                 350

His Arg Ala Tyr His Gly Gly Ser Arg Tyr Tyr Leu Ser Pro Asp Cys
                355                 360                 365

Phe Leu Phe Phe Met Ser Arg Leu Leu Lys Arg Ala Asp Asp Pro Ala
        370                 375                 380

Val Gln Ala Arg Leu Arg Pro Leu Phe Val Glu Arg Val Asn Glu Arg
385                 390                 395                 400

Val Gly Ala Ala Gly Asp Ser Met Asp Leu Ala Phe Arg Ile Leu Ala
                405                 410                 415

Ala Ala Ser Val Gly Val Gln Cys Pro Arg Asp Leu Glu Arg Leu Thr
                420                 425                 430
```

```
Ala Gly Gln Cys Asp Asp Gly Gly Trp Asp Leu Cys Trp Phe Tyr Val
            435                 440                 445

Phe Gly Ser Thr Gly Val Lys Ala Gly Asn Arg Gly Leu Thr Thr Ala
    450                 455                 460

Leu Ala Val Thr Ala Ile Gln Thr Ala Ile Gly Arg Pro Pro Ser Pro
465                 470                 475                 480

Ser Pro Ser Ala Ala Ser Ser Ser Phe Arg Pro Ser Ser Pro Tyr Lys
            485                 490                 495

Phe Leu Gly Ile Ser Arg Pro Ala Ser Pro Ile Arg Phe Gly Asp Leu
                500                 505                 510

Leu Arg Pro Trp Arg Lys Met Ser Arg Ser Asn Leu Lys Ser Gln
            515                 520                 525

<210> SEQ ID NO 30
<211> LENGTH: 1584
<212> TYPE: DNA
<213> ORGANISM: Dichomitus squalens
<220> FEATURE:
<221> NAME/KEY: misc_feature
<223> OTHER INFORMATION: cDNA

<400> SEQUENCE: 30
atggcaagca ttcatcgtcg ctatactacg ctgattctgg acctgggtga tgttttgttc      60
cgctggagcc cgaaaaccga gactgcgatt cctccgcaac aactgaaaga catcctgagc     120
agcgtcacct ggttcgagta cgagcgtggc cgtctgagcc aagaggcttg ctacgagcgt     180
tgcgccgaag agttcaagat tgaagccagc gtgattgcgg aagcgttcaa acaagcgcgt     240
ggtagcctgc gtccgaacga agaatttatc gcactgatcc gtgatctgcg tcgcgagatg     300
catggtgacc tgaccgttct ggctctgagc aatatctcgt tgccggatta cgagtatatt     360
atgtctctga gcagcgactg gacgacggtc tttgatcgtg tgttcccgtc agctctggtg     420
ggcgagcgta aaccgcactt gggttgctat cgcaaggtca tcagcgagat gaacctggaa     480
cctcagacca cggtctttgt ggacgataaa ctggataatg tcgcaagcgc gcgtagcctg     540
ggtatgcacg gtatcgtgtt tgataatcaa gcgaatgtgt tcgccagct gcgtaatatt     600 ttcggtgatc caatccgtcg cggtcaagag tatctgcgtg gccatgccgg taaattggag     660
agcagcacgg acaatggttt gatctttgaa gagaacttca cccagctgat catttatgaa     720
ctgacccagg accgcacgtt gatcagcctg tcggagtgtc cgcgtacctg gaacttcttc     780
cgtggcgagc gttgttttc tgaaaccttc ccggacgacg tggacaccac gtccgttgca     840
ctgacggttc tgcaaccgga tcgcgcactg gttaacagcg tgctggacga aatgctggaa     900
tatgtcgatg cggatggcat catgcagacg tatttcgacc gctcgcgtcc gcgtatggac     960
ccgtttgttt gcgtcaacgt actgagcctg ttttacgaga cggtcgtgg tcacgaactg    1020 ccgcgcactc tggattgggt gtacgaagtc ctgctccacc gcgcctacca cggtggttcc    1080
cgttactacc tgagcccgga ctgtttcttg ttttttatga ccgtctgct gaaacgtgca    1140 gacgacccag cggttcaggc gagattgcgt ccgctgtttg tggaacgcgt taacgaacgt    1200
gttggcgcgg ccggtgatag catggacctg gcgtttcgca ttctggccgc agcgagcgtg    1260
ggtgtgcagt gtccgcgcga cctggagcgt ctgaccgctg tcaatgcga tgatggcggc    1320 tgggatctgt gttggttcta cgttttcggc agcaccggcg ttaaggcggg taatcgtggt    1380
ctgaccacgg cgctggcagt caccgcgatc cagaccgcca tcggccgtcc gcctagcccg    1440
agcccgtccg cggcaagctc cagcttccgc ccgagcagcc cgtacaagtt tctgggtatt    1500
```

```
agccgtccgg cgtccccaat tcgcttcggt gaccttctgc gtccgtggcg taaaatgtct    1560
cgctctaacc tgaagtccca gtaa                                           1584
```

<210> SEQ ID NO 31
<211> LENGTH: 1584
<212> TYPE: DNA
<213> ORGANISM: Artificial Sequence
<220> FEATURE:
<223> OTHER INFORMATION: codon optimized cDNA

<400> SEQUENCE: 31

```
atggcctcaa tccaccgtcg atacactact ctcatcctcg acctcggcga cgtactcttt     60
cgttggtctc caaagactga daccgccatt ccacctcaac aactcaagga tatcctctcc    120
tctgtcacct ggtttgagta cgaacgcggc agactatccc aggaagcatg ctacgagcgc    180
tgcgccgagg agttcaagat agaggcctcg gtcattgcag aagcctttaa gcaggctcgc    240
gggtcactgc ggcccaacga ggagttcatc gccttgatcc gtgacctccg ccgtgagatg    300
cacggtgacc ttaccgttct tgccctctcc aacatctccc tccccgacta cgaatacatc    360
atgtcgctaa gctcagattg gacgaccgtc ttcgatcgcg tattccccctc tgcactcgtt    420 ggcgagcgca agcctcatct gggatgctat cgcaaggtca tctcggagat gaacctagaa    480
cctcagacga ctgtgttcgt ggatgacaag cttgacaacg tcgcgtctgc tgctcacttt    540
ggtatgcacg gcatcgtgtt tgacaaccaa gccaacgtct tccgccaact ccgcaatatc    600
ttcggagacc ccatccgccg tggccaagag tatctccgtg gcatgctgg caaactcgag     660 tcttcgaccg acaacgggtt gatcttcgag agaacttca cacagctgat catctacgag     720
ttgacgcaag acaggactct catctcgctt tcagaatgtc ctcgtacttg gaatttcttc    780
cgaggcgaac cgctattctc ggagaccttc ccggatgatg tcgacacaac atctgtggcg    840
ttgacggtat tgcaaccgga cagagcactg gtcaactccg ttctagacga gatgctggag    900
tatgtcgacg ccgatggcat catgcagaca tacttcgatc gttcacgacc acgcatggac    960
cccttcgtct gcgtgaacgt actctcccctg ttctacgaga acggtcgtgg tcacgagctc   1020
cctcgcacat tggactgggt ctacgagtgc tcctccatc gcgcgtacca cggcggttcg     1080
cgttattacc tgtcgcccga ctgcttccta ttcttcatga ccgcctact caagcgcgca    1140 gacgatccag cagtccaggc tcggctccgc ccgctcttcg tcgagcgggt gaacgagcga    1200
gtaggcgccg ctggcgactc gatggacctc gccttccgca tcctcgccgc agcgtctgtt   1260
ggcgtccagt gccccgcga tctggaaagg ttgactgccg gcaatgcga cgacggtgga    1320 tgggacctct gctggttcta cgtgttcggc tcgacgggcg tgaaggcggg caaccgcggc    1380
ctcacaacgg ccctcgctgt cacggccata cagacggcca tcggacgccc ccttcgccc    1440 agtccctccg cggcctcctc gtctttcaga cctagttccc cttacaaatt cctaggcatt   1500
tcgcgcccag ctagccccat tcgcttggc gacttacttc gcccatggcg gaagatgagc    1560
aggtcgaact tgaagtctca atga                                          1584
```

<210> SEQ ID NO 32
<211> LENGTH: 495
<212> TYPE: PRT
<213> ORGANISM: Antrodia cinnamomea

<400> SEQUENCE: 32

```
Met Arg Arg Asn Val Leu Asn Lys Ala Thr His Ser Gln Ser Pro Leu
 1               5                  10                  15
```

```
Lys Pro Asn Ile Thr Thr Leu Ile Phe Asp Leu Gly Asp Val Leu Leu
                20                  25                  30

Thr Trp Ser Asp Ser Thr Pro Lys Ser Pro Leu Pro Lys Ile Val
        35                  40                  45

Lys Gly Ile Leu Arg Ser Leu Thr Trp Phe Glu Tyr Glu Lys Gly Asn
 50                  55                  60

Leu Thr Glu Ser Gln Thr Tyr Gly Gln Val Ala Gln Glu Phe Gly Val
 65                  70                  75                  80

Asp Ala Ser Glu Val Lys Ala Ser Phe Glu Ala Ala Arg Asp Ser Leu
                85                  90                  95

Lys Ser Asn Pro Met Leu Leu Gln Leu Ile Arg Ser Leu Lys Asp Ser
                100                 105                 110

Gly His Val Ile Tyr Ala Met Ser Asn Ile Ser Ala Pro Asp Trp Glu
                115                 120                 125

Phe Leu Lys Thr Arg Ala Asp Leu Ser Asp Trp Ala Leu Phe Asp Arg
        130                 135                 140

Val Phe Pro Ser Ala Glu Ala His Asp Arg Lys Pro Asn Ile Gly Phe
145                 150                 155                 160

Tyr Gln His Val Ile Asn Glu Thr Gly Leu Asn Pro Ser Asn Thr Val
                165                 170                 175

Phe Val Asp Asp Arg Ile Glu Asn Val Val Ser Ala Arg Ser Ala Gly
                180                 185                 190

Met His Gly Ile Val Phe Asp Asp Ile Asn Asn Val Ile Arg Gln Leu
        195                 200                 205

Lys Asn Leu Cys Glu Asp Pro Ile His Arg Ala Arg Ser Phe Leu Tyr
210                 215                 220

Ala Asn Lys Lys Cys Leu Asn Thr Val Ser Thr Asp Gly Thr Ile Val
225                 230                 235                 240

Ser Glu Asn Phe Ser Gln Leu Leu Ile Leu Glu Ala Ile Gly Asp Glu
                245                 250                 255

Ser Leu Val Asp Phe Val Arg His Glu Gly Arg Phe Asn Phe Phe Gln
                260                 265                 270

Gly Glu Ala Lys Leu Ile Met Thr Asn His Tyr Pro Asp Asp Phe Asp
        275                 280                 285

Thr Thr Ser Ile Gly Leu Thr Val Val Pro Tyr Ile Asp Asp Lys Thr
        290                 295                 300

Arg Asn Arg Val Met Asp Glu Ile Leu Ala Tyr Gln Ser Glu Asp Gly
305                 310                 315                 320

Ile Val Leu Val Tyr Phe Asp His Lys Arg Pro Arg Ile Asp Pro Val
                325                 330                 335

Val Cys Val Asn Val Leu Thr Leu Phe Tyr Arg Tyr Gly Arg Gly His
                340                 345                 350

Gln Leu Gln Lys Thr Leu Asp Trp Val Glu Gln Val Leu Ile Asn Arg
        355                 360                 365

Ala Cys Ala Ser Gly Thr Phe Tyr Tyr Ala Thr Glu Glu Gln Phe Leu
        370                 375                 380

Phe Phe Leu Ser Arg Leu Ile Gln Ser Ser Pro Asp Val Arg Gln Arg
385                 390                 395                 400

Leu Glu Gly Val Phe Lys Arg Val Val Glu Arg Phe Gly Ala Asp
                405                 410                 415

Gly Asp Ala Leu Ala Met Ala Met Arg Ile His Thr Ala Ala Ser Val
        420                 425                 430
```

```
Gly Leu Val Asp His Val Asp Leu Asp Lys Leu Phe Ala Leu Gln Gln
            435                 440                 445

Asn Asp Gly Ser Trp Arg Asp Ser Ala Phe Tyr Arg Phe Pro Ser Ala
        450                 455                 460

Arg Gln Leu Ala Ser Asn Asp Gly Leu Thr Thr Ala Ile Ala Ile Gln
465                 470                 475                 480

Ala Ile Gln Ala Ala Glu Arg Leu Arg Glu Asp Gly Asn Val Leu
                485                 490                 495
```

<210> SEQ ID NO 33
<211> LENGTH: 1488
<212> TYPE: DNA
<213> ORGANISM: Antrodia cinnamomea
<220> FEATURE:
<221> NAME/KEY: misc_feature
<223> OTHER INFORMATION: cDNA

<400> SEQUENCE: 33

| | | | | |
|---|---|---|---|---|
| atgaggcgaa | acgtactcaa | caaagcaaca | cattctcagt | caccattgaa gcccaacatc | 60 |
| acgacgctca | tatttgactt | gggcgacgta | cttctcacgt | ggtccgactc aacacctaaa | 120 |
| tctccactgc | ccccaaaaat | tgtcaaggga | atactacgtt | cactgacctg gtttgagtac | 180 |
| gagaaaggga | acttgacaga | gtcccagacc | tacgggcaag | ttgctcagga atttggagtg | 240 |
| gatgcttccg | aagtcaaagc | ttccttcgaa | gcagctcgcg | actcgctcaa gagcaaccca | 300 |
| atgcttctcc | agttgatccg | tagcctcaaa | gactctggcc | acgtcattta cgcaatgtct | 360 |
| aacatatctg | ctcccgactg | gaattttttg | aagacgcggg | cagacctctc agattgggct | 420 |
| cttttttgaca | gagtcttccc | ttctgccgaa | gcgcatgacc | gcaagccgaa cattggtttc | 480 |
| tatcagcacg | tcataaacga | gactggtctg | aacccgtcca | acactgtctt tgtcgatgac | 540 |
| aggatcgaga | atgttgtatc | cgcacgctca | gcaggaatgc | acgggatcgt gtttgacgac | 600 |
| ataaataatg | tgatccgaca | gttgaaaaac | ctctgcgagg | atccgattca ccgcgcacga | 660 |
| tctttttcttt | atgcaaataa | gaagtgtttg | aatacggtta | gcacagatgg cacaattgtg | 720 |
| agcgagaact | tctcgcaatt | gttgatcctt | gaggccattg | gcgacgaaag cctagtcgac | 780 |
| tttgtgaggc | atgagggccg | attcaacttc | ttccagggg | aggccaaact catcatgacg | 840 |
| aatcactacc | ccgatgattt | cgatactaca | tccataggtt | taaccgttgt tccatatatt | 900 |
| gacgacaaga | ctagaaatag | agttatggat | gagatcctgg | cctaccaaag cgaagacggc | 960 |
| attgtgctgg | tatactttga | ccacaagcgc | cccaggattg | atcctgttgt ctgtgtcaat | 1020 |
| gtcctcaccc | tcttctatag | gtatggccgt | gggcaccagc | ttcaaaagac actggattgg | 1080 |
| gtcgaacagg | tcctgatcaa | ccgtgcgtgt | gcgtccggca | cgttctatta cgcaacagag | 1140 |
| gaacaattcc | tctttttcct | ctcccgcctg | atccaaagct | ctccggacgt acgacagcgg | 1200 |
| ttggaagggg | tctttaaaag | aagagtagtc | gagcggtttg | gtgcagacgg cgacgctctc | 1260 |
| gctatggcga | tgcgcattca | caccgcggcg | agcgtgggcc | tcgttgacca tgtcgatctt | 1320 |
| gacaagctgt | tcgcattgca | gcaaaatgac | ggttcttgga | gagacagcgc tttctacaga | 1380 |
| tttccgtcgg | ccaggcaact | ggctagtaac | gacggcttga | cgactgcaat cgctattcag | 1440 |
| gccattcaag | ctgcggagag | gctcagggag | gatgggaacg | tgctttga | 1488 |

<210> SEQ ID NO 34
<211> LENGTH: 1488
<212> TYPE: DNA
<213> ORGANISM: Artificial Sequence
<220> FEATURE:

-continued

<223> OTHER INFORMATION: codon optimized cDNA

<400> SEQUENCE: 34

```
atgcgccgta atgtcctgaa caaagcaacc catagccagt caccgttgaa accgaatatc      60
accacgctga tttttgactt gggcgatgtc ctgctgacct ggagcgacag cactccgaaa     120
tctccgttgc cgccgaagat cgtcaagggc atcctgcgta gcctgacttg gttcgagtac     180
gaaaagggca atttgaccga aagccaaacg tatggtcagg tcgcgcaaga atttggtgtg     240
gatgcctctg aagtgaaggc cagctttgag gctgcgcgtg atagcttgaa atcgaatccg     300
atgctgctgc agctgattcg cagcctgaaa gattccggtc acgtgatcta cgccatgagc     360
aacatcagcg cgcctgattg ggaatttctg aaaacccgcg ctgacctgtc tgactgggcc     420
ctgtttgacc gcgtgttccc gtctgccgag gcacatgacc gcaaaccgaa cattggcttt     480
taccaacacg tgatcaatga acgggtctg aatccatcca taccgtgtt cgttgacgac      540
cgtattgaaa cgttgttag cgcacgtagc gctggtatgc acggtatcgt tttcgatgac     600
attaacaacg tcattcgcca gctgaagaat ctgtgcgagg acccaattca ccgtgcacgt     660
tcctttttgt atgcgaacaa aaagtgcctg aataccgtga gcaccgatgg tacgatcgtc     720
agcgagaact ttagccagct tctgattctg aagccattg gtgacgagtc cctggtagac     780
ttcgtccgcc atgagggccg ttttaacttc ttccagggtg aggcaaagct gatcatgacc     840
aatcactacc cggacgattt cgataccacg agcattggtc tgaccgttgt cccgtatatc     900
gatgacaaaa cgcgtaatcg tgtgatggat gaaatcctgg cgtatcagtc cgaggatggt     960
atcgttctgg tgtacttcga tcacaagcgt ccgcgcattg acccggtcgt ttgtgtgaac    1020
gttctgacgc tgttctaccg ctatggtcgt ggccatcaac tgcagaaaac cctggactgg    1080
gttgagcaag tcctgattaa tcgtgcgtgt gcgagcggca cgttctacta cgcgaccgaa    1140
gaacagttcc tgttttcct gagccgtctg attcagtcga gccctgacgt cgccaacgt     1200
ctggaaggcg tgttcaagcg tcgtgtcgtt gagcgctttg gtgcgacgg tgatgccctg    1260
gcaatggcga tgcgtatcca taccgcagcg agcgttggcc tggtggacca cgtggatctg    1320
gataagctgt tcgcgctgca acagaacgac ggtagctggc gcgatagcgc gttttatcgt    1380
tttccgagcg cgcgtcaact cgcgagcaac gacggcttga ccacggcaat tgctattcag    1440
gccatccaag cggctgagag attacgtgag gatggtaacg ttctgtaa                 1488
```

<210> SEQ ID NO 35
<211> LENGTH: 543
<212> TYPE: PRT
<213> ORGANISM: Aspergillus ustus

<400> SEQUENCE: 35

```
Met Val Arg Ala Leu Ile Leu Asp Leu Gly Asp Val Leu Phe Asn Trp
1               5                  10                  15

Asp Ala Pro Lys Ser Thr Pro Val Ser Arg Lys Thr Leu Ser Gln Met
            20                  25                  30

Leu His Ser Asp Ile Trp Gly Glu Tyr Glu Cys Gly Gln Leu Thr Glu
        35                  40                  45

Pro Glu Ser Tyr Lys Ala Leu Ala Ser Arg Tyr Ser Cys Gln Ala Gln
    50                  55                  60

Asp Val Ala Asp Thr Phe Tyr Leu Ala Arg Glu Ser Leu Arg Leu Asp
65                  70                  75                  80

Ala Thr Phe Lys Thr Phe Leu Gln Asp Leu Lys Gln Arg Ala Asn Gly
                85                  90                  95
```

-continued

Ser Leu Arg Val Tyr Gly Met Ser Asn Ile Ser Gln Pro Asp Tyr Glu
                100                 105                 110

Val Leu Leu Ser Lys Ala Asp Asp Leu Ser Leu Phe Asp Lys Ile Phe
                115                 120                 125

Pro Ser Gly His Val Gly Met Arg Lys Pro Asp Leu Ala Phe Phe Arg
            130                 135                 140

His Val Leu Arg Glu Ile Ser Thr Ala Ser Glu Asp Ile Val Phe Val
145                 150                 155                 160

Asp Asp Asn Leu Glu Asn Val Thr Ser Ala Arg Ser Leu Gly Met Gln
                165                 170                 175

Gly Ile Val Phe Arg Asp Lys Glu Asp Val Gln Arg Gln Leu Arg Asn
            180                 185                 190

Leu Phe Gly Ser Pro Ala Glu Arg Gly Arg Glu Tyr Leu Ser Ile Asn
            195                 200                 205

Lys Thr Lys Leu Gln Ser Val Thr Thr Thr Asn Ile Pro Ile Leu Asp
    210                 215                 220

Asn Phe Gly Gln Leu Leu Ile Leu Glu Ala Thr Arg Asp Pro Asp Leu
225                 230                 235                 240

Val Ser Met His Pro Gly Gln Arg Thr Trp Asn Phe Phe Ile Gly Ser
                245                 250                 255

Pro Thr Leu Thr Thr Asp Ala Phe Pro Asp Asp Met Asp Thr Thr Ser
            260                 265                 270

Leu Gly Leu Ser Ile Ile Pro Pro Ser Pro Glu Ile Ala Ala Ser Val
        275                 280                 285

Met Asp Glu Ile Val Thr Arg Leu Asn Lys Asp Gly Ile Val Pro Thr
            290                 295                 300

Tyr Phe Asp Ser Thr Arg Pro Arg Val Asp Pro Ile Val Cys Val Asn
305                 310                 315                 320

Val Leu Thr Leu Phe Ala Lys Tyr Gly Arg Glu Asp Glu Leu Ser Gly
                325                 330                 335

Thr Ile Ala Trp Val Arg Asp Val Leu Tyr His Arg Ala Tyr Leu Ala
            340                 345                 350

Gly Thr Arg Tyr Tyr Ala Ser Pro Glu Ala Phe Leu Phe Phe Phe Thr
        355                 360                 365

Arg Phe Thr Arg Asn Leu Arg Pro Gly Pro Arg Lys Gln Glu Leu Thr
    370                 375                 380

Ala Leu Leu Ser Gln Arg Leu Gln Glu Arg Asn Lys Thr Pro Val Asp
385                 390                 395                 400

Ala Leu Ala Leu Ser Met Arg Ile Ile Ala Cys Leu Thr Leu Gly Ile
                405                 410                 415

Glu Ser Pro Ala Asp Asp Val Ala Thr Leu Thr Gly Met Gln Cys Gly
            420                 425                 430

Asp Gly Gly Trp Pro Ala Cys Val Ile Tyr Lys Tyr Gly Ala Gly Gly
        435                 440                 445

Leu Gly Ile Thr Asn Arg Gly Val Ser Thr Ala Phe Ala Val Lys Ala
    450                 455                 460

Ile Thr Thr Thr Pro Leu Ala Val Gln Pro Glu Val Ser Val Ser Ala
465                 470                 475                 480

Gly Ala Gly Gly Ser Ser Arg Pro Val Gly Ala Asp Ala Ala Val
                485                 490                 495

Ser Leu Arg Pro Arg Trp Arg Ala Val Val Gln Ser Leu His Pro Leu
            500                 505                 510

Ser Arg Val Gly Gly Leu Val Ala Val Ile Phe Ala Ala Leu His Phe
    515                 520                 525

Asn Leu Ala Trp Leu Tyr Asn Val Ser Leu Ala Ser Arg Ile Val
    530                 535                 540

<210> SEQ ID NO 36
<211> LENGTH: 1632
<212> TYPE: DNA
<213> ORGANISM: Aspergillus ustus
<220> FEATURE:
<221> NAME/KEY: misc_feature
<223> OTHER INFORMATION: cDNA

<400> SEQUENCE: 36

```
atggttcgtg cattgatttt ggatttgggt gatgtgttgt ttaactggga tgcgcctaag      60
agcaccccgg tttcccgcaa gactctgagc caaatgctgc actcggatat ttggggcgag     120
tacgagtgtg gtcaactgac tgagccggag tcctataaag ccctggcgag ccgctatagc     180
tgccaggcgc aagatgtcgc tgacaccttt tacctggcgc gtgagagcct gcgtctggac     240
gcaacgttta agaccttcct gcaagatctg aagcaacgcg ccaacggttc tctgcgtgtc     300
tatggtatga gcaatatcag ccagccggat tacgaagtcc tgctgagcaa agctgacgat     360
ctcagcctgt ttgacaaaat cttccgtcg gtcacgttg gtatgagaaa gcctgacctg      420
gcgttttcc gtcacgttct gcgtgagatc agcacggcta gcgaagatat tgtgtttgtt     480
gacgacaatt tggaaaacgt cacgtctgca cgctccctgg gtatgcaagg catcgtcttt     540
cgtgataagg aagatgtcca gcgccagctg cgcaatctgt tcggttcccc ggcagagcgc     600
ggtcgtgagt atctgagcat taataagacc aaactgcaga gcgtgaccac caccaatatc     660
ccgattctgg acaacttcgg tcagttgctg atcctggaag ctacccgtga cccggattta     720
gtcagcatgc atccaggcca acgtacgtgg aacttcttca ttggcagccc gaccttgacg     780
accgacgcgt ttccggacga tatggacacg acttctctgg gcctgagcat catcccgccg     840
agcccggaaa ttgcagcaag cgttatggac gaaatcgtca cccgtctgaa taaagatggt     900
attgtgccga cctacttcga cagcacgcgt ccacgtgtgg acccgatcgt ctgcgttaac     960
gtcctgacct tgtttgcgaa atatggtcgt gaagatgaac tgagcggcac gattgcgtgg    1020
gtccgcgacg ttctgtatca tcgcgcatac ctggcgggca cgcgctacta cgcgtcccca    1080
gaggccttcc tgttcttctt tacgcgtttc acccgcaatc tgcgtccggg tccgcgtaaa    1140
caagaactta cggcgctgct gagccagcgt ctgcaggaac gcaacaagac gccggttgac    1200
gctctggccc tgagcatgcg tatcatcgcc tgtctgaccc tgggcattga gagcccggca    1260
gacgacgtgg ccaccctgac cggtatgcag tgtggtgatg gtggctggcc ggcgtgcgtg    1320
atctacaaat atggtgcggg tggcttgggt atcacgaatc gtggcgttag cactgccttc    1380
gcggtgaaag cgattacgac caccccgctg gcagtgcagc cagaagtcag cgtcagcgct    1440
ggtgccggcg gctccagccg cccggttggt gcggatgcgg cagcggttag cttgcgtccg    1500
cgttggcgtg cggttgtgca gagcctgcat ccgctgagcc gcgtgggtgg cctggttgcc    1560
gtgatcttcg cggcactgca ctttaacctg gcgtggctgt acaacgtaag cctggctagc    1620
cgtattgtgt aa                                                        1632
```

<210> SEQ ID NO 37
<211> LENGTH: 1632
<212> TYPE: DNA
<213> ORGANISM: Artificial Sequence
<220> FEATURE:

<223> OTHER INFORMATION: codon optimized cDNA

<400> SEQUENCE: 37

```
atggtccgcg cactgattct cgatctcggc gacgtcctct tcaactggga cgccccaaag    60
tcaaccccg tttcccgcaa gacactcagc cagatgctgc atagcgacat ctggggcgaa   120
tacgaatgtg ccaactgac agagccggaa agctacaagg cgcttgccag ccgctattct   180
tgccaggctc aagatgttgc agataccttc tatctagccc gcgaatcgct gaggctcgat   240
gcgaccttca agaccttcct gcaggacttg aagcagaggg ccaacggctc acttcgcgta   300
tatgggatgt ccaacatctc ccagcccgat atgaggtcc tgctgtccaa ggcggatgac   360
ttgagcctgt ttgacaagat cttcccatcc ggccacgtcg ggatgcgtaa gcctgacctt   420
gcgttttttc gacatgtcct gcgtgagatc tcgacggcca gcgaggatat tgtgtttgtt   480
gacgacaacc tggagaacgt gacatctgcc cggtctctgg gcatgcaggg gattgtcttt   540
cgcgacaagg aggatgtaca gagacagctg cggaacctct ttggcagtcc tgctgaacgt   600
ggaagggagt atttgtccat caacaagaca agctccaga gcgtcacgac gaccaatatc   660
cccattctcg acaactttgg ccagctcctt atcctcgaag ccaccagaga cccagacctg   720
gtgtccatgc atcctggaca gaggacctgg aactttttca tcggatctcc aactctgaca   780
acggacgcct tcccagacga tatggacacc acctcacttg gcctttctat tatacccca   840
agtcccgaga ttgcagcgtc cgtgatggat gagattgtga cccgcctgaa caaggacggc   900
attgtcccaa catattttga cagcaccaga ccccgcgtcg acccgatcgt ctgcgtcaac   960
gttctcaccc tcttcgctaa atacggccgc gaagacgagc tgtccgggac atagcctgg   1020
gtgcgcgatg tgctgtatca cagggcctac cttgcaggga ccagatacta cgcatcccca   1080
gaagcattcc ttttcttctt cacgcgcttc acccgaaacc tgcgcccggg cccgcgcaag   1140
caggagctca cggcgctgct gtcccagcgc ctgcaggagc gcaacaagac gcccgttgac   1200
gcacttgcgc tctcgatgcg gattattgcg tgcctcacgc tgggtattga atccccgct   1260
gacgacgtgg ctaccctcac gggcatgcag tgtggggatg gcgggtggcc ggcctgtgtc   1320
atctacaagt acggcgccgg tgggctgggg atcacgaaca gggggtctc gaccgcgttt   1380
gctgtcaagg caatcactac tactccttgg gcggtgcagc ctgaagttag tgtcagcgca   1440
ggtgcaggag gcagcagtcg ccctgtgggt gccgatgctg ctgcagtctc gctccgcccg   1500
agatggcgag ctgttgtgca gagtctccat ccgctctctc gggttggtgg gttggtggcc   1560
gtcattttg ctgcactgca tttcaacttg gcctggcttt ataatgtgtc ccttgctagt   1620
aggatcgttt ag                                                      1632
```

<210> SEQ ID NO 38
<211> LENGTH: 477
<212> TYPE: PRT
<213> ORGANISM: Aspergillus oryzae

<400> SEQUENCE: 38

```
Met Thr Arg Trp Lys Ser Ser Gln Tyr Gln Ala Ile Ile Phe Asp Leu
1               5                   10                  15

Gly Gly Val Ile Leu Thr Trp Asp Leu Pro Glu Asp Thr Val Ile Ser
            20                  25                  30

Ala Gln Ile Phe Lys Arg Met Leu Thr Ser Gln Thr Trp Ser Asp Tyr
        35                  40                  45

Glu Arg Gly Asn Leu Ser Glu Asn Gly Cys Tyr Gln Arg Leu Ala Glu
    50                  55                  60
```

```
Asp Phe Gly Ile Asp Ser Ala Asp Ile Ala His Thr Val Arg Gln Ala
 65                  70                  75                  80

Arg Glu Ser Leu Val Thr Asp Thr Ala Ile Met Asn Ile Ile Ser Glu
                 85                  90                  95

Ile Arg Ala Gly Ala Asn His Ile Ala Ile Phe Ala Met Ser Asn Ile
            100                 105                 110

Ser Gln Pro Asp Tyr Ala Ala Leu Leu Leu Asp His Arg Gly Met Cys
        115                 120                 125

Ser Phe Asp Arg Val Phe Pro Ser Gly Cys Tyr Gly Thr Arg Lys Pro
    130                 135                 140

Glu Leu Ser Phe Tyr Asn Lys Val Leu Arg Glu Ile Asp Thr Pro Pro
145                 150                 155                 160

Glu Asn Val Ile Phe Val Asp Asp Gln Leu Glu Asn Val Ile Ser Ala
                165                 170                 175

Gln Ser Ile Gly Ile His Gly Ile Ala Tyr Thr Asn Ala Ala Glu Leu
            180                 185                 190

Gly Arg Gln Leu Arg Asn Leu Ile Phe Asp Pro Val Glu Arg Gly Arg
        195                 200                 205

Glu Phe Leu Arg Arg Asn Ala Gly Glu Phe His Ser Ile Thr Glu Thr
    210                 215                 220

Asp Gln Ile Val Arg Glu Asn Phe Ser Gln Leu Leu Ile Leu Glu Ala
225                 230                 235                 240

Thr Gly Asp Lys Ser Leu Val Ser Leu Glu Tyr His Gln Lys Ser Trp
                245                 250                 255

Asn Phe Phe Gln Gly Asn Pro Ile Leu Thr Thr Glu Thr Phe Pro Asp
            260                 265                 270

Asp Val Asp Thr Thr Ser Leu Ala Leu Met Thr Leu Pro Thr Asp Thr
        275                 280                 285

Lys Thr Ala Asn Leu Leu Leu Asp Gln Ile Leu Gly Leu Val Asn Ala
    290                 295                 300

Asp Glu Ile Val Thr Thr Tyr Phe Asp Gln Thr Arg Glu Arg Ile Asp
305                 310                 315                 320

Pro Val Val Cys Val Asn Val Leu Arg Leu Phe Cys Thr Tyr Gly Arg
                325                 330                 335

Gly Ile Ala Leu Pro Leu Thr Leu Gln Trp Val Tyr Asp Val Leu Ala
            340                 345                 350

His Arg Ala Tyr Ile Asn Gly Thr Arg Tyr Tyr Thr Ser Pro Glu Ser
        355                 360                 365

Phe Leu Tyr Phe Val Gly Gln Leu Cys Arg Phe Ser Thr Gly Val Leu
    370                 375                 380

Ala Leu Arg Pro Leu Glu Thr Leu Leu Ile Asp Arg Leu Lys Glu Arg
385                 390                 395                 400

Leu Gln Val Lys Ala Asp Pro Leu Ser Leu Ala Met Arg Ile Leu Thr
                405                 410                 415

Cys Leu Ser Val Gly Val Ser Gln Val Glu Val Asp Leu Arg Glu Leu
            420                 425                 430

Leu Ser Met Gln Cys Glu Asp Gly Ser Trp Glu His Cys Pro Phe Thr
        435                 440                 445

Arg Tyr Gly Leu Ser Lys Val Ser Ile Gly Asn Arg Gly Leu Thr Thr
    450                 455                 460

Ala Phe Val Val Lys Ala Val Glu Met Cys Arg Gly Ser
465                 470                 475
```

-continued

<210> SEQ ID NO 39
<211> LENGTH: 1434
<212> TYPE: DNA
<213> ORGANISM: Aspergillus oryzae
<220> FEATURE:
<221> NAME/KEY: misc_feature
<223> OTHER INFORMATION: cDNA

<400> SEQUENCE: 39

| | | | | | |
|---|---|---|---|---|---|
| atgactcgat | ggaaatcgtc | ccaataccaa | gcaattatct | tgacctagg | cggtgtcatt | 60 |
| ttaacatggg | acctcccgga | agacactgtg | atatcggccc | agatctttaa | gagaatgctc | 120 |
| acatcgcaga | catggtcaga | ttatgagcgc | ggaaatctca | gcgaaaatgg | ttgctaccag | 180 |
| aggttggccg | aggattttgg | cattgactct | gccgacattg | cacataccgt | tagacaagca | 240 |
| cgggaatccc | ttgtcactga | taccgctatc | atgaacatta | tatctgagat | cagagctggg | 300 |
| gctaaccata | ttgctatctt | cgctatgtcg | aacatctccc | aaccagatta | tgcggctctg | 360 |
| ctccttgatc | atcgcgggat | gtgcagtttt | gaccgggtgt | tcccatctgg | atgctacggg | 420 |
| acaaggaaac | cagagctctc | attctataac | aaagtcttgc | gggagattga | cacgccaccg | 480 |
| gaaaacgtca | tctttgtcga | tgatcagctg | aaaatgtga | tctctgcgca | gtccattggc | 540 |
| atacacggga | ttgcctatac | gaatgctgct | gaactcggtc | gacagcttag | gaacctaata | 600 |
| tttgaccctg | tagagagggg | tagggaattc | ttacggcgca | atgctggaga | gttccatagc | 660 |
| atcactgaaa | ccgatcaaat | tgttcgggaa | aatttctcac | agttgctcat | tctagaagcg | 720 |
| actggtgata | agagtctggt | atctcttgaa | tatcaccaga | agagctggaa | tttcttccaa | 780 |
| ggaaaccccta | ttctcacgac | agagacattc | ccagatgatg | ttgacacaac | atctcttgcc | 840 |
| ttgatgactc | tacctacaga | cacaaaaaact | gcaaatttgt | tactcgacca | gattttgggg | 900 |
| ctagtcaacg | ctgatgaaat | cgtaacaaca | tactttgacc | agacccgaga | acggatcgat | 960 |
| ccagtagtct | gcgtcaatgt | ccttcgtctc | ttttgcacct | acggccgggg | cattgcgctc | 1020 |
| cctttgactc | ttcagtgggt | gtacgacgtc | ctcgctcatc | gggcatatat | aaacggtaca | 1080 |
| cgttactaca | caagtcccga | aagcttccta | tacttgtcg | gtcaactttg | tcgattctca | 1140 |
| acaggggtac | tggcacttcg | gccgctggaa | acgttgctta | tagatcgtct | caaggaacgt | 1200 |
| cttcaggtca | aagcagatcc | tctatcactc | gctatgcgga | tcttgacctg | tttgtccgtt | 1260 |
| ggtgtgtctc | aagttgaagt | cgatctccga | gagttgctct | cgatgcagtg | tgaagatggc | 1320 |
| tcgtgggaac | attgtccatt | cacccggtat | ggtttgtcca | aagtgagcat | tggcaatcgg | 1380 |
| ggccttacaa | ctgcttttgt | ggtcaaggcg | gttgaaatgt | gtcgaggcag | ttag | 1434 |

<210> SEQ ID NO 40
<211> LENGTH: 1434
<212> TYPE: DNA
<213> ORGANISM: Artificial Sequence
<220> FEATURE:
<223> OTHER INFORMATION: codon optimized cDNA

<400> SEQUENCE: 40

| | | | | | |
|---|---|---|---|---|---|
| atgactcgtt | ggaaaagctc | tcaatatcag | gcaatcattt | tcgatctggg | cggtgttatt | 60 |
| ctgacctggg | acttgccgga | agatacggtt | atctccgcgc | aaatctttaa | gcgtatgctg | 120 |
| accagccaga | cctggtccga | ttatgagcgc | ggtaatctga | gcgagaacgg | ctgctatcaa | 180 |
| cgtttggcgg | aagatttcgg | catcgatagc | gccgatattg | cccacaccgt | ccgtcaggca | 240 |
| cgtgagtccc | tggtgaccga | caccgccatc | atgaatatca | tctccgagat | ccgtgcaggc | 300 |

-continued

```
gcgaaccaca tcgcaattttt cgcgatgagc aacatctcac agccggatta cgctgcgctg      360
ctgctggacc atcgcgggtat gtgcagcttt gaccgcgtct ttccgagcgg ttgttacggc      420
acccgtaagc ctgagctgag cttctacaat aaagtgctgc gtgaaattga caccccgccg      480
gaaaatgtta ttttcgttga cgatcaattg gaaaatgtga ttagcgcgca agcattggt       540 attcatggca ttgcgtatac gaatgccgcg gaactgggcc gccagctgag aaacctgatc      600
ttcgatccgg tggagcgcgg tcgtgagttc ctgcgtcgta cgctggtga gtttcactct       660 attacggaaa cggaccagat tgtgcgcgag aacttcagcc agctgctgat tctggaagcg      720
accggtgaca aaagcctggt tagcctggaa taccaccaaa agtcgtggaa cttcttccaa      780
ggtaacccaa tcctgacgac ggaaaccttc ccggacgatg ttgacactac tagcctggct      840
ctgatgacgc tgccgacgga caccaagacc gcgaatctgt tgctggacca gattctgggt      900
ttggttaatg ccgatgaaat tgtgactacg tacttcgacc agacccgtga gcgtatcgat      960
ccagtggtct gtgtgaatgt cctgcgcctg ttctgtacgt acggccgcgg catcgcgctg     1020
ccgctgaccc tgcaatgggt ctacgatgtg ctggcgcacc gcgcatacat taacggtacg     1080
cgttattaca ccagcccgga gagctttctg tattttgtcg gtcagctctg tcgttttagc     1140
accggtgtgc tggcactgcg tccgctggag actctgctga ttgatcgtct gaaagagcgc     1200
ctgcaagtta aagctgaccc gctgagcctg gcaatgcgca tccttacgtg cttatctgtc     1260
ggtgtcagcc aggttgaagt ggacttgcgt gagttgttga gcatgcagtg cgaggacggt     1320
agctgggagc attgcccgtt cacccgctac ggcctgagca aggtttccat cggtaaccgt     1380
ggcctgacca cggcgtttgt ggttaaagcc gtcgagatgt gccgtggcag ctaa            1434
```

<210> SEQ ID NO 41
<211> LENGTH: 528
<212> TYPE: PRT
<213> ORGANISM: Aspergillus calidoustus

<400> SEQUENCE: 41

```
Met Val Arg Ala Leu Ile Leu Asp Leu Gly Asp Val Leu Phe Asn Trp
1               5                   10                  15

Asp Ala Pro Ala Ser Thr Pro Ile Ser Arg Lys Thr Leu Gly Gln Met
            20                  25                  30

Leu His Ser Glu Ile Trp Gly Glu Tyr Glu Arg Gly His Leu Thr Glu
        35                  40                  45

Asp Glu Ala Tyr Asn Ala Leu Ala Lys Arg Tyr Ser Cys Glu Ala Lys
    50                  55                  60

Asp Val Ala His Thr Phe Val Leu Ala Arg Glu Ser Leu Arg Leu Asp
65                  70                  75                  80

Thr Lys Phe Lys Thr Phe Leu Gln Thr Leu Lys Gln Asn Ala Asn Gly
                85                  90                  95

Ser Leu Arg Val Tyr Gly Met Ser Asn Ile Ser Lys Pro Asp Phe Glu
            100                 105                 110

Val Leu Leu Gly Lys Ala Asp Asp Trp Thr Leu Phe Asp Lys Ile Phe
        115                 120                 125

Pro Ser Gly His Val Gly Met Arg Lys Pro Asp Leu Ala Phe Phe Arg
    130                 135                 140

Tyr Val Leu Lys Asp Ile Ser Thr Pro Val Glu Asp Val Phe Val
145                 150                 155                 160

Asp Asp Asn Leu Asp Asn Val Thr Ser Ala Arg Ser Leu Gly Met Arg
                165                 170                 175
```

```
Ser Val Leu Phe His Lys Lys Asp Glu Val Gln Arg Gln Leu Thr Asn
            180                 185                 190
Ile Phe Gly Ser Pro Ala Glu Arg Gly Leu Glu Tyr Leu Ser Ala Asn
        195                 200                 205
Lys Thr Asn Leu Gln Ser Ala Thr Thr Thr Asp Ile Pro Ile Gln Asp
    210                 215                 220
Asn Phe Gly Gln Leu Leu Ile Leu Glu Ala Thr Glu Asp Pro Ser Leu
225                 230                 235                 240
Val Arg Met Glu Pro Gly Lys Arg Thr Trp Asn Phe Phe Ile Gly Ser
                245                 250                 255
Pro Ser Leu Thr Thr Asp Thr Phe Pro Asp Asp Leu Asp Thr Thr Ser
            260                 265                 270
Leu Ala Leu Ser Ile Val Pro Thr Ser Pro Asp Val Val Asn Ser Val
        275                 280                 285
Ile Asp Glu Ile Ile Ser Arg Arg Asp Lys Asp Gly Ile Val Pro Thr
    290                 295                 300
Tyr Phe Asp Asn Thr Arg Pro Arg Val Asp Pro Ile Val Cys Val Asn
305                 310                 315                 320
Val Leu Ser Met Phe Ala Lys Tyr Gly Arg Glu His Asp Leu Pro Ala
                325                 330                 335
Thr Val Ala Trp Val Arg Asp Val Leu Tyr His Arg Ala Tyr Leu Gly
            340                 345                 350
Gly Thr Arg Tyr Tyr Gly Ser Ala Glu Ala Phe Leu Phe Phe Thr
        355                 360                 365
Arg Phe Val Arg Asn Leu Arg Pro Gly Thr Leu Lys Gln Asp Leu His
370                 375                 380
Ala Leu Leu Ser Glu Arg Val Arg Glu Arg Leu Asn Thr Pro Val Asp
385                 390                 395                 400
Ala Leu Ala Leu Ser Met Arg Ile Gln Ala Cys His Ala Leu Gly Phe
                405                 410                 415
Asp Ala Pro Ala Asp Ile Ala Thr Leu Ile Thr Met Gln Asp Glu Asp
            420                 425                 430
Gly Gly Trp Pro Ala Ala Val Ile Tyr Lys Tyr Gly Ala Gly Gly Leu
        435                 440                 445
Gly Ile Thr Asn Arg Gly Val Ser Thr Ala Phe Ala Val Lys Ala Ile
    450                 455                 460
Thr Gly Ser Pro Val Lys Thr Glu Thr Asn Ile Gly Gly Asp Gly Ala
465                 470                 475                 480
Arg Ala Val Ser Ala Met Ser Ser Leu Glu Ala Arg Arg Leu Gln Pro
                485                 490                 495
Ile Ser Ser Val Gly Asp Trp Val Arg Phe Ile Ile Ala Ser Leu His
            500                 505                 510
Val His Leu Ala Trp Leu Trp Asn Val Leu Leu Leu Ser Lys Val Val
        515                 520                 525

<210> SEQ ID NO 42
<211> LENGTH: 1587
<212> TYPE: DNA
<213> ORGANISM: Aspergillus calidoustus
<220> FEATURE:
<221> NAME/KEY: misc_feature
<223> OTHER INFORMATION: cDNA

<400> SEQUENCE: 42
atggtccgcg cactcatcct cgatctcggc gatgtcctct tcaactggga cgcgcctgcg    60
```

| | |
|---|---|
| tccacccccca tttcacgcaa gaccctcggc cagatgctgc atagtgagat ctggggtgag | 120 |
| tatgaacgtg gccatttgac agaagacgag gcatacaacg cactcgcgaa gcggtattcc | 180 |
| tgcgaggcca aggatgtcgc acatacctttt gtcctggcac gagaatcgct gcggctcgac | 240 |
| acgaaattca aaacgtttct gcagactcta aagcagaatg ccaacggctc ccttcgtgtc | 300 |
| tatggcatgt cgaatatatc gaaaccggat ttcgaagtcc tgctgggcaa ggccgatgac | 360 |
| tggactctgt ttgacaagat cttcccctct ggccatgtcg gtatgcgcaa gccagatctt | 420 |
| gccttcttcc gctatgtgct caaggacatt tcaacgcctg tcgaggatgt ggtgttttgtt | 480 |
| gacgataacc tggacaacgt gacgagtgct cggtctctgg gcatgcgcag cgtcctctttt | 540 |
| cataagaaag acgaggtcca gcgacagctc accaacatct ttggcagccc tgctgagcgg | 600 |
| ggcttggagt atctctccgc caacaagacg aatctgcaga gtgctaccac gacagatatc | 660 |
| ccaatccagg ataactttgg ccaacttctg attctcgagg ccactgaaga cccatcgctg | 720 |
| gtccgcatgg agcccggtaa gcgaacctgg aatttcttca tcggttctcc atccctcaca | 780 |
| accgacacct tccccgacga tctcgacacc acatcccttg ccctctccat cgtacccaca | 840 |
| agccccgacg tcgtcaactc ggtcatcgac gagattatca gccgtcgcga caaggacggt | 900 |
| atcgtcccga cttacttcga caacacccgc ccccgcgtgg acccaatcgt ctgcgtaaac | 960 |
| gtcctctcca tgttcgcaaa gtacggccgc gagcacgacc tccccgcaac agttgcgtgg | 1020 |
| gtccgcgacg tcttgtatca tcgagcatac ctcggcggaa cacggtacta cgggtcagct | 1080 |
| gaggccttcc tcttcttctt cactcgcttc gttcgcaacc tccgaccggg aactctcaag | 1140 |
| caggatctac acgcattgct atcagagcgc gtgcgcgagc gactcaatac ccccgtcgac | 1200 |
| gcactcgccc tgtcaatgcg catccaggcc tgtcatgcgc tgggctttga cgcccccgca | 1260 |
| gacattgcga cgctcatcac aatgcaggac gaggacggcg ggtggccggc agccgtcatc | 1320 |
| tacaagtacg gggccggggg gttggggatc acgaaccggg gtgtttcgac tgcgtttgcc | 1380 |
| gtaaaggcga ttacagggtc gcccgtgaag actgaaacca acataggcgg cgatggagct | 1440 |
| cgcgctgtct cggccatgtc ctccttggag gcgaggaggc tacagccgat ctcgtcggtt | 1500 |
| ggggactggg tgcggtttat cattgcgtcg ttgcatgtcc atctggcttg gctttggaat | 1560 |
| gttttgcttt tgagcaaggt tgtttga | 1587 |

<210> SEQ ID NO 43
<211> LENGTH: 1587
<212> TYPE: DNA
<213> ORGANISM: Artificial Sequence
<220> FEATURE:
<223> OTHER INFORMATION: codon optimized cDNA

<400> SEQUENCE: 43

| | |
|---|---|
| atggttcgtg cgttgatttt ggatttgggt gatgtgttgt ttaattggga cgcccctgca | 60 |
| agcactccga tcagccgtaa gaccctgggc cagatgctgc attccgagat ttggggtgag | 120 |
| tatgagcgtg gtcacctgac cgaagatgaa gcgtacaacg cgctggcaaa gcgctacagc | 180 |
| tgcgaggcaa agacgtggc gcatactttt gttttggcgc gtgaaagcct gcgcctggat | 240 |
| accaagttta agactttcct gcagaccctg aaacagaacg cgaacggctc gctgcgtgtt | 300 |
| tatggtatgt ccaatatcag caaaccggat tttgaagtgc tgctgggtaa gctgacgac | 360 |
| tggaccttgt tcgacaagat cttcccgagc ggtcatgtcg gtatgcgcaa accggacctg | 420 |
| gctttctttc gttacgtgct gaaagacatc agcaccccgg ttgaggatgt tgtgttttgtt | 480 |
| gacgataacc tggataatgt gacgtctgcc cgttccctgg gtatgcgtag cgtcctgttc | 540 |

```
cacaaaaaag acgaagtcca acgtcagctg accaacattt tcggtagccc tgctgagcgc    600
ggtctggagt atctgtccgc gaacaagacc aatctgcaaa gcgcaaccac caccgacatc    660
cctatccaag acaactttgg tcaattactg attctggaag ccaccgaaga tccgagcctg    720
gtacgcatgg aaccgggcaa gcgtacctgg aatttcttca ttggctctcc gagcctgacg    780
acggatacct tcccggatga cctggacacg acgagcctcg cactgtccat cgtgccgacc    840
agcccagatg ttgttaatag cgtgatcgat gagatcatca gccgtcgcga caaggacggt    900
attgtgccga cgtactttga taacacgcgc ccgcgtgtgg acccgattgt tgtgttaac     960
gttctgtcta tgttcgcgaa atatggccgt gagcacgatc tgccggcgac ggtcgcgtgg   1020
gtccgcgacg tcctctatca tcgcgcatac ctgggtggca ccagatacta cggtagcgcg   1080
gaagccttcc ttttcttctt tacgcgcttt gtgcgtaatc tgcgtccggg cacgctgaaa   1140
caagatctgc acgcgttgct gagcgagcgt gtccgtgagc gcctgaatac cccggtggat   1200
gcgctggcgc tgagcatgcg cattcaggct tgccacgcac tgggctttga cgccccagct   1260
gacatcgcga cgctgattac catgcaagat gaagatggtg gctggccggc ggcagttatc   1320
tacaaatatg gtgcgggtgg cctgggcatt acgaaccgtg gtgtgtccac ggcattcgcg   1380
gtgaaggcaa tcacgggtag cccggttaaa accgaaacca acatcggcgg cgacggtgcc   1440
cgtgcagtgt cggccatgag cagcctggaa gcccgtcgtt tgcagccgat ttctagcgtc   1500
ggcgactggg tccgtttcat catcgcatca ctgcacgtcc acctggcgtg gctgtggaat   1560
gtcctgctgc tgagcaaagt cgtttaa                                       1587

<210> SEQ ID NO 44
<211> LENGTH: 531
<212> TYPE: PRT
<213> ORGANISM: Heterobasidion irregulare

<400> SEQUENCE: 44

Met Ser Met Ile Pro Arg Cys Ser Asn Leu Ile Leu Asp Ile Gly Asp
1               5                   10                  15

Val Leu Phe Thr Trp Ser Pro Lys Thr Ser Thr Ser Ile Ser Pro Arg
            20                  25                  30

Thr Met Lys Ser Ile Leu Ser Ser Thr Thr Trp His Gln Tyr Glu Thr
        35                  40                  45

Gly His Ile Ser Gln Gly Asp Cys Tyr Arg Leu Ile Gly Asn Gln Phe
    50                  55                  60

Ser Ile Asp Pro Gln Glu Val Gly Leu Ala Phe Gln Gln Ala Arg Asp
65                  70                  75                  80

Ser Leu Gln Pro Asn Val Asp Phe Ile His Phe Ile Arg Ala Leu Lys
                85                  90                  95

Ala Glu Ser His Gly Thr Leu Arg Val Phe Ala Met Ser Asn Ile Ser
            100                 105                 110

Gln Pro Asp Tyr Ala Val Leu Arg Thr Lys Ala Asp Trp Ala Val
        115                 120                 125

Phe Asp Asp Ile Phe Thr Ser Ala Asp Ala Gly Val Arg Lys Pro His
    130                 135                 140

Leu Gly Phe Tyr Lys Leu Val Leu Gly Lys Ile Gly Ala Asp Pro Asn
145                 150                 155                 160

Asp Thr Val Phe Val Asp Asp Lys Gly Asp Asn Val Leu Ser Ala Arg
                165                 170                 175

Ser Leu Gly Leu His Gly Ile Val Phe Asp Ser Met Asp Asn Val Lys
```

180                 185                 190
Arg Ala Leu Arg Tyr Leu Ile Ser Asp Pro Ile Arg Arg Gly Arg Glu
            195                 200                 205

Phe Leu Gln Ala Arg Ala Gly His Leu Glu Ser Glu Thr Asn Thr Gly
        210                 215                 220

Ile Glu Ile Gly Asp Asn Phe Ala Gln Leu Leu Ile Leu Glu Ala Thr
225                 230                 235                 240

Lys Asp Arg Thr Leu Val Asn Tyr Met Asp His Pro Asn Lys Trp Asn
                245                 250                 255

Phe Phe Arg Asp Gln Pro Leu Leu Thr Thr Glu Glu Phe Pro Phe Asp
            260                 265                 270

Leu Asp Thr Thr Ser Ile Gly Thr Leu Ala Thr Gln Arg Asp Asp Gly
        275                 280                 285

Thr Ala Asn Leu Val Met Asp Glu Met Leu Gln Tyr Arg Asp Glu Asp
        290                 295                 300

Gly Ile Ile Gln Thr Tyr Phe Asp His Glu Arg Pro Arg Ile Asp Pro
305                 310                 315                 320

Ile Val Cys Val Asn Val Leu Ser Leu Phe Tyr Ser Arg Gly Arg Gly
                325                 330                 335

Ser Glu Leu Ala Pro Thr Leu Glu Trp Val Arg Gly Val Leu Lys His
            340                 345                 350

Arg Ala Tyr Leu Asp Gly Thr Arg Tyr Tyr Glu Thr Gly Glu Cys Phe
        355                 360                 365

Leu Phe Phe Leu Ser Arg Leu Leu Gln Ser Thr Lys Asp Ala Ala Leu
370                 375                 380

His Ala Ser Leu Lys Ser Leu Phe Ala Glu Arg Val Lys Glu Arg Ile
385                 390                 395                 400

Gly Ala Pro Gly Asp Ala Leu Ala Leu Ala Met Arg Ile Leu Ala Cys
                405                 410                 415

Ala Ala Val Gly Val Arg Asp Glu Ile Asp Leu Arg Ser Leu Leu Pro
            420                 425                 430

Leu Gln Cys Glu Asp Gly Gly Trp Glu Ala Gly Trp Val Tyr Lys Tyr
        435                 440                 445

Gly Ser Ser Gly Val Lys Ile Gly Asn Arg Gly Leu Thr Thr Ala Leu
        450                 455                 460

Ala Leu Asn Ala Ile Glu Ala Val Glu Gly Arg Arg Thr Arg Pro Lys
465                 470                 475                 480

Ser Gly Lys Ile Ser Arg Val Ser Arg His Ser Glu Val Ala Ala Ala
                485                 490                 495

Pro Arg Ser Ser Thr Ser Ser His Arg Ser Asn Arg Ser Ile Ser Arg
            500                 505                 510

Thr Phe Gln Ala Tyr Phe Lys Ala Ser Trp Thr Ser Met Lys Gln Val
        515                 520                 525

Ala Val Ala
    530

<210> SEQ ID NO 45
<211> LENGTH: 1596
<212> TYPE: DNA
<213> ORGANISM: Heterobasidion irregulare
<220> FEATURE:
<221> NAME/KEY: misc_feature
<223> OTHER INFORMATION: cDNA

<400> SEQUENCE: 45

| | |
|---|---|
| atgtccatga tacccagatg ctcgaatctc atcctcgaca tcggggatgt tctcttcaca | 60 |
| tggtctccga agacgtccac ttcgatctcc ccccgcacca tgaagagcat actgtcatcg | 120 |
| acgacctggc accaatacga gaccgggcac atttcacagg gcgactgcta ccgcctcata | 180 |
| ggcaaccagt tctccatcga tcctcaggaa gtcggacttg cattccaaca agctcgggac | 240 |
| tcattgcagc ctaatgttga cttcattcac ttcatccgcg ccctcaaggc ggaatcacac | 300 |
| gggacgctgc gcgtcttcgc tatgtccaac atctctcagc ccgattacgc agttcttcgg | 360 |
| actaaggacg ccgactgggc cgttttttgac gatatattca cgtctgcaga tgctggggtt | 420 |
| cgaaagccac accttgggtt ctacaagttg gtactcggaa agatcggcgc cgatccaaac | 480 |
| gataccgtct tcgtcgatga caaggggggac aatgtcctct ctgcacggtc tctcggcctt | 540 |
| catggaatcg tctttgacag tatggacaac gtcaagcgag ccctgcgcta cttgatcagc | 600 |
| gacccccatac ggcgaggacg agagtttctc caagcgcgag ccggccattt ggagtcggag | 660 |
| accaatacgg gcatcgaaat cggtgataat tttgcccagc tccttattct cgaggccacg | 720 |
| aaggatagga cactcgtcaa ttatatggac catccgaaca aatggaatt cttccgagat | 780 |
| caaccgctcc tcacaacgga ggagttccct ttcgatctcg atacgacatc tattggaacg | 840 |
| cttgcgacgc agcgcgatga tgggactgcc aatctagtaa tggatgagat gcttcagtac | 900 |
| cgtgatgagg atggcataat acaaacatat ttcgatcatg aacgaccgag gatagatccc | 960 |
| atcgtctgtg tcaacgtctt gagccttttc tactcccggg tcgtggttc ggagctagca | 1020 |
| ccgacactag agtgggtgcg tggtgtcctc aagcaccgcg cgtatctcga tggaacgcga | 1080 |
| tactacgaga caggcgaatg cttccttttc ttcctcagcc ggctcttgca atcaaccaag | 1140 |
| gacgccgcct tgcacgcatc gttgaaatct ttgttcgccg aacgggtcaa ggagcgcata | 1200 |
| ggggcaccag gggacgcgct ggcgctggcg atgcgtatac tggcatgcgc agcagtgggc | 1260 |
| gtgcgggacg agatcgatct tcgatcacta ttacctctgc agtgcgagga tgggggtgg | 1320 |
| gaggcaggct gggtgtacaa gtatgggtct cgggagtca agatcggcaa tcgtggcctc | 1380 |
| acgactgcgc ttgcgctcaa tgccatcgag gctgtggagg acgtcgcac gaggccgaag | 1440 |
| tcgggtaaga tcagccgagt cagccgtcat tctgaggtcg cagcagcgcc acggtcttcc | 1500 |
| accagcagtc atcgttctaa tcgctcgatc tcaaggacat tccaggcgta cttcaaggcg | 1560 |
| tcgtggacat cgatgaaaca ggtggccgtg gcgtga | 1596 |

<210> SEQ ID NO 46
<211> LENGTH: 1596
<212> TYPE: DNA
<213> ORGANISM: Artificial Sequence
<220> FEATURE:
<223> OTHER INFORMATION: codon optimized cDNA

<400> SEQUENCE: 46

| | |
|---|---|
| atgagcatga ttccacgttg tagcaatctg attctcgaca tcggtgatgt gttgtttacg | 60 |
| tggagcccga aaaccagcac cagcattagc ccgcgtacca tgaaatctat cctgagctct | 120 |
| accacctggc atcaatatga gactggccac atcagccagg gtgattgcta ccgcctgatc | 180 |
| ggtaatcagt tctccatcga cccgcaagag gtcggtttgg ccttccagca agccagagac | 240 |
| agcctgcaac cgaatgttga tttcatccat ttcattcgtg ccctgaaagc tgagtcgcac | 300 |
| ggcaccctgc gcgttttttgc gatgagcaat atcagccaac ctgactatgc agtcctgcgt | 360 |
| acgaaagacg cggactgggc tgtttttgat gatatcttca cgagcgcgga tgctggtgtt | 420 |
| cgtaaaccgc acctgggttt ttataaactg gtcttaggca agattggcgc ggaccctaac | 480 |

```
gacaccgttt tgtggatga taagggtgac aacgtcctct ctgcacgttc cctgggtctg    540
cacggtatcg tttttgattc aatggacaac gtgaagcgcg cactgcgcta cctgattagc    600
gacccgatcc gccgcggccg tgaatttctg caggcccgtg cgggtcacct ggagtccgaa    660
acgaacacgg gtattgagat tggtgataat ttcgcgcaat tgctgatcct ggaagcgacc    720
aaagatcgta ctctggtgaa ctacatggac cacccgaaca agtggaactt cttccgtgac    780
cagccgctgc tgaccaccga gaatttccg ttcgacctgg acacgaccag cattggcacg    840
ctggccaccc aacgtgacga tggtacggcg aatctggtaa tggacgaaat gttgcagtat    900
cgtgacgaag atggcatcat tcagacctat ttcgatcatg agcgcccgcg tattgatccg    960
attgtttgtg tgaatgtgct gtctctgttc tacagccgtg gccgtggctc tgagttggcg   1020
ccgacgctgg aatgggtgcg cggtgtgttg aaacatcgtg cgtacctgga tggtacgcgt   1080
tattacgaga ctggtgagtg tttcctgttt ttcctgagcc gtctgctgca gagcaccaaa   1140
gacgcagccc tgcacgcgag cctgaagtcc ctgtttgcag agcgtgttaa agagcgcatc   1200
ggtgcgccgg gcgatgctct ggcgctggct atgcgcatcc tggcgtgcgc cgctgttggt   1260
gtgcgcgatg aaattgattt gcgtagcctg ctgccgctgc aatgcgaaga tggcggctgg   1320
gaagcgggct gggtctacaa atacggcagc agcggtgtga agattggcaa tcgcggtctt   1380
accacggcgc tggcattgaa tgctatcgaa gccgttgagg gccgtcgcac ccgcccaaag   1440
tccggtaaga tcagccgtgt tagccgtcat agcgaagtcg cagcggcacc gcgttcctcg   1500
acgagcagcc accgtagcaa ccgtagcatt agccgcacct tccaggcata ttttaaagcg   1560
agctggacca gcatgaaaca gtcgcagtg gcgtaa                              1596
```

<210> SEQ ID NO 47
<211> LENGTH: 518
<212> TYPE: PRT
<213> ORGANISM: Schizopora paradoxa

<400> SEQUENCE: 47

```
Met Ser Ile His Gly Ser Ser Met Ser Ser Tyr Ser Ser Thr Val Pro
1               5                   10                  15

Ser Met Thr Ser Ser Pro Ala Ser Thr Ser Pro Ser Ser Pro Ala
            20                  25                  30

Ser Ser Ile His Glu Ile Gly Pro Val Pro Glu Ala Arg Arg Lys Gly
        35                  40                  45

Gln Cys Asn Ala Leu Ile Phe Asp Leu Gly Asp Val Leu Phe Thr Trp
    50                  55                  60

Ser Ala Glu Thr Lys Thr Thr Ile Ser Pro Lys Leu Leu Lys Lys Ile
65                  70                  75                  80

Leu Asn Ser Leu Thr Trp Phe Glu Tyr Glu Lys Gly Asn Ile Gly Glu
                85                  90                  95

Gln Glu Ala Tyr Asp Ala Val Ala Lys Glu Phe Gly Val Pro Ser Ser
            100                 105                 110

Glu Val Gly Ala Ala Phe Gln Cys Ala Arg Asp Ser Leu Gln Ser Asn
        115                 120                 125

Pro Arg Leu Val Ser Leu Ile Arg Glu Leu Lys Ser Gln Tyr Asp Leu
    130                 135                 140

Lys Val Tyr Ala Met Ser Asn Ile Ser Ala Pro Asp Trp Glu Val Leu
145                 150                 155                 160

Arg Thr Lys Ala Thr Pro Glu Glu Trp Ala Met Phe Asp Arg Val Phe
                165                 170                 175
```

Thr Ser Ala Ala Ala Arg Glu Arg Lys Pro Asn Leu Gly Phe Tyr Arg
            180                 185                 190

Gln Val Val Glu Ala Thr Gly Val Asp Pro Ala Arg Ser Val Phe Val
        195                 200                 205

Asp Asp Lys Leu Asp Asn Val Ile Ser Ala Arg Ser Val Gly Leu Asn
210                 215                 220

Ala Ile Ile Phe Asp Ser Phe Glu Asn Val Ala Arg Gln Leu Lys Asn
225                 230                 235                 240

Tyr Val Ala Asp Pro Ile Gly Arg Ala Glu Ala Trp Leu Arg Asp Asn
                245                 250                 255

Ala Lys Lys Met Leu Ser Ile Thr Asp Ala Gly Val Val Val Tyr Glu
            260                 265                 270

Asn Phe Gly Gln Met Leu Ile Leu Glu Ala Thr Gly Asp Arg Ser Leu
        275                 280                 285

Val Asp Tyr Val Glu Tyr Pro Arg Leu Phe Asn Phe Phe Gln Gly Asn
    290                 295                 300

Gly Val Phe Thr Thr Glu Ser Phe Pro Cys Asp Leu Asp Ser Thr Ser
305                 310                 315                 320

Ile Gly Leu Thr Val Thr Asn His Val Asp Glu Lys Thr Arg His Ser
                325                 330                 335

Val Met Asp Glu Met Leu Thr Tyr Lys Asn Glu Asp Gly Ile Ile Ala
            340                 345                 350

Thr Tyr Phe Asp Ala Thr Arg Pro Arg Ile Asp Pro Val Val Cys Ala
        355                 360                 365

Asn Val Leu Thr Phe Phe Tyr Lys Asn Gly Arg Gly Glu Glu Leu Asn
    370                 375                 380

Glu Thr Leu Asp Trp Val Tyr Asp Ile Leu Leu His Arg Ala Tyr Leu
385                 390                 395                 400

Asp Gly Thr Arg Tyr Tyr Phe Gly Ser Asp Thr Phe Leu Phe Phe Leu
                405                 410                 415

Ser Arg Leu Leu Ser Glu Ser Pro Ser Val Tyr Ala Arg Phe Ala Pro
            420                 425                 430

Val Phe Gln Glu Arg Val Lys Glu Arg Met Gly Ala Thr Gly Asp Ala
        435                 440                 445

Met Ser Leu Ala Met Arg Ile Ile Ala Ala Thr Val Lys Ile Gln
    450                 455                 460

Asp Arg Val Asp Cys Asp Ala Leu Leu Gln Thr Gln Glu Asp Asp Gly
465                 470                 475                 480

Gly Phe Pro Ile Gly Trp Met Tyr Lys Tyr Gly Ala Thr Gly Met Leu
                485                 490                 495

Leu Gly Asn Lys Gly Leu Ser Thr Ala Leu Ala Ile Gln Ala Ile Lys
            500                 505                 510

Ala Val Glu Ser Phe Pro
        515

<210> SEQ ID NO 48
<211> LENGTH: 1557
<212> TYPE: DNA
<213> ORGANISM: Schizopora paradoxa
<220> FEATURE:
<221> NAME/KEY: misc_feature
<223> OTHER INFORMATION: cDNA

<400> SEQUENCE: 48
atgtcgattc acggttcttc tatgtcctcc tattcctcga ctgtgccgtc aatgacttcc        60

```
tctcccgcgt ccacttctac tccgtcgtct cctgcatcgt cgatccatga gattggtcct    120
gtcccagaag ctcgacgaaa gggacagtgc aacgcgctga tcttcgacct cggagacgtc    180
ctcttcacct ggtcggcaga gactaagacc accatttccc cgaaactcct gaaaagatc     240 cttaactcct taacatggtt cgaatacgag aagggaaaca tcggggagca ggaggcgtat    300
gacgcagtcg caaaggagtt tggcgtcccg tcgtccgagg tcggggccgc tttccagtgc    360
gcgcgcgatt cgctacagag caatcccgc ctcgtctcgc tcatccgtga gctgaagtcg     420
caatatgatc tcaaggtgta cgccatgtcc aacatctctg cgccggactg ggaagtccta    480
aggacgaagg cgaccccctga ggagtgggca atgtttgacc cgtcttcac gagcgcggcc    540 gcgcgcgagc gtaagccaaa cctcggattc tacagacagg ttgttgaggc gaccggcgtc    600
gaccccgctc gctccgtgtt cgtcgacgat aaactcgaca atgtcatctc tgcgcgttca    660
gtcggattaa atgcgatcat cttcgactca tttgagaacg tcgcccggca gctcaaaaac    720
tatgtcgctg atcctatcgg acgggcgagg cgtggttgc gcgataacgc aaagaagatg     780
ttgtcaatta cggatgccgg ggtggtcgta tacgagaatt cggccagat gctgatcttg      840 gaggcaacag cgataggtc gcttgtgac tacgtcgagt accctcgtct cttcaacttc       900
ttccaaggca atggcgtctt tacgaccgag tcattccctt gcgaccttga ttcgacttcc     960
atcggcttaa ccgtcacgaa ccacgtcgat gagaaaacaa ggcacagcgt catggatgag    1020
atgctgacct acaaaaatga ggatggtatc attgcgactt actttgatgc cacgcgtccc    1080
cgaattgacc ccgtcgtctg cgccaatgtc ttgacgttct tctacaagaa cggccgaggg    1140
gaggagctca atgaaacact tgactgggtc tacgacatcc tccttcatcg cgcgtacctc    1200
gatggcacac gctattattt cggctcagac accttcctct tcttcctttc tcgacttctc    1260
tccgaatcgc catccgttta cgcccgtttc gctccggtgt tccaggagag agtcaaggag    1320
cgcatggggg cgacgggaga tgcgatgtcc cttgcgatgc gcatcatcgc ggccgcaact    1380
gtcaagatcc aagaccgagt cgactgcgac gctctgctgc agacgcagga agacgacggt    1440
ggattcccga taggttggat gtacaagtac ggggcgaccg ggatgcttct gggtaacaag    1500
ggcttgtcga cagctctggc aatccaagct atcaaagcgg tcgaatcttt cccttga       1557
```

<210> SEQ ID NO 49
<211> LENGTH: 1557
<212> TYPE: DNA
<213> ORGANISM: Artificial Sequence
<220> FEATURE:
<223> OTHER INFORMATION: codon optimized cDNA

<400> SEQUENCE: 49

```
atgtcgattc acggtagcag catgtcgtct tatagcagca cggttccatc tatgactagc     60
agcccggctt ccacgagcac gccgtccagc ccggccagca gcatccacga aatcggcccg    120
gtccctgagg cgcgtcgcaa gggccaatgc aatgcactga tcttcgacct gggtgatgtt    180
ctgtttacct ggagcgcaga aaccaagacc acgatcagcc gaagctgct gaaaaagatt      240 ctgaacagct tgacctggtt tgagtatgag aaaggcaaca tcggtgaaca agaagcctat    300
gacgccgttg cgaaagagtt cggtgtgccg agctctgagg ttggcgctgc gtttcaatgt    360
gcgcgtgact ccctgcaaag caatccgcgt ttggttagcc tgattcgtga gctgaagtcc    420
cagtacgacc tgaaagtgta cgctatgagc aatattagcg cgccagactg ggaagtgctg    480
cgtactaaag cgacccccgga agagtgggca atgttcgatc gtgtctttac ttctgcggcg    540
```

```
gcgcgtgagc gtaagccgaa cttgggcttt taccgccaag tcgtggaagc aaccggtgtc   600
gatccggcgc gtagcgtttt cgtcgatgat aaactggaca atgtgatcag cgcgcgctct   660
gtcggtctga acgctattat cttcgactcc ttcgaaaacg tcgcccgtca gctgaagaat   720
tacgtcgcag acccgattgg tcgcgctgag gcgtggctgc gcgacaacgc aaagaaaatg   780
ctgagcatca ccgatgcggg tgttgtggtt tacgagaatt ttggccagat gctgatcctg   840
gaagctaccg gtgaccgtag cctggtggac tatgtggagt atccgcgcct ctttaacttc   900
ttccagggta acggcgtttt tacgaccgag agctttccat gcgatctgga cagcaccagc   960
atcggtctga ctgtgaccaa tcatgtggac gaaaagactc gccacagcgt catggacgaa  1020
atgctgacct acaaaaatga agatggtatt attgcgacgt actttgacgc gacgcgcccg  1080
cgcattgacc ctgttgtctg tgccaatgtt ctgaccttct tctacaaaaa cggtcgtggt  1140
gaagaattga acgaaaccct ggattgggtg tacgacattc tgctgcatcg cgcgtatctg  1200
gacggtacgc gttattattt cggctccgat acgttcctgt ttttcctgag ccgtctgctg  1260
agcgagtctc cgagcgttta cgcgcgtttt gccccggtgt ttcaagagcg cgtgaaagag  1320
cgtatgggcg cgaccggtga tgcgatgagc ctggccatgc gtatcattgc agcagcaacc  1380
gtaaagatcc aggatcgtgt ggattgcgac gcactgttgc agaccaagaa gatgatggc   1440 ggtttcccga ttggttggat gtacaaatat ggtgcgaccg gtatgttgct gggcaacaaa  1500
ggcctgagca cggccctggc gatccaggca attaaagccg tcgagtcgtt cccgtaa     1557
```

<210> SEQ ID NO 50
<211> LENGTH: 507
<212> TYPE: PRT
<213> ORGANISM: Aspergillus versicolor

<400> SEQUENCE: 50

```
Met Gly Ser Thr Lys Ala Leu Val Val Asp Phe Gly Asn Val Leu Cys
1               5                   10                  15

Thr Trp Thr Pro Pro Arg Glu Leu Ser Ile Pro Lys Lys Leu Lys
            20                  25                  30

Gln Ile Met Ser Ser Asp Ile Trp Leu Asp Tyr Glu Arg Gly Ile Tyr
        35                  40                  45

Lys Ser Glu Asp Glu Cys Tyr Leu Ala Val Ala Thr Arg Phe Gly Val
    50                  55                  60

Ser Pro Ser Asp Leu Ser Ser Val Met Lys Lys Ala Arg Glu Ser Leu
65                  70                  75                  80

Gln Pro Asn Thr Ala Thr Leu Asn His Leu Ser His Leu Lys Lys Thr
                85                  90                  95

Gln Pro Gly Leu Arg Ile Tyr Gly Leu Thr Asn Thr Pro Leu Pro Glu
            100                 105                 110

Gln Ser Ser Val Arg Ser Ile Ala Gln Glu Trp Pro Ile Phe Asp His
        115                 120                 125

Ile Tyr Ile Ser Gly Ile Leu Gly Met Arg Lys Pro Asp Ile Gly Cys
    130                 135                 140

Tyr Arg Leu Val Leu Arg Lys Ile Gly Leu Pro Ala Glu Ser Val Val
145                 150                 155                 160

Phe Ile Asp Asp Ser Pro Glu Asn Ile Leu Ala Ala Gln Ser Leu Gly
                165                 170                 175

Val His Ser Ile Leu Phe Gln Ser His Asp Gln Leu Ser Arg Gln Leu
            180                 185                 190

Gly Asn Val Leu Gly Asp Pro Ile Gln Arg Gly His Asn Phe Leu Leu
```

```
            195                 200                 205
Ser Asn Ala Lys Gln Met Asn Ser Thr Thr Asp Lys Gly Val Ile Ile
        210                 215                 220

Arg Asp Asn Phe Ala Gln Leu Leu Ile Ile Glu Leu Thr Gln Asn Pro
225                 230                 235                 240

Asp Leu Val Ala Leu Glu Thr Trp Asp Arg Thr Trp Asn Phe Phe Ile
                245                 250                 255

Gly Pro Pro Gln Leu Thr Thr Glu Ser Phe Pro Asn Asp Leu Asp Thr
            260                 265                 270

Thr Ser Ile Ala Leu Ser Val Leu Pro Val Asp Lys Glu Val Val Trp
        275                 280                 285

Ser Val Met Asp Glu Met Leu Thr Phe Thr Asn Ala Asp Gly Ile Phe
290                 295                 300

Met Thr Tyr Phe Asp Arg Ser Arg Pro Arg Val Asp Pro Val Val Cys
305                 310                 315                 320

Thr Asn Val Leu Asn Leu Phe Cys Met His Gly Arg Glu Ser Glu Val
                325                 330                 335

Ala Ala Thr Phe Asp Trp Val Leu Asp Val Leu Arg Asn Ser Ala Tyr
            340                 345                 350

Leu Ser Gly Ser Arg Tyr Tyr Ser Ser Pro Asp Cys Phe Leu Tyr Phe
        355                 360                 365

Leu Ser Arg Leu Ser Cys Val Val Arg Asp Gly Thr Arg Arg Arg Glu
370                 375                 380

Leu Lys Ser Leu Leu Lys Gln Gln Val Ser Gln Arg Ile Gly Ala Asp
385                 390                 395                 400

Gly Asp Ser Val Ser Leu Ala Thr Arg Leu Leu Ala Ser Asn Ile Leu
                405                 410                 415

Gly Ile Thr Asn Gly Arg Asp Arg Ser Arg Leu Leu Ala Leu Gln Glu
            420                 425                 430

Thr Asp Gly Gly Trp Pro Ala Gly Trp Val Tyr Lys Phe Gly Ser Ser
        435                 440                 445

Gly Val Gln Ile Gly Asn Arg Gly Leu Ser Thr Ala Leu Ala Leu Lys
450                 455                 460

Ser Ile Glu Arg Gln Lys Gly Pro Val Glu Ala Ile Ser Ser Glu Pro
465                 470                 475                 480

Glu Ala Trp Trp Pro Ser Leu Arg Leu Asp Arg Leu Leu Asn Val Trp
                485                 490                 495

Pro Phe Ile Asp Trp Lys Gly Tyr Ser Pro Ser
            500                 505

<210> SEQ ID NO 51
<211> LENGTH: 1524
<212> TYPE: DNA
<213> ORGANISM: Aspergillus versicolor
<220> FEATURE:
<221> NAME/KEY: misc_feature
<223> OTHER INFORMATION: cDNA

<400> SEQUENCE: 51
atgggttcca ccaaggctct tgttgttgac tttgggaatg ttttgtgtac ctggacacca      60
cccagggagt tatccatccc gcccaagaag ctgaaacaaa tcatgtcttc tgacatttgg     120
ctcgactatg aacggggtat ctataagtcg gaggacgagt gctacttggc ggttgcaact     180
cgcttcggcg tctctcccag cgacctctcc tcggtgatga aaaaggcccg cgagagcctg     240
caaccaaaca ccgcaaccct gaatcatctg tctcatctca aaaagaccca gcctggcctc     300
```

```
aggatatacg gtttgaccaa caccoctctc ccagaacaaa gcagtgtacg atccatcgcc      360
caggaatggc ctatcttcga ccatatctac atatcaggca tcctcggaat gcgcaagccg      420
gacattggct gctacaggct ggtgctgcga aagattgggc ttccagcgga gtccgtggtc      480
ttcattgatg attcacccga gaacatcctg gccgcgcagt cactgggagt acacagcata      540
ctgttccaaa gccacgacca gctctctcgt cagcttggca atgtgctggg tgatccaatc      600
cagcggggcc ataacttcct actctcgaac gcaaagcaaa tgaatagtac gaccgacaag      660
ggagttatta tccgggacaa ctttgcgcaa ctgctgatca tcgagctgac gcagaaccca      720
gaccttgtgg cgttagaaac atgggaccgt acctggaatt tttttattgg acctccacaa      780
ttgacaactg aaagctttcc caatgatctt gacactacct ccatcgctct ctcggttctt      840
ccggttgaca aagaagtggt atggtctgtg atggacgaga tgctaacgtt taccaatgcg      900
gatgggattt ttatgaccta tttcgaccga tcacgccctc gagttgatcc ggtagtttgc      960
accaatgtcc tgaatctttt ctgcatgcat ggacgggaaa gcgaagttgc agccacattt     1020
gactgggtgc tggacgttct tcgaaattcg gcctatttat caggatccag atactattct     1080
tcgcctgatt gctttctata ctttctttca cggctgagct gtgtggtccg agacggcacg     1140
cgacgcaggg agctcaagtc actgttgaaa caacaagtga gccagcgtat tggcgctgat     1200
ggtgattccg tctctctcgc cactaggcta cttgcatcga acattttagg aatcacaaat     1260
ggccgtgatc gctccaggct tcttgctctg caggaaactg acggtggatg gcctgctggg     1320
tgggtttata aattcggaag ctcggggta cagattggca atcggggct cagtacagcc       1380 ttggcgttaa aatcaattga gcgtcagaag gggcctgttg aggcgatatc cagtgagcca     1440
gaagcgtggt ggccatccct caggcttgac cgacttctca acgtttggcc tttcatcgac     1500
tggaagggat attcgccgag ttga                                             1524

<210> SEQ ID NO 52
<211> LENGTH: 1524
<212> TYPE: DNA
<213> ORGANISM: Artificial Sequence
<220> FEATURE:
<223> OTHER INFORMATION: codon optimized cDNA

<400> SEQUENCE: 52
atgggttcta cgaaagcgtt ggttgttgat tttggtaatg ttctgtgcac ttggacgcca       60
ccacgtgaat tgtccatccc gccgaagaaa ctgaagcaaa tcatgagcag cgacatttgg      120
ctggactatg agcgtggtat ctacaaatcg gaagatgagt gctacctggc agttgcgacg      180
cgctttggtg tcagcccgtc cgacctgagc tccgttatga aaaagcccg tgagagcctg       240 cagccgaata ccgcaacgct gaaccacttg agccatctga agaaaaccca gcctggcctt      300
cgtatctacg gcctgacgaa cacccgttg ccggaacaga gctcagtccg tagcattgcg        360
caggaatggc cgatttttga ccacatctac attagcggca tcttgggtat gcgcaaaccg      420
gatattggtt gttaccgtct ggttctgcgt aagatcggtc tgccagcgga gtccgtcgta      480
ttcatcgacg acagcccgga gaacattctg gcagctcaat cgttgggtgt ccatagcatc      540
ctgttccagt cccacgatca gctgagccgt cagctgggca atgtgctggg tgatccgatt      600
cagcgcggtc acaacttcct cctgtccaac gcgaagcaaa tgaacagcac caccgataag      660
ggtgtgatta tccgcgacaa cttcgcccag ctgctgatta ttgagctgac ccaaaatccg      720
gatctggttg cgctggagac ttgggaccgt acgtggaatt tctttattgg tccgccgcaa      780
```

```
ctgaccaccg agagctttcc gaacgacctg gacaccacga gcattgccct gagcgtgttg     840
ccggtggata agaagtcgt ttggtctgtg atggatgaga tgctgacctt caccaacgca      900
gacggcatct tcatgaccta tttcgatcgt agccgtccgc gtgttgaccc ggtcgtttgt     960
accaatgtcc tgaatctgtt ttgcatgcat ggtcgcgaga gcgaagtggc cgcgacgttc    1020
gactgggtgc tggacgtgct gcgcaacagc gcgtacctga gcggttcccg ttattacagc    1080
agcccggatt gttttctgta tttcctgtct cgtctgagct gcgtcgtccg tgatggcacg    1140
cgtcgtcgtg aactgaaaag cctgctgaag caacaagttt ctcaacgtat cggcgctgac    1200
ggtgattccg tcagcctggc cacccgtttg ctggcgagca acatcctggg cattactaac    1260
ggtcgtgacc gcagccgtct gctggcattg caagaaaccg atggtggctg gcctgcaggc    1320
tgggtctata agtttggtag cagcggcgtg caaattggca atcgcggtct gagcaccgcg    1380
ctggctctga agtctatcga gcgccagaaa ggtccggtgg aagcaatcag cagcgagccg    1440
gaagcgtggt ggcctagctt acgcttggac cgcttgctga atgtttggcc atttatcgac    1500
tggaagggct actccccgag ctaa                                           1524
```

<210> SEQ ID NO 53
<211> LENGTH: 5
<212> TYPE: PRT
<213> ORGANISM: Artificial Sequence
<220> FEATURE:
<223> OTHER INFORMATION: Type I synthase motif
<220> FEATURE:
<221> NAME/KEY: MISC_FEATURE
<222> LOCATION: (3)..(3)
<223> OTHER INFORMATION: where X is K, N, R, S, or Q
<220> FEATURE:
<221> NAME/KEY: MISC_FEATURE
<222> LOCATION: (4)..(4)
<223> OTHER INFORMATION: where X is  L, I, G, P, or T
<220> FEATURE:
<221> NAME/KEY: MISC_FEATURE
<222> LOCATION: (5)..(5)
<223> OTHER INFORMATION: where X is  D or E

<400> SEQUENCE: 53

Asp Asp Xaa Xaa Xaa
1               5

<210> SEQ ID NO 54
<211> LENGTH: 7
<212> TYPE: PRT
<213> ORGANISM: Artificial Sequence
<220> FEATURE:
<223> OTHER INFORMATION: Type I synthase motif
<220> FEATURE:
<221> NAME/KEY: MISC_FEATURE
<222> LOCATION: (3)..(3)
<223> OTHER INFORMATION: where X is K, Q or R
<220> FEATURE:
<221> NAME/KEY: MISC_FEATURE
<222> LOCATION: (4)..(4)
<223> OTHER INFORMATION: where X is L, I or T
<220> FEATURE:
<221> NAME/KEY: MISC_FEATURE
<222> LOCATION: (5)..(5)
<223> OTHER INFORMATION: where X is D or E

<400> SEQUENCE: 54

Asp Asp Xaa Xaa Xaa Asn Val
1               5

<210> SEQ ID NO 55
<211> LENGTH: 7

```
<212> TYPE: PRT
<213> ORGANISM: Artificial Sequence
<220> FEATURE:
<223> OTHER INFORMATION: Type I synthase motif
<220> FEATURE:
<221> NAME/KEY: MISC_FEATURE
<222> LOCATION: (3)..(3)
<223> OTHER INFORMATION: where X is N, K, S or Q
<220> FEATURE:
<221> NAME/KEY: MISC_FEATURE
<222> LOCATION: (4)..(4)
<223> OTHER INFORMATION: where X is L, P or G
<220> FEATURE:
<221> NAME/KEY: MISC_FEATURE
<222> LOCATION: (5)..(5)
<223> OTHER INFORMATION: where X is D or E
<220> FEATURE:
<221> NAME/KEY: MISC_FEATURE
<222> LOCATION: (7)..(7)
<223> OTHER INFORMATION: where X is V or I

<400> SEQUENCE: 55

Asp Asp Xaa Xaa Xaa Asn Xaa
1               5

<210> SEQ ID NO 56
<211> LENGTH: 5
<212> TYPE: PRT
<213> ORGANISM: Artificial Sequence
<220> FEATURE:
<223> OTHER INFORMATION: Type II synthase motif
<220> FEATURE:
<221> NAME/KEY: MISC_FEATURE
<222> LOCATION: (2)..(2)
<223> OTHER INFORMATION: where X is V, M, F or L
<220> FEATURE:
<221> NAME/KEY: MISC_FEATURE
<222> LOCATION: (4)..(4)
<223> OTHER INFORMATION: where X is T or S

<400> SEQUENCE: 56

Asp Xaa Asp Xaa Thr
1               5

<210> SEQ ID NO 57
<211> LENGTH: 6
<212> TYPE: PRT
<213> ORGANISM: Artificial Sequence
<220> FEATURE:
<223> OTHER INFORMATION: Type II synthase motif
<220> FEATURE:
<221> NAME/KEY: MISC_FEATURE
<222> LOCATION: (2)..(2)
<223> OTHER INFORMATION: where X is V, M, L or F

<400> SEQUENCE: 57

Asp Xaa Asp Thr Thr Ser
1               5

<210> SEQ ID NO 58
<211> LENGTH: 6
<212> TYPE: PRT
<213> ORGANISM: Artificial Sequence
<220> FEATURE:
<223> OTHER INFORMATION: Type II synthase motif
<220> FEATURE:
<221> NAME/KEY: MISC_FEATURE
<222> LOCATION: (2)..(2)
<223> OTHER INFORMATION: where X is V, M or L
<220> FEATURE:
<221> NAME/KEY: MISC_FEATURE
<222> LOCATION: (4)..(4)
<223> OTHER INFORMATION: where X is T or S
```

<400> SEQUENCE: 58

Asp Xaa Asp Xaa Thr Ser
1               5

<210> SEQ ID NO 59
<211> LENGTH: 10
<212> TYPE: PRT
<213> ORGANISM: Artificial Sequence
<220> FEATURE:
<223> OTHER INFORMATION: Conserved motif A
<220> FEATURE:
<221> NAME/KEY: MISC_FEATURE
<222> LOCATION: (2)..(9)
<223> OTHER INFORMATION: where X is any amino acid

<400> SEQUENCE: 59

Ser Xaa Xaa Trp Xaa Xaa Tyr Glu Xaa Gly
1               5                   10

<210> SEQ ID NO 60
<211> LENGTH: 9
<212> TYPE: PRT
<213> ORGANISM: Artificial Sequence
<220> FEATURE:
<223> OTHER INFORMATION: Conserved motif B
<220> FEATURE:
<221> NAME/KEY: MISC_FEATURE
<222> LOCATION: (3)..(5)
<223> OTHER INFORMATION: where X is any amino acid
<220> FEATURE:
<221> NAME/KEY: MISC_FEATURE
<222> LOCATION: (6)..(6)
<223> OTHER INFORMATION: where X is I or L
<220> FEATURE:
<221> NAME/KEY: MISC_FEATURE
<222> LOCATION: (8)..(8)
<223> OTHER INFORMATION: where X is any amino acid

<400> SEQUENCE: 60

Asn Phe Xaa Gln Xaa Xaa Ile Xaa Glu
1               5

<210> SEQ ID NO 61
<211> LENGTH: 24
<212> TYPE: PRT
<213> ORGANISM: Artificial Sequence
<220> FEATURE:
<223> OTHER INFORMATION: Conserved motif C
<220> FEATURE:
<221> NAME/KEY: MISC_FEATURE
<222> LOCATION: (1)..(1)
<223> OTHER INFORMATION: where X is D or E
<220> FEATURE:
<221> NAME/KEY: MISC_FEATURE
<222> LOCATION: (2)..(2)
<223> OTHER INFORMATION: where X is G or E
<220> FEATURE:
<221> NAME/KEY: MISC_FEATURE
<222> LOCATION: (4)..(5)
<223> OTHER INFORMATION: where X is any amino acid
<220> FEATURE:
<221> NAME/KEY: MISC_FEATURE
<222> LOCATION: (6)..(6)
<223> OTHER INFORMATION: where X is T or V
<220> FEATURE:
<221> NAME/KEY: MISC_FEATURE
<222> LOCATION: (10)..(21)
<223> OTHER INFORMATION: where X is any amino acid

<400> SEQUENCE: 61

Xaa Xaa Ile Xaa Xaa Xaa Tyr Phe Asp Xaa Xaa Arg Xaa Arg Xaa Asp

Pro Xaa Val Xaa Xaa Asn Val Leu
         20

<210> SEQ ID NO 62
<211> LENGTH: 7
<212> TYPE: PRT
<213> ORGANISM: Artificial Sequence
<220> FEATURE:
<223> OTHER INFORMATION: Conserved motif D
<220> FEATURE:
<221> NAME/KEY: MISC_FEATURE
<222> LOCATION: (2)..(6)
<223> OTHER INFORMATION: where X is any amino acid
<220> FEATURE:
<221> NAME/KEY: MISC_FEATURE
<222> LOCATION: (7)..(7)
<223> OTHER INFORMATION: where X is W or F

<400> SEQUENCE: 62

Gln Xaa Xaa Asp Gly Xaa Xaa
1               5

<210> SEQ ID NO 63
<211> LENGTH: 540
<212> TYPE: PRT
<213> ORGANISM: Agaricus bisporus

<400> SEQUENCE: 63

Met Ala Pro Pro Gln Arg Pro Phe Thr Ala Ile Val Phe Asp Ile Gly
1               5                   10                  15

Asp Val Leu Phe Gln Trp Ser Ala Thr Thr Lys Thr Ser Ile Ser Pro
            20                  25                  30

Lys Thr Leu Arg Ser Ile Leu Asn Cys Pro Thr Trp Phe Asp Tyr Glu
        35                  40                  45

Arg Gly Arg Leu Ala Glu Asn Ala Cys Tyr Ala Ala Ile Ser Gln Glu
    50                  55                  60

Phe Asn Val Asn Pro Asp Glu Val Arg Asp Ala Phe Ser Gln Ala Arg
65                  70                  75                  80

Asp Ser Leu Gln Ala Asn His Asp Phe Ile Ser Leu Ile Arg Glu Leu
                85                  90                  95

Lys Ala Gln Ala Asn Gly Arg Leu Arg Val Tyr Ala Met Ser Asn Ile
            100                 105                 110

Ser Leu Pro Asp Trp Glu Val Leu Arg Met Lys Pro Ala Asp Trp Asp
        115                 120                 125

Ile Phe Asp His Val Phe Thr Ser Gly Ala Val Gly Glu Arg Lys Pro
    130                 135                 140

Asn Leu Ala Phe Tyr Arg His Val Ile Ala Thr Asp Leu Gln Pro
145                 150                 155                 160

His Gln Thr Ile Phe Val Asp Asp Lys Leu Glu Asn Val Leu Ser Ala
                165                 170                 175

Arg Ser Leu Gly Phe Thr Gly Ile Val Phe Asp Glu Pro Ser Glu Val
            180                 185                 190

Lys Arg Ala Leu Arg Asn Leu Ile Gly Asp Pro Val Gln Arg Gly Gly
        195                 200                 205

Glu Phe Leu Val Arg Asn Ala Gly Lys Leu Gly Ser Ile Thr Arg Thr
    210                 215                 220

Thr Ala Lys His Glu Ser Ile Pro Leu Asp Glu Asn Phe Ala Gln Leu
225                 230                 235                 240

-continued

```
Leu Ile Leu Glu Ile Thr Gly Asn Arg Ala Leu Val Asn Leu Val Glu
                245                 250                 255

His Pro Gln Thr Trp Asn Phe Phe Gln Gly Lys Gly Gln Leu Thr Thr
            260                 265                 270

Glu Glu Phe Pro Phe Asp Leu Asp Thr Thr Ser Leu Gly Leu Thr Ile
        275                 280                 285

Leu Lys Arg Ser Arg Glu Ile Ala Asp Ser Val Met Asp Glu Met Leu
    290                 295                 300

Glu Tyr Val Asp Pro Asp Gly Ile Ile Gln Thr Tyr Phe Asp His Arg
305                 310                 315                 320

Arg Pro Arg Phe Asp Pro Val Val Cys Val Asn Ala Leu Ser Leu Phe
                325                 330                 335

Tyr Ala Tyr Gly Arg Gly Glu Gln Leu Arg Ser Thr Leu Thr Trp Val
            340                 345                 350

His Glu Val Leu Leu Asn Arg Ala Tyr Leu Asp Gly Thr Arg Tyr Tyr
        355                 360                 365

Glu Thr Ala Glu Cys Phe Leu Tyr Phe Met Ser Arg Leu Leu Ala Thr
    370                 375                 380

Ser Gly Asp Pro Asp Leu His Ser Leu Leu Lys Pro Leu Leu Lys Glu
385                 390                 395                 400

Arg Val Gln Glu Arg Ile Gly Ala Asp Gly Asp Ser Leu Ala Leu Ala
                405                 410                 415

Met Arg Ile Leu Ala Cys Asp Phe Val Gly Ile Arg Asp Glu Val Asp
            420                 425                 430

Leu Arg Thr Leu Leu Thr Leu Gln Cys Glu Asp Gly Gly Trp Glu Val
        435                 440                 445

Gly Trp Met Tyr Lys Tyr Gly Ser Ser Gly Ile Ser Ile Gly Asn Arg
    450                 455                 460

Gly Leu Ala Thr Ala Leu Ala Ile Lys Ala Val Asp Thr Met Phe Gln
465                 470                 475                 480

Pro Gln Ile Arg Phe Ser Glu Ser Pro Thr Asp Thr Leu Val Glu Asn
                485                 490                 495

Ala Ile His Lys Arg Arg Pro Ser Phe Ser Glu Lys Phe Leu Gly Lys
            500                 505                 510

Arg Pro Arg Ser Gly Ser Phe Arg Lys Pro Leu Gln Trp Ile Leu Gln
        515                 520                 525

Gly Ser Lys Leu Arg Lys Ser Val Glu Ile Gly Ser
    530                 535                 540
```

<210> SEQ ID NO 64
<211> LENGTH: 1808
<212> TYPE: DNA
<213> ORGANISM: Agaricus bisporus
<220> FEATURE:
<221> NAME/KEY: misc_feature
<223> OTHER INFORMATION: cDNA

<400> SEQUENCE: 64

| | | |
|---|---|---|
| atggctccgc ctcagcgacc ctttactgcg attgtctttg acatcgggga tgttctattc | 60 |
| caatggtctg caaccaccaa aacctctatc tcaccaaaga cactccgctc tattctcaac | 120 |
| tgtccgacat ggtttgacta tgaacgtgga cgcctggcag aaaacgcttg ttatgccgct | 180 |
| atctcacaag aattcaacgt caacccagac gaagttcgcg acgctttcag ccaagcgcgc | 240 |
| gactctctcc aagcaaacca cgacttcatc agtctcatcc gtgagctgaa ggcacaagca | 300 |
| aatggtcgtt tacgtgtgta cgccatgtcg aacatatctc ttcctgattg ggaagtgctg | 360 |

-continued

```
cggatgaaac ctgctgattg ggatattttc gaccacgtct tcacatccgg tgcggttggg      420
gaacgcaagc ccaatctcgc cttttatcgc catgttatcg cggccaccga tctgcagcct      480
catcagacaa tatttgttga cgataagctg gagaatgttc tctcagcacg ttccctcggg      540
ttcacaggca tcgtgtttga cgagccctcc gaggtcaaac gtgcgcttcg taacctcatt      600
ggggatcctg ttcaacgagg aggtgaattc ttggttcgga atgccggaaa gcttggctct      660
atcacaagga ctactgcaaa gcacgagtca atcccctcg acgagaattt tgctcagctt       720
cttattctcg agataacggg gaacaggtgc gttagcttct tgtagggtct tctgtcgtaa      780
tactaaattt tttctggtgt ttagggcttt ggtcaacctc gttgagcatc ctcaaacgtg      840
gaatttcttc caaggtgcgc tgctaaaata acatccagt tgcgtttcga agctcattgt       900
gggcgtcccg tcacaggcaa gggccagctg acaacagaag aatttccatt cgatctcgat      960
acaacttctc ttggtctcac gatcctcaag cgaagcaggg aaatcgccga ttcagtcatg     1020
gatgaaatgc tggagtatgt cgatcctgat ggtatcattc aggcaagttt catttatcgg     1080
cttgagaaaa taaagacaaa aacgttctga tgggggggatg tttctagacg tatttcgatc    1140
atcggagacc acgttttgat ccagtcgtgt gtgtcaatgc attaagcctc ttctatgctt     1200
acggccgcgg ggagcaactg cggtcgactt tgacatgggt acatgaagtc cttctcaatc     1260
gagcctactt ggatggcaca cggtactacg aaacagccga atgcttcctc tatttcatga    1320
gccgacttct cgccacttca ggcgaccctg accttcactc ccttcttaaa cctcttctca    1380
aagaacgggt gcaagaacgc attggagctg atggagactc tcttgcactc gcaatgcgta    1440
ttctcgcctg tgatttcgtc ggaatcagag atgaagtgga tttacgcaca cttctgactt    1500
tgcaatgtga agatggaggt tgggaagtgg gttggatgta caagtatgga tcttccggta    1560
tcagtatcgg aaatcgtgga ctggccaccg cgctcgctat caaggccgtc gacacgatgt    1620 ttcaaccca aattcggttc tctgaatcac ccacagatac tttggttgaa aacgctatcc     1680
acaaacgccg tccctcattt tccgaaaaat tcctcggcaa acgtcctcgc agcggatcgt    1740
tcaggaaacc tttacagtgg atactgcaag gttccaagct tcgcaaatct gtcgaaatag    1800
gaagctaa                                                             1808
```

<210> SEQ ID NO 65
<211> LENGTH: 1623
<212> TYPE: DNA
<213> ORGANISM: Artificial Sequence
<220> FEATURE:
<223> OTHER INFORMATION: codon optimized cDNA

<400> SEQUENCE: 65

```
atggcaccac cgcaacgtcc gttcactgca attgttttcg atattggcga tgttttgttc       60
caatggtctg cgaccacgaa accagcatt agcccgaaaa ccctgcgcag cattctgaat       120
tgtccgacct ggtttgatta tgagcgcggc cgtctggcgg aaaatgcgtg ttacgctgcg      180
atcagccaag aatttaacgt caacccggac gaagttcgcg acgccttcag ccaagcgcgc      240
gacagcctgc aggcgaatca cgacttcatc agcctgattc gtgagctgaa agctcaggcg     300
aacggtcgtc tgcgtgtcta cgccatgtct aatatcagcc tgccggattg ggaagtcctg     360
cgtatgaagc cagccgattg ggacatcttt gaccatgtat ttaccagcgg tgcggtgggt     420
gagcgcaagc cgaacctggc cttttatcgt cacgtcatcg cggccaccga tctgcagccg     480
caccagacga tcttcgtgga tgacaaactg gaaaacgtgc tgtctgcgcg ctcgctgggc     540
```

```
ttcacgggta tcgtgttcga cgagccaagc gaagtcaaac gtgcgctgcg taatctgatc    600
ggcgacccgg tgcagcgtgg tggcgagttc ctggttcgta atgctggcaa actgggttct    660
atcacccgta cgaccgcaaa acatgagagc atcccgctgg atgagaattt tgcacaactg    720
ttgattctgg aaattactgg taaccgcgca ctggtcaatc tggttgagca cccgcagacg    780
tggaacttct tccagggtaa gggccagctg acgaccgaag aatttccttt tgacctggat    840
acgacgagcc tggtctgac gatcctgaag cgtagccgcg agattgccga ctccgtcatg    900
gacgaaatgt tggaatacgt tggaccctgac ggcatcattc agacctactt cgatcatcgt    960
cgcccgcgct ttgacccggt tgtttgcgtt aatgccctga cctgttctac tgcatacggc   1020
cgtggtgagc aactgcgttc caccttgacc tgggtgcacg aagttctgtt gaaccgtgcg   1080
tatttggatg gtacgcgtta ctatgaaacg gccgagtgct ttctgtattt catgtcccgt   1140
ctgctggcaa ccagcggtga cccggatctg cattccctgc tgaagccgtt gctgaaggaa   1200
cgcgtgcaag agcgcatcgg cgctgacggt gacagcctgg cgctggcgat gcgcattttg   1260
gcatgtgatt ttgttggcat ccgtgatgaa gtggatctgc gtaccctgct gaccttacag   1320
tgcgaggatg gcggttggga agtgggctgg atgtacaaat acggtagcag cggtattagc   1380
attggtaacc gtggtctggc aaccgcattg gcgatcaaag ctgttgacac catgtttcaa   1440
ccgcaaatcc gtttcagcga gagcccgacc gacactctgg tggagaacgc gattcacaag   1500
cgccgcccga gcttttcaga gaattttta ggtaagcgtc cgcgttccgg ttcgttccgt   1560
aaaccgctgc aatggattct gcagggcagc aagctgcgca agagcgtcga gatcggtagc   1620
taa                                                                 1623
```

<210> SEQ ID NO 66
<211> LENGTH: 1584
<212> TYPE: DNA
<213> ORGANISM: Artificial Sequence
<220> FEATURE:
<223> OTHER INFORMATION: codon optimized cDNA

<400> SEQUENCE: 66

```
atggcttcta tccacagaag atacactact ttgatcttgg acttgggtga cgttttgttc     60
agatggtctc caaagactga aactgctatc ccaccacaac aattgaagga catcttgtct    120
tctgttactt ggttcgaata cgaaagaggt agattgtctc aagaagcttg ttacgaaaga    180
tgtgctgaag aattcaagat cgaagcttct gttatcgctg aagctttcaa gcaagctaga    240
ggttctttga gaccaaacga agaattcatc gctttgatca gagacttgag aagagaaatg    300
cacggtgact tgactgtttt ggctttgtct aacatctctt tgccagacta cgaatacatc    360
atgtctttgt cttctgactg gactactgtt tcgacagag ttttcccatc tgctttggtt    420
ggtgaaagaa agccacactt gggttgttac agaaaggtta tctctgaaat gaacttggaa    480
ccacaaacta ctgttttcgt tgacgacaag ttggacaacg ttgcttctgc tagatctttg    540
ggtatgcacg gtatcgtttt cgacaaccaa gctaacgttt cagacaatt gagaaacatc    600
ttcggtgacc caatcagaag aggtcaagaa tacttgagag tcacgctgg taagttggaa    660
tcttctactg acaacggttt gatcttcgaa gaaaacttca ctcaattgat catctacgaa    720
ttgactcaag acagaacttt gatctctttg tctgaatgtc aagaacttg gaacttcttc    780
agaggtgaac cattgttctc tgaaactttc ccagacgacg ttgacactac ttctgttgct    840
ttgactgttt tgcaaccaga cagagctttg gttaactctg ttttgacga aatgttggaa    900
tacgttgacg ctgacggtat catgcaaact tacttcgaca gatctagacc aagaatggac    960
```

```
ccattcgttt gtgttaacgt tttgtctttg ttctacgaaa acggtagagg tcacgaattg    1020
ccaagaactt tggactgggt ttacgaagtt ttgttgcaca gagcttacca cggtggttct    1080
agatactact tgtctccaga ctgtttcttg ttcttcatgt ctagattgtt gaagagagct    1140
gacgacccag ctgttcaagc tagattgaga ccattgttcg ttgaaagagt taacgaaaga    1200
gttggtgctg ctggtgactc tatggacttg gctttcagaa tcttggctgc tgcttctgtt    1260
ggtgttcaat gtccaagaga cttggaaaga ttgactgctg tcaatgtgga cgacggtggt    1320
tgggacttgt gttggttcta cgttttcggt tctactggtg ttaaggctgg taacagaggt    1380
ttgactactc ctttggctgt tactgctatc caaactgcta tcggtagacc accatctcca    1440
tctccatctg ctgcttcttc ttctttcaga ccatcttctc catacaagtt cttgggtatc    1500
tctagaccag cttctccaat cagattcggt gacttgttga gaccatggag aaagatgtct    1560
agatctaact tgaagtctca ataa                                           1584
```

<210> SEQ ID NO 67
<211> LENGTH: 1623
<212> TYPE: DNA
<213> ORGANISM: Artificial Sequence
<220> FEATURE:
<223> OTHER INFORMATION: codon optimized cDNA

<400> SEQUENCE: 67

```
atggctccac cacaaagacc attcactgct atcgttttcg acatcggtga cgttttgttc      60
caatggtctg ctactactaa gacttctatc tctccaaaga ctttgagatc tatcttgaac     120
tgtccaactt ggttcgacta cgaaagaggt agattggctg aaaacgcttg ttacgctgct     180
atctctcaag aattcaacgt taacccagac gaagttagag acgctttctc tcaagctaga     240
gactctttgc aagctaacca cgacttcatc tctttgatca gagaattgaa ggctcaagct     300
aacggtagat tgagagttta cgctatgtct aacatctctt tgccagactg gaagttttg     360 agaatgaagc cagctgactg ggacatcttc gaccacgttt tcacttctgg tgctgttggt     420
gaaagaaagc caaacttggc tttctacaga cacgttatcg ctgctactga cttgcaacca     480
caccaaacta tcttcgttga cgacaagttg gaaaacgttt tgtctgctag atctttgggt     540
ttcactggta tcgttttcga cgaaccatct gaagttaaga gagctttgag aaacttgatc     600
ggtgacccag ttcaaagagg tggtgaattc ttggttagaa cgctggtaa gttgggttct     660 atcactagaa ctactgctaa gcacgaatct atcccattgg acgaaaactt cgctcaattg     720
ttgatcttgg aaatcactgg taacagagct ttggttaact tggttgaaca cccacaaact     780
tggaacttct ccaaggtaa gggtcaattg actactgaag aattcccatt cgacttggac     840
actacttctt tgggtttgac tatcttgaag agatctagaa aaatcgctga ctctgttatg     900
gacgaaatgt tggaatacgt tgacccagac ggtatcatcc aaacttactt cgaccacaga     960
agaccaagat cgacccagt tgtttgtgtt aacgctttgt ctttgttcta cgcttacggt    1020
agaggtgaac aattgagatc tactttgact tgggttcacg aagttttgtt gaacagagct    1080
tacttggacg gtactagata ctacgaaact gctgaatgtt tcttgtactt catgtctaga    1140
ttgttggcta cttctggtga cccagacttg cactctttgt tgaagccatt gttgaaggaa    1200
agagttcaag aaagaatcgg tgctgacggt gactctttgg ctttggctat gagaatcttg    1260
gcttgtgact cgttggtat cagagacgaa gttgacttga aacttttgtt gacttttgcaa    1320 tgtgaagacg gtggttggga agttggttgg atgtacaagt acggttcttc tggtatctct    1380
```

```
atcggtaaca gaggtttggc tactgctttg ctatcaagg ctgttgacac tatgttccaa      1440
ccacaaatca gattctctga atctccaact gacactttgg ttgaaaacgc tatccacaag    1500
agaagaccat ctttctctga aaagttcttg ggtaagagac caagatctgg ttctttcaga    1560
aagccattgc aatggatctt gcaaggttct aagttgagaa agtctgttga atcggttct     1620 taa                                                                  1623
```

<210> SEQ ID NO 68
<211> LENGTH: 1566
<212> TYPE: DNA
<213> ORGANISM: Artificial Sequence
<220> FEATURE:
<223> OTHER INFORMATION: codon optimized cDNA

<400> SEQUENCE: 68

```
atgtacactg ctttgatctt ggacttgggt gacgttttgt tctcttggtc ttctactact      60
aacactacta tcccaccaag acaattgaag gaaatcttgt cttctccagc ttggttcgaa    120
tacgaaagag gtagaatcac tcaagctgaa tgttacgaaa gagtttctgc tgaattctct    180
ttggacgcta ctgctgttgc tgaagctttc agacaagcta gagactcttt gagaccaaac    240
gacaagttct tgactttgat cagagaattg agacaacaat ctcacggtga attgactgtt    300 ttggcttttgt ctaacatctc tttgccagac tacgaattca tcatggcttt ggactctaag    360
tggacttctg ttttcgacag agttttccca tctgctttgg ttggtgaaag aaagccacac    420
ttgggtgctt tcagacaagt tttgtctgaa atgaacttgg acccacacac tactgttttc    480
gttgacgaca agttggacaa cgttgttcct gctagatctt gggtatgca cggtgttgtt    540 ttcgactctc aagacaacgt tttcagaatg ttgagaaaca tcttcggtga cccaatccac    600
agaggtagag actacttgag acaacacgct ggtagattgg aaacttctac tgacgctggt    660
gttgttttcg aagaaaactt cactcaattg atcatctacg aattgactaa cgacaagtct    720
ttgatcacta cttctaactg tgctagaact tggaacttct tcagaggtaa gccattgttc    780
tctgcttctt cccagacga catggacact acttctgttg ctttgactgt tttgagattg    840
gaccacgctt tggttaactc tgtttttggac gaaatgttga agtacgttga cgctgacggt    900
atcatgcaaa cttacttcga ccacactaga ccaagaatgg acccattcgt tgtgtttaac    960
gttttgtctt gttccacga acaaggtaga ggtcacgaat tgccaaacac tttgaatgg     1020 gttcacgaag ttttgttgca cagagcttac atcggtggtt ctagatacta cttgtctgct   1080
gactgtttct tgttcttcat gtctagattg ttgcaaagaa tcactgaccc atctgttttg   1140
ggtagattca gaccattgtt catcgaaaga gttagagaaa gagttggtgc tactggtgac   1200
tctatcgact ggctttcag aatcatcgct gcttctactg ttggtatcca atgtccaaga   1260
gacttggaat ctttgttggc tgctcaatgt gaagacggtg gttgggactt gtgttggttc    1320
taccaatacg gttctactgg tgttaaggct ggtaacagag ttttgactac tgctttggct   1380
atcaaggcta tcgactctgc tatcgctaga ccaccatctc cagctttgtc tgttgcttct   1440
tcttctaagt ctgaaatccc aaagccaatc caaagatctt tgagaccatt gtctccaaga   1500
agattcggtg ttttcttgat gccatggaga agatctcaaa gaaacggtgt tgctgttttct   1560 tcttaa                                                              1566
```

<210> SEQ ID NO 69
<211> LENGTH: 1602
<212> TYPE: DNA
<213> ORGANISM: Artificial Sequence
<220> FEATURE:
<223> OTHER INFORMATION: codon optimized cDNA

<400> SEQUENCE: 69

```
atgtctgctg ctgctcaata cactactttg atcttggact tgggtgacgt tttgttcact      60
tggtctccaa agactaagac ttctatccca ccaagaactt tgaaggaaat cttgaactct     120
gctacttggt acgaatacga aagaggtaga atctctcaag acgaatgtta cgaaagagtt     180
ggtactgaat tcggtatcgc tccatctgaa atcgacaacg ctttcaagca agctagagac     240
tctatggaat ctaacgacga attgatcgct ttggttagag aattgaagac tcaattggac     300
ggtgaattgt tggttttcgc tttgtctaac atctctttgc agactacgga atacgttttg     360
actaagccag ctgactggtc tatcttcgac aaggttttcc catctgcttt ggttggtgaa     420
agaaagccac acttgggtgt ttacaagcac gttatcgctg aaactggtat cgacccaaga     480
actactgttt tcgttgacga caagatcgac aacgttttgt ctgctagatc tgttggtatg     540
cacggtatcg ttttcgaaaa gcaagaagac gttatgagag ctttgagaaa catcttcggt     600
gacccagtta agaggtag agaatacttg agaagaaacg ctatgagatt ggaatctgtt       660
actgaccacg tgttgctttt cggtgaaaac ttcactcaat tgttgatctt ggaattgact     720
aacgacccat ctttggttac tttgccagac agaccaagaa cttggaactt cttcagaggt     780
aacggtggta gaccatctaa gccattgttc tctgaagctt tcccagacga cttggacact     840
acttctttgg ctttgactgt tttgcaaaga gacccaggtg ttatctcttc tgttatggac     900
gaaatgttga actacagaga cccagacggt atcatgcaaa cttacttcga cgacggtaga     960
caaagattgg acccattcgt taacgttaac gttttgactt tcttctacac taacggtaga    1020
ggtcacgaat tggaccaatg tttgacttgg gttagagaag ttttgttgta cagagcttac    1080
ttgggtggtt ctagatacta cccatctgct gactgtttct tgtacttcat ctctagattg    1140
ttcgcttgta ctaacgaccc agttttgcac caccaattga agccattgtt cgttgaaaga    1200
gttcaagaac aaatcggtgt tgaaggtgac gctttggaat tggctttcag attgttggtt    1260
tgtgcttctt tggacgttca aaacgctatc gacatgagaa gattgttgga atgcaatgt     1320
gaagacggtg ttgggaagg tggtaacttg tacagattcg gtactactgg tttgaaggtt    1380
actaacagag gtttgactac tgctgctgct gttcaagcta tcgaagcttc tcaaagaaga    1440
ccaccatctc catctccatc tgttaatct actaagtctc caatcactcc agttactcca     1500
atgttggaag ttccatcttt gggtttgtct atctctagac atcttctcc attgttgggt     1560
tacttcagat tgccatggaa gaagtctgct gaagttcact aa                       1602
```

<210> SEQ ID NO 70
<211> LENGTH: 1461
<212> TYPE: DNA
<213> ORGANISM: Artificial Sequence
<220> FEATURE:
<223> OTHER INFORMATION: codon optimized cDNA

<400> SEQUENCE: 70

```
atggctatca ctaagggtcc agttaaggct ttgatcttgg acttctctaa cgttttgtgt      60
tcttggaagc accatctaa cgttgctgtt ccaccacaaa tcttgaagat gatcatgtct      120
tctgacatct ggcacgacta cgaatgtggt agatactcta gagaagactg ttacgctaga     180
gttgctgaca gattccacat ctctgctgct gacatggaag acactttgaa gcaagctaga     240
aagtctttgc aagttcacca cgaaactttg ttgttcatcc aacaagttaa gaaggacgct     300
```

```
ggtggtgaat tgatggtttg tggtatgact aacactccaa gaccagaaca agacgttatg     360
cactctatca acgctgaata cccagttttc gacagaatct acatctctgg tttgatgggt     420
atgagaaagc catctatctg tttctaccaa agagttatgg aagaaatcgg tttgtctggt     480
gacgctatca tgttcatcga cgacaagttg gaaaacgtta tcgctgctca atctgttggt     540
atcagaggtg ttttgttcca atctcaacaa gacttgagaa gagttgtttt gaacttcttg     600
ggtgacccag ttcacagagg tttgcaattc ttggctgcta acgctaagaa gatggactct     660
gttactaaca ctggtgacac tatccaagac aacttcgctc aattgttgat cttggaattg     720
gctcaagaca gagaattggt taagttgcaa gctggtaaga gaacttggaa ctacttcatc     780
ggtccaccaa agttgactac tgctactttc ccagacgaca tggacactac ttctatggct     840
ttgtctgttt gccagttgc tgaagacgtt gtttcttctg ttttggacga aatgttgaag      900
ttcgttactg acgacggtat cttcatgact tacttcgact cttctagacc aagagttgac     960
ccagttgttt gtatcaacgt tttgggtgtt ttctgtagac acaacagaga aagagacgtt    1020
ttgccaactt ccactggat cagagacatc ttgatcaaca gagcttactt gtctggtact     1080
agatactacc catctccaga cttgttcttg ttcttcttgg ctagattgtg tttggctgtt    1140
agaaaccaat ctttgagaga acaattggtt ttgccattgg ttgacagatt gagagaaaga    1200
gttggtgctc aggtgaagc tgtttctttg gctgctagaa tcttggcttg tagatctttc     1260
ggtatcgact ctgctagaga catggactct ttgagaggta agcaatgtga agacggtggt    1320
tggccagttg aatgggttta cagattcgct tctttcggtt tgaacgttgg taacagaggt    1380
ttggctactg ctttcgctgt tagagctttg gaatctccat acggtgaatc tgctgttaag    1440
gttatgagaa gaatcgtttaa                                                1461

<210> SEQ ID NO 71
<211> LENGTH: 79
<212> TYPE: DNA
<213> ORGANISM: Artificial Sequence
<220> FEATURE:
<223> OTHER INFORMATION: Primer for construction of fragment "a" (LEU2
      yeast marker)

<400> SEQUENCE: 71
aggtgcagtt cgcgtgcaat tataacgtcg tggcaactgt tatcagtcgt accgcgccat     60
tcgactacgt cgtaaggcc                                                   79

<210> SEQ ID NO 72
<211> LENGTH: 80
<212> TYPE: DNA
<213> ORGANISM: Artificial Sequence
<220> FEATURE:
<223> OTHER INFORMATION: Primer for construction of fragment "a" (LEU2
      yeast marker)

<400> SEQUENCE: 72
tcgtggtcaa ggcgtgcaat tctcaacacg agagtgattc ttcggcgttg ttgctgacca     60
tcgacggtcg aggagaactt                                                  80

<210> SEQ ID NO 73
<211> LENGTH: 85
<212> TYPE: DNA
<213> ORGANISM: Artificial Sequence
<220> FEATURE:
<223> OTHER INFORMATION: Primer for construction of fragment "b" (AmpR
      E. coli marker)
```

<400> SEQUENCE: 73
tggtcagcaa caacgccgaa gaatcactct cgtgttgaga attgcacgcc ttgaccacga    60
cacgttaagg gattttggtc atgag                                         85

<210> SEQ ID NO 74
<211> LENGTH: 80
<212> TYPE: DNA
<213> ORGANISM: Artificial Sequence
<220> FEATURE:
<223> OTHER INFORMATION: Primer for construction of fragment "b" (AmpR
      E. coli marker)

<400> SEQUENCE: 74
aacgcgtacc ctaagtacgg caccacagtg actatgcagt ccgcactttg ccaatgccaa    60
aaatgtgcgc ggaacccta                                                80

<210> SEQ ID NO 75
<211> LENGTH: 84
<212> TYPE: DNA
<213> ORGANISM: Artificial Sequence
<220> FEATURE:
<223> OTHER INFORMATION: Primer for construction of fragment "c" (Yeast
      origin of replication)

<400> SEQUENCE: 75
ttggcattgg caaagtgcgg actgcatagt cactgtggtg ccgtacttag ggtacgcgtt    60
cctgaacgaa gcatctgtgc ttca                                          84

<210> SEQ ID NO 76
<211> LENGTH: 85
<212> TYPE: DNA
<213> ORGANISM: Artificial Sequence
<220> FEATURE:
<223> OTHER INFORMATION: Primer for construction of fragment "c" (Yeast
      origin of replication)

<400> SEQUENCE: 76
ccgagatgcc aaaggatagg tgctatgttg atgactacga cacagaactg cgggtgacat    60
aatgatagca ttgaaggatg agact                                         85

<210> SEQ ID NO 77
<211> LENGTH: 82
<212> TYPE: DNA
<213> ORGANISM: Artificial Sequence
<220> FEATURE:
<223> OTHER INFORMATION: Primer for construction of fragment "d" (E.
      coli origin of replication)

<400> SEQUENCE: 77
atgtcacccg cagttctgtg tcgtagtcat caacatagca cctatccttt ggcatctcgg    60
tgagcaaaag gccagcaaaa gg                                            82

<210> SEQ ID NO 78
<211> LENGTH: 81
<212> TYPE: DNA
<213> ORGANISM: Artificial Sequence
<220> FEATURE:
<223> OTHER INFORMATION: Primer for construction of fragment "d" (E.
      coli origin of replication)

```
<400> SEQUENCE: 78
ctcagatgta cggtgatcgc caccatgtga cggaagctat cctgacagtg tagcaagtgc    60
tgagcgtcag accccgtaga a                                              81
```